(12) United States Patent
Marder et al.

(10) Patent No.: US 7,994,423 B2
(45) Date of Patent: Aug. 9, 2011

(54) CHARGE-TRANSPORT MATERIALS, METHODS OF FABRICATION THEREOF, AND METHODS OF USE THEREOF

(75) Inventors: Seth Marder, Atlanta, GA (US); Bilal Kaafarani, Beirut (LB); Steve Barlow, Atlanta, GA (US); Bernhard Kippelen, Decatur, GA (US); Benoit Domercq, Atlanta, GA (US); Qing Zhang, Shanghai (CN); Takeshi Kondo, Duluth, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 855 days.

(21) Appl. No.: 11/629,262

(22) PCT Filed: Jun. 14, 2005

(86) PCT No.: PCT/US2005/020998
§ 371 (c)(1),
(2), (4) Date: Feb. 6, 2008

(87) PCT Pub. No.: WO2005/123737
PCT Pub. Date: Dec. 29, 2005

(65) Prior Publication Data
US 2009/0065057 A1  Mar. 12, 2009

Related U.S. Application Data

(60) Provisional application No. 60/579,308, filed on Jun. 14, 2004.

(51) Int. Cl.
*H01L 31/00* (2006.01)
*H01L 29/00* (2006.01)
*C07D 241/36* (2006.01)
*C07D 241/00* (2006.01)

(52) U.S. Cl. ........ 136/263; 544/338; 544/340; 544/341; 257/40

(58) Field of Classification Search .................. 136/263; 544/338, 340, 341; 257/40, E51.006; 256/259; 428/704; 526/259
See application file for complete search history.

(56) References Cited

U.S. PATENT DOCUMENTS
6,436,559 B1   8/2002   Ueno et al.

OTHER PUBLICATIONS

G. Kestemont, V. de Halleux, M. Lehmann, D. A. Ivanov, M. Watson, Y. H. Geerts. Discotic mesogens with potential electron carrier properties, Chem. Comm. 2001, 2074-2075.*

V. Lemaur, D. A. da Silva Filho, V. Coropceanu, M. Lehmann, Y. Geerts, J. Piris,I M. G. Debije, A. M. van de Craats, K. Senthilkumar, L. D. A. Siebbeles, J. M. Warman, J.-L. Bredas, J. Cornil. Charge Transport Properties in Discotic Liquid Crystals: A Quantum-Chemical Insight into Structure-Property Relationships, JACS 2004, 126, 3271-3279.*

Skujins, et al., "Spectroscopic and Structural Studies of Some Oxocarbon Condensation Products-1" Tetrahedron, vol. 25, pp. 3935-3945 (1969).

(Continued)

*Primary Examiner* — Jennifer K. Michener
*Assistant Examiner* — Carlos Barcena
(74) *Attorney, Agent, or Firm* — Thomas, Kayden, Horstemeyer & Risley, LLP

(57) ABSTRACT

Briefly described, embodiments of this disclosure include charge-transport materials, methods of forming charge-transport materials, and methods of using the charge-transport materials.

15 Claims, 55 Drawing Sheets

OTHER PUBLICATIONS

Bock, et al., "Electron-Deficient Columnar Plastic Crystals" ChemPhysChem, vol. 3(6), pp. 532-535 (2002).
Budd, et al., "A Nanoporous Network Polymer Derived from Hexaazaatrinaphthalene with Potential as an Adsorbent an Catalyst Support" Journal of Materials Chemistry, vol. 13, pp. 2721-2726 (2003).
Int'l Search Report, Dec. 14, 2006.

* cited by examiner

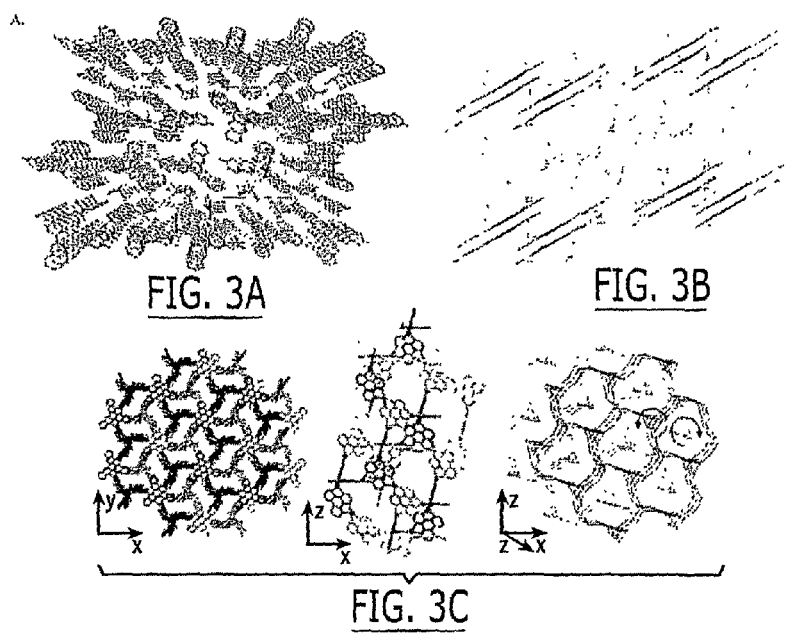
FIG. 3A
FIG. 3B
FIG. 3C
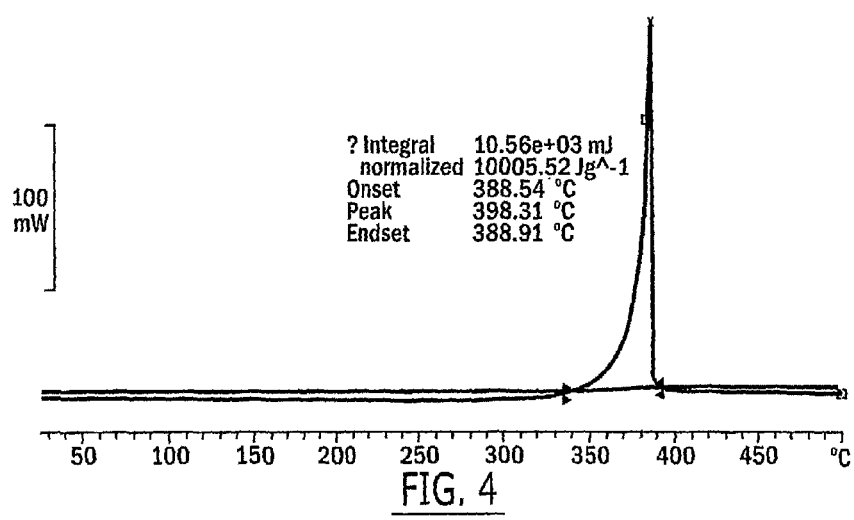
FIG. 4

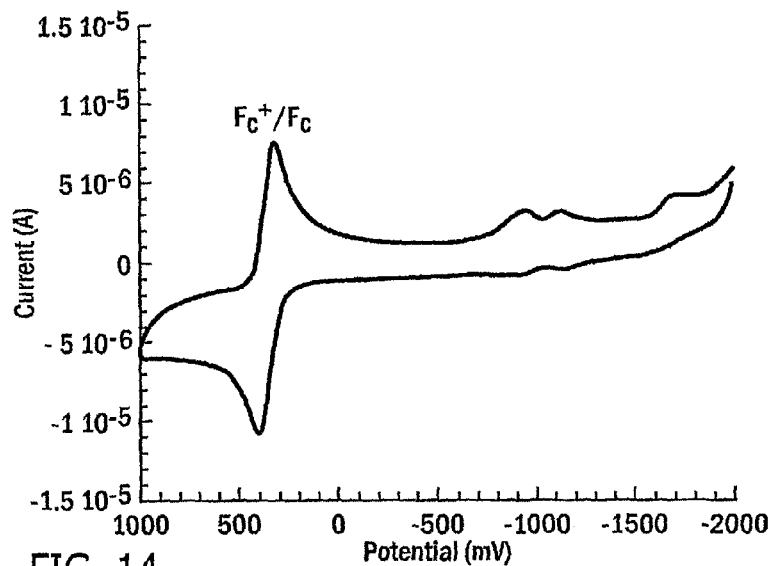
FIG. 14
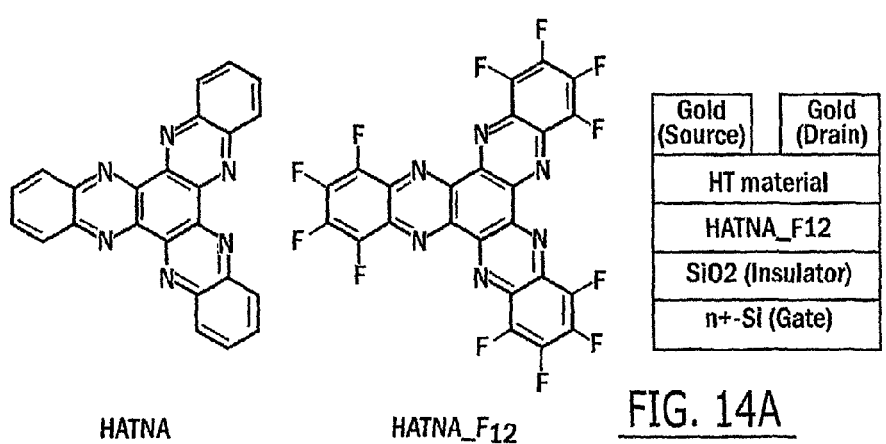
HATNA   HATNA_F12   FIG. 14A

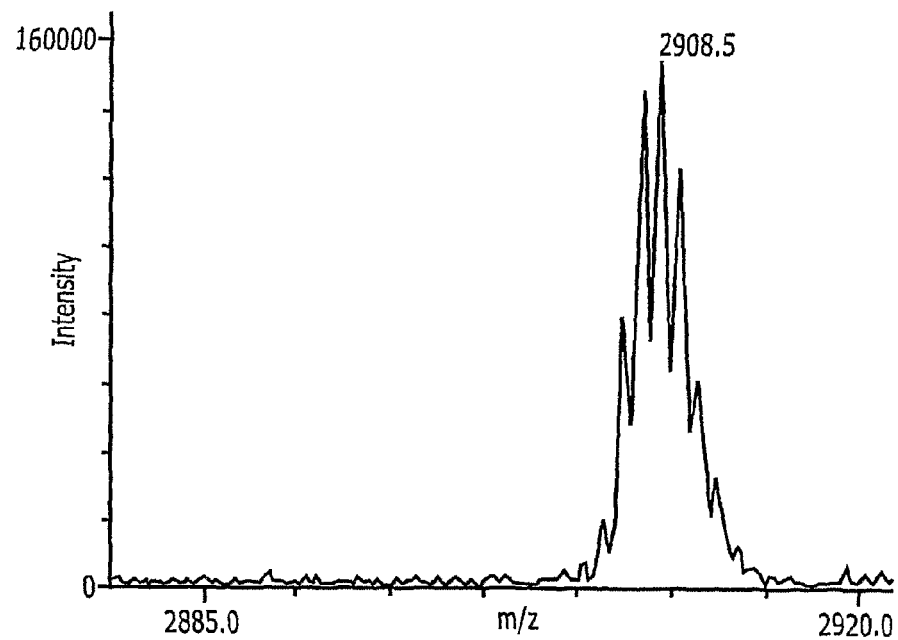
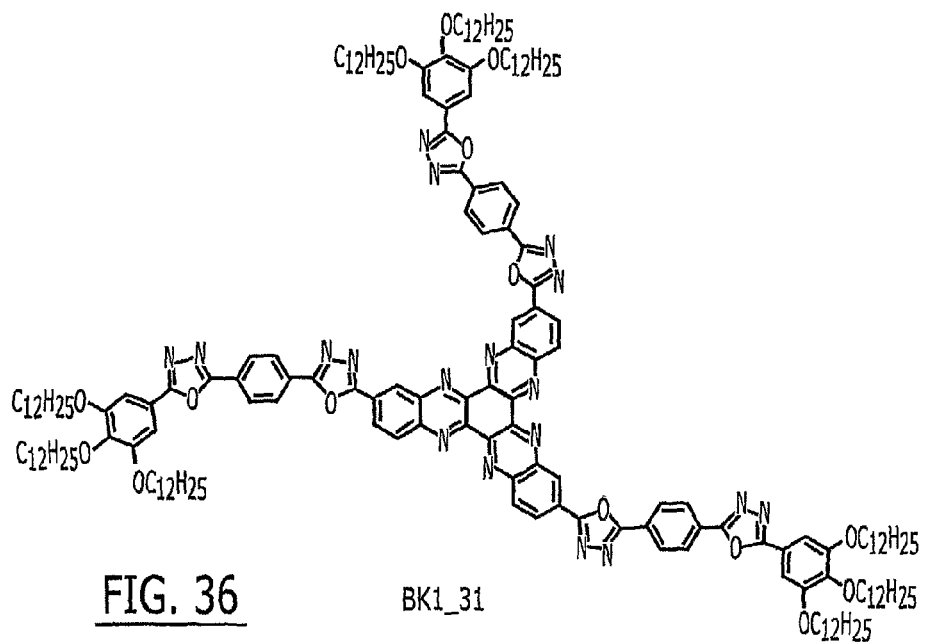
FIG. 36  BK1_31

CHARGE-TRANSPORT MATERIALS, METHODS OF FABRICATION THEREOF, AND METHODS OF USE THEREOF

CROSS-REFERENCE TO RELATED APPLICATION

This application claims priority to U.S. provisional patent application entitled "Electron Deficient Materials For Use In Organic Electronics And Optoelectronics" filed on Jun. 14, 2004 and accorded Ser. No. 60/579,308, which is entirely incorporated herein by reference.

STATEMENT REGARDING FEDERALLY SPONSORED RESEARCH OR DEVELOPMENT

The U.S. government may have a paid-up license in embodiments of this disclosure and the right in limited circumstances to require the patent owner to license others on reasonable terms as provided for by the terms of grants awarded by the Office of Naval Research (N00014-04-1-0120) and the National Science Foundation (DMR 0120967 and ECS-0309131) of the U.S. Government.

BACKGROUND

Charge-transport molecular and polymeric materials are semiconducting materials in which charges can migrate under the influence of an electric field. These charges may be present due to doping with oxidizing or reducing agents, so that some fraction of the transport molecules or polymer repeat units is present as radical cations or anions. More usually, charges are introduced by injection from another material under the influence of an electric field. Charge-transport materials may be classified into hole- and electron-transport materials. In a hole-transport material, electrons are removed, either by doping or injection, from a filled manifold of orbitals to give positively charged molecules or polymer repeat units. Transport takes place by electron-transfer between a molecule or polymer repeat unit and the corresponding radical cation; this can be regarded as movement of a positive charge (hole) in the opposite direction to this electronic motion. In an electron-transport material, extra electrons are added, either by doping or injection; here the transport process includes electron-transfer from the radical anion of a molecule or polymer repeat unit to the corresponding neutral species. In addition, some material—ambi-polar materials—may transport both holes and electrons.

SUMMARY

Briefly described, embodiments of this disclosure include charge-transport materials; polymers, co-polymers, and homopolymers, including charge-transport materials; polymer layers including charge-transport materials, and devices including charge-transport materials.

One exemplary charge-transport material, among others, includes a hexaazatrinaphthylene (HATNA)-$[X]_6$ monomer having a structure:

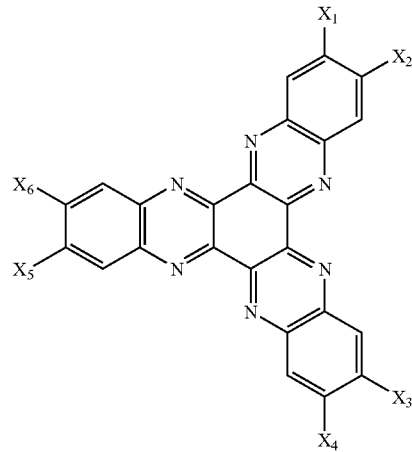

wherein $X_1$, $X_2$, $X_3$, $X_4$, $X_5$, and $X_6$ each are independently selected from: Br; F; I; CN; $NO_2$; CHO; linear or branched, alkyl groups with from 2 to 25 carbons; linear or branched, perfluoronated alkyl groups with up to 25 carbons; fused aromatic rings; donor groups; acceptor groups; aryl groups; polymerizable groups; —$(CH_2CH_2O)_\alpha$—$(CH_2)_\beta OR_{a1}$; —$(CH_2CH_2O)_\alpha$—$(CH_2)_\beta NR_{a2}R_{a3}$; —$(CH_2CH_2O)_\alpha$—$(CH_2)_\beta CONR_{a2}R_{a3}$; —$(CH_2CH_2O)_\alpha$—$(CH_2)_\beta CN$; —$(CH_2CH_2O)_\gamma$—$(CH_2)_\delta F$; —$(CH_2CH_2O)_\gamma$—$(CH_2)_\delta NO_2$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\alpha$—$(CH_2CH_2O)_\alpha$—$(CH_2)_\beta$-Phenyl; —$(CH_2)_\beta$—$(OCH_2CH_2)_\alpha R_{a1}$; —$(CH_2)_\beta$—$(OCH_2CH_2)_\alpha NR_{a2}R_{a3}$; —$(CH_2)_\beta$—$(OCH_2CH_2)_\alpha CONR_{a2}R_{a3}$; —$(CH_2)_\beta$—$(OCH_2CH_2)_\alpha CN$; —$(CH_2)_\beta$—$(OCH_2CH_2)_\alpha F$; —$(CH_2)_\beta$—$(OCH_2CH_2)_\alpha NO_2$; —$(CH_2)_\beta$—$(OCH_2CH_2)_\alpha Cl$; —$(CH_2)_\beta$—$(OCH_2CH_2)_\alpha Br$; —$(CH_2)_\beta$—$(OCH_2CH_2)_\alpha I$; —$(CH_2)_\beta$—$(OCH_2CH_2)_\alpha$Phenyl; —$(CF_2)_\beta OR_{a1}$; —$(CF_2)_\beta CH_2NR_{a2}R_{a3}$; —$(CF_2)_\beta CF_3$; —$O(CF_2)_\beta OR_{a1}$; —$OCH_2CH_2(CF_2)OR_{a1}$; —$OCH_2CH_2(CF_2)_\beta CH_2NR_{a2}R_{a3}$; —$O(CF_2)_\beta CH_2NR_{a2}R_{a3}$; —$OCH_2CH_2(CF_2)_\beta CF_3$; —$(CH_2)_\beta$—$(OCH_2CH_2)_\alpha$Phenyl; —$(CF_2)_\alpha$—$(OCH_2CH_2)_\alpha$Phenyl; —$(CH_2)_\beta$—$(OCH_2CH_2)_\alpha$Aryl; —$(CF_2)_\beta$—$(OCH_2CH_2)_\alpha$Aryl; —$(OCH_2CH_2)_\alpha$—$(CF_2)_\beta$Aryl; —$(OCH_2CH_2)_\alpha$, —$(CH_2)_\beta$Aryl; —$O(CH_2)_\beta$Aryl; and —$O(CF_2)_\beta$Aryl; and combinations thereof; wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript $\alpha$ is an integer number from 0 to 25, wherein subscript $\beta$ is an integer number from 0 to 25; and with the proviso that $X_1$, $X_2$, $X_3$, $X_4$, $X_5$, and $X_6$ are not an alkoxy group, —OR, where $R=C_nH_{2n+1}$, where n=6, 8, 10, or 12; an alkylthio, —SR, where $R=C_nH_{2n+1}$, where n=6, 8, 10, or 12; H; Cl; or a methyl (—$CH_3$) group.

Another exemplary charge-transport material, among others, includes a hexaazatrinaphthylene (HATNA)-$[CO_2Y]_3$ monomer having a structure:

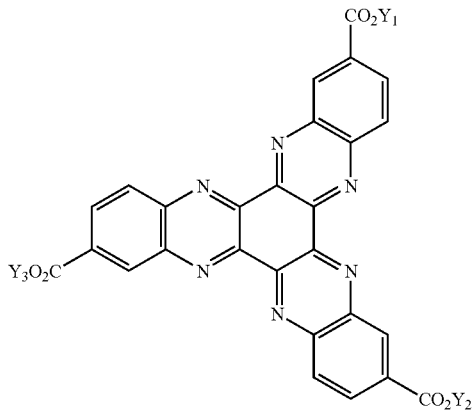

wherein $Y_1$, $Y_2$, and $Y_3$ each are independently selected from: H; linear or branched, alkyl groups with up to 25 carbons; linear or branched, perfluoronated alkyl groups with up to 25 carbons; fused aromatic rings; donor groups; acceptor groups; aryl groups; polymerizable groups; —$(CH_2CH_2O)_\alpha$—$(CH_2)_\beta CH_2$—$OR_{a1}$; —$(CH_2CH_2O)_\alpha$—$(CH_2)_\beta CH_2$—$NR_{a2}R_{a3}$; —$(CH_2CH_2O)_\alpha$—$(CH_2)_\beta CH_2$—$CONR_{a2}R_{a3}$; —$(CH_2CH_2O)_\alpha$—$(CH_2)_\beta CH_2$—$CN$; —$(CH_2CH_2O)_\gamma$—$(CH_2)_\delta CH_2$—$F$; —$(CH_2CH_2O)_\gamma$—$(CH_2)_\delta CH_2$—$NO_2$; —$(CH_2CH_2O)_\alpha$—$(CH_2)_\beta CH_2$—$Cl$; —$(CH_2CH_2O)_\alpha$—$(CH_2)_\beta CH_2$—$Br$; —$(CH_2CH_2O)_\alpha$—$(CH_2)_\beta CH_2$—$I$; —$(CH_2CH_2O)_\alpha$—$(CH_2)_\beta$-Phenyl; —$CH_2$—$(CH_2)_\beta$—$(OCH_2CH_2)_\alpha R_{a1}$; —$CH_2$—$(CH_2)_\beta$—$(OCH_2CH_2)_\alpha NR_{a2}R_{a3}$; —$(CH_2)_\beta CH_2$—$(OCH_2CH_2)_\alpha CONR_{a2}R_{a3}$; —$CH_2$—$(CH_2)_\beta$—$(OCH_2CH_2)_\alpha CN$; —$CH_2$—$(CH_2)_\beta$—$(OCH_2CH_2)_\alpha F$; —$CH_2$—$(CH_2)_\beta$—$(OCH_2CH_2)_\alpha NO_2$; —$CH_2$—$(CH_2)_\beta$—$(OCH_2CH_2)Cl$; —$CH_2$—$(CH_2)_\beta$—$(OCH_2CH_2)_\alpha Br$; —$CH_2$—$(CH_2)_\beta$—$(OCH_2CH_2)_\alpha I$; —$CH_2(CH_2)_\beta$—$(OCH_2CH_2)_\alpha$Phenyl; —$CF_2$—$(CF_2)_\beta OR_{a1}$; —$CF_2$—$(CF_2)_\beta CH_2 NR_{a2}R_{a3}$; —$(CF_2)_\beta CF_3$; —$(CF_2)_\beta OR_{a1}$; —$CH_2CH_2(CF_2)_\beta OR_{a1}$; —$CH_2CH_2(CF_2)_\beta CH_2 NR_{a2}R_{a3}$; —$(CF_2)_\beta CH_2 NR_{a2}R_{a3}$; —$CH_2CH_2(CF_2)_\beta CF_3$; —$CH_2$—$(CH_2)_\beta$—$(OCH_2CH_2)_\alpha$Phenyl; —$CF_2$—$(CF_2)_\beta$—$(OCH_2CH_2)_\alpha$Phenyl; —$CH_2$—$(CH_2)_\beta$—$(OCH_2CH_2)_\alpha$Aryl; —$CF_2$—$(CF_2)_\beta$—$(OCH_2CH_2)_\alpha$Aryl; —$CH_2CH_2$—$(OCH_2CH_2)_\alpha$—$O(CF_2)_\beta$Aryl; $CH_2CH_2$—$(OCH_2CH_2)_\alpha$—$O(CH_2)_\beta$Aryl; —$CH_2O(CH_2)_\beta$Aryl; and —$(CF_2)_\beta$Aryl; and combinations thereof; and wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript $\alpha$ is an integer number from 0 to 25, and wherein subscript $\beta$ is an integer number from 0 to 25.

Another exemplary charge-transport material, among others, includes a hexaazatrinaphthylene (HATNA)-$[CO_2Y']_3$ monomer having a structure:

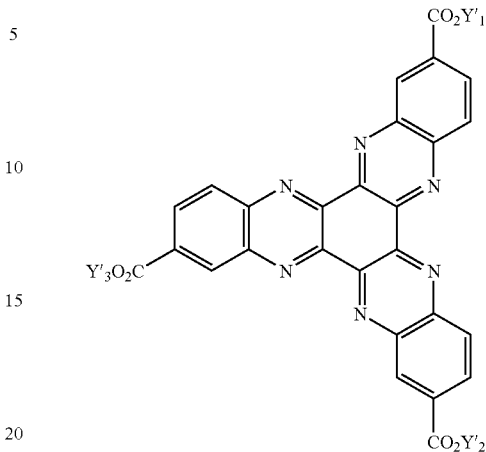

wherein $Y'_1$, $Y'_2$, and $Y'_3$ each are independently selected from: H; linear or branched, alkyl groups with up to 25 carbons; linear or branched, perfluoronated alkyl groups with up to 25 carbons; fused aromatic rings; donor groups; acceptor groups; aryl groups; polymerizable groups; —$(CH_2CH_2O)_\alpha$—$(CH_2)_\beta CH_2$—$OR_{a1}$; —$(CH_2CH_2O)_\alpha$—$(CH_2)_\beta CH_2$—$NR_{a2}R_{a3}$; —$(CH_2CH_2O)_\alpha$—$(CH_2)_\beta CH_2$—$CONR_{a2}R_{a3}$; —$(CH_2CH_2O)_\alpha$—$(CH_2)_\beta CH_2$—$CN$; —$(CH_2CH_2O)_\gamma$—$(CH_2)_\delta CH_2$—$F$; —$(CH_2CH_2O)_\gamma$—$(CH_2)_\delta CH_2$—$NO_2$; —$(CH_2CH_2O)_\alpha$—$(CH_2)_\beta CH_2$—$Cl$; —$(CH_2CH_2O)_\alpha$—$(CH_2)_\beta CH_2$—$Br$; —$(CH_2CH_2O)_\alpha$—$(CH_2)_\beta CH_2$—$I$; —$(CH_2CH_2O)$, —$(CH_2)_\beta$-Phenyl; —$CH_2$—$(CH_2)_\beta$—$(OCH_2CH_2)_\alpha R_{a1}$; —$CH_2$—$(CH_2)_\beta$—$(OCH_2CH_2)_\alpha$ $NR_{a2}R_{a3}$; —$(CH_2)_\beta CH_2$—$(OCH_2CH_2)_\alpha CONR_{a2}R_{a3}$; —$CH_2$—$(CH_2)_\beta$—$(OCH_2CH_2)_\alpha CN$; —$CH_2$—$(CH_2)_\beta$—$(OCH_2CH_2)_\alpha F$; —$CH_2$—$(CH_2)_\beta$—$(OCH_2CH_2)_\alpha NO_2$; —$CH_2$—$(CH_2)_\beta$—$(OCH_2CH_2)_\alpha Cl$; —$CH_2$—$(CH_2)_\beta$—$(OCH_2CH_2)_\alpha Br$; —$CH_2$—$(CH_2)_\beta$—$(OCH_2CH_2)_\alpha I$; —$CH_2(CH_2)_\beta$—$(OCH_2CH_2)_\alpha$Phenyl; —$CF_2$—$(CF_2)_\beta OR_{a1}$; —$CF_2$—$(CF_2)_\beta CH_2 NR_{a2}R_{a3}$; —$(CF_2)_\beta CF_3$; —$(CF_2)_\beta OR_{a1}$; —$CH_2CH_2(CF_2)_\beta OR_{a1}$; —$CH_2CH_2(CF_2)_\beta CH_2 NR_{a2}R_{a3}$; —$(CF_2)_\beta CH_2 NR_{a2}R_{a3}$; —$CH_2CH_2(CF_2)_\beta CF_3$; —$CH_2$—$(CH_2)_\beta$—$(OCH_2CH_2)_\alpha$Phenyl; —$CF_2$—$(CF_2)_\beta$—$(OCH_2CH_2)_\alpha$Phenyl; —$CH_2$—$(CH_2)_\beta$—$(OCH_2CH_2)_\alpha$Aryl; —$CF_2$—$(CF_2)_\beta$—$(OCH_2CH_2)_\alpha$Aryl; —$CH_2CH_2$—$(OCH_2CH_2)_\alpha$—$O(CF_2)_\beta$Aryl; $CH_2CH_2$—$(OCH_2CH_2)_\alpha$—$O(CH_2)_\beta$Aryl; —$CH_2O(CH_2)_\beta$Aryl; and —$(CF_2)_\beta$Aryl; and combinations thereof; and wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript $\alpha$ is an integer number from 0 to 25, and wherein subscript $\beta$ is an integer number from 0 to 25.

Another exemplary charge-transport material, among others, includes a hexaazatrinaphthylene (HATNA)-$[CCU]_6$ monomer having a structure:

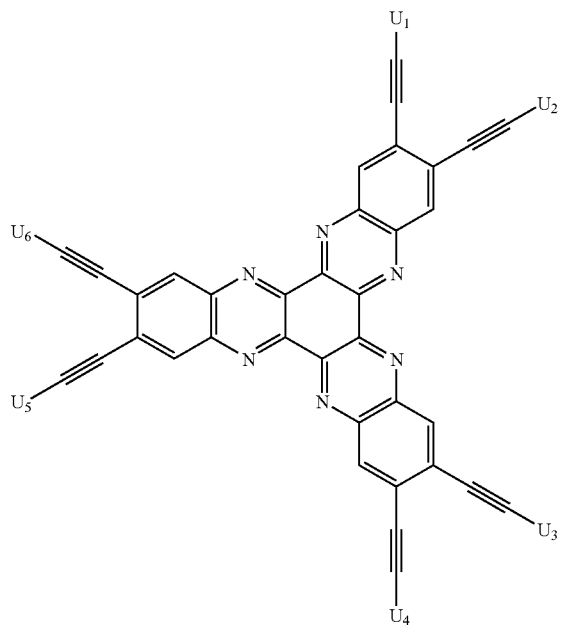

wherein $U_1$, $U_2$, $U_3$, $U_4$, $U_5$, and $U_6$ each are independently selected from: H; halogens; CN; $NO_2$; CHO; linear or branched, alkyl groups with up to 25 carbons; linear or branched, perfluoronated alkyl groups with up to 25 carbons; fused aromatic rings; donor groups; acceptor groups; aryl groups; polymerizable groups; $—(CH_2CH_2O)_\alpha—(CH_2)_\beta OR_{a1}$; $—(CH_2CH_2O)_\alpha—(CH_2)_\beta NR_{a2}R_{a3}$; $—(CH_2CH_2O)_\alpha—(CH_2)_\beta CONR_{a2}R_{a3}$; $—(CH_2CH_2O)_\alpha—(CH_2)_\beta CN$; $—(CH_2CH_2O)_\gamma—(CH_2)_\delta F$; $—(CH_2CH_2O)_\gamma—(CH_2)_\delta NO_2$; $—(CH_2CH_2O)_\alpha—(CH_2)_\beta Cl$; $—(CH_2CH_2O)_\alpha—(CH_2)_\beta Br$; $—(CH_2CH_2O)_\alpha—(CH_2)_\alpha I$; $—(CH_2CH_2O)_\alpha—(CH_2)_\beta$-Phenyl; $—(CH_2)_\beta—(OCH_2CH_2)_\alpha R_{a1}$; $—(CH_2)_\beta—(OCH_2CH_2)_\alpha NR_{a2}R_{a3}$; $—(CH_2)_\beta—(OCH_2CH_2)_\alpha CONR_{a2}R_{a3}$; $—(CH_2)_\beta—(OCH_2CH_2)_\alpha CN$; $—(CH_2)_\beta—(OCH_2CH_2)_\alpha F$; $—(CH_2)_\beta—(OCH_2CH_2)_\alpha NO_2$; $—(CH_2)_\beta—(OCH_2CH_2)_\alpha Cl$; $—(CH_2)_\beta—(OCH_2CH_2)_\alpha Br$; $—(CH_2)_\beta—(OCH_2CH_2)_\alpha I$; $—(CH_2)_\beta—(OCH_2CH_2)_\alpha Phenyl$; $—(CF_2)_\beta OR_{a1}$; $—(CF_2)_\beta CH_2 NR_{a2}R_{a3}$; $—(CF_2)_\beta CF_3$; $—O(CF_2)_\beta OR_{a1}$; $—OCH_2CH_2(CF_2)_\beta OR_{a1}$; $—OCH_2CH_2(CF_2)_\beta CH_2 NR_{a2}R_{a3}$; $—O(CF_2)_\beta CH_2 NR_{a2}R_{a3}$; $—OCH_2CH_2(CF_2)_\beta CF_3$; $—(CH_2)_\beta—(OCH_2CH_2)_\alpha Phenyl$; $—(CF_2)_\beta—(OCH_2CH_2)_\alpha Phenyl$; $—(CH_2)_\beta—(OCH_2CH_2)_\alpha Aryl$; $—(CF_2)_\beta—(OCH_2CH_2)_\alpha Aryl$; $—(OCH_2CH_2)_\alpha—(CF_2)_\beta Aryl$; $—(OCH_2CH_2)_\alpha—(CH_2)_\beta Aryl$; $—O(CH_2)_\beta Aryl$; and $—O(CF_2)_\beta Aryl$; and combinations thereof; and wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript $\alpha$ is an integer number from 0 to 25, and wherein subscript $\beta$ is an integer number from 0 to 25.

Another exemplary charge-transport material, among others, includes a hexaazatrinaphthylene (HATNA)-[Z]$_3$ monomer having a structure:

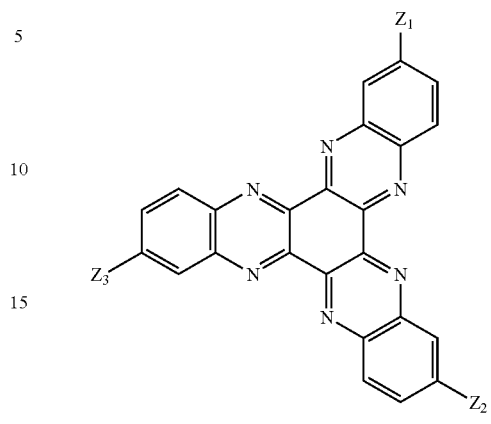

wherein $Z_1$, $Z_2$, and $Z_3$ each are independently selected from: H; halogens; CN; $NO_2$; CHO; $CO_2Hal$, where Hal is a halogen selected from F, Cl, Br; linear or branched, alkyl groups with up to 25 carbons; linear or branched, perfluoronated alkyl groups with up to 25 carbons; fused aromatic rings; donor groups; acceptor groups; aryl groups; polymerizable groups; $—(CH_2CH_2O)_\alpha—(CH_2)_\beta OR_{a1}$; $—(CH_2CH_2O)_\alpha—(CH_2)_\beta NR_{a2}R_{a3}$; $—(CH_2CH_2O)_\alpha—(CH_2)_\beta CONR_{a2}R_{a3}$; $—(CH_2CH_2O)_\alpha—(CH_2)_\beta CN$; $—(CH_2CH_2O)_\gamma—(CH_2)_\delta F$; $—(CH_2CH_2O)_\gamma—(CH_2)_\delta NO_2$; $—(CH_2CH_2O)_\alpha—(CH_2)_\beta Cl$; $—(CH_2CH_2O)_\alpha—(CH_2)_\beta Br$; $—(CH_2CH_2O)_\alpha—(CH_2)_\beta I$; $—(CH_2CH_2O)_\alpha—(CH_2)_\beta$-Phenyl; $—(CH_2)_\beta—(OCH_2CH_2)_\alpha R_{a1}$; $—(CH_2)—(OCH_2CH_2)_\alpha NR_{a2}R_{a3}$; $—(CH_2)_\beta—(OCH_2CH_2)_\alpha CONR_{a2}R_{a3}$; $—(CH_2)_\beta—(OCH_2CH_2)_\alpha CN$; $—(CH_2)_\beta—(OCH_2CH_2)_\alpha F$; $—(CH_2)_\beta—(OCH_2CH_2)_\alpha NO_2$; $—(CH_2)_\beta—(OCH_2CH_2)_\alpha Cl$; $—(CH_2)_\beta—(OCH_2CH_2)_\alpha Br$; $—(CH_2)_\beta—(OCH_2CH_2)_\alpha I$; $—(CH_2)—(OCH_2CH_2)_\alpha Phenyl$; $—(CF_2)_\beta OR_{a1}$; $—(CF_2)_\beta CH_2 NR_{a2}R_{a3}$; $—(CF_2)_\beta CF_3$; $—O(CF_2)_\beta OR_{a1}$; $—OCH_2CH_2(CF_2)_\beta OR_{a1}$; $—OCH_2CH_2(CF_2)_\beta CH_2 NR_{a2}R_{a3}$; $—O(CF_2)_\beta CH_2 NR_{a2}R_{a3}$; $—OCH_2CH_2(CF_2)_\beta CF_3$; $—(CH_2)_\beta—(OCH_2CH_2)_\alpha Phenyl$; $—(CF_2)_\beta—(OCH_2CH_2)_\alpha Phenyl$; $—(CH_2)_\beta—(OCH_2CH_2)_\alpha Aryl$; $—(CF_2)_\beta—(OCH_2CH_2)_\alpha Aryl$; $—(OCH_2CH_2)_\alpha—(CF_2)_\beta Aryl$; $—(OCH_2CH_2)_\alpha—(CH_2)_\beta Aryl$; $—O(CH_2)_\beta Aryl$; and $—O(CF_2)_\beta Aryl$; and combinations thereof; and wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript $\alpha$ is an integer number from 0 to 25, and wherein subscript $\beta$ is an integer number from 0 to 25.

Another exemplary charge-transport material, among others, includes a hexaazatrinaphthylene (HATNA)-[Z']$_3$ monomer having a structure:

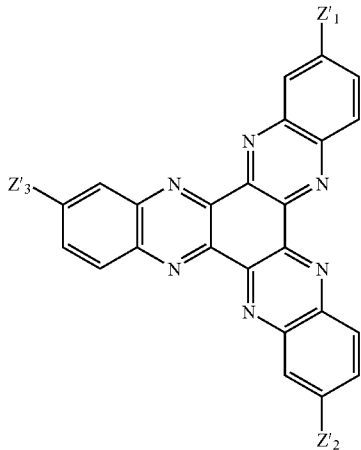

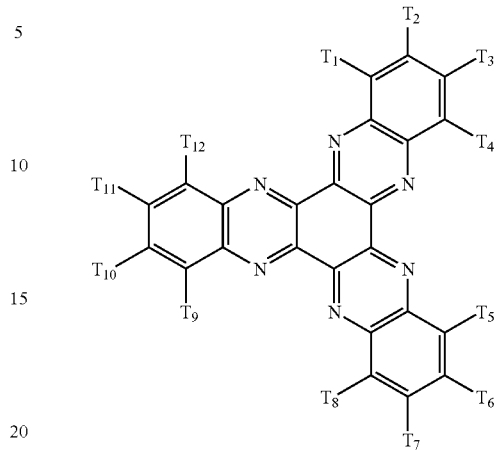

wherein $Z'_1$, $Z'_2$, and $Z'_3$ each are independently selected from: H; halogens; CN; $NO_2$; CHO; $CO_2$Hal where Hal is a halogen selected from F, Cl, Br; linear or branched, alkyl groups with up to 25 carbons; linear or branched, perfluoronated alkyl groups with up to 25 carbons; fused aromatic rings; donor groups; acceptor groups; aryl groups; polymerizable groups; $—(CH_2CH_2O)_\alpha—(CH_2)_\beta OR_{a1}$; $—(CH_2CH_2O)_\alpha—(CH_2)_\beta NR_{a2}R_{a3}$; $—(CH_2CH_2O)_\alpha—(CH_2)_\beta CONR_{a2}R_{a3}$; $—(CH_2CH_2O)_\beta—(CH_2)_\beta CN$; $—(CH_2CH_2O)_\gamma—(CH_2)_\delta F$; $—(CH_2CH_2O)_\gamma—(CH_2)_\delta NO_2$; $—(CH_2CH_2O)_\alpha—(CH_2)_\beta Cl$; $—(CH_2CH_2O)_\alpha—(CH_2)_\beta Br$; $—(CH_2CH_2O)_\alpha—(CH_2)_\beta I$; $—(CH_2CH_2O)_\alpha—(CH_2)_\beta$-Phenyl; $—(CH_2)_\beta—(OCH_2CH_2)_\alpha R_{a1}$; $—(CH_2)—(OCH_2CH_2)_\alpha NR_{a2}R_{a3}$; $—(CH_2)_\beta—(OCH_2CH_2)_\alpha CONR_{a2}R_{a3}$; $—(CH_2)_\beta—(OCH_2CH_2)_\alpha CN$; $—(CH_2)_\beta—(OCH_2CH_2)_\alpha F$; $—(CH_2)_\beta—(OCH_2CH_2)_\alpha NO_2$; $—(CH_2)_\beta—(OCH_2CH_2)_\alpha Cl$; $—(CH_2)_\beta—(OCH_2CH_2)_\alpha Br$; $—(CH_2)_\beta—(OCH_2CH_2)_\alpha I$; $—(CH_2)_\beta—(OCH_2CH_2)_\alpha$Phenyl; $—(CF_2)_\beta OR_{a1}$; $—(CF_2)_\beta CH_2NR_{a2}R_{a3}$; $—(CF_2)_\beta CF_3$; $—O(CF_2)_\beta OR_{a1}$; $—OCH_2CH_2(CF_2)_\beta OR_{a1}$; $—OCH_2CH_2(CF_2)_\beta CH_2NR_{a2}R_{a3}$; $—O(CF_2)_\beta CH_2NR_{a2}R_{a3}$; $—OCH_2CH_2(CF_2)_\beta CF_3$; $—(CH_2)_\beta—(OCH_2CH_2)_\alpha$Phenyl; $—(CF_2)_\beta—(OCH_2CH_2)_\alpha$Phenyl; $—(CH_2)_\beta—(OCH_2CH_2)_\alpha$Aryl; $—(CF_2)_\beta—(OCH_2CH_2)_\alpha$Aryl; $—(OCH_2CH_2)_\alpha—(CF_2)_\beta$Aryl; $—(OCH_2CH_2)_\alpha—(CH_2)_\beta$Aryl; $—O(CH_2)_\beta$Aryl; and $—O(CF_2)_\beta$Aryl; and combinations thereof; and wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript α is an integer number from 0 to 25, and wherein subscript β is an integer number from 0 to 25.

Another exemplary charge-transport material, among others, includes a hexaazatrinaphthylene (HATNA)-[T]$_{12}$ monomer having a structure:

wherein $T_1$, $T_2$, $T_3$, $T_4$, $T_5$, $T_6$, $T_7$, $T_8$, $T_9$, $T_{10}$, $T_{11}$, and $T_{12}$, each are independently selected from: H; halogens; CN; $NO_2$; CHO; linear or branched, alkyl groups with up to 25 carbons; linear or branched, perfluoronated alkyl groups with up to 25 carbons; fused aromatic rings; donor groups; acceptor groups; aryl groups; polymerizable groups; $—(CH_2CH_2O)_\alpha—(CH_2)_\beta OR_{a1}$; $—(CH_2CH_2O)_\alpha—(CH_2)_\beta NR_{a2}R_{a3}$; $—(CH_2CH_2O)_\alpha—(CH_2)_\beta CONR_{a2}R_{a3}$; $—(CH_2CH_2O)_\beta—(CH_2)_\beta CN$; $—(CH_2CH_2O)_\gamma—(CH_2)_\delta F$; $—(CH_2CH_2O)_\gamma—(CH_2)_\delta NO_2$; $—(CH_2CH_2O)_\alpha—(CH_2)_\beta Cl$; $—(CH_2CH_2O)_\alpha—(CH_2)_\beta Br$; $—(CH_2CH_2O)_\alpha—(CH_2)_\beta I$; $—(CH_2CH_2O)_\alpha—(CH_2)_\beta$-Phenyl; $—(CH_2)_\beta—(OCH_2CH_2)_\alpha R_{a1}$; $—(CH_2)_\beta—(OCH_2CH_2)_\alpha NR_{a2}R_{a3}$; $—(CH_2)_\beta—(OCH_2CH_2)_\alpha CONR_{a2}R_{a3}$; $—(CH_2)_\beta—(OCH_2CH_2)_\alpha CN$; $—(CH_2)_\beta—(OCH_2CH_2)_\alpha F$; $—(CH_2)_\beta—(OCH_2CH_2)_\alpha NO_2$; $—(CH_2)_\beta—(OCH_2CH_2)_\alpha Cl$; $—(CH_2)_\beta—(OCH_2CH_2)_\alpha Br$; $—(CH_2)_\beta—(OCH_2CH_2)_\alpha I$; $—(CH_2)_\beta—(OCH_2CH_2)_\alpha$Phenyl; $—(CF_2)_\beta OR_{a1}$; $—(CF_2)_\beta CH_2NR_{a2}R_{a3}$; $—(CF_2)_\beta CF_3$; $—O(CF_2)_\beta OR_{a1}$; $—OCH_2CH_2(CF_2)_\beta OR_{a1}$; $—OCH_2CH_2(CF_2)_\beta CH_2NR_{a2}R_{a3}$; $—O(CF_2)_\beta CH_2NR_{a2}R_{a3}$; $—OCH_2CH_2(CF_2)_\beta CF_3$; $—(CH_2)_\beta—(OCH_2CH_2)_\alpha$Phenyl; $—(CF_2)_\beta—(OCH_2CH_2)_\alpha$Phenyl; $—(CH_2)_\beta—(OCH_2CH_2)_\alpha$Aryl; $—(CF_2)_\beta—(OCH_2CH_2)_\alpha$Aryl; $—(OCH_2CH_2)_\alpha—(CF_2)_\beta$Aryl; $—(OCH_2CH_2)_\alpha—(CH_2)_\beta$Aryl; $—O(CH_2)_\beta$Aryl; and $—O(CF_2)_\beta$Aryl; and combinations thereof; and wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript α is an integer number from 0 to 25, and wherein subscript β is an integer number from 0 to 25.

Another exemplary charge-transport material, among others, includes a dodecaazatrianthracene (DATAN)-[W]$_{12}$ monomer having a structure:

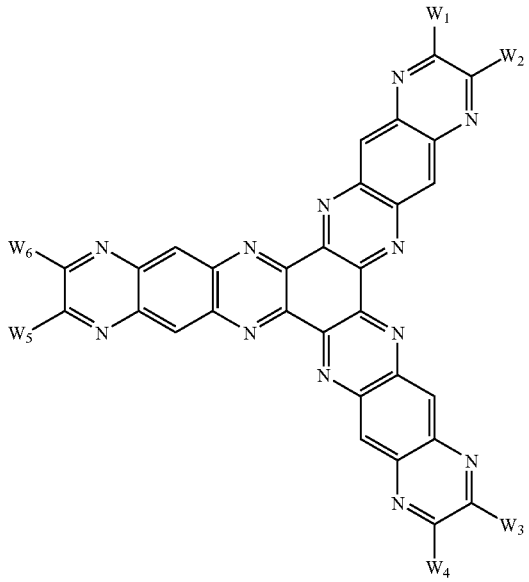

wherein $W_1$, $W_2$, $W_3$, $W_4$, $W_5$, and $W_6$, each are independently selected from: H; halogens; CN; $NO_2$; CHO; linear or branched, alkyl groups with up to 25 carbons; linear or branched, perfluoronated alkyl groups with up to 25 carbons; fused aromatic rings; donor groups; acceptor groups; aryl groups; polymerizable groups; —$(CH_2CH_2O)_\alpha$—$(CH_2)_\beta$ $OR_{a1}$; —$(CH_2CH_2O)_\alpha$—$(CH_2)_\beta NR_{a2}R_{a3}$; —$(CH_2CH_2O)_\alpha$ —$(CH_2)_\beta CONR_{a2}R_{a3}$; —$(CH_2CH_2O)_\alpha$—$(CH_2)_\beta CN$; —$(CH_2CH_2O)_\gamma$—$(CH_2)_\delta F$; —$(CH_2CH_2O)_\gamma$—$(CH_2)_\delta NO_2$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$; —$(CH_2CH_2O)_\alpha$,—$(CH_2)_\beta$-Phenyl; —$(CH_2)_\beta$—$(OCH_2CH_2)_\alpha R_{a1}$; —$(CH_2)$—$(OCH_2CH_2)_\alpha NR_{a2}R_{a3}$; —$(CH_2)_\beta$—$(OCH_2CH_2)_\alpha CONR_{a2}R_{a3}$; —$(CH_2)_\beta$ —$(OCH_2CH_2)_\alpha CN$; —$(CH_2)_\beta$—$(OCH_2CH_2)_\alpha F$; —$(CH_2)_\beta$ —$(OCH_2CH_2)_\alpha NO_2$; —$(CH_2)_\beta$—$(OCH_2CH_2)_\alpha Cl$; —$(CH_2)_\beta$ —$(OCH_2CH_2)_\alpha Br$; —$(CH_2)_\beta$—$(OCH_2CH_2)_\alpha I$; —$(CH_2)_\beta$ —$(OCH_2CH_2)_\alpha$Phenyl; —$(CF_2)_\beta OR_{a1}$; —$(CF_2)_\beta CH_2NR_{a2}R_{a3}$; —$(CF_2)_\beta CF_3$; —$O(CF_2)_\beta OR_{a1}$; —$OCH_2CH_2(CF_2)_\beta OR_{a1}$; —$OCH_2CH_2(CF_2)_\beta CH_2NR_{a2}R_{a3}$; —$O(CF_2)_\beta CH_2NR_{a2}R_{a3}$; —$OCH_2CH_2(CF_2)_\beta CF_3$; —$(CH_2)_\beta$—$(OCH_2CH_2)_\alpha$Phenyl; —$(CF_2)_\beta$—$(OCH_2CH_2)_\alpha$Phenyl; —$(CH_2)_\beta$—$(OCH_2CH_2)_\alpha$Aryl; —$(CF_2)_\beta$—$(OCH_2CH_2)_\alpha$Aryl; —$(OCH_2CH_2)_\alpha$—$(CF_2)_\beta$Aryl; —$(OCH_2CH_2)_\alpha$—$(CH_2)_\beta$Aryl; —$O(CH_2)_\beta$Aryl; and —$O(CF_2)_\beta$Aryl; and combinations thereof; and wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript $\alpha$ is an integer number from 0 to 25, and wherein subscript $\beta$ is an integer number from 0 to 25.

Another exemplary charge-transport material, among others, includes a hexaazatrinaphthylene (HATNA)-[Imide]$_3$ monomer having a structure:

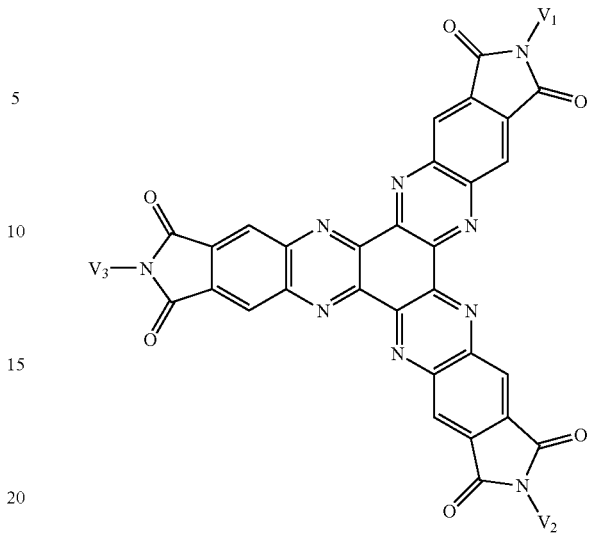

wherein $V_1$, $V_2$, and $V_3$, each are independently selected from: H; linear or branched, alkyl groups with up to 25 carbons; linear or branched, perfluoronated alkyl groups with up to 25 carbons; fused aromatic rings; donor groups; acceptor groups; aryl groups; polymerizable groups; —$(CH_2CH_2O)_\alpha$—$(CH_2)_\beta CH_2$—$OR_{a1}$; —$(CH_2CH_2O)_\alpha$—$(CH_2)_\beta CH_2$—$NR_{a2}R_{a3}$; —$(CH_2CH_2O)_\alpha$—$(CH_2)_\beta CH_2$—$CONR_{a2}R_{a3}$; —$(CH_2CH_2O)_\alpha$—$(CH_2)_\beta CH_2$—CN; —$(CH_2CH_2O)_\gamma$—$(CH_2)_\delta CH_2$—F; —$(CH_2CH_2O)_\gamma$—$(CH_2)_\delta CH_2$—$NO_2$; —$(CH_2CH_2O)_\alpha$—$(CH_2)_\beta CH_2$—Cl; —$(CH_2CH_2O)_\alpha$—$(CH_2)_\beta CH_2$—Br; —$(CH_2CH_2O)_\alpha$—$(CH_2)_\beta CH_2$—I; —$(CH_2CH_2O)_\alpha$—$(CH_2)_\beta$-Phenyl; —$CH_2$—$(CH_2)_\beta$—$(OCH_2CH_2)_\alpha R_{a1}$; —$CH_2$—$(CH_2)_\beta$—$(OCH_2CH_2)_\alpha NR_{a2}R_{a3}$; —$(CH_2)_\beta CH_2$—$(OCH_2CH_2)_\alpha$ $CONR_{a2}R_{a3}$; —$CH_2$—$(CH_2)_\beta$—$(OCH_2CH_2)_\alpha CN$; —$CH_2$—$(CH_2)_\beta$—$(OCH_2CH_2)_\alpha F$; —$CH_2$—$(CH_2)_\beta$—$(OCH_2CH_2)_\alpha NO_2$; —$CH_2$—$(CH_2)_\beta$—$(OCH_2CH_2)_\alpha Cl$; —$CH_2$—$(CH_2)_\beta$—$(OCH_2CH_2)_\alpha Br$; —$CH_2$—$(CH_2)_\beta$—$(OCH_2CH_2)_\alpha I$; —$CH_2(CH_2)_\beta$—$(OCH_2CH_2)_\alpha$Phenyl; —$CF_2$—$(CF_2)_\beta OR_{a1}$; —$CF_2$—$(CF_2)_\beta CH_2NR_{a2}R_{a3}$; —$(CF_2)_\beta CF_3$; —$(CF_2)_\beta OR_{a1}$; —$CH_2CH_2(CF_2)_\beta OR_{a1}$; —$CH_2CH_2(CF_2)_\beta CH_2NR_{a2}R_{a3}$; —$(CF_2)_\beta CH_2NR_{a2}R_{a3}$; —$CH_2CH_2(CF_2)_\beta CF_3$; —$CH_2$—$(CH_2)_\beta$—$(OCH_2CH_2)_\alpha$Phenyl; —$CF_2$—$(CF_2)_\beta$—$(OCH_2CH_2)_\alpha$Phenyl; —$CH_2$—$(CH_2)_\beta$—$(OCH_2CH_2)_\alpha$Aryl; —$CF_2$—$(CF_2)_\beta$ $(OCH_2CH_2)_\alpha$ Aryl; —$CH_2CH_2$—$(OCH_2CH_2)_\alpha$—$O(CF_2)_\beta$ Aryl; $CH_2CH_2$—$(OCH_2CH_2)_\alpha$—$O(CH_2)_\beta$Aryl; —$CH_2$—O $(CH_2)_\beta$Aryl; and —$(CF_2)_\beta$Aryl; and combinations thereof; and wherein $R_{a1}$, $R_{a2}$, and $R_{a3}$ can each be independently selected from, but not limited to, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript $\alpha$ is an integer number from 0 to 25, and wherein subscript $\beta$ is an integer number from 0 to 25.

Another exemplary charge-transport material, among others, includes a polymer, co-polymer, or a homopolymer, among others that can include one or more of a monomer such as, but not limited to, a HATNA-[X]$_6$ monomer, a HATNA-[CO$_2$Y]$_3$, a HATNA-[CCU]$_6$ monomer, a HATNA-[Z]$_3$ monomer, a DATAN-[W]$_{12}$ monomer, a HATNA-[Imide]$_3$ monomer, a HATNA-[CO$_2$Y']$_3$ monomer, a HATNA-[Z']$_3$ monomer, a HATNA-[T]$_{12}$ monomer, and combinations thereof.

A device, among others, that can include one or more of a monomer such as, but not limited to, a HATNA-$[X]_6$ monomer, a HATNA-$[CO_2Y]_3$, a HATNA-$[CCU]_6$ monomer, a HATNA-$[Z]_3$ monomer, a DATAN-$[W]_{12}$ monomer, a HATNA-$[Imide]_3$ monomer, a HATNA-$[CO_2Y']_3$ monomer, a HATNA-$[Z']_3$ monomer, a HATNA-$[T]_{12}$ monomer, and combinations thereof.

A polymer layer, among others, that can include one or more of a monomer such as, but not limited to, a HATNA-$[X]_6$ monomer, a HATNA-$[CO_2Y]_3$, a HATNA-$[CCU]_6$ monomer, a HATNA-$[Z]_3$ monomer, a DATAN-$[W]_{12}$ monomer, a HATNA-$[Imide]_3$ monomer, a HATNA-$[CO_2Y']_3$ monomer, a HATNA-$[Z']_3$ monomer, a HATNA-$[T]_{12}$ monomer, and combinations thereof.

A device, among others, that includes a first electrode and a second electrode. The first electrode includes: a hole-transport layer disposed adjacent the first electrode; and an electron-transport layer disposed adjacent the hole-transport layer, and wherein the electron-transport material is selected from: HATNA-$[X]_6$, HATNA-$[CO_2Y]_3$, HATNA-$[CO_2Y']_3$, HATNA-$[CCU]_6$, HATNA-$[Z]_3$, HATNA-$[Z']_3$, HATNA-$[T]_{12}$, DATAN-$[W]_{12}$, HATNA-$[Imide]_3$, and combinations thereof. The second electrode is disposed adjacent the electron-transport layer.

An organic photovoltaic cell, among others, that includes a first electrode and a second electrode. The first electrode includes a hole-transport layer disposed adjacent the first electrode; an electron-transport layer disposed adjacent the hole-transport layer, and wherein the electron-transport material is selected from: HATNA-$[X]_6$, HATNA-$[CO_2Y]_3$, HATNA-$[CO_2Y']_3$, HATNA-$[CCU]_6$, HATNA-$[Z]_3$, HATNA-$[Z']_3$, HATNA-$[T]_{12}$, DATAN-$[W]_{12}$, HATNA-$[Imide]_3$, and combinations thereof; and an exciton blocking layer disposed adjacent the electron-transport layer. The second electrode is disposed adjacent the exciton blocking layer.

An organic field-effect transistor, among others, that includes: a substrate; a gate electrode disposed on a first side of the substrate; a gate insulator disposed on a second side of the substrate; a source electrode disposed on a first portion of the gate insulator; a drain electrode disposed on a second portion of the gate insulator; and an electron-transport layer disposed on a third portion of the gate insulator, the source electrode, and the drain electrode, and wherein the electron-transport material is selected from: HATNA-$[X]_6$, HATNA-$[CO_2Y]_3$, HATNA-$[CO_2Y']_3$, HATNA-$[CCU]_6$, HATNA-$[Z]_3$, HATNA-$[Z']_3$, HATNA-$[T]_{12}$, DATAN-$[W]_{12}$, HATNA-$[Imide]_3$, and combinations thereof.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3 illustrates the X-ray structure of HATNA (reproduced from references 10, 11, and 12).

FIG. 4 illustrates the DSC of BK2_93, HATNA_$[NO_2]_6$.

FIG. 14 illustrates the cyclic DC voltammogram of HATNA_$Cl_6$, BK2_67C, in dichloromethane with 0.1 M $TBAPF_6$ (vs Ag/AgCl); $E_1^{red}=-1.286$ V; $E_2^{red}=-1.514$ V; $E_3^{red}=-2.022$ V. The reduction potentials are calculated vs. $F_c^+/F_c$.

FIG. 14A illustrates the proposed design of an OFET based on HATNA_$F_{12}$ and a HT material.

FIG. 36 illustrates the MALDI-TOF of BK1__31 (BK2__9F).

DETAILED DESCRIPTION

Figure 1:
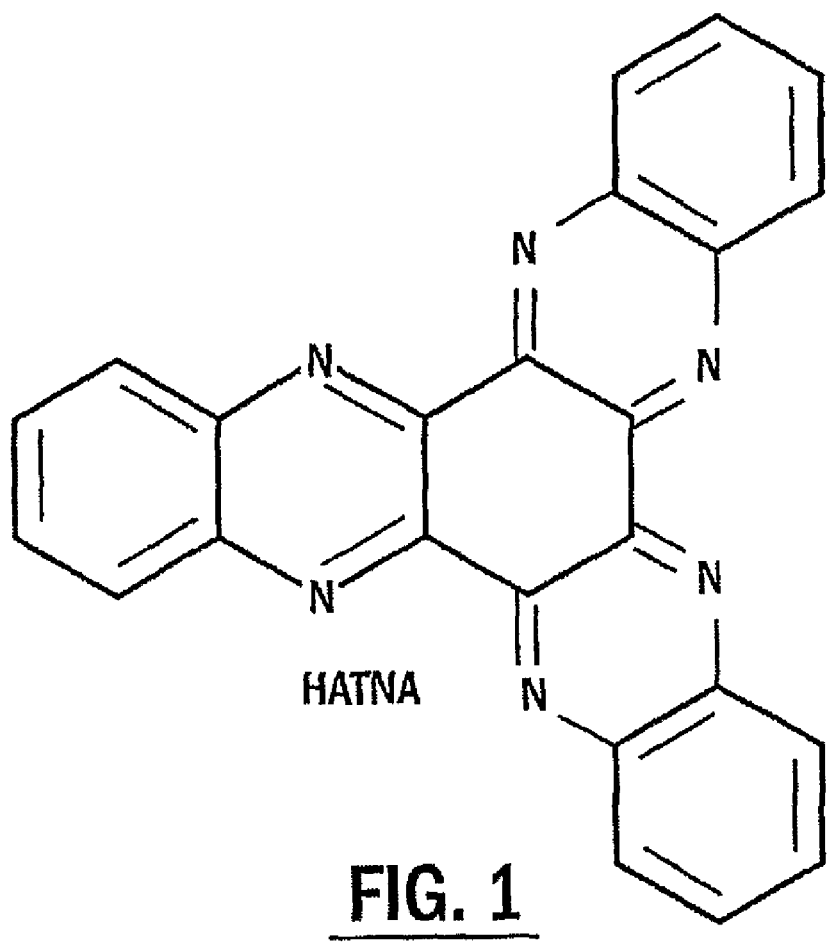
FIG. 1 illustrates a chemical structure of hexaazatrinaphthylene (HATNA) compound.

In accordance with the purpose(s) of the present disclosure, as embodied and broadly described herein, embodiments of the present disclosure, in one aspect, relate to charge-transport material, methods of making charge-transport materials, and methods of using charge-transport materials. In particular, the charge-transport materials include, but are not limited to, compounds having hexaazatrinaphthylenes (HATNA) cores and dodecaazatrianthracenes (DATAN) cores, and having side chains (groups or mesogens) attached to the core. HATNA and DATAN charge-transport materials have strong intermolecular overlap and low reorganization energies, coupled with the tunability of redox potentials, of glass-, crystal-, and liquid-crystal-forming abilities, of the delocalization of electronic structure, and of the degree of molecular and materials anisotropy. In particular, the side chains of HATNA and DATAN cores can be selected to provide charge-transport materials having various volatilities, solubilities, crystallinity, and charge transport ability, as well as being a hole-transport material or an electron-transport material. In other words, the side chains can be selected to tune the characteristics of the charge-transport material as necessary.

The charge-transport materials described herein can be used in a wide variety of electronic applications that include, but are not limited to, electroluminescent (EL) devices (e.g., organic light emitting devices (OLEDs)), photovoltaic cells, light-emitting diodes, field-effect transistors, phototransistors, radio-frequency ID tags, semiconductor devices, photoconductive diodes, metal-semiconductor junctions (e.g., Schottky barrier diodes), p-n junction diodes, p-n-p-n switching devices, photodetectors, optical sensors, phototransducers, bipolar junction transistors (BJTs), heterojunction bipolar translators, switching transistors, charge transfer devices, thin film transistors, organic radiation detectors, infra-red emitters, tunable microcavities for variable output wavelength, telecommunications devices and applications, optical computing devices, optical memory devices, chemical detectors, combinations thereof, and the like.

In addition, the charge-transport materials may also be used to modify the surfaces of other material components with the aim of improving mechanical contact between materials and/or to improve charge-transport from one material to another.

The charge-transport materials may exist as crystals, mesoscopic phases, polymers, glasses, liquids, gases, and combinations thereof. The state of charge-transport materials can be altered by processing the charge-transport materials, mixing the charge-transport materials with other materials, using different side chains in the charge-transport materials relative to other charge-transport materials, and the like. One skilled in the art could modify embodiments of the present disclosure to alter the state of the charge-transport materials.

The charge-transport materials can be processed to produce a highly ordered mesophase morphology. When the charge-transport materials are used to form a layered thin film, the molecules have a preferential orientation in space. In particular, the charge-transport materials can have a certain degree of long-range orientational molecular order and long-range translational molecular order. The mesophase ordering allows close packing of molecular pi-electron systems (e.g., closely packed conjugated aromatic rings, in which very close pi-pi stacking can occur). Pi-pi stacking allows intermolecular charge transport to occur more easily, leading to high charge carrier mobilities, which increases intermolecular charge transfer that occurs through a hopping mechanism between adjacent molecules. In particular, the charge-transport material compounds can stack in the form of well-defined columns (e.g., the aromatic cores in one layer are substantially aligned with the aromatic cores in adjacent layers) forming one dimensional paths for charge transport along the stacked conjugated cores due to the good intermolecular overlap within the stacks.

This ordered, and oriented microstructure can be made substantially permanent by polymerizing the charge-transport materials, which can also create a structure with long-range order, or a "monodomain." Formation of a monodomain also maximizes charge transfer by eliminating charge trap sites at grain boundaries, while the polymerization also improves the mechanical properties of the film. Further, by cross-linking the charge-transport material compounds, a highly stable structure results, which has an additional advantage of being substantially impervious to subsequent processing solvents during device fabrication, thus allowing a wider range of solvents to be used in deposition of the next layer of the device by solution techniques. In addition, the cross-linking may increase the density of the film, leading to smaller intermolecular distances and improved charge transport.

The charge-transport materials may be in a liquid crystalline phase, may show liquid crystal phase behavior in mixtures with other compounds, or when the compounds or materials, or the mixtures thereof, are polymerized, they are in a liquid crystalline phase. As used herein, a "liquid crystalline phase" or "liquid crystal phase" includes a phase that is intermediate to a liquid phase and a crystalline phase. In the liquid crystalline phase, the orientations of a portion of the charge-transport material compounds are correlated to each other (e.g., the orientation of each individual charge-transport material compound is affected and is affecting the orientation of the neighboring charge-transport material compound), and the correlation can extend to a large scale (e.g., equal to or larger than 1 micron so that a substantial portion of the charge-transport material compounds are orientated (e.g., the central aromatic cores are substantially aligned in subsequent layers to form a one dimensional column for charge transport)). The orientation-correlation in the liquid crystals allows one to control the orientations of the charge-transport material compounds with the aid of an electrical field, a magnetic field, or a pre-treated surface, so that one can switch the orientation or diminish the unwanted effect of the local environment (e.g., impurities). This is unlike an isotropic phase where the orientations of charge-transport material compounds in solution are random.

The alignment of the molecules of the liquid crystals is conventionally regarded as being alignment with respect to a vector called the director. Unlike in the solid phase, in the crystalline state the positions of the molecules in the liquid crystal phase do not have long range order in at least one direction. For example, discotic liquid-crystalline mesophases include quasi-two-dimensional molecules, which include a rigid conjugated core and flexible side chains (e.g., HATNA and DATAN charge-transport molecules). The charge-transport material compounds in the discotic liquid-crystalline mesophase can stack in the form of well-defined columns, forming one-dimensional paths for charge transport along the stacked conjugated cores due to the good intermolecular overlap within the stacks.

Alignment of the liquid crystal material can be achieved for example by application of a magnetic and/or electric field (e.g., oscillating electromagnetic radiation), by treatment of the substrate onto which the material is coated, by shearing the material during or after coating, by application of a magnetic and/or electric field (e.g., oscillating electromagnetic radiation) to the coated material, or by the addition of surface-active compounds to the liquid crystal material. Reviews of alignment techniques are given for example by 1. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement. (1981), pages 1-77.

As mentioned above, the charge-transport materials includes HATNA or DATAN cores. The following structures illustrate the HATNA core and the DATAN core:

The HATNA or DATAN can be monomer units in a polymer of the charge-transport material, such as a homopolymer or a copolymer (e.g., block copolymers, random copolymers, alternating copolymers, periodic copolymers, and combinations thereof). The monomer units in embodiments of the copolymers can include the HATNA and/or DATAN core (e.g., see various structures below), as well as other monomer units consistent with the purposes and characteristics of the charge-transport materials described herein.

Various groups (e.g., atoms and compounds) or mesogenic units can be bonded to the HATNA core and/or the DATAN core to form a variety of charge-transport materials. The type of group and/or the combinations of groups and/or the location of the groups bonded to the HATNA core and/or the DATAN core can be selected to tune or manipulate the volatility, solubility, crystallinity, melting point, phase transitions, shelf life, and charge transport ability, of the charge-transport material. In addition, the type of group and/or the combinations of groups that can be bonded to the HATNA core and/or the DATAN core can be selected to form a hole-transport material or an electron-transport material. For example, see the discussion corresponding to Scheme 7 in Example 1.

The following structures describe non-limited embodiments of the charge-transport material compounds having the HATNA core or the DATAN core:

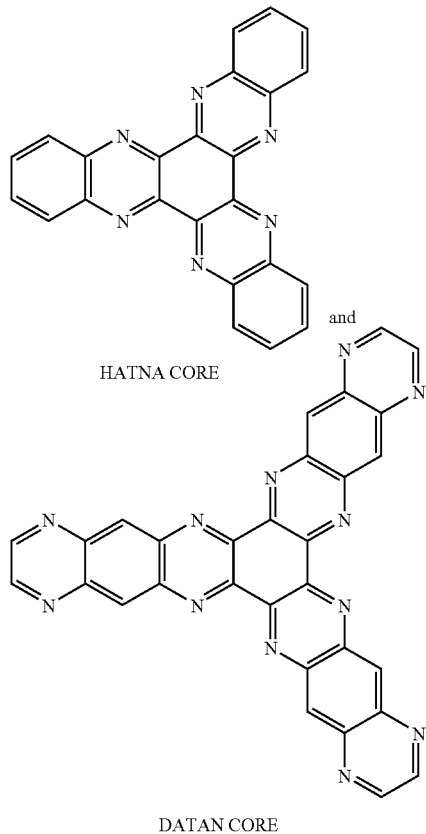

HATNA CORE and

DATAN CORE

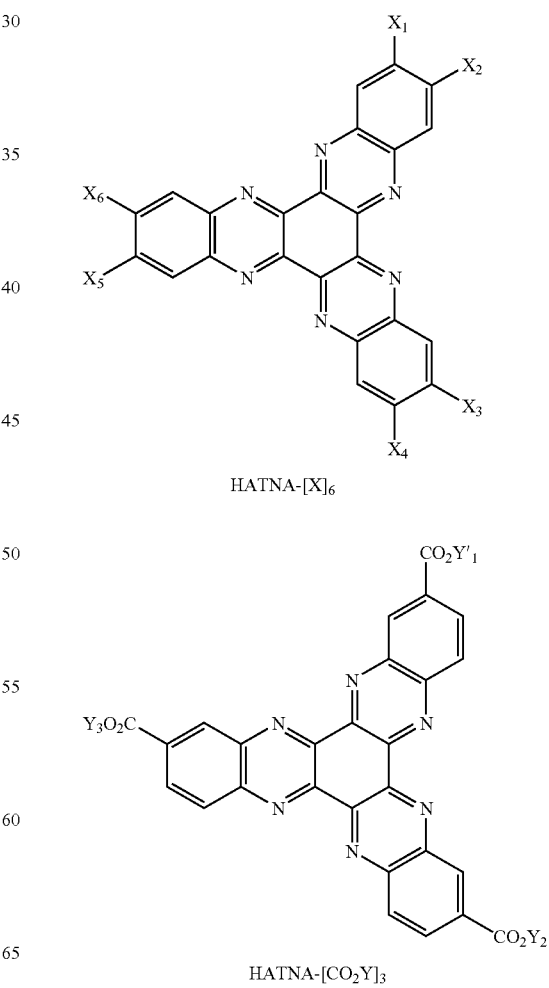

HATNA-$[X]_6$

HATNA-$[CO_2Y]_3$

-continued
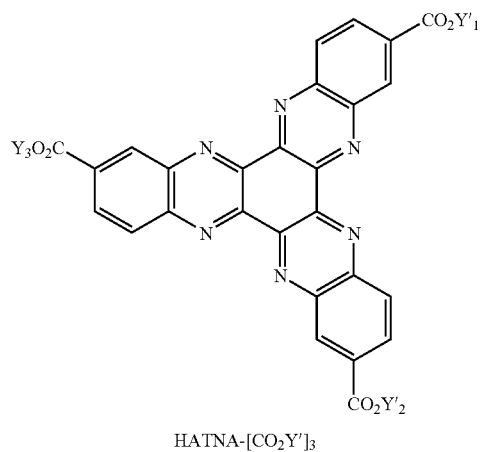
HATNA-[CO₂Y′]₃
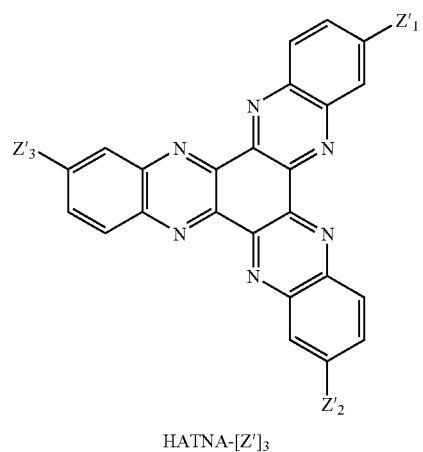
HATNA-[Z′]₃
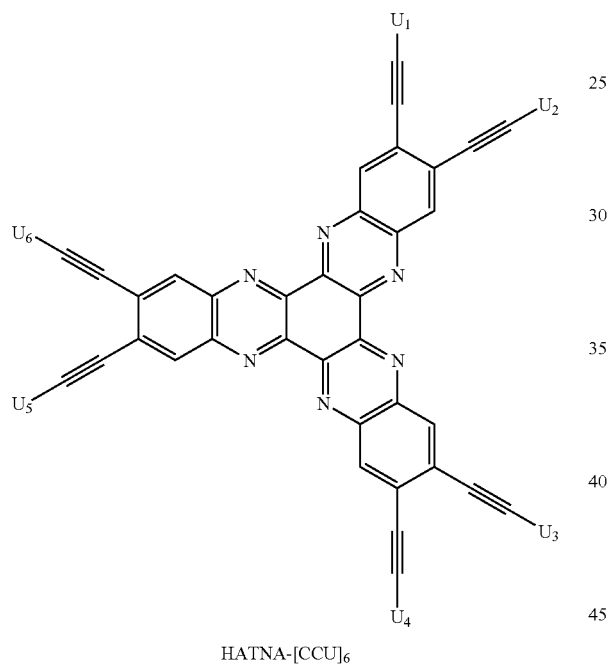
HATNA-[CCU]₆
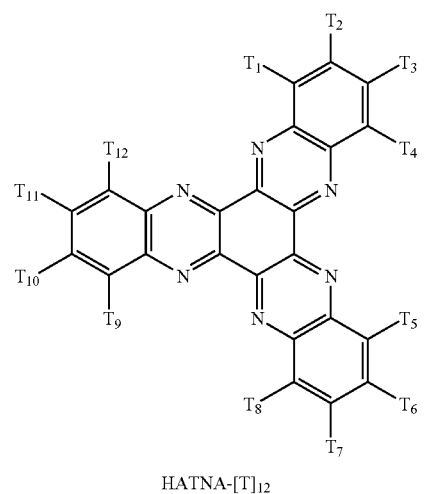
HATNA-[T]₁₂
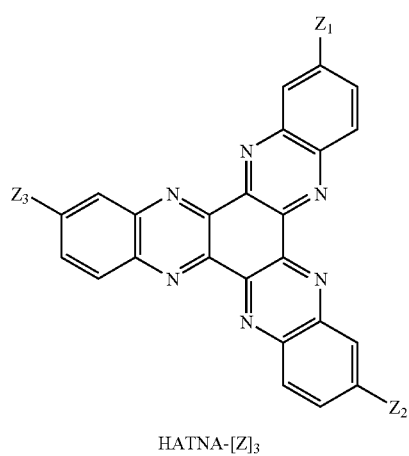
HATNA-[Z]₃
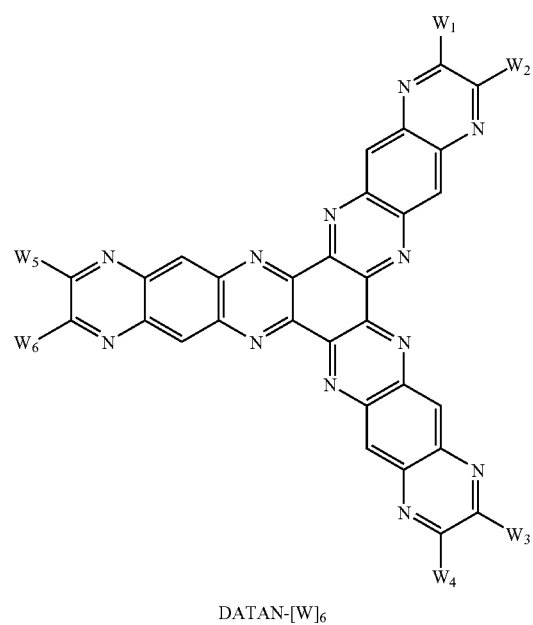
DATAN-[W]₆

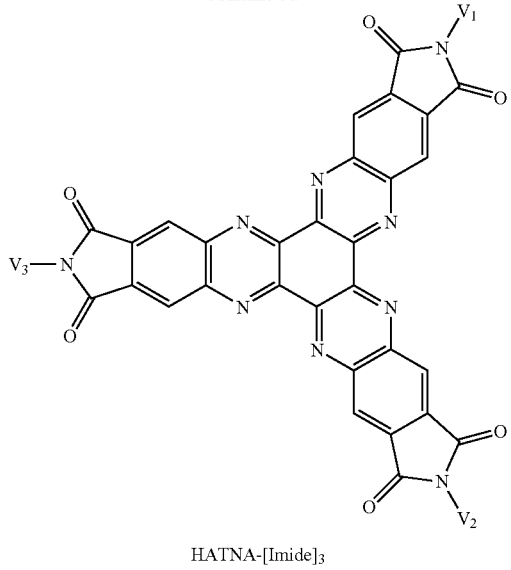

HATNA-[Imide]$_3$

In HATNA-[X]$_6$, HATNA-[CO$_2$Y]$_3$, HATNA-[CO$_2$Y']$_3$, HATNA-[CCU]$_6$, HATNA-[Z]$_3$, HATNA-[Z']$_3$, HATNA-[T]$_{12}$, HATNA-[Imide]$_3$, and DATNA-[W]$_6$, an asterisk (*) in the structures shown below identifies the atom of attachment to a functional group and implies that the atom is missing one hydrogen that would normally be implied by the structure in the absence of the asterisk. Also note the following: "—" indicates a single bond between 2 atoms, "=" indicates a double bond between 2 atoms, and "≡" indicates a triple bond between 2 atoms.

In HATNA-[X]$_6$, HATNA-[CO$_2$Y]$_3$, HATNA-[CO$_2$Y']$_3$, HATNA-[CCU]$_6$, HATNA-[Z]$_3$, HATNA-[Z']$_3$, HATNA-[T]$_{12}$, HATNA-[Imide]$_3$, and DATNA-[W]$_6$, the groups can include from one type of group to up to twelve types of groups depending on the particular charge-transport material (e.g., HATNA-[CO$_2$Y]$_3$ as compared to HATNA-[T]$_{12}$). For example, X$_1$, X$_2$, X$_3$, X$_4$, X$_5$, and X$_6$, could be the same type of group, two types of groups, three types of groups, four types of groups, five types of groups, or six types of groups. It should also be noted that the configuration (e.g., position on the molecule) of the groups on the molecules can vary depending on the number of different groups bonded to the molecules to produce charge-transport materials having a particular characteristic.

Groups R$_3$, R$_4$, T$_1$, T$_2$, T$_3$, T$_4$, T$_5$, T$_6$, T$_7$, T$_8$, T$_9$, T$_{10}$, T$_{11}$, T$_{12}$, U$_1$, U$_2$, U$_3$, U$_4$, U$_5$, U$_6$, W$_1$, W$_2$, W$_3$, W$_4$, W$_5$, W$_6$, X$_1$, X$_2$, X$_3$, X$_4$, X$_5$, X$_6$, Z$_1$, Z$_2$, Z$_3$, Z'$_1$, Z'$_2$, and Z'$_3$, can each be independently selected from, but not limited to, the one or more of following groups: H; halogens; CN; NO$_2$; CHO; linear or branched, alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, and 25 carbons in all isomer-forms such as normal, secondary, iso- and neo-isomers); linear or branched, perfluoronated alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, and 25 carbons in all isomer forms such as normal, secondary, iso- and neo-isomers); fused aromatic rings (e.g., two to four rings); donor groups (e.g., those having low ionization potentials, see discussion below); acceptor groups (e.g., those having high electron affinity, see discussion below); aryl groups (see discussion below); and polymerizable groups (see discussion below).

In addition, groups R$_3$, R$_4$, T$_1$, T$_2$, T$_3$, T$_4$, T$_5$, T$_6$, T$_7$, T$_8$, T$_9$, T$_{10}$, T$_{11}$, T$_{12}$, U$_1$, U$_2$, U$_3$, U$_4$, U$_5$, U$_6$, W$_1$, W$_2$, W$_3$, W$_4$, W$_5$, W$_6$, X$_1$, X$_2$, X$_3$, X$_4$, X$_5$, X$_6$, Z$_1$, Z$_2$, Z$_3$, Z'$_1$, Z'$_2$, and Z'$_3$, can each be independently selected from, but not limited to, one or more of the following groups: —(CH$_2$CH$_2$O)$_\alpha$—(CH$_2$)$_\beta$OR$_{a1}$; —(CH$_2$CH$_2$O)$_\alpha$—(CH$_2$)$_\beta$NR$_{a2}$R$_{a3}$; —(CH$_2$CH$_2$O)$_\alpha$—(CH$_2$)$_\beta$CONR$_{a2}$R$_{a3}$; —(CH$_2$CH$_2$O)$_\alpha$—(CH$_2$)$_\beta$CN; —(CH$_2$CH$_2$O)$_\gamma$—(CH$_2$)$_\delta$F; —(CH$_2$CH$_2$O)$_\gamma$—(CH$_2$)$_\delta$NO$_2$; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; —(CH$_2$)$_\beta$—(OCH$_2$CH$_2$)$_\alpha$R$_{a1}$; —(CH$_2$)$_\beta$—(OCH$_2$CH$_2$)$_\alpha$NR$_{a2}$R$_{a3}$; —(CH$_2$)$_\beta$—(OCH$_2$CH$_2$)$_\alpha$CONR$_{a2}$R$_{a3}$; —(CH$_2$)$_\beta$—(OCH$_2$CH$_2$)$_\alpha$CN; —(CH$_2$)$_\beta$—(OCH$_2$CH$_2$)$_\alpha$F; —(CH$_2$)$_\beta$—(OCH$_2$CH$_2$)$_\alpha$NO$_2$; —(CH$_2$)$_\beta$—(OCH$_2$CH$_2$)$_\alpha$Cl; —(CH$_2$)$_\beta$—(OCH$_2$CH$_2$)$_\alpha$Br; —(CH$_2$)$_\beta$—(OCH$_2$CH$_2$)$_\alpha$I; —(CH$_2$)$_\beta$—(OCH$_2$CH$_2$)$_\alpha$Phenyl; —(CF$_2$)$_\beta$OR$_{a1}$; —(CF$_2$)OCH$_2$NR$_{a2}$R$_{a3}$; —(CF$_2$)$_\beta$CF$_3$; —O(CF$_2$)$_\beta$OR$_{a1}$; —OCH$_2$CH(CF$_2$)$_\beta$OR$_{a1}$; —OCH$_2$CH(CF$_2$)$_\beta$CH$_2$NR$_{a2}$R$_{a3}$; —O(CF$_2$)$_\beta$CH$_2$NR$_{a2}$R$_{a3}$; —OCH$_2$CH$_2$(CF$_2$)$_\beta$ CF$_3$; —(CH$_2$)$_\beta$—(OCH$_2$CH$_2$)$_\alpha$Phenyl; —(CF$_2$)$_\beta$—(OCH$_2$CH$_2$)$_\alpha$Phenyl; —(CH$_2$)$_\beta$—(OCH$_2$CH$_2$)$_\alpha$Aryl; (see discussion below); —(CF$_2$)$_\beta$—(OCH$_2$CH$_2$)$_\alpha$Aryl (see discussion below); —(OCH$_2$CH$_2$)$_\alpha$—(CF$_2$)$_\beta$Aryl (see discussion below); —(OCH$_2$CH$_2$)$_\alpha$—(CH$_2$)$_\beta$Aryl (see discussion below); —O(CH$_2$)$_\beta$Aryl; (see discussion below); and —O(CF$_2$)$_\alpha$Aryl (see discussion below). Groups V$_1$, V$_2$, V$_3$, Y$_1$, Y$_2$, Y$_3$, Y'$_1$, Y'$_2$, and Y'$_3$ each are independently selected from: H; linear or branched, alkyl groups with up to 25 carbons; linear or branched, perfluoronated alkyl groups with up to 25 carbons; fused aromatic rings; donor groups; acceptor groups; aryl groups; polymerizable groups; —(CH$_2$CH$_2$O)$_\alpha$—(CH$_2$)$_\beta$CH$_2$—OR$_{a1}$; —(CH$_2$CH$_2$O)$_\alpha$—(CH$_2$)$_\beta$CH$_2$—NR$_{a2}$R$_{a3}$; —(CH$_2$CH$_2$O)$_\alpha$—(CH$_2$)OCH$_2$—CONR$_{a2}$R$_{a3}$; —(CH$_2$CH$_2$O)$_\alpha$—(CH$_2$)$_\beta$CH$_2$—CN; —(CH$_2$CH$_2$O)$_\gamma$—(CH$_2$)$_\delta$CH$_2$—F; —(CH$_2$CH$_2$O)$_\gamma$—(CH$_2$)$_\delta$CH$_2$—NO$_2$; —(CH$_2$CH$_2$O)$_\alpha$—(CH$_2$)OCH$_2$—Cl; —(CH$_2$CH$_2$O)$_\alpha$—(CH$_2$)OCH$_2$—Br; —(CH$_2$CH$_2$O)$_\alpha$—(CH$_2$)OCH$_2$—I; —(CH$_2$CH$_2$O)$_\alpha$—(CH$_2$)$_\beta$-Phenyl; —CH$_2$—(CH$_2$)$_\beta$—(OCH$_2$CH$_2$)$_\alpha$R$_{a1}$; —CH$_2$—(CH$_2$)—(OCH$_2$CH$_2$)$_\alpha$NR$_{a2}$R$_{a3}$; —(CH$_2$)$_\beta$CH$_2$—(OCH$_2$CH$_2$)$_\alpha$CONR$_{a2}$R$_{a3}$; —CH$_2$—(CH$_2$)$_\beta$—(OCH$_2$CH$_2$)$_\alpha$CN; —CH$_2$—(CH$_2$)$_\beta$—(OCH$_2$CH$_2$)$_\alpha$F; —CH$_2$—(CH$_2$)$_\beta$—(OCH$_2$CH$_2$)$_\alpha$NO$_2$; —CH$_2$—(CH$_2$)$_\beta$—(OCH$_2$CH$_2$)$_\alpha$Cl; —CH$_2$—(CH$_2$)$_\beta$—(OCH$_2$CH$_2$)$_\alpha$Br; —CH$_2$—(CH$_2$)$_\beta$—(OCH$_2$CH$_2$)$_\alpha$I; —CH$_2$(CH$_2$)$_\beta$—(OCH$_2$CH$_2$)$_\alpha$Phenyl; —CF$_2$—(CF$_2$)$_\beta$OR$_{a1}$; —CF$_2$—(CF$_2$)$_\beta$CH$_2$NR$_{a2}$R$_{a3}$; —(CF$_2$)$_\beta$CF$_3$; —(CF$_2$)OR$_{a1}$; —CH$_2$CH$_2$(CF$_2$)$_\beta$OR$_{a1}$; —CH$_2$CH$_2$(CF$_2$)$_\beta$CH$_2$NR$_{a2}$R$_{a3}$; (CF$_2$)CH$_2$NR$_{a2}$R$_{a3}$; —CH$_2$CH$_2$(CF$_2$)$_\beta$CF$_3$; —CH$_2$—(CH$_2$)$_\beta$—(OCH$_2$CH$_2$)$_\alpha$Phenyl; —CF$_2$—(CF$_2$)$_\beta$—(OCH$_2$CH$_2$)$_\alpha$Phenyl; —CH$_2$—(CH$_2$)$_\beta$—(OCH$_2$CH$_2$)$_\alpha$Aryl; —CF$_2$—(CF$_2$)$_\beta$—(OCH$_2$CH$_2$)$_\alpha$ Aryl; —CH$_2$CH$_2$—(OCH$_2$CH$_2$)$_\alpha$—O(CF$_2$)$_\beta$Aryl; CH$_2$CH$_2$—(OCH$_2$CH$_2$)$_\alpha$—O(CH$_2$)$_\beta$Aryl; —CH$_2$O(CH$_2$)$_\beta$Aryl; and —(CF$_2$)$_\beta$Aryl; and combinations thereof. In addition, groups V$_1$, V$_2$, V$_3$, Y$_1$, Y$_2$, Y$_3$, Y'$_1$, Y'$_2$, and Y'$_3$ can each be independently selected from, but not limited to, one or more of the following groups: —(CH$_2$CH$_2$O)$_\alpha$—(CH$_2$)$_\beta$CH$_2$—OR$_{a1}$; —(CH$_2$CH$_2$O)$_\alpha$—(CH$_2$)$_\beta$CH$_2$—NR$_{a2}$R$_{a3}$; —(CH$_2$CH$_2$O)$_\alpha$—(CH$_2$)$_\beta$CH$_2$—CONR$_{a2}$R$_{a3}$; —(CH$_2$CH$_2$O)$_\alpha$—(CH$_2$)$_\beta$CH$_2$—CN; —(CH$_2$CH$_2$O)$_\gamma$—(CH$_2$)$_\delta$CH$_2$—F; —(CH$_2$CH$_2$O)$_\gamma$—(CH$_2$)$_\delta$CH$_2$—NO$_2$; —(CH$_2$CH$_2$O)$_\alpha$—(CH$_2$)$_\beta$CH$_2$—Cl; —(CH$_2$CH$_2$O)$_\alpha$—(CH$_2$)$_\beta$CH$_2$—Br; —(CH$_2$CH$_2$O)$_\alpha$—(CH$_2$)$_\beta$CH$_2$—I; —(CH$_2$CH$_2$O)$_\alpha$—(CH$_2$)$_\beta$-Phenyl; —CH$_2$—(CH$_2$)$_\beta$—(OCH$_2$CH$_2$)$_\alpha$R$_{a1}$; —CH$_2$—(CH$_2$)$_\beta$—(OCH$_2$CH$_2$)$_\alpha$NR$_{a2}$R$_{a3}$; —(CH$_2$)$_\beta$CH$_2$—(OCH$_2$CH$_2$)$_\alpha$CONR$_{a2}$R$_{a3}$; —CH$_2$—(CH$_2$)$_\beta$—(OCH$_2$CH$_2$)$_\alpha$CN; —CH$_2$—(CH$_2$)$_\beta$—

—(OCH$_2$CH$_2$)$_\alpha$F; —CH$_2$—(CH$_2$)$_\beta$—(OCH$_2$CH$_2$)$_\alpha$NO$_2$; —CH$_2$—(CH$_2$)$_\beta$—(OCH$_2$CH$_2$)$_\alpha$Cl; —CH$_2$—(CH$_2$)$_\beta$—(OCH$_2$CH$_2$)$_\alpha$Br; —CH$_2$—(CH$_2$)$_\beta$—(OCH$_2$CH$_2$)$_\alpha$I; —CH$_2$(CH$_2$)$_\beta$—(OCH$_2$CH$_2$)$_\alpha$Phenyl; —CF$_2$—(CF$_2$)$_\beta$OR$_{a1}$; —CF$_2$—(CF$_2$)$_\beta$CH$_2$NR$_{a2}$R$_{a3}$; —(CF$_2$)$_\beta$CF$_3$; —(CF$_2$)$_\beta$OR$_{a1}$; —CH$_2$CH$_2$(CF$_2$)$_\beta$OR$_{a1}$; —CH$_2$CH$_2$(CF$_2$)$_\beta$CH$_2$NR$_{a2}$R$_{a3}$; (CF$_2$)$_\beta$CH$_2$—NR$_{a2}$R$_{a3}$; —CH$_2$CH$_2$(CF$_2$)$_\beta$CF$_3$; —CH$_2$—(CH$_2$)$_\beta$—(OCH$_2$CH$_2$)$_\alpha$Phenyl; —CF$_2$—(CF$_2$)$_\beta$—(OCH$_2$CH$_2$)$_\alpha$Phenyl; —CH$_2$—(CH$_2$)$_\beta$—(OCH$_2$CH$_2$)$_\alpha$Aryl; —CF$_2$—(CF$_2$)$_\beta$—(OCH$_2$CH$_2$)$_\alpha$Aryl (see discussion below); —CH$_2$CH$_2$—(OCH$_2$CH$_2$)$_\alpha$—O(CF$_2$)$_\beta$Aryl (see discussion below); CH$_2$CH$_2$—(OCH$_2$CH$_2$)$_\alpha$—O(CH$_2$)$_\beta$Aryl (see discussion below); —CH$_2$O(CH$_2$)$_\beta$Aryl (see discussion below); and —(CF$_2$)$_\beta$Aryl (see discussion below).

R$_{a1}$, R$_{a2}$, and R$_{a3}$ can each be independently selected from, but not limited to, one or more of the following groups: H; linear or branched, alkyl groups with up to 25 carbons (e.g., 0, 1, 2, 3, 4, 5, 6, 7, 8, 9, 10, 11, 12, 13, 14, 15, 16, 17, 18, 19, 20, 21, 22, 23, 24, 25 carbons in all isomer forms such as normal, secondary, iso- and neo-isomers); and a functional group derived from amino acids, nucleic acids, biotin, ferrocene, ruthenocene, cyanuric chloride, methacryloyl chloride, and derivatives thereof. Subscript $\alpha$ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25). Subscript $\beta$ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25).

The aryl group can include aromatic ring systems having up to 20 carbons in the aromatic ring framework (e.g., 0, 1, 2, 3, 4, 5, 6, 7, 8, 9, 10, 11, 12, 13, 14, 15, 16, 17, 18, 19, and 20 carbons in all isomer forms), (e.g., does not include carbons on the substituents). The aryl group can include, but is not limited to the following structures:

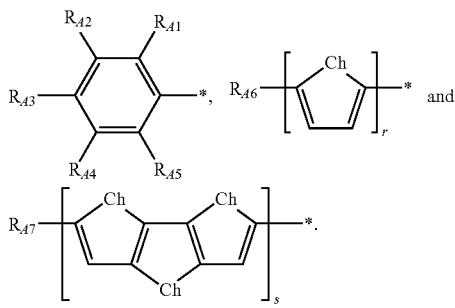

It should be noted that Ch can be an atom such as, but not limited to, Se, S, O, and a combination thereof when more than one Ch is present in the aryl ring system. R$_{A1}$, R$_{A2}$, R$_{A3}$, R$_{A4}$, R$_{A5}$, R$_{A6}$, R$_{A7}$, can each be independently selected from, but not limited to, the following groups: H; a linear or branched alkyl group with up to 25 carbons (e.g., 0, 1, 2, 3, 4, 5, 6, 7, 8, 9, 10, 11, 12, 13, 14, 15, 16, 17, 18, 19, 20, 21, 22, 23, 24, and 25 carbons in all isomer forms such as normal, secondary, iso- and neo-isomers); —(CH$_2$CH$_2$O)$_\gamma$—(CH$_2$)$_\delta$OCH$_3$; —(CH$_2$CH$_2$O)$_\gamma$—(CH$_2$)$_\delta$N(CH$_3$)$_2$; —(CH$_2$CH$_2$O)$_\gamma$—(CH$_2$)$_\delta$CON(CH$_3$)$_2$; —(CH$_2$CH$_2$O)$_\gamma$—(CH$_2$)$_\delta$CN; —(CH$_2$CH$_2$O)$_\gamma$—(CH$_2$)$_\delta$F; —(CH$_2$CH$_2$O)$_\gamma$—(CH$_2$)$_\delta$NO$_2$; —(CH$_2$CH$_2$O)$_\gamma$—(CH$_2$)$_\delta$Cl; —(CH$_2$CH$_2$O)$_\gamma$—(CH$_2$)$_\gamma$Br; —(CH$_2$CH$_2$O)$_\gamma$—(CH$_2$)$_\delta$I; —(CH$_2$CH$_2$O)$_\gamma$—(CH$_2$)$_\delta$-Phenyl; —(CH$_2$)$_\delta$—(OCH$_2$CH$_2$)$_\gamma$CH$_3$; —(CH$_2$)$_\delta$—(OCH$_2$CH$_2$)$_\delta$N(CH$_3$)$_2$; —(CH$_2$)$_\delta$—(OCH$_2$CH$_2$)$_\gamma$C(O)N(CH$_3$)$_2$; —(CH$_2$)$_\delta$—(OCH$_2$CH$_2$)$_\gamma$CN; —(CH$_2$)$_\delta$—(OCH$_2$CH$_2$)$_\gamma$F; —(CH$_2$)$_\delta$—(OCH$_2$CH$_2$)$_\alpha$NO$_2$; —(CH$_2$)$_\delta$—(OCH$_2$CH$_2$)$_\gamma$Cl; —(CH$_2$)$_\delta$—(OCH$_2$CH$_2$)$_\gamma$Br; —(CH$_2$)$_\delta$—(OCH$_2$CH$_2$)$_\gamma$; —(CH$_2$)$_\delta$—(OCH$_2$CH$_2$)$_\gamma$Phenyl; —(CF$_2$)$_\beta$OCH$_3$; —(CF$_2$)$_\beta$OCH$_3$; —(CF$_2$)$_\beta$CH$_2$N(CH$_3$)$_2$; —(CF$_2$)$_\beta$CF$_3$; —O(CF$_2$)$_\beta$OCH$_3$; —OCH$_2$CH$_2$(CF$_2$)$_\beta$OCH$_3$; —OCH$_2$CH$_2$(CF$_2$)$_\beta$CH$_2$N(CH$_3$)$_2$; —O(CF$_2$)$_\beta$CH$_2$N(CH$_3$)$_2$; —OCH$_2$CH$_2$(CF$_2$)$_\beta$CF$_3$; —(CH$_2$)$_\beta$—(OCH$_2$CH$_2$)$_\alpha$Phenyl; and —(CF$_2$)$_\beta$—(OCH$_2$CH$_2$)$_\alpha$Phenyl.

The subscript $\gamma$ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25). The subscript $\delta$ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25). The subscript r is an integer number from 0 to 6 (e.g., 0, 1, 2, 3, 4, 5, and 6). The subscript s is an integer number from 0 to 3 (e.g., 0, 1, 2, and 3).

The polymerizable group (functionalities) can include, but is not limited to, vinyl, allyl, 4-styryl, acroyl, epoxide, oxetane, cyclic-carbonate, methacroyl, and acrylonitrile, each of which may be polymerized by either a radical, cationic, atom transfer, or anionic polymerization process.

In addition, the polymerizable group can include, but is not limited to, isocyanate, isothiocyanate, and epoxides, such that they can be copolymerized with difunctional amines or alcohols such as HO(CH$_2$)$_\chi$OH, H$_2$N(CH$_2$)$_\chi$NH$_2$, where $\chi$ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, 24, and 25).

Also the polymerizable group can include, but is not limited to, strained ring olefins such as, but not limited to, dicyclopentadienyl, norbornenyl, and cyclobutenyl. Such monomers can be polymerized via ring opening metathesis polymerization using an appropriate metal catalyst as would be known to those skilled in the art.

Further, the polymerizable group can include, but is not limited to, (—CH$_2$)$_\eta$SiCl$_3$, (—CH$_2$)$_\eta$Si(OCH$_2$CH$_3$)$_3$, or (—CH$_2$)$_\eta$Si(OCH$_3$)$_3$, where the monomers can be reacted with water under conditions known to those skilled in the art to form either thin film or monolithic organically modified sol-gel glasses, or modified silicated surfaces, where $\eta$ is an integer number from 0 to 25 (e.g., 0, 1, 2, 3, 4, 5, 6, 7, 8, 9, 10, 11, 12, 13, 14, 15, 16, 17, 18, 19, 20, 21, 22, 23, and 25).

Furthermore, the polymerizable group can include, but is not limited to, polymerizable groups that can be photochemically dimerized or polymerized, and these include the following structures:

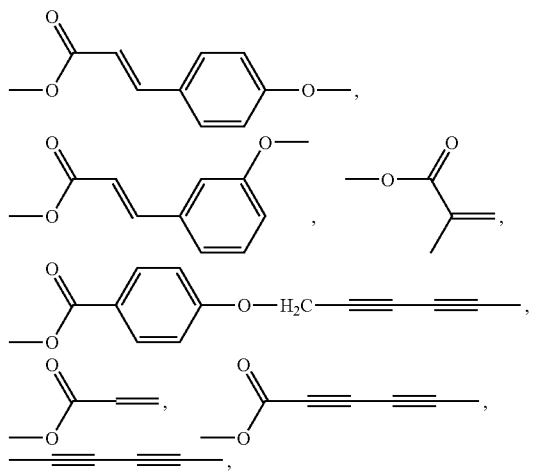

-continued
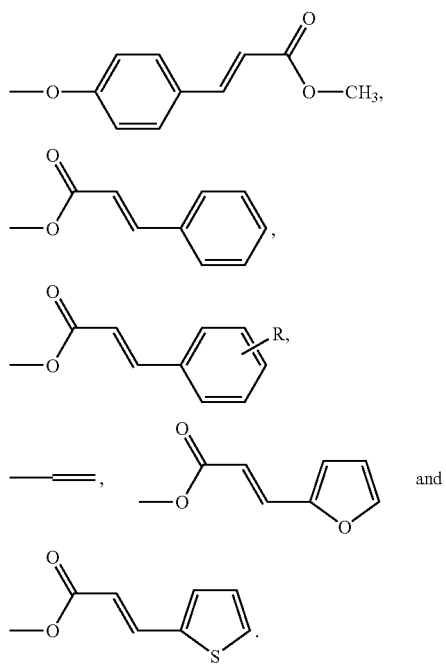
The donor groups (donors) can include structures such as, but not limited to, the following:
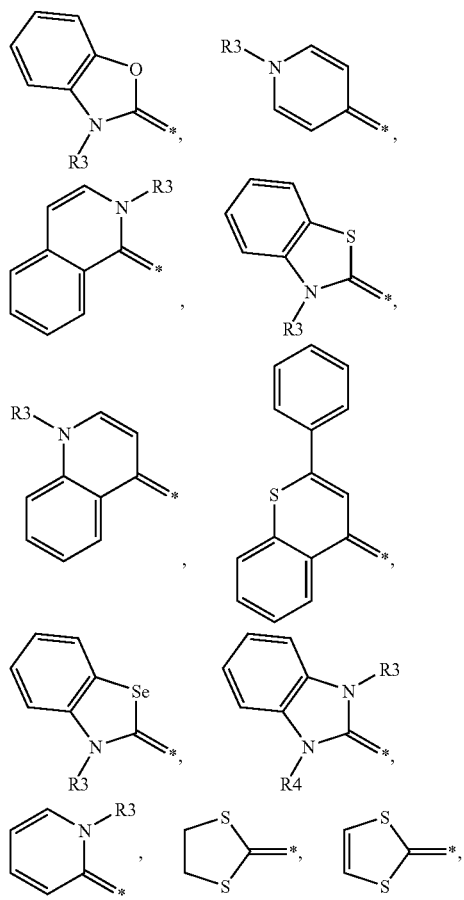
-continued
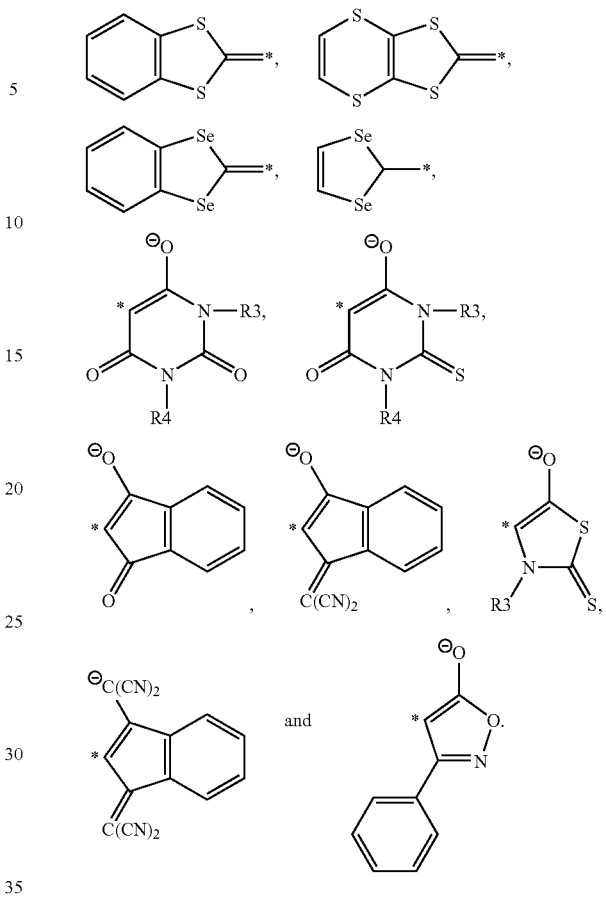
The acceptor groups (acceptors) can include structures such as, but not limited to, the following:
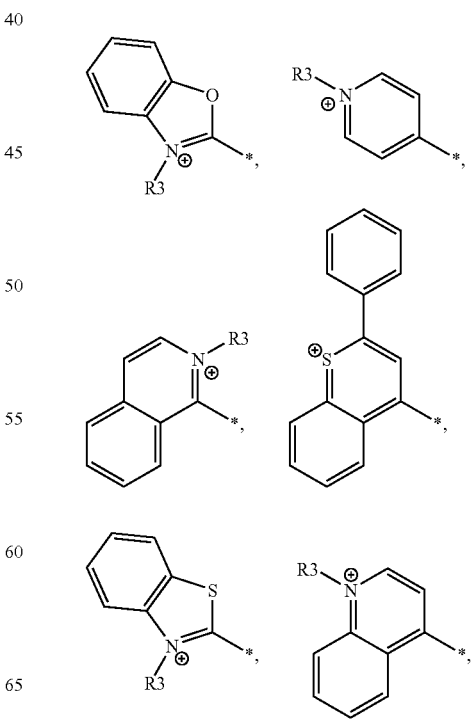

27
-continued
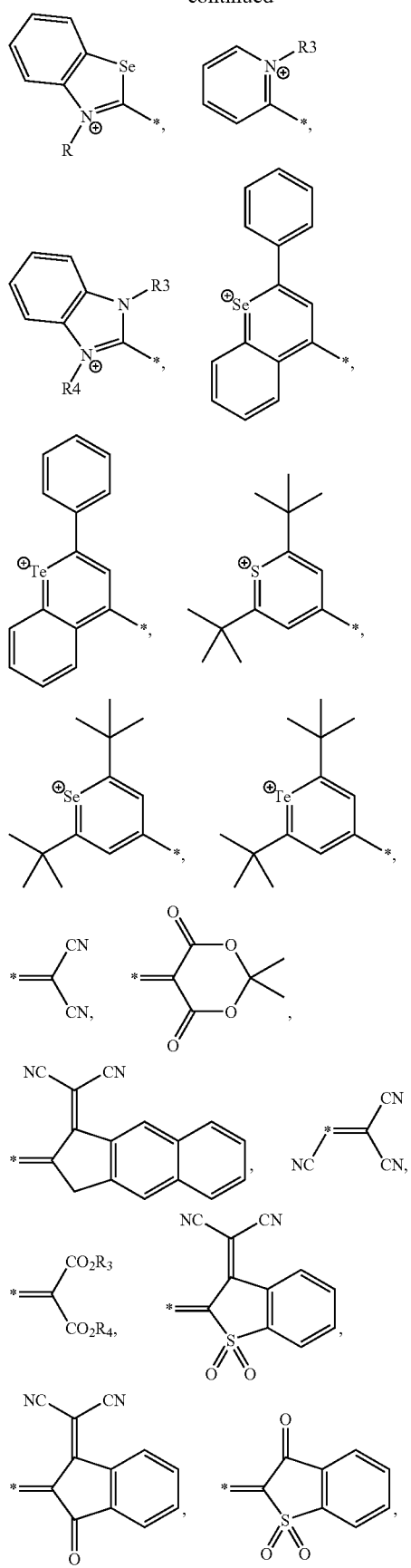
28
-continued
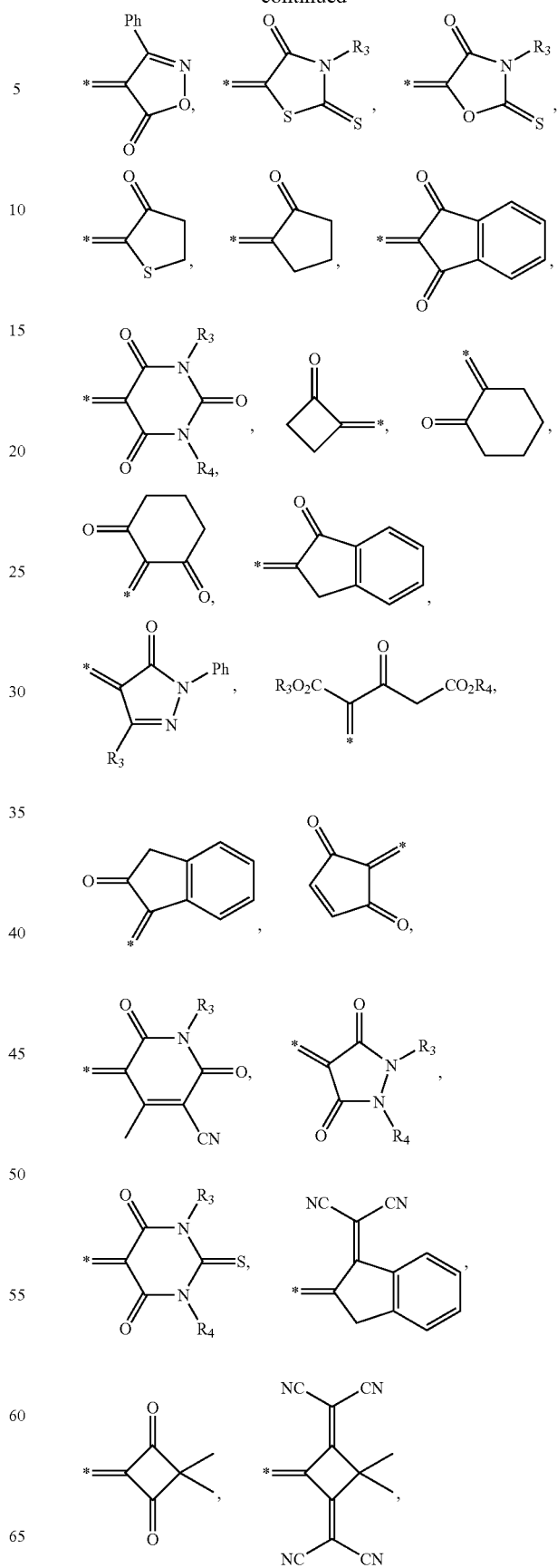

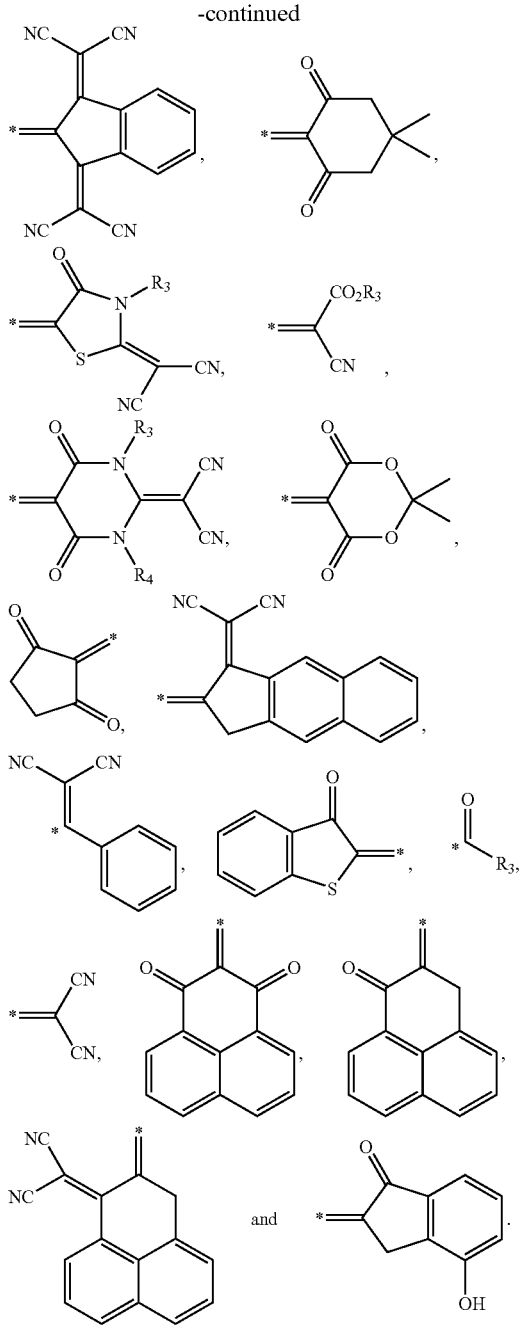

It should also be noted that $X_1, X_2, X_3, X_4, X_5$, and $X_6$, can each be independently selected from, but not limited to, one or more of the following groups: a halogen or an alkyl chain bonded directly to the core or via a linking group such as, but not limited to, a methylene, an oxygen, a sulfur, or a selenium linkage. In addition, $X_1, X_2, X_3, X_4, X_5$, and $X_6$ can each be independently selected from, but not limited to, one or more of the following groups: substituted or unsubstituted alkyl, aryl (including aromatic and heteroaromatic groups, which are explained in J. March, "Advanced Organic Chemistry: Reactions, Mechanisms and Structure", Fourth edition, Wiley-Interscience, New York, 1992, Chapter 2, which is included herein by reference in its entirety), cycloalkyl, or heterocyclic groups which are bonded to the carbon-atom either directly or via a linking group. Also, $X_1, X_2, X_3, X_4, X_5$, and $X_6$ can each be independently selected from, but not limited to, one or more of the following groups: donors and/or acceptors such as those described herein and in U.S. Pat. No. 6,267,913, which is included herein by reference in its entirety. Further, $X_1, X_2, X_3, X_4, X_5$, and $X_6$ can each be independently selected from, but not limited to, the following groups: any of the groups described above linked through a pi-conjugated linking group as described in U.S. Pat. No. 6,267,913. In one embodiment of HATNA-$[X]_6$, $X_1, X_2, X_3, X_4, X_5$, and $X_6$ are not an alkoxy (—OR, where R=$C_nH_{2n+1}$, where n=6, 8, 10, or 12)), an alkylthio (—SR, where R=$C_nH_{2n+1}$, where n=6, 8, 10, or 12)), H, Cl, or methyl (—$CH_3$).

It should also be noted that $C_2X_2$ (e.g., $X_1$ and $X_2$, $X_3$ and $X_4$, and $X_5$ and $X_6$) could also be, but is not limited to, a part of a heterocyclic group such as, but not limited to, naphtyl, phenanthryl, and benzo[b]triphenylene. In addition, $C_2X_2$ (e.g., $X_1$ and $X_2$, $X_3$ and $X_4$, and $X_5$ and $X_6$) could also include polymerizable groups including, but not limited to, acrylates, epoxides, oxetanes, chalcones, cinnamates, alkynes, and olefins.

It should also be noted that $Y_1, Y_2, Y_3, Y'_1, Y'_2$, and $Y'_3$, can each be independently selected from, but not limited to, one or more of the following groups: an alkyl chain, perfluoro aliphatic chain, aryl group, or heterocyclic group. In addition, $Y_1, Y_2, Y_3, Y'_1, Y'_2$, and $Y'_3$, can each be independently selected from, but not limited to, one or more of the following groups: substituted or unsubstituted alkyl, aryl (including aromatic and heteroaromatic groups, which are explained in J. March, "Advanced Organic Chemistry: Reactions, Mechanisms and Structure", Fourth edition, Wiley-Interscience, New York, 1992, Chapter 2), cycloalkyl, or heterocyclic groups which are bonded to the carbon atom either directly or via a linking group. $Y_1, Y_2, Y_3, Y'_1, Y'_2$, and $Y'_3$, can each be independently selected from, but not limited to, the following polymerizable groups: acrylates, epoxides, oxetanes, chalcones, cinnamates, alkynes, and olefins. $Y_1, Y_2, Y_3, Y'_1, Y'_2$, and $Y'_3$, can each be independently selected from, but not limited to, the following groups: donors and/or acceptors as described herein and in U.S. Pat. No. 6,267,913. $Y_1, Y_2, Y_3, Y'_1, Y'_2$, and $Y'_3$, can each be independently selected from, but not limited to, the following groups: any of the groups described above linked through a pi-conjugated linking group as described in U.S. Pat. No. 6,267,913. $Y_1, Y_2, Y_3, Y'_1, Y'_2$, and $Y'_3$, can each be independently selected from, but not limited to, one or more of the following groups: a part of a heterocyclic group such as naphtyl, phenanthryl, and benzo[b]triphenylene.

It should also be noted that $Z_1, Z_2, Z_3, Z'_1, Z'_2$, and $Z'_3$, can each be independently selected from, but not limited to, one or more of the following groups: an aryl group substituted with alkoxy chains, thiol chains, selenium chains, linked directly to the core or via a spacer of alternative phenyl and oxadiazole rings. $Z_1, Z_2, Z_3, Z'_1, Z'_2$, and $Z'_3$, can each be independently selected from, but not limited to, $CO_2Hal$, where Hal is a halogen selected from F, Cl, or Br. $Z_1, Z_2, Z_3, Z'_1, Z'_2$, and $Z'_3$, can each be independently selected from, but not limited to, one or more of the following groups: substituted or unsubstituted alkyl, aryl (including aromatic and heteroaromatic groups, which are explained in J. March, "Advanced Organic Chemistry: Reactions, Mechanisms and Structure", Fourth edition, Wiley-Interscience, New York, 1992, Chapter 2), cycloalkyl, or heterocyclic groups, which are bonded to the carbon atom either directly or via a linking group. $Z_1, Z_2, Z_3, Z'_1, Z'_2$, and $Z'_3$, can each be independently selected from, but not limited to, one or more of the following polymerizable groups: acrylates, epoxides, oxetanes, chalcones, cinnamates, alkynes, and olefins. $Z_1$, $Z_2$, $Z_3$, $Z'_1$, $Z'_2$, and $Z'_3$, can each be independently selected from, but not limited to, one or more of the following groups: donors and/or acceptors as described herein and in U.S. Pat. No. 6,267,913. $Z_1$, $Z_2$, $Z_3$, $Z'_1$, $Z'_2$, and $Z'_3$, can each be independently selected from, but not limited to, one or more of the following groups: any of the groups described above linked through a pi-conjugated linking group as described in U.S. Pat. No. 6,267,913.

It should also be noted that $U_1$, $U_2$, $U_3$, $U_4$, $U_5$, and $U_6$, can each be independently selected from, but not limited to, one or more of the following groups: an aryl group substituted with alkoxy chains, thiol chains, selenium chains connected directly to the acetylene or via a spacer of alternative phenyl and oxadiazole rings. $U_1$, $U_2$, $U_3$, $U_4$, $U_5$, and $U_6$, can each be independently selected from, but not limited to, the following groups: triisopropyl silane and t-butyl. $U_1$, $U_2$, $U_3$, $U_4$, $U_5$, and $U_6$, can each be independently selected from, but not limited to, the following groups: substituted or unsubstituted alkyl, aryl (including aromatic and heteroaromatic groups, which are explained in J. March, "Advanced Organic Chemistry: Reactions, Mechanisms and Structure", Fourth edition, Wiley-Interscience, New York, 1992, Chapter 2), cycloalkyl, or heterocyclic groups, which are bonded to the carbon atom either directly or via a linking group. $U_1$, $U_2$, $U_3$, $U_4$, $U_5$, and $U_6$, can each be independently selected from, but not limited to, the following polymerizable groups: acrylates, epoxides, oxetanes, chalcones, cinnamates, alkynes, and olefins. $U_1$, $U_2$, $U_3$, $U_4$, $U_5$, and $U_6$, can each be independently selected from, but not limited to, the following groups: donors and/or acceptors as described herein and in U.S. Pat. No. 6,267,913. $U_1$, $U_2$, $U_3$, $U_4$, $U_5$, and $U_6$, can each be independently selected from, but not limited to, the following groups: any of the groups described above linked through a pi-conjugated linking group as described in U.S. Pat. No. 6,267,913.

It should also be noted that $V_1$, $V_2$, and $V_3$, can each be independently selected from, but not limited to, one or more of the following groups: an alkyl chain, an aryl group, an aryl group substituted with alkoxy chains, thiol chains, selenium chains, linked directly to the core or via a spacer of alternative phenyl and oxadiazole rings. $V_1$, $V_2$, and $V_3$, can each be independently selected from, but not limited to, the following groups: substituted or unsubstituted alkyl, aryl (including aromatic and heteroaromatic groups, which are explained in J. March, "Advanced Organic Chemistry: Reactions, Mechanisms and Structure", Fourth edition, Wiley-Interscience, New York, 1992, Chapter 2), cycloalkyl, or heterocyclic groups which are bonded to the carbon atom either directly or via a linking group. $V_1$, $V_2$, and $V_3$, can each be independently selected from, but not limited to, the following polymerizable groups: acrylates, epoxides, oxetanes, chalcones, cinnamates, alkynes, and olefins. $V_1$, $V_2$, and $V_3$, can each be independently selected from, but not limited to, the following groups: donors and/or acceptors as described herein and in U.S. Pat. No. 6,267,913. $V_1$, $V_2$, and $V_3$, can each be independently selected from, but not limited to, the following groups: any of the groups described above linked through a pi-conjugated linking group as described in U.S. Pat. No. 6,267,913.

It should also be noted that $W_1$, $W_2$, $W_3$, $W_4$, $W_5$, and $W_6$, can each be independently selected from, but not limited to, one or more of the following groups: alkyl chain, aryl group, aryl group substituted with alkoxy chains, thiol chains, selenium chains, linked directly to the core or via a spacer of alternative phenyl and oxadiazole rings. $W_1$, $W_2$, $W_3$, $W_4$, $W_5$, and $W_6$, can each be independently selected from, but not limited to, one or more of the following groups: substituted or unsubstituted alkyl, aryl (including aromatic and heteroaromatic groups, which are explained in J. March, "Advanced Organic Chemistry: Reactions, Mechanisms and Structure", Fourth edition, Wiley-Interscience, New York, 1992, Chapter 2), cycloalkyl, or heterocyclic groups, which are bonded to the carbon atom either directly or via a linking group. $W_1$, $W_2$, $W_3$, $W_4$, $W_5$, and $W_6$, can each be independently selected from, but not limited to, the following groups: donors and/or acceptors as described herein and in U.S. Pat. No. 6,267,913. $W_1$, $W_2$, $W_3$, $W_4$, $W_5$, and $W_6$, can each be independently selected from, but not limited to, the following groups: any of the groups described above linked through a pi-conjugated linking group as described in U.S. Pat. No. 6,267,913.

It should also be noted that $C_2W_2$ (e.g., $W_1$ and $W_2$, $W_3$ and $W_4$, and $W_5$ and $W_6$) could also be, but is not limited to, a part of a heterocyclic, group such as, but not limited to, naphtyl, phenanthryl, and benzo[b]triphenylene. In addition, $C_2W_2$ could also include polymerizable groups including, but not limited to, acrylates, epoxides, oxetanes, chalcones, cinnamates, alkynes, and olefins.

It should also be noted that $T_1$, $T_2$, $T_3$, $T_4$, $T_5$, $T_6$, $T_7$, $T_8$, $T_9$, $T_{10}$, $T_{11}$, and $T_{12}$, can each be independently selected from, but not limited to, one or more of the following groups: a halogen or an alkyl chain bonded directly to the core or via a linking group such as, but not limited to, a methylene, an oxygen, a sulfur, or a selenium linkage. In addition, $T_1$, $T_2$, $T_3$, $T_4$, $T_5$, $T_6$, $T_7$, $T_8$, $T_9$, $T_{10}$, $T_{11}$, and $T_{12}$, can each be independently selected from, but not limited to, the following groups: substituted or unsubstituted alkyl, aryl (including aromatic and heteroaromatic groups, which are explained in J. March, "Advanced Organic Chemistry: Reactions, Mechanisms and Structure", Fourth edition, Wiley-Interscience, New York, 1992, Chapter 2, which is included herein by reference in its entirety), cycloalkyl, or heterocyclic groups which are bonded to the carbon atom either directly or via a linking group. Also, $T_1$, $T_2$, $T_3$, $T_4$, $T_5$, $T_6$, $T_7$, $T_8$, $T_9$, $T_{10}$, $T_{11}$, and $T_{12}$, can each be independently selected from, but not limited to, the following groups: donors and/or acceptors such as those described herein and in U.S. Pat. No. 6,267,913, which is included herein by reference in its entirety. Further, $T_1$, $T_2$, $T_3$, $T_4$, $T_5$, $T_6$, $T_7$, $T_8$, $T_9$, $T_{10}$, $T_{11}$, and $T_{12}$, can each be independently selected from, but not limited to, the following groups: any of the groups described above linked through a π-conjugated linking group as described in U.S. Pat. No. 6,267,913.

The charge-transport materials have a room temperature, zero field electron mobility of at least about $10^{-6}$ to $10^2$ $cm^2/Vs$, $10^{-4}$ to $10^2$ $cm^2/Vs$, and $10^{-2}$ to $10^2$ $cm^2/Vs$.

The distance between adjacent molecules in adjacent layers is about 3.6 Å and 3.1 Å.

The charge-transport materials should be capable of reduction by a metalless reducing agent other than sodium.

In an embodiment, a polymer layer of the charge-transport material can be formed by disposing a layer of a polymerizable material including monomers, oligomers, and/or polymers of the charge-transport material, onto a surface. The molecules of the charge-transport material can be optionally aligned into a substantially uniform orientation or a patterned orientation such that in each pattern the orientation is substantially uniform. Then, a polymerization reaction is initiated and the monomers, oligomers, and/or polymers of the charge-transport material form a layer of polymerized charge-transport material. The polymerization process can be repeated to produce a plurality of layers. In addition, cross-linking processes can also be performed to cross-link the molecules in adjacent layers. One skilled in the art could perform a polymerization process in a manner different than described here and obtain the polymer layer of the charge-transport material, and such processes are intended to be included herein.

A plurality of layers of charge-transport material can be produced to form a charge-transport layer that can have a thickness of about 0.01 to 1000 µm, 0.05 to 100 µm, 0.05 to 10 µm. The length and width of the charge-transport layer can vary depending on the application, but in general, the length can be about 0.01 µm to 1000 cm, and the width can be about 0.01 µm to 1000 cm.

It should be noted that in some embodiments is it advantageous to have the aromatic core aligned parallel to the substrate materials (e.g., in photovoltaic cells and others devices where a perpendicular alignment may be more preferable (e.g., transistor configurations)).

It should also be noted that the charge-transport materials could be used as mixtures with other electron transport materials including those described herein, as well as others. Likewise the charge-transport materials could be used in combination with other hole transport materials, sensitizers, emitters, chromophores, and the like, to add other functionality to devices.

The polymerization and cross-linking of the charge-transport material molecules can be performed using methods understood by those skilled in the art. In general, polymerization may take place by exposure to heat or actinic radiation in the presence of an initiator. In general, cross-linking may occur due to internal reactions and/or by the addition of a cross-linking additive. Additional details regarding preparation of the charge-transport materials are described in Example 1.

Actinic radiation means irradiation with radiation (e.g., UV light, IR light or visible light, irradiation with X-rays or gamma rays or irradiation with high-energy particles, such as ions or electrons). In an embodiment, a polymerization initiator can be used that decomposes when heated to produce free radicals or ions that start the polymerization. In another embodiment, the polymerization can be carried out in the presence of an initiator absorbing at the wavelength of the actinic radiation. For example, when polymerizing using UV light, a UV initiator can be used that decomposes under UV irradiation to produce free radicals or ions which start the polymerization reaction.

The UV initiator can include chemicals such as, but not limited to, a free radical initiator, a cationic initiator, or combinations thereof. The free-radical initiator includes compounds that produce a free radical on exposure to UV radiation. The free-radical is capable of initiating a polymerization reaction among the monomers and/or oligomers present.

Examples of free-radical initiators include, but are not limited to, benzophenones (e.g., benzophenone, methyl benzophenone, Michler's ketone, and xanthones), acylphosphine oxide type free radical initiators (e.g., 2,4,6-trimethylbenzoyldiphenyl phosphine oxide (TMPO), 2,4,6-trimethylbenzoylethoxyphenyl phosphine oxide (TEPO), and bisacylphosphine oxides (BAPO's)), azo compounds (e.g., AIBN), benzoins, and benzoin alkyl ethers (e.g., benzoin, benzoin methyl ether and benzoin isopropyl ether).

In addition, the free radical photoinitiator can include, but is not limited to: acyloin; a derivative of acyloin, such as benzoin ethyl ether, benzoin isobutyl ether, desyl bromide, and α-methylbenzoin; a diketone, such as benzil and diacetyl; an organic sulfide, such as diphenyl monosulfide, diphenyl disulfide, desyl phenyl sulfide, and tetramethylthiuram monosulfide; a thioxanthone; an S-acyl dithiocarbamate, such as S-benzoyl-N,N-dimethyldithiocarbamate and S-(p-chlorobenzoyl)-N,N-dimethyldithiocarbamate; a phenone, such as acetophenone, α-α-α-tribromoacetophenone, o-nitro-α-α-α-tribromoacetophenone, benzophenone, and p,p'-tetramethyldiaminobenzophenone; a quinone; a triazole; a sulfonyl halide, such as p-toluenesulfonyl chloride; a phosphorus-containing photoinitiator, such as an acylphosphine oxide; an acrylated amine; or mixtures thereof.

The free-radical initiator can be used alone or in combination with a co-initiator. Co-initiators are used with initiators that need a second molecule to produce a radical that is active in UV-systems. For example, benzophenone uses a second molecule, such as an amine, to produce a reactive radical. A preferred class of co-initiators are alkanolamines such as, but not limited to, triethylamine, methyldiethanolamine, and triethanolamine Suitable cationic initiators include, but are not limited to, compounds that form aprotic acids or Brønsted acids upon exposure to UV light sufficient to initiate polymerization. The cationic initiator used may be a single compound, a mixture of two or more active compounds, or a combination of two or more different compounds (e.g., co-initiators).

The cationic photoinitiator can include, but is not limited to, onium salt, such as a sulfonium salt, an iodonium salt, or mixtures thereof. In addition, the cationic photoinitiatior can include, but is not limited to, an aryldiazonium salt, a bis-diaryliodonium salt, a diaryliodonium salt of sulfonic acid, a triarylsulfonium salt of sulfonic acid, a diaryliodonium salt of boric acid, a diaryliodonium salt of boronic acid, a triarylsulfonium salt of boric acid, a triarylsulfonium salt of boronic acid, or mixtures thereof. Examples of cationic photoinitiatiors include, but are not limited to, diaryliodonium hexafluoroantimonate, aryl sulfonium hexafluorophosphate, aryl sulfonium hexafluoroantimonate, bis(dodecyl phenyl) iodonium hexafluoroarsenate, tolyl-cumyliodonium tetrakis(pentafluorophenyl) borate, bis(dodecylphenyl) iodonium hexafluoroantimonate, dialkylphenyl iodonium hexafluoroantimonate, diaryliodonium salts of perfluoroalkylsulfonic acids (such as diaryliodonium salts of perfluorobutanesulfonic acid, perfluoroethanesulfonic acid, perfluorooctanesulfonic acid, and trifluoromethane sulfonic acid), diaryliodonium salts of aryl sulfonic acids (such as diaryliodonium salts of para-toluene sulfonic acid, dodecylbenzene sulfonic acid, benzene sulfonic acid, and 3-nitrobenzene sulfonic acid), triarylsulfonium salts of perfluoroalkylsulfonic acids (such as triarylsulfonium salts of perfluorobutanesulfonic acid, perfluoroethanesulfonic acid, perfluorooctanesulfonic acid, and trifluoromethane sulfonic acid), triarylsulfonium salts of aryl sulfonic acids (such as triarylsulfonium salts of para-toluene sulfonic acid, dodecylbenzene sulfonic acid, benzene sulfonic acid, and 3-nitrobenzene sulfonic acid), diaryliodonium salts of perhaloarylboronic acids, triarylsulfonium salts of perhaloarylboronic acid, or mixtures thereof.

The visible radiation initiator can include, but is not limited to, diketones (e.g., camphorquinone, 1,2-acenaphthylenedione, 1H-indole-2,3-dione, 5H-dibenzo[a,d]cycloheptene-10, and 11-dione), phenoxazine dyes (e.g., Resazurin, Resorufin), acylphosphine oxides, (e.g., diphenyl (2,4,6-trimethylbenzoyl) phosphine oxide), and the like.

In an embodiment, the polymerization of the charge-transport materials can be carried out as in-situ polymerization of a coated layer of the material, possibly during fabrication of the device of interest that includes the charge-transport material. In the case of liquid crystal materials, these are preferably aligned in their liquid crystal state into homeotropic orientation prior to polymerization, where the conjugated pi-electron systems are orthogonal to the direction of charge transport. This ensures that the intermolecular distances are minimized and hence the energy required to transport charge between molecules is minimized. The molecules are then polymerized and/or cross-linked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45-66.

The polymers including the HATNA core and/or the DATAN core can have a molecular weight from about 3000 to 300,000 daltons, and about 2000 to 200,0000 daltons.

Example 1

Now having described the embodiments of the charge-transport materials in general, Examples 1-3 describe some specific embodiments of the charge-transport materials. While embodiments of charge-transport materials are described in connection with Examples 1-3 and the corresponding text and figures, there is no intent to limit embodiments of the charge-transport materials to these descriptions. On the contrary, the intent is to cover all alternatives, modifications, and equivalents included within the spirit and scope of embodiments of the present disclosure.

It should also be noted that in each Example, in particular Example 3, one skilled in the art of organic chemistry would understand that esters of carboxylic acids could be converted to their corresponding carboxylic acids. In his manner either pure 5,6,11,12,17,18-Hexaaza-trinaphthylene-2,8,15-tricarboxylic acid 1 ester or 5,6,11,12,17,18-Hexaaza-trinaphthylene-2,8,15-tricarboxylic acid can be synthesized from the 1a and 1b'. This pure acid can therefore be used as starting point to synthesize any isomerically pure compounds described herein that would be derived from this acid.

Organic semiconducting materials having high carrier mobility are used for a wide range of electronic applications such as, light-emitting diodes, solar cells, and field-effect transistors.[1,2,3,4,5,6] Discotic liquid-crystalline mesophases are typically quasi-two-dimensional molecules, which are often constituted of a rigid central aromatic core and extended flexible chains. These molecules usually pack in the form of well-defined columns forming one-dimensional paths for charge transport along the stacked conjugated cores due to good intermolecular orbital overlap within the stacks.[7] Only a limited number of electron mobility measurements in columnar discotic liquid crystals have been so far reported.[8,9]

Hexaazatrinaphylene, HATNA, FIG. 1, has been investigated for electron-transport materials applications. Because of the nitrogen presence in HATNA, these compounds are anticipated to be electron-poor relative to all-hydrocarbon analogues. It should be relatively easy to inject electrons into these compounds from other materials. Therefore, HATNA derivatives are likely to act principally, although not necessarily exclusively, as electron-transport materials.

Figure 2:
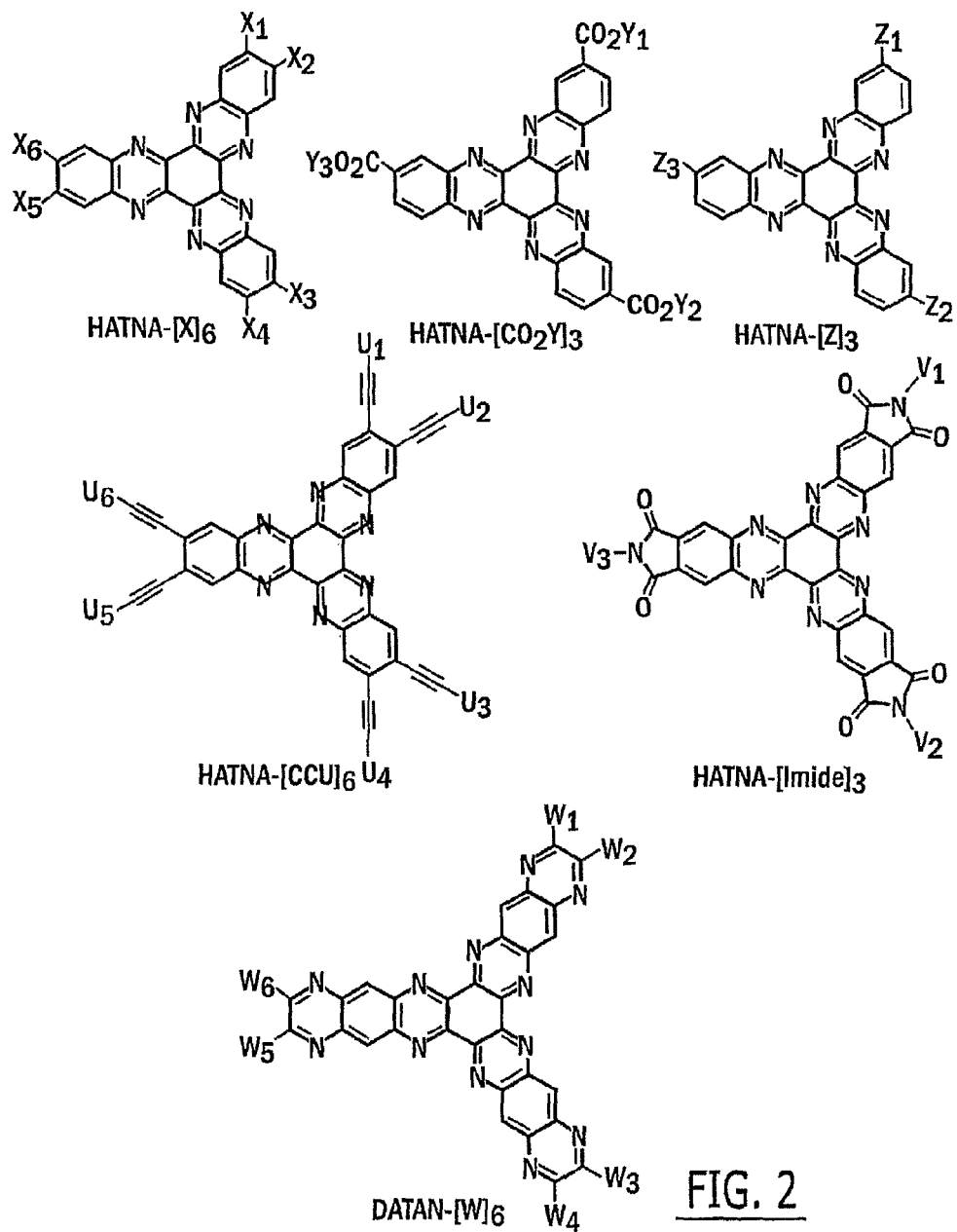
FIG. 2 illustrates general chemical structures of HATNA and dodecaazatrianthracene (DATAN) compounds.

The HATNA cores and the dodecaazatrianthracenes, DATAN, cores are shown in FIG. 2.

Small Molecules with HATNA Core:

A series of HATNA compounds with different substitutions, Scheme 1, have been synthesized. These compounds have low solubility in most organic solvents. HATNA, BK2_73, is the model core. A previous X-ray structure investigation of HATNA.CHCl$_3$, BK2_73, showed that this compound stacked in the solid state, FIG. 3.[10,11]

HATNA_Cl$_6$, BK2_67, HATNA_Me$_6$, BK2_25, and HATNA_Br$_6$, BK2_31, can be used in the synthesis of other HATNA compounds, which are described herein. No further purification is needed for these syntheses. An investigation has been conducted in regard to the effect of core size of hexaazatrianthracene, HATAN, BK3_25, and hexaazatristriphenylene HATT (also referred to as "Mickey-Mouse" HATNA), BK3_31, on their mobility and, in cases where suitable crystals can be obtained, their solid state packing. The substitution with six nitro groups in HATNA_[NO$_2$]$_6$, BK2_93, further increases the electron acceptor capability of this compound due the strong electron withdrawing effect of the nitro-substituent. Doping HATNA_[NO$_2$]$_6$, BK2_93, with the strong electron donor tetrathiofulvalene TTF is anticipated to generate a charge transfer complex. DSC investigation of HATNA_[NO$_2$]$_6$, BK2_93, showed that this compound is potentially explosive at 398° C. (ΔH=−658 KJ/mol), FIG. 4.

Figure 5:
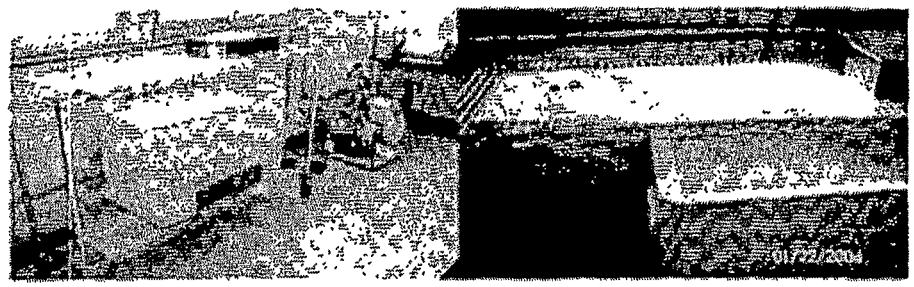
FIG. 5 illustrates the train purification system; sublimation of HATNA, BK2_73.
Figure 6:
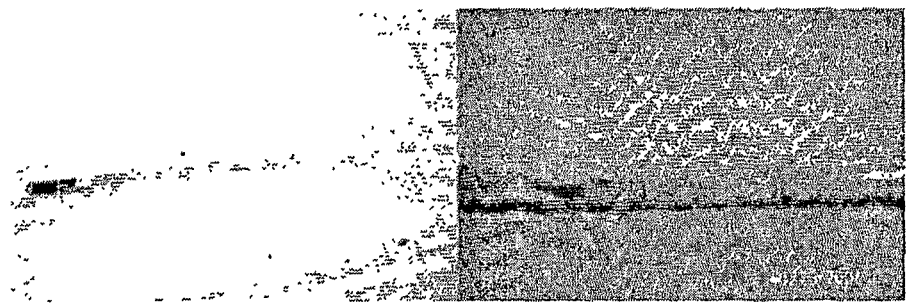
FIG. 6 illustrates the sublimation of HATNA-$Cl_6$, BK2_67.
Figure 7:
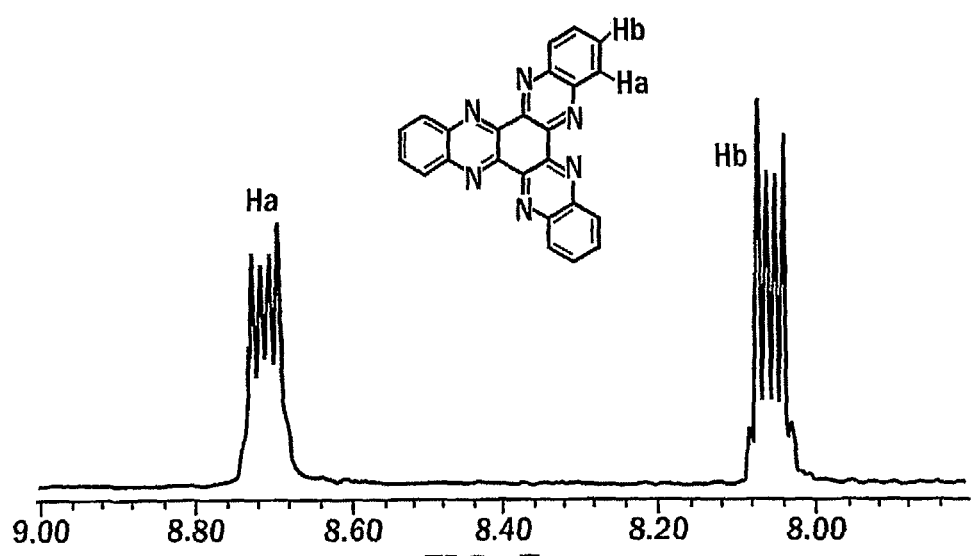
FIG. 7 illustrates the $^1$H NMR of sublimed HATNA, BK2_73C.
Figures 8A, 8B:
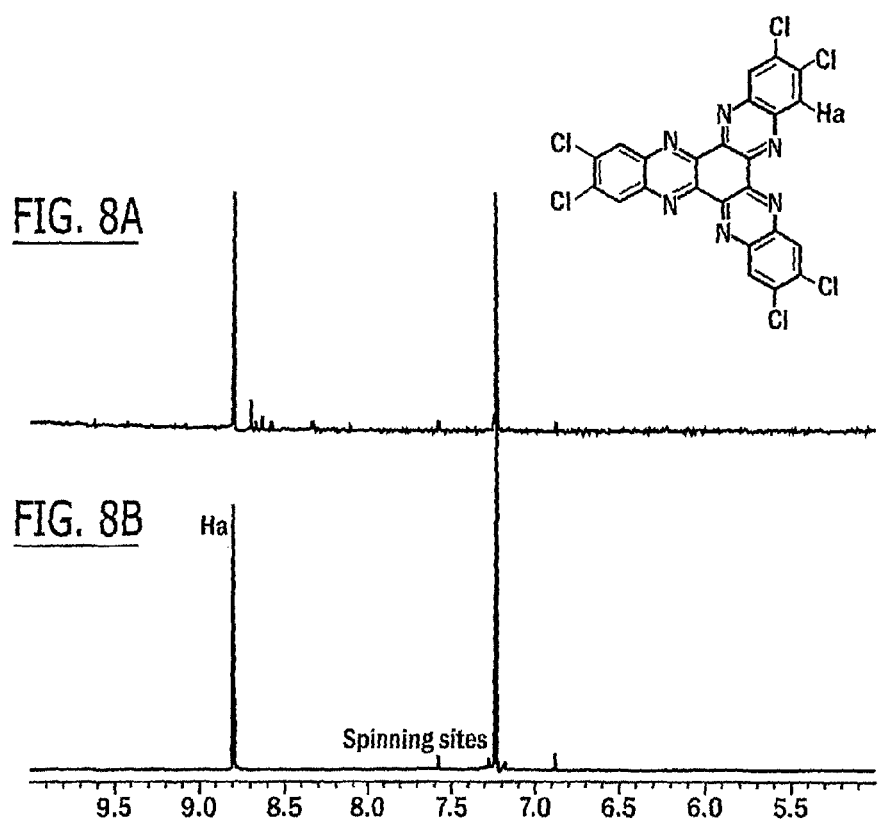
FIG. 8 illustrates the $^1$H NMR of HATNA-$Cl_6$, BK2_67, (a) before and (b) after sublimation.
Figure 9A:
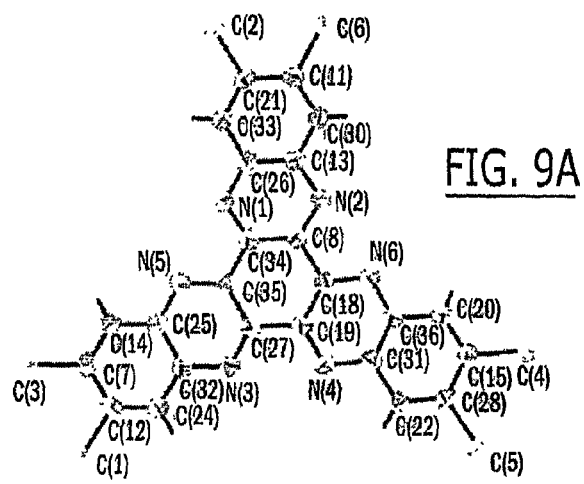
FIG. 9A illustrates the ORTEP of HATNA-$Cl_6$, BK2_67C.
Figure 9B:
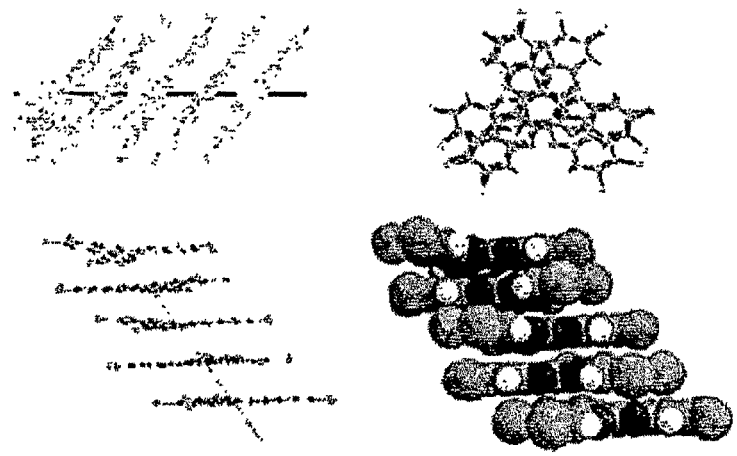
FIG. 9B illustrates the molecular packing of sublimed HATNA-$Cl_6$, BK2_67C.

HATNA, BK2_73, HATNA_Cl$_6$, BK2_67, HATNA_Br$_6$, BK2_31, and HATNA_[Me]$_6$, BK2_25 were purified by high-power vacuum train sublimation (ca. 10$^{-6}$, torr), FIGS. 5 and 6. There are three zones in the sublimation tube whilst two tubes are in zone one and labeled as 1.1 and 1.2 tubes, four tubes are present in zone two and are labeled as tubes 2.1, 2.2, 2.3, and 2.4, and two tubes are present in zone three and are labeled as tubes 3.1 and 3.2. The sublimation step has resulted in isolating pure compounds. The elemental analysis for the sublimed HATNA, HATNA-Cl$_6$, and HATNA_Br$_6$ passed; however, that of sublimed HATNA_Me$_6$ passed on N, H but not C (low by 0.75%). 300 MHz $^1$H NMR of sublimed BK2_73 and BK2_67 are shown in FIGS. 7 and 8, respectively. The sublimation of HATNA_Cl$_6$, BK2_67 has resulted in yellow crystals that were suitable for X-ray structure determination. The X-ray structure and molecular packing of HATNA_Cl$_6$ are shown in FIGS. 9A and 9B, respectively. The distance between the different molecules is ca. 3.21 Å. Such columnar packing in HATNA_Cl$_6$ may be attributed to effective electronic coupling and intermolecular coulombic interactions between the different molecules. The X-ray data and parameters of HATNA_Cl$_6$ are shown in Tables 1-6.

Scheme 1. Structures of HATNA-[X]$_6$ compounds.

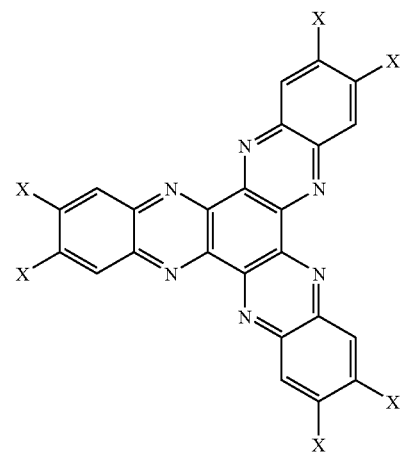

BK2_73 (X = H)
BK2_67 (X = Cl)
BK2_31 (X = Br)
BK2_25 (X = Me)
BK2_93 (X = NO$_2$)

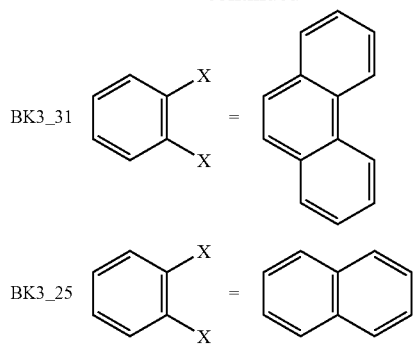

TABLE 1

Crystal data and structure refinement for z29b, HATNA-Cl$_6$.

| | |
|---|---|
| Identification code | z29b (HATNA-Cl$_6$) |
| Empirical formula | C$_{42}$H$_{38}$Cl$_4$N$_2$O$_4$ |
| Formula weight | 776.54 |
| Temperature | 293(2) K |
| Wavelength | 0.71073 Å |
| Crystal system | Monoclinic |
| Space group | P2(1)/c |
| Unit cell dimensions | a = 10.964(2) Å   α = 90°. |
| | b = 26.634(5) Å   β = 108.91(3)°. |
| | c = 8.0160(16) Å   γ = 90°. |
| Volume | 2214.5(8) Å$^3$ |
| Z | 3 |
| Density (calculated) | 1.747 Mg/m$^3$ |
| Absorption coefficient | 0.459 mm$^{-1}$ |
| F(000) | 1212 |
| Crystal size | ? X ? X ? mm$^3$ |
| Theta range for data collection | 1.96 to 30.21°. |
| Index ranges | −15 <= h <= 15, −37 <= k <= 36, −11 <= l <= 11 |
| Reflections collected | 26555 |
| Independent reflections | 6532 [R(int) = 0.0592] |
| Completeness to theta = 30.21° | 99.3% |
| Absorption correction | None |
| Refinement method | Full-matrix least-squares on F$^2$ |
| Data/restraints/parameters | 6532/0/349 |
| Goodness-of-fit on F$^2$ | 0.909 |
| Final R indices [I > 2sigma(I)] | R1 = 0.0518, wR2 = 0.1176 |
| R indices (all data) | R1 = 0.0841, wR2 = 0.1273 |
| Largest diff. peak and hole | 1.034 and −0.494 e · Å$^{-3}$ |

Figure 10:
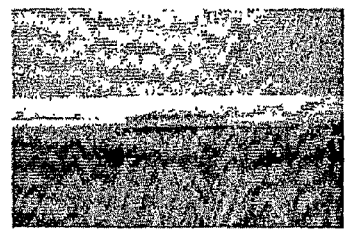
FIG. 10 illustrates the crystals in tubes 2.3 and 2.4 upon the sublimation of HATNA-$[Me]_6$ (refer to BRK_III_92 for details).
Figure 10A:
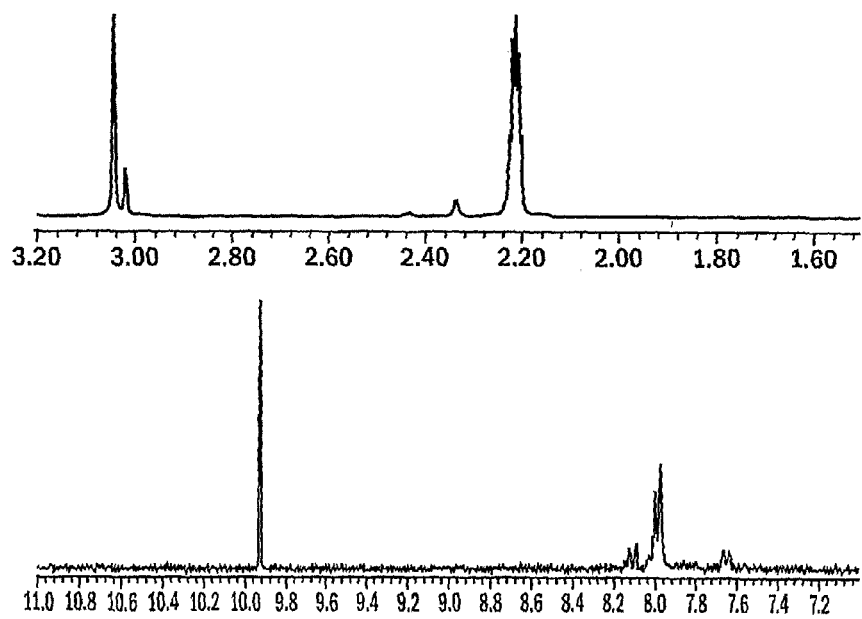
Figure 10B:
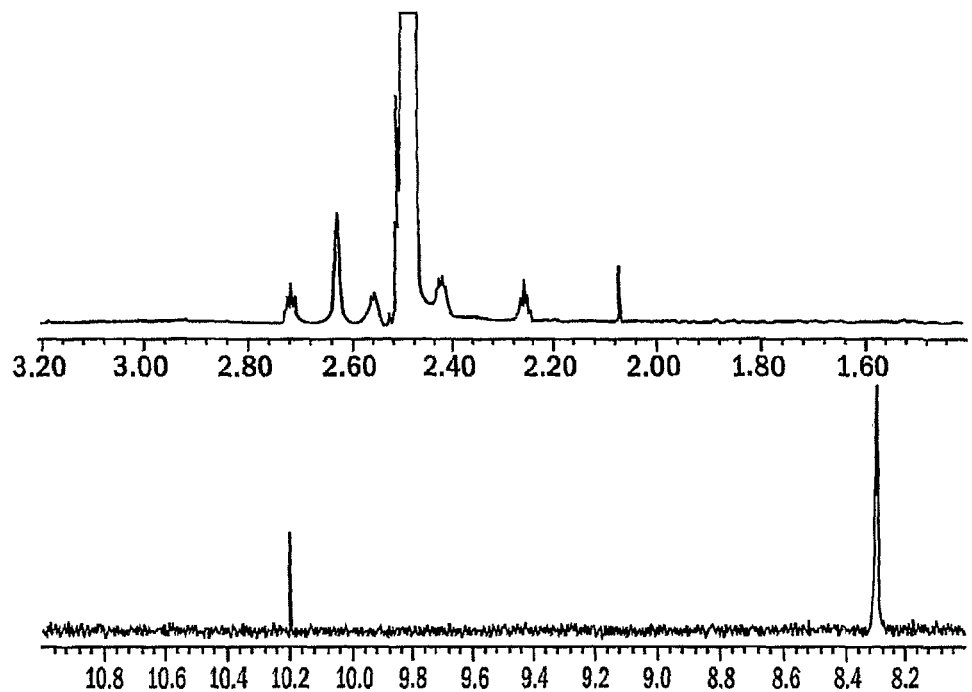

Sublimation of HATNA-Me$_6$ has resulted in blue crystals in zones 2.3 and 2.4. The HR-FAB MW indicated that the crystals in tubes 2.3 and 2.4 as well as the powder in tube 3.2 correspond to the same compound. The presence of the compound in different zones may be attributed to the nucleation effect since there is formation of crystals in the earlier tubes. Cheesman and Cookson[13] originally reported the tautomerization of dimethyl quinoxaline, Scheme 1A. Aumiller, W. D. et al.[14] reported oxidation of hexamethylheazatriphenylene. Alternatively, the compound in different zones may be due to tautomerization of HATNA-Me$_6$ as shown in Scheme 1A. Crystals could be the result of intermolecular H-bonding in one of the tautomer's isomers. $^1$H NMR spectra of BRK_III_92D and BRK_III_92B, with low solubility in DMSO, are shown in FIGS. 10A and 10B, respectively. The two doublets in the aromatic region of the $^1$H NMR of BRK_III_92D, FIG. 10A, could be associated with vinyl H's, i.e. evidence for tautomerism in this compound.

Scheme 1A. Possible tautomirism of HATNA_Me$_6$.

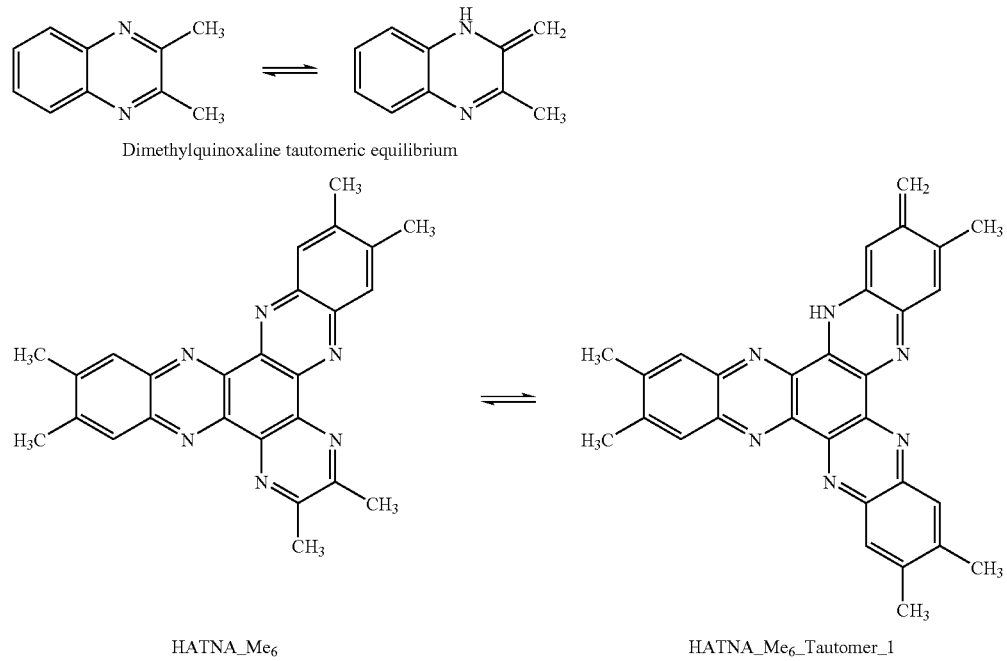

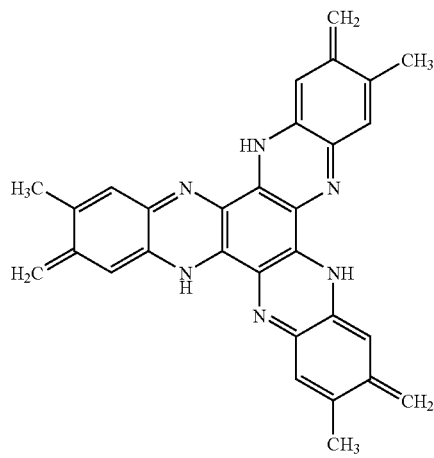

HATNA_Me₆_Tautomer_3

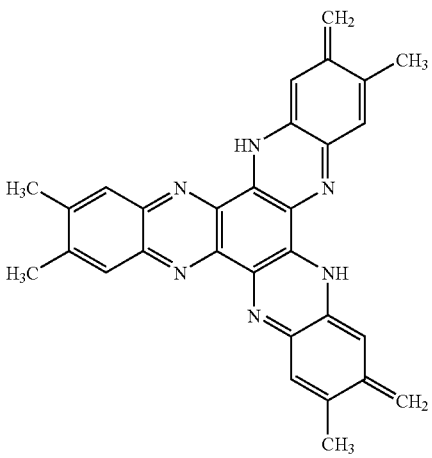

HATNA_Me₆_Tautomer_2

HATNA_Me₆_Tautomer_4 ⇌ HATNA_Me₆_Tautomer_5 ⇌ HATNA_Me₆_Tautomer_6

Figure 11:
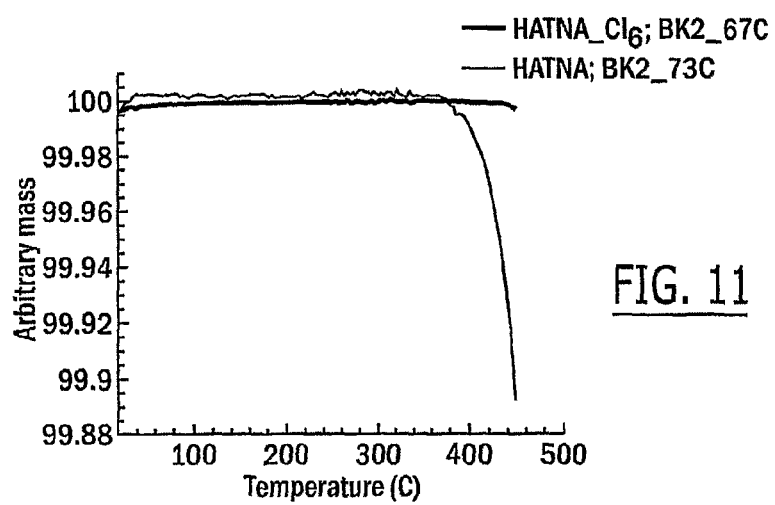
FIG. 11 illustrates the TGA (thermal stability) of BK2_67C (sublimed HATNA-$Cl_6$) and BK2_73C (sublimed HATNA).
Figure 12:
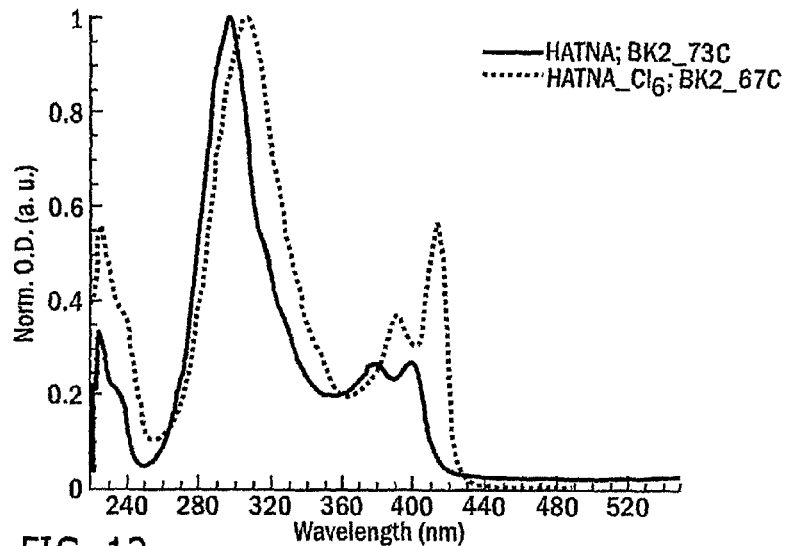
FIG. 12 illustrates the normalized absorption of BK2_73C and BK2_67C in $CH_2Cl_2$. The sample was filtered before acquiring the data because of the low solubility; therefore, the concentration was not determined.
Figure 13:
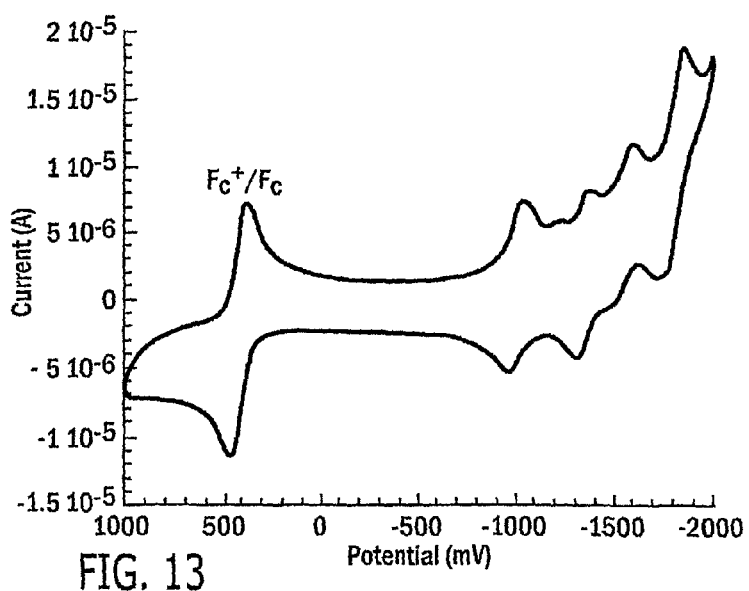
FIG. 13 illustrates the cyclic DC voltammogram of HATNA, BK2_73C, in dichloromethane with 0.1 M $TBAPF_6$ (vs Ag/AgCl); $E_1^{red}=-1.442V$; $E_2^{red}=-1.793$ V; $E_3^{red}=-1.870V$; $E_4^{red}=-2.203$ V. The reduction potentials are calculated vs. $F_c^+/F_c$.

The TGA plots of BK2__67C (sublimed HATNA-Cl₆) and BK2__73C (sublimed HATNA) are shown in FIG. 11. HATNA-Cl₆ did not decompose up to 450° C.; the afterheating crystals were of the same quality as they were before. HATNA seems to decompose at ca. 413° C.; however, sublimation of this compound cannot be ruled out. The chlorine substitution in HATNA-Cl₆ has increased its thermal stability relative to HATNA. The absorbance of HATNA_Cl₆ is redshifted with respect to that of HATNA, FIG. 12. HATNA_Cl₆ has three distinctive absorbing bands at $\lambda_1$=307, $\lambda_2$=392, and $\lambda_3$=414 mm. HATNA has three distinctive absorbing bands at $\lambda_1$=297, $\lambda_2$=379, and $\lambda_3'$=399 mm. The ratio $\lambda_2/\lambda_2 2$=1.41, $\lambda_3/\lambda_3$=2.04. The cyclic DC voltammograms of HATNA and HATNA_Cl₆ are shown in FIGS. 13 and 14, respectively.

In the course of the synthesis of hexaazatristriphenylene HATT (also referred to as "Mickey-Mouse" HATNA), BK3__31, a different product was observed, Scheme 2. The threefold condensation of hexaketocyclohexane octahydrate SM4 with 9,10-diaminophenanthrene SM7 in acetic acid/ethanol under air resulted in an orange solid phenanthrazine BK2__97E, which was sublimed under high vacuum. Phenanthrazine was confirmed by ¹H NMR and E1 mass analysis. In this regard, 9,10-diaminophenanthrene SM7 may have been partially oxidized to phenanthrene-9,10-dione SM34 under air. The double bond (9=10) in 9,10-diaminophenanthrene SM7 behaves more like a single double bond rather than one in an aromatic system, i.e. it can be oxidized more easily. Condensation of SM7 and SM34 led to BK2__97E. To give evidence for the proposed mechanism, two control experiments were performed. 9,10-diaminophenanthrene SM7 was refluxed in acetic acid/ethanol for 24 hours. E1 mass analysis showed the presence of phenanthrazine, BK3__29. Hexaazatristriphenylene HATT, BK3__31 was obtained when the condensation was performed in acetic acid under nitrogen (MALDI TOF measurement confirmed the presence of HATT).

Scheme 2. Proposed mechanism for the formation of BK2_97E.

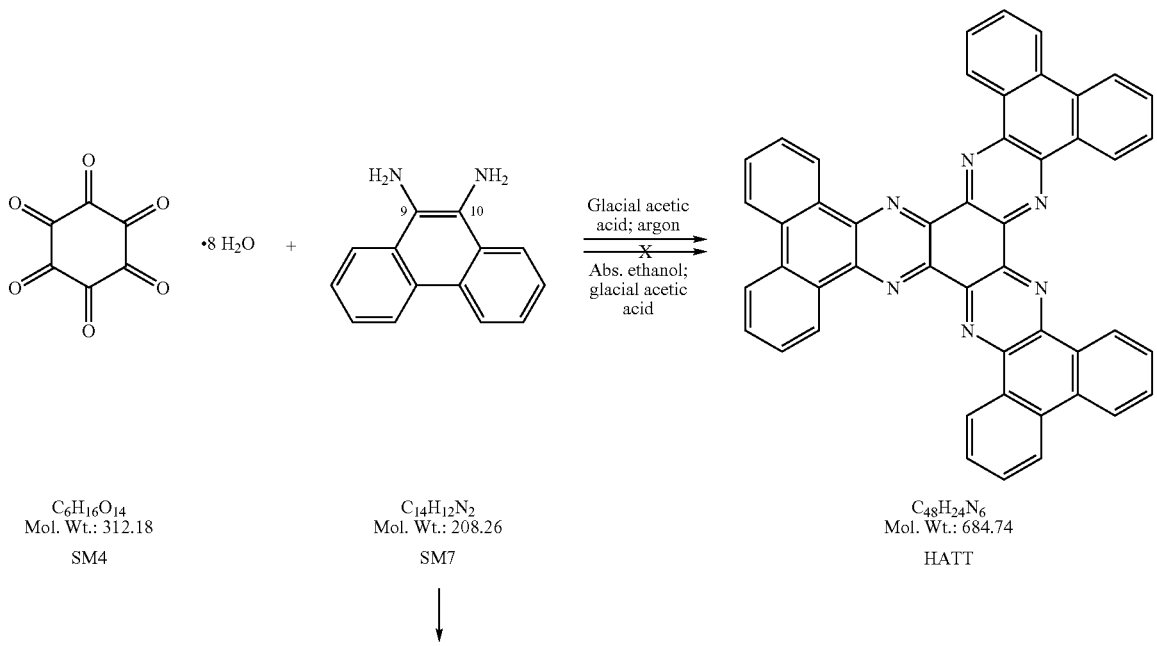

C₆H₁₆O₁₄
Mol. Wt.: 312.18
SM4

C₁₄H₁₂N₂
Mol. Wt.: 208.26
SM7

C₄₈H₂₄N₆
Mol. Wt.: 684.74
HATT

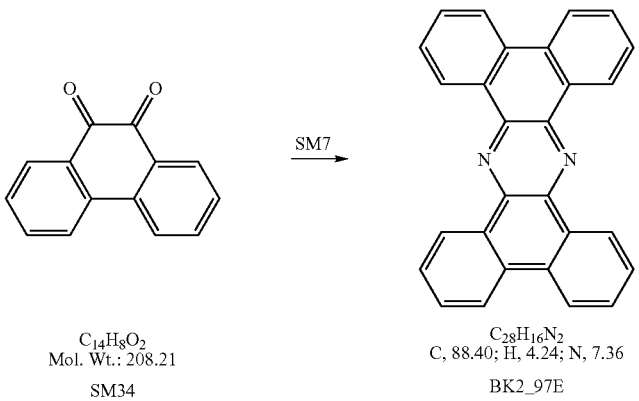

C₁₄H₈O₂
Mol. Wt.: 208.21
SM34

SM7 →

C₂₈H₁₆N₂
C, 88.40; H, 4.24; N, 7.36
BK2_97E

The synthesis of HATNA_F$_{12}$ and fabrication of an OFET as shown in FIG. 14A is proposed. 3,4,5,6-tetrafluoro-1,2-phenylenediamine can be synthesized according to a literature procedure reported by Heaton, A. et al.[16] and upon its condensation with hexaketocyclohexane octahydrate, HATNA_F$_{12}$ could be obtained. Perfluorophenyl-phenyl interactions have been reported in the case of alkenes,[17] diynes,[18] and enediynes.[19] Such stacking interactions is anticipated, upon mixing HATNA and HATNA_F$_{12}$. It is worth noting that co-sublimation of HATNA and HATNA_F$_{12}$ could lead to a crystal formed of a stack of alternate molecules of HATNA and HATNA_F$_{12}$.

1,2-diamino-4,5-dicyanobenzene could be synthesized according to a literature procedure. Upon its condensation with hexaketocyclohexane octahydrate, HATNA_[CN]$_6$ was obtained. The seven membered ring in compound BK1_53 is expected to disturb its planarity; thus, affecting its mobility.

-continued

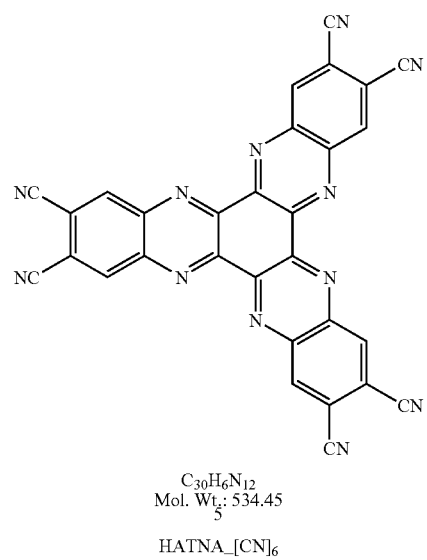

C₃₀H₆N₁₂
Mol. Wt.: 534.455

HATNA_[CN]₆

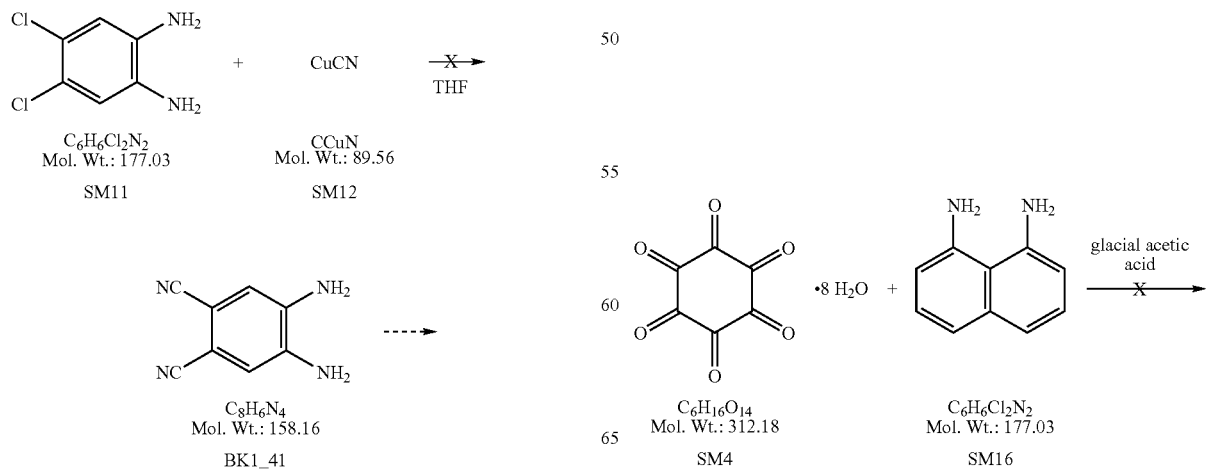

Scheme 2A. Synthetic approaches to HATNA_[CN]₆ and BK1_53.

SM11 C₆H₆Cl₂N₂ Mol. Wt.: 177.03

SM12 CCuN Mol. Wt.: 89.56

BK1_41 C₈H₆N₄ Mol. Wt.: 158.16

SM4 C₆H₁₆O₁₄ Mol. Wt.: 312.18

SM16 C₆H₆Cl₂N₂ Mol. Wt.: 177.03

-continued

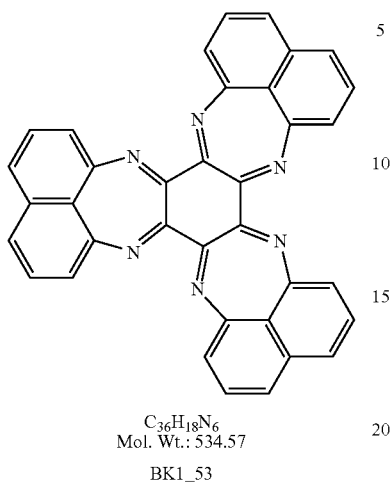

C₃₆H₁₈N₆
Mol. Wt.: 534.57
BK1_53

HATNA with Thiols and Alkoxy Chains

Discotic thermotropic liquid crystals are generally constituted of a rigid disk-like core substituted with extended flexible chains. Five different types of discotic liquid crystals are yet known. The five different discotic structures are the nematic discotic, the disordered columnar, the tilted disordered columnar, the ordered columnar, and the tilted columnar phases.[20] Kestmont, G. et. al.'s[21] reported the synthesis of HATNA_[SR]₆. The authors reported that HATNA_[SR]₆ showed mesophase behavior, Table 2.

Scheme 3. Synthetic Scheme of HATNA_[SC₁₂H₂₅]₆, BK2_71, and HATNA_[SC₈H₁₇]₆, BK2_99.

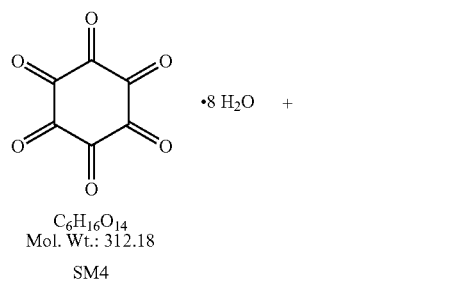

C₆H₁₆O₁₄
Mol. Wt.: 312.18
SM4

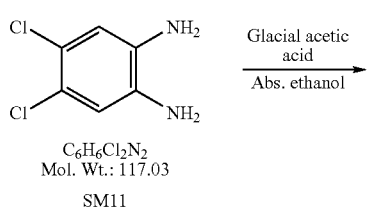

C₆H₆Cl₂N₂
Mol. Wt.: 117.03
SM11

-continued

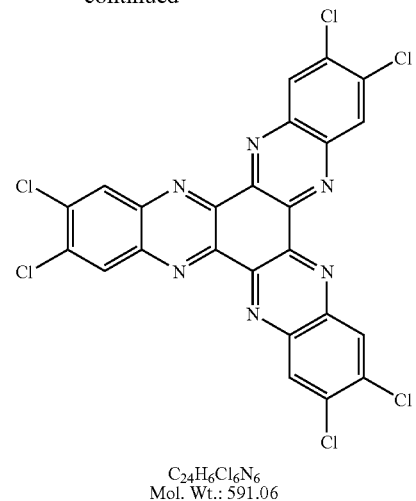

C₂₄H₆Cl₆N₆
Mol. Wt.: 591.06
BK2_67

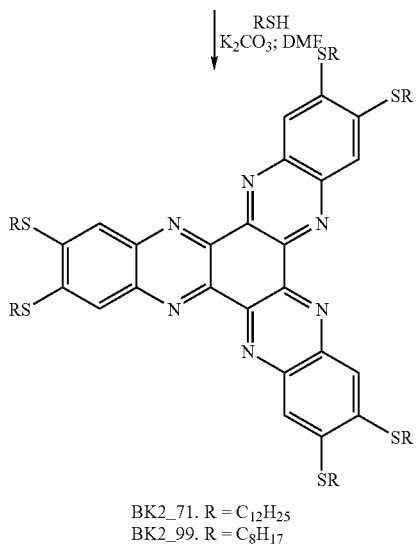

BK2_71. R = C₁₂H₂₅
BK2_99. R = C₈H₁₇

Figure 15:
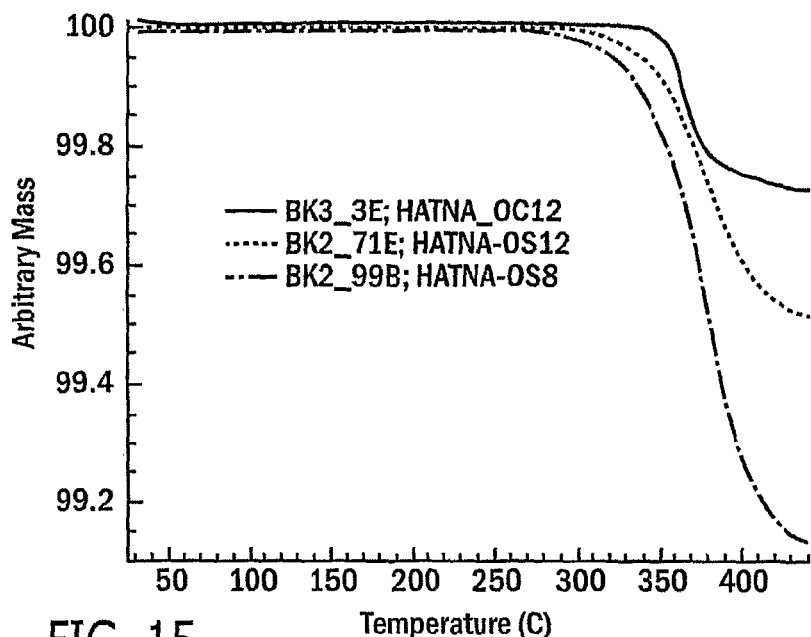
FIG. 15 illustrates the thermal stability of BK2_71E, BK2_99B, and BK3_3E.
Figure 16A:
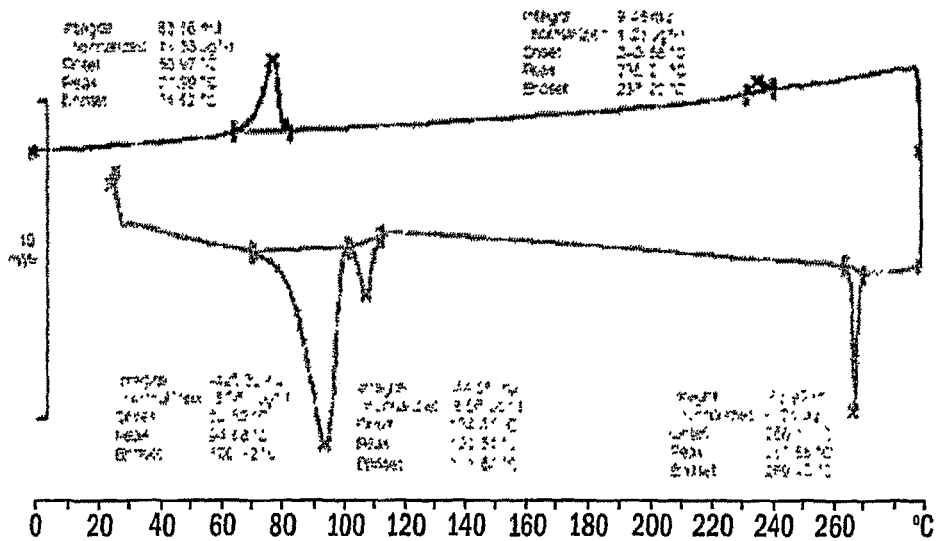
FIG. 16A illustrates the DSC of HATNA_$[SC_{12}H_{25}]_6$, BK2_71E; first cycle of heating and cooling.
Figure 16B:
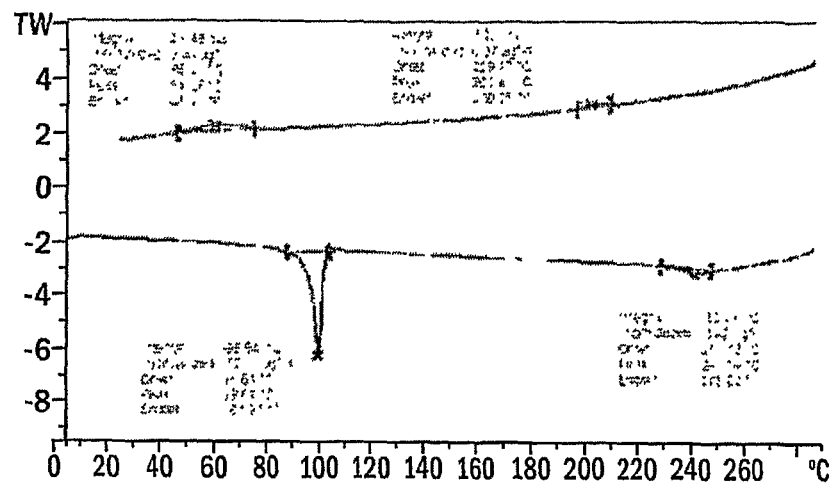
FIG. 16B illustrates the DSC of HATNA_$[SC_{12}H_{25}]_6$, BK2_71E; second cycle of heating and cooling.
Figure 16C:
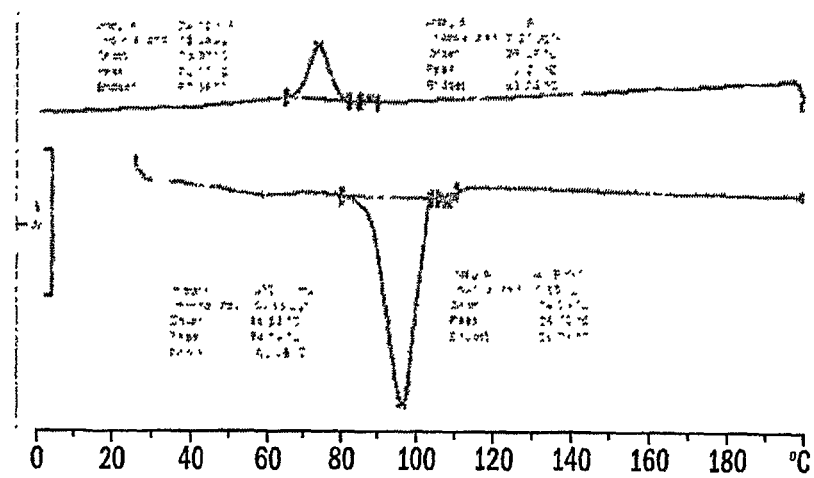
FIG. 16C illustrates the DSC of HATNA_$[SC_{12}H_{25}]_6$, BK2_71E; first cycle of heating (till 200° C.) and cooling.
Figure 16D:
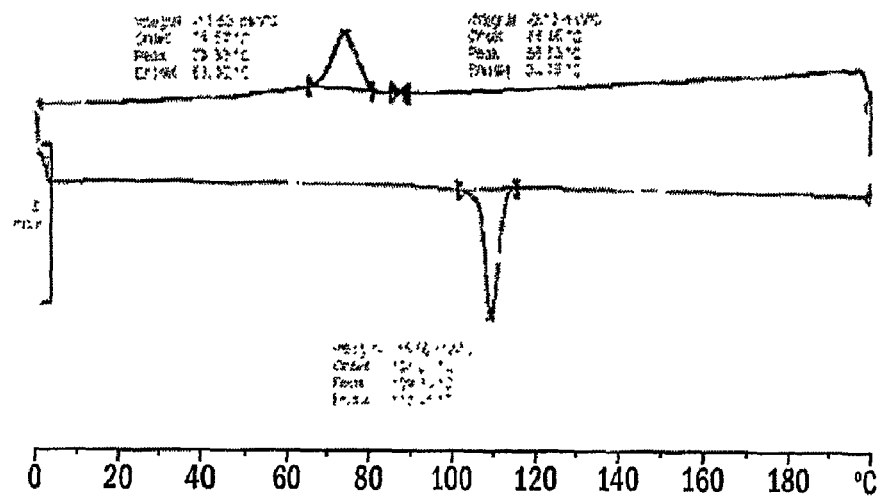
FIG. 16D illustrates the DSC of HATNA_$[SC_{12}H_{25}]_6$, BK2_71E; second cycle of heating (till 200° C.) and cooling.
Figure 17A:
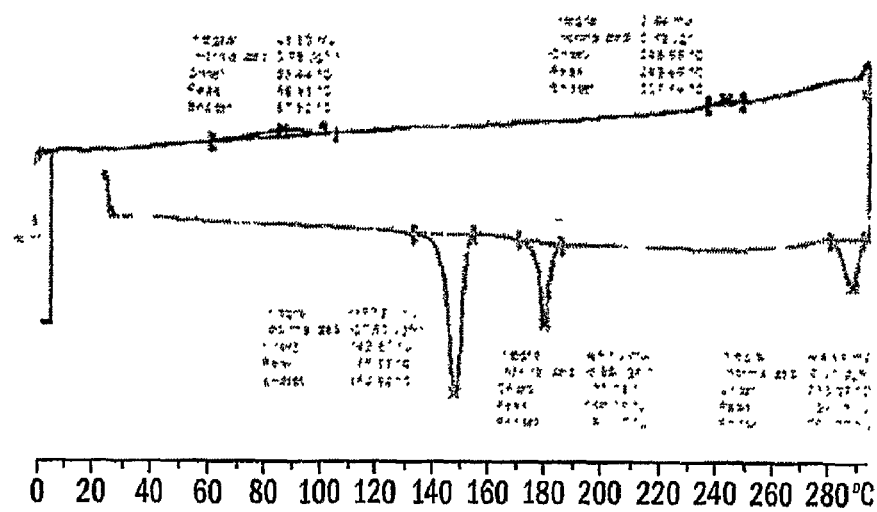
FIG. 17A illustrates the DSC of HATNA_$[SC_8H_{17}]_6$, BK2_99B; first cycle of heating and cooling.
Figure 17B:
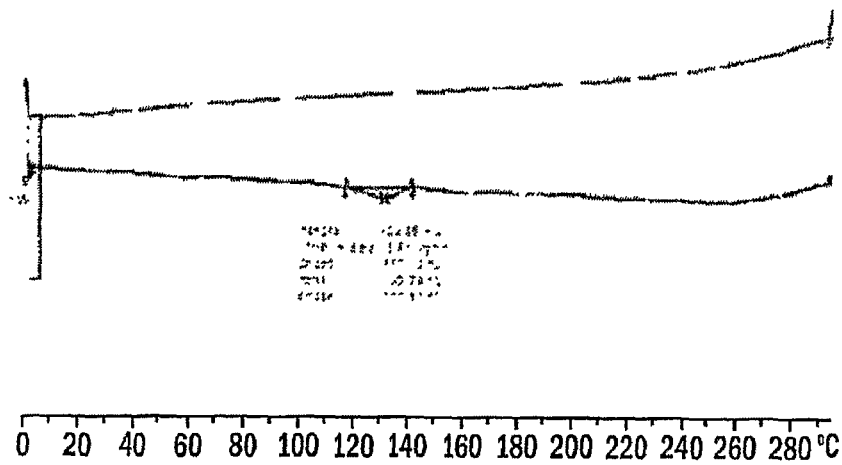
FIG. 17B illustrates the DSC of HATNA_$[SC_8H_{17}]_6$, BK2_99B; second cycle of heating and cooling.
Figure 17C:
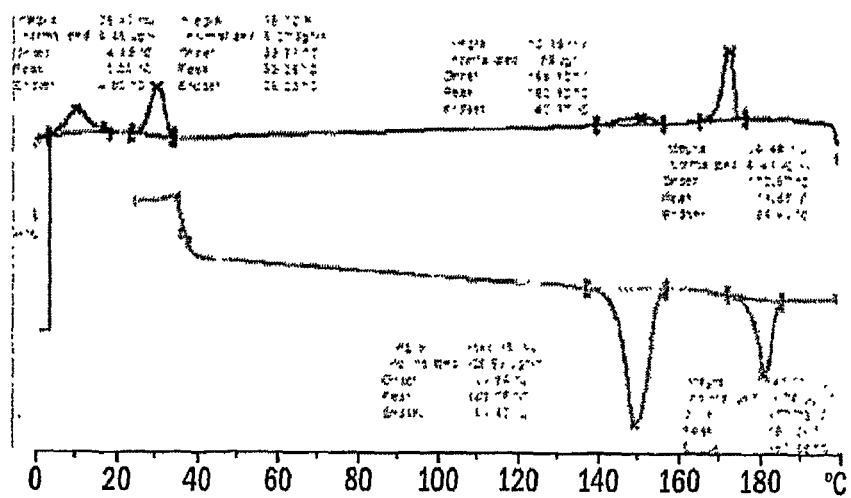
FIG. 17C illustrates the DSC of HATNA_$[SC_8H_{17}]_6$, BK2_99B; first cycle of heating (till 200° C.) and cooling.
Figure 17D:
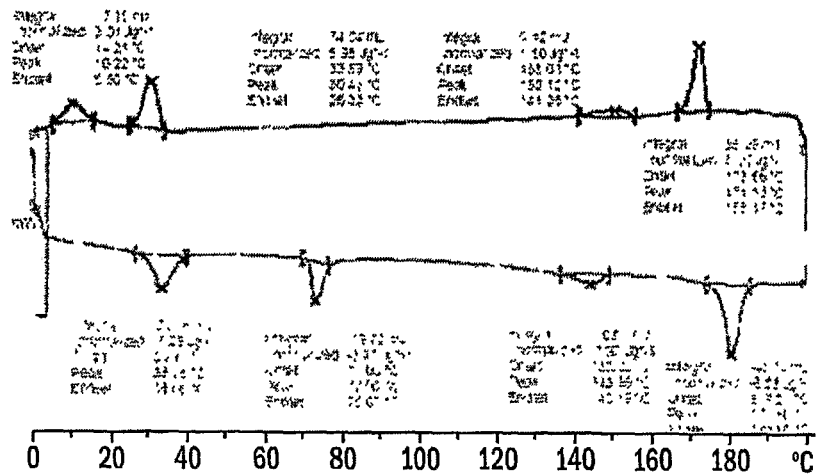
FIG. 17D illustrates the DSC of HATNA_$[SC_8H_{17}]_6$, BK2_99B; second cycle of heating (till 200° C.) and cooling.
Figure 18:
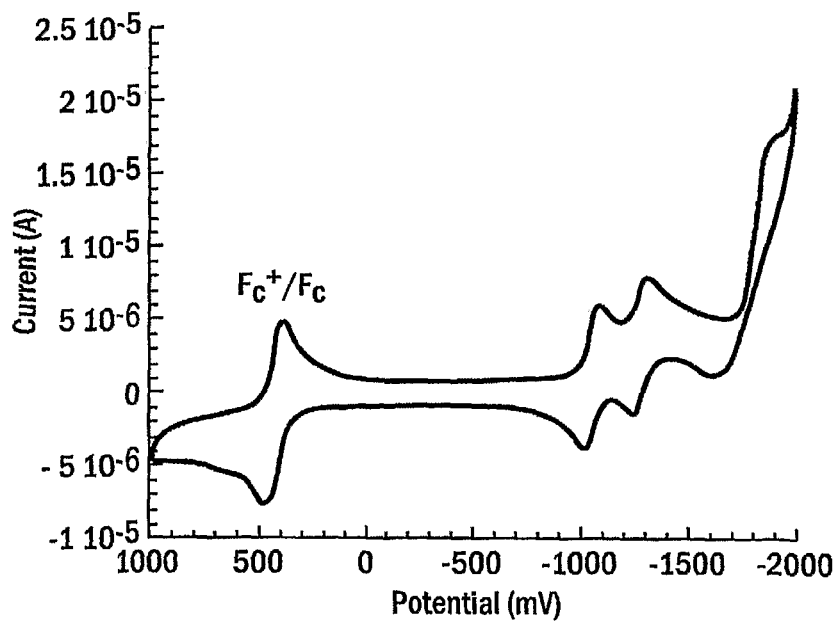
FIG. 18 illustrates the cyclic DC voltammogram of HATNA_$[SC_{12}H_{25}]_6$, BK2_71E, in dichloromethane with 0.1 M $TBAPF_6$ (vs. a Ag/AgCl pseudoreference); half-wave reduction potentials of $E_1^{red}=-1.449$ V; $E_2^{red}=-1.881$ V; $E_1=-2.026$ V are calculated vs ferrocenium/ferrocene.
Figure 19:
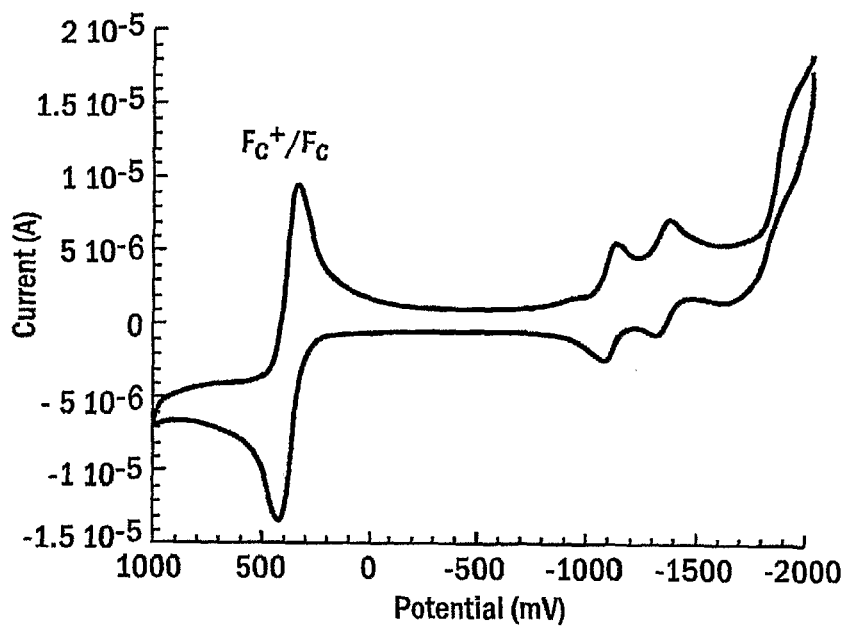
FIG. 19 illustrates the cyclic DC voltammogram of HATNA_$[SC_8H_{17}]_6$, BK2_99B, in dichloromethane with 0.1 M $TBAPF_6$ (vs a Ag/AgCl pseudoreference); half-wave reduction potentials of $E_1^{red}=-1.468$ V; $E_2^{red}=-1.708$ V; $E_3=-1.980$ V are calculated vs ferrocenium/ferrocene.
Figure 20:
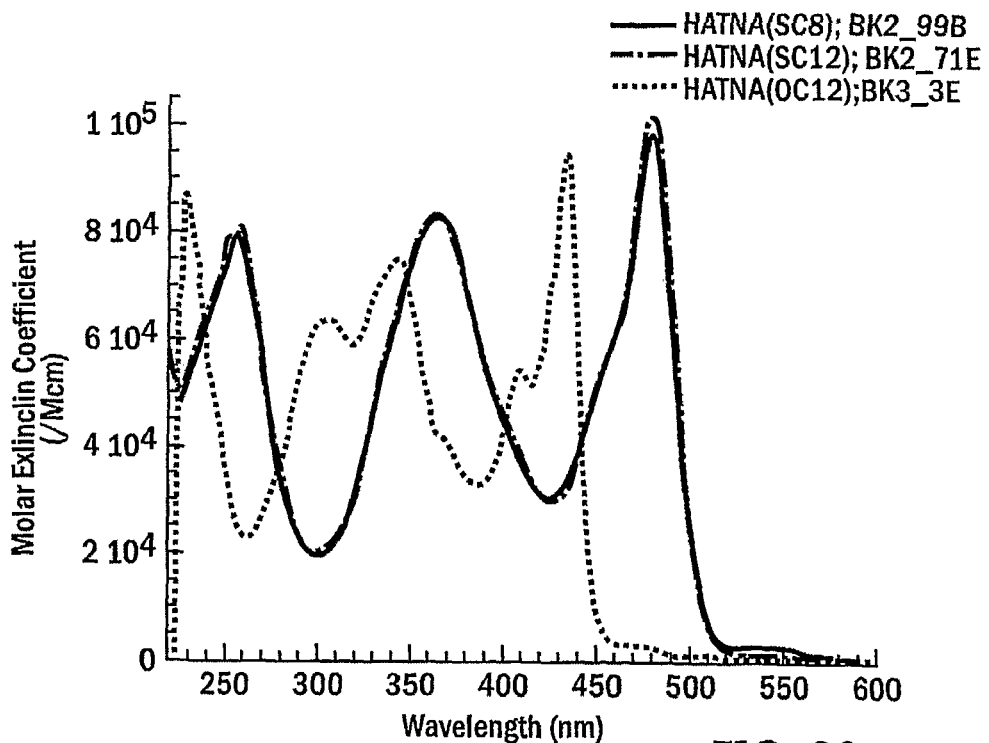
FIG. 20 illustrates the absorbance of HATNA_$[SC_8H_{17}]_6$, BK2_99B, HATN_$[SC_{12}H_{25}]_6$, BK2_71E, and HATNA_$[OC_{12}H_{25}]_6$, BK3-3E, in $CH_2Cl_2$.
Figure 21:
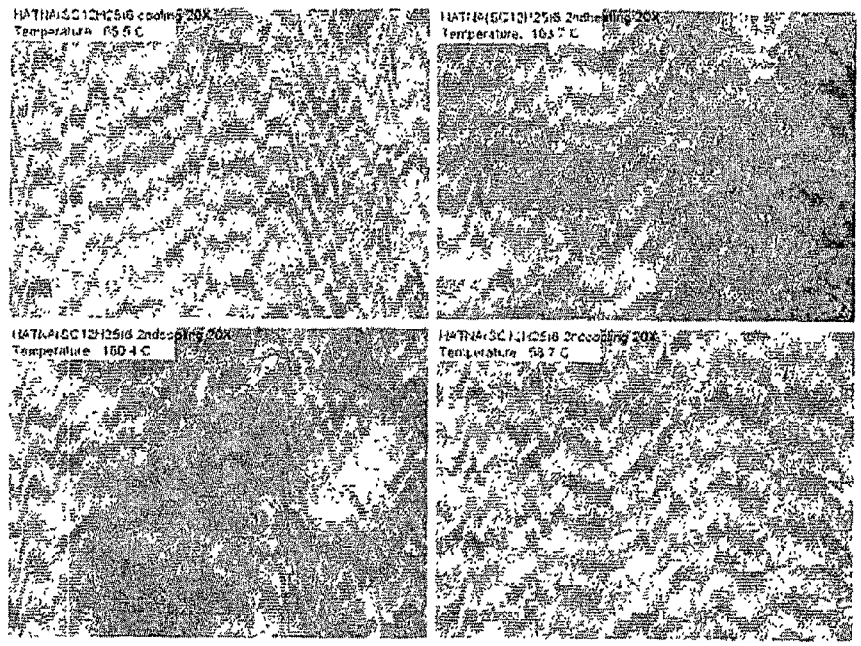
FIG. 21 illustrates the textures of HATNA_$[SC_{12}H_{25}]_6$, BK2_71E, between cross-polarizers.
Figure 22:
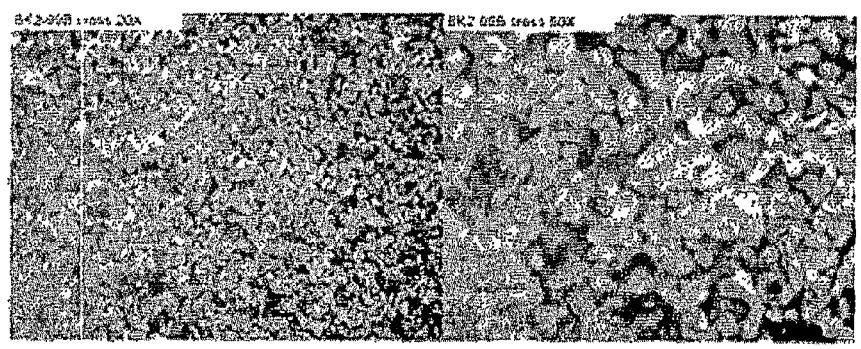
FIG. 22 illustrates the textures of HATNA_$[SC_8H_{17}]_6$, BK2_99B, between cross-polarizers.

The synthesis of HATNA_[SR]₆ for R=C₁₂H₂₅ (BK2_71) and R=C₈H₁₇ (BK2_99). HATNA-Cl₆ was repeated, BK2_67, was used in the synthesis of BK2-71 and BK2_99 without the sublimation step, Scheme 3. The thermal stability of BK2_71 and BK2_99 is shown in FIG. 15. BK2_71 decomposes at ca. 320° C., while BK2_99 decomposes at ca. 330° C. The DSC data of BK2_71E and BK2_99B are shown in FIGS. 16 and 17, respectively. The data is summarized in Table 8. The results are not in agreement with Kestmont, G. et. al's.[21] The CV data of BK2_71E and BK2_99B are shown in FIGS. 18 and 19, respectively. The UV-vis spectra of BK2_71 and BK2_99 are shown in FIG. 20. The chain length does not affect the absorbance of HATNA-[SR]₆, which has three distinctive absorbance bands at 255, 363, and 479 nm. Polarized optical microscope investigation of BK2_71 and BK2_99 showed their textures as depicted in FIGS. 21 and 22, respectively. It was observed that upon HATNA_[SC₁₂H₂₅]₆ solution in CH₂Cl₂ exposure to a latex glove, the color changes immediately from yellow to red. Weck et al.[22] reported the increase of the clearing temperature of triphenylene upon mixing it in 1:1 ratio with perfluorotriphenylene due to intermolecular coulombic interactions between these molecules. Mixing it in 1:1 ratio of HATNA_F₁₂ and HATNA_[XR]₆ where X=O, S could lead to such a behavior.

TABLE 2

Literature mesophase assignment, transition temperatures (° C.), and transient enthalpies (kJ/mol).[21]

| | | | | | | | | | |
|---|---|---|---|---|---|---|---|---|---|
| HATNA_(SC$_8$H$_{17}$)$_6$ | Cr | $\xrightarrow{77\ (5.6)}$ | X$_1$ | $\xrightarrow{142\ (14.0)}$ | X$_2$ | $\xrightarrow{178\ (13.5)}$ | LC | $\longrightarrow$ | decomp. at ca. 250° C. |
| | Cr | $\xleftarrow{43\ (-7.6)}$ | X$_1$ | $\xleftarrow{174\ (-12.5)}$ | LC | | | | |
| HATNA_(SC$_{12}$H$_{25}$)$_6$ | X | $\xrightarrow{99\ (31.7)}$ | LC | $\longrightarrow$ | decomp. at ca. 250° C. | | | | |
| | X | $\xleftarrow{79\ (-32.4)}$ | LC | | | | | | |

TABLE 3

Mesophase assignment, transition temperatures (° C.), and transient enthalpies (kJ/mol).[a]

| | | | | | | | | | |
|---|---|---|---|---|---|---|---|---|---|
| BK2_71E HATNA_(SC$_{12}$H$_{25}$)$_6$ | 1st cycle | X | $\xrightarrow{95\ (91.4)}$ | X$_1$ | $\xrightarrow{109\ (9.6)}$ | LC | $\xrightarrow{268\ (11.6)}$ | I | |
| | | X | $\xleftarrow{80\ (-18.0)}$ | LC | $\xleftarrow{236\ (-2.0)}$ | I | | | |
| | 2nd cycle | X | $\xrightarrow{100\ (20.5)}$ | LC | $\xrightarrow{242\ (2.3)}$ | I | | | |
| | | X | $\xleftarrow{61\ (-5.5)}$ | LC | $\xleftarrow{203\ (-0.6)}$ | I | | | |
| BK2_99B HATNA_(SC$_8$H$_{17}$)$_6$ | 1st cycle | X | $\xrightarrow{149\ (34.4)}$ | X$_1$ | $\xrightarrow{180\ (12.3)}$ | LC | $\xrightarrow{289\ (9.0)}$ | I | |
| | | X | $\xleftarrow{87\ (-4.7)}$ | LC | $\xleftarrow{244\ (-0.74)}$ | I | | | |
| | 2nd cycle | X | $\xrightarrow{131\ (4.8)}$ | I | | | | | |

[a]X is unknown phase; LC = liquid crystalline; I = isotropic (liquid).

Recently, Ong, C. W. et al. reported that HATNA_[OR]$_6$ exhibited liquid-crystalline behavior.[23] HATNA_[OR]$_6$ BK3_3 having 6 arms of OC$_{12}$H$_{25}$ extended chains (Scheme 4) was synthesized. 4,5-Bis-dodecyloxy benzene-1,2-diamine BK3_1 was synthesized according to a literature procedure.[24] Three-fold condensation of BK3_1 with hexaketocyclohexane octahydrate afforded BK3_3 (Scheme 4).

Figure 23:
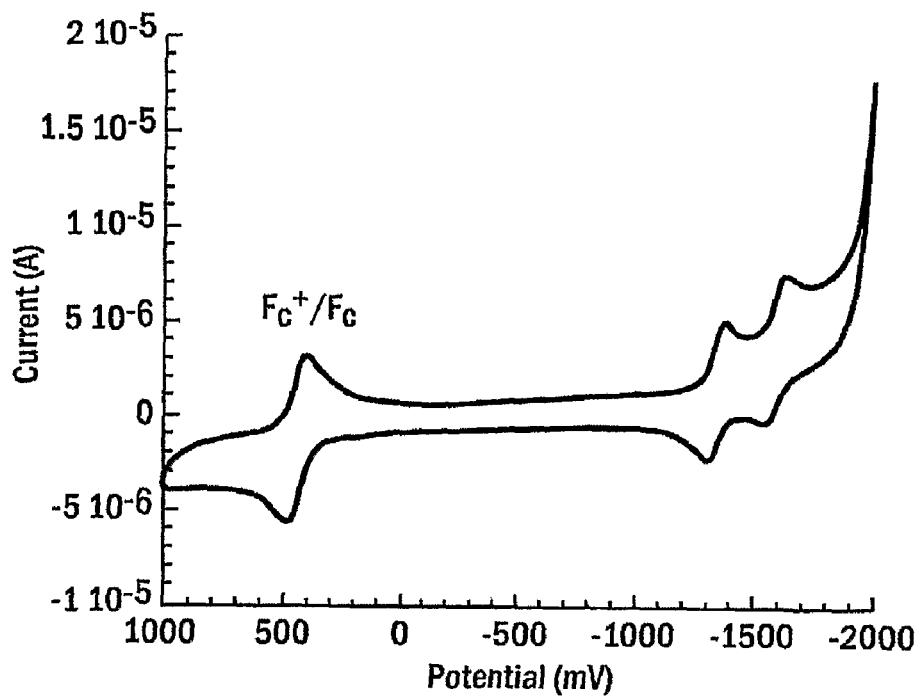
FIG. 23 illustrates the cyclic DC voltammogram of HATNA_[OC$_{12}$H$_{25}$]$_6$, BK3__3G in dichloromethane with 0.1 M TBAPF$_6$ (vs. a Ag/AgCl pseudoreference); half-wave reduction potentials of E$_1^{red}$=1.775 V; E$_2$=−2.020 V are calculated vs ferrocenium/ferrocene.
Figure 24A:
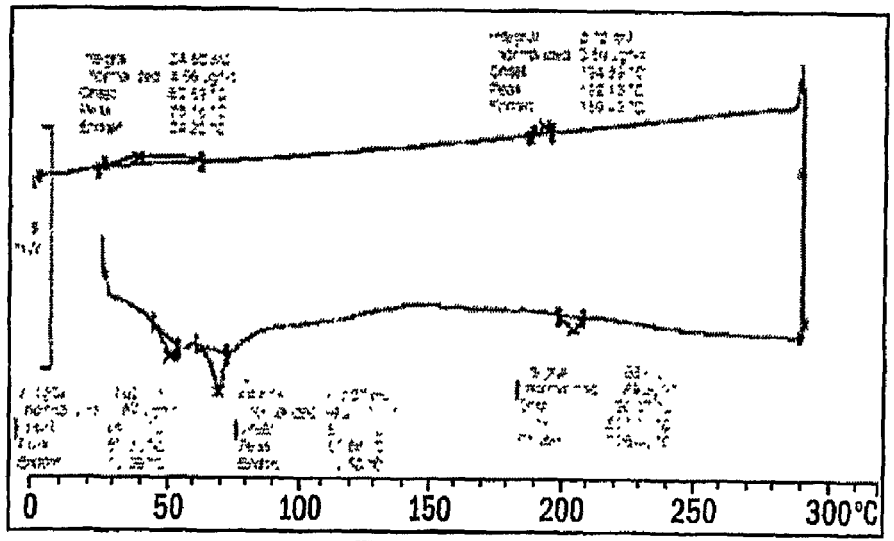
FIG. 24A illustrates the DSC of HATNA_[OC$_{12}$H$_{25}$]$_6$, BK3__3G; first cycle of heating and cooling.
Figure 24B:
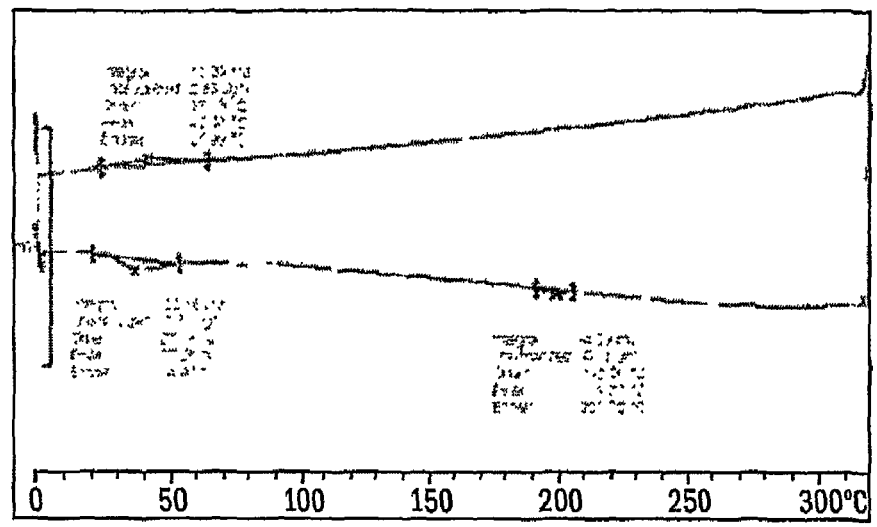
FIG. 24B illustrates the DSC of HATNA_[OC$_{12}$H$_{25}$]$_6$, BK3__3G; second cycle of heating and cooling.
Figure 25:
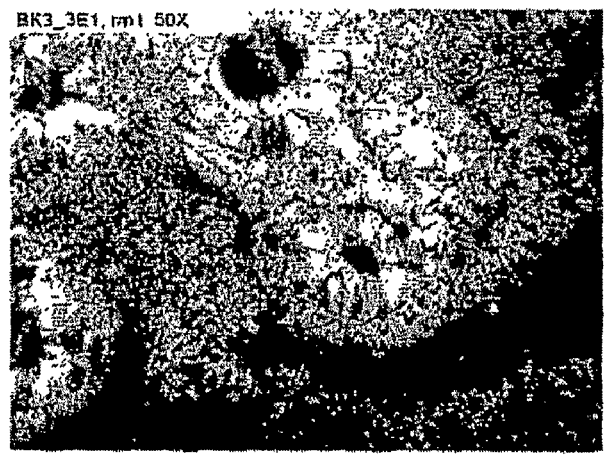
FIG. 25 illustrates the textures of BK3__3E between cross-polarizers.

The TGA plot of BK3_3 is shown in FIG. 15. HATNA_[OC$_{12}$H$_{25}$]$_6$ decomposes at ca. 350° C. The UV-vis spectrum of BK3-3 is shown in FIG. 20. BK3_3 has four distinctive absorbance bands at 228, 303, 341, and 433 nm in addition to a shoulder at 409 nm. The cyclic DC voltammogram of BK3_3 is shown in FIG. 23. DSC data of BK3_3 is shown in FIG. 24. Preliminary polarized optical microscope photos of the textures of BK3_3 are shown in FIG. 25. The sample was dissolved in CH$_2$Cl$_2$ and was slowly evaporated on a glass slide, and it was then heated on an aluminum block for 5 min at 280° C.

Scheme 4. Synthetic Scheme of HATNA_[OC$_{12}$H$_{25}$]$_6$, BK3_3.

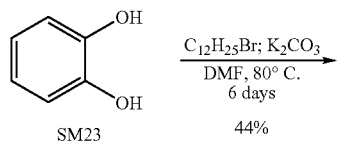

SM23    44%

-continued

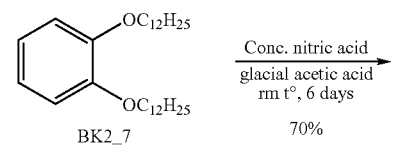

BK2_7    70%

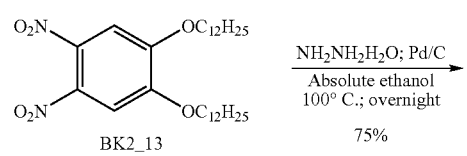

BK2_13    75%

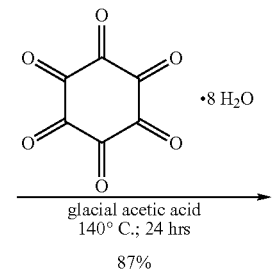

BK2_33
BK3_1    87%

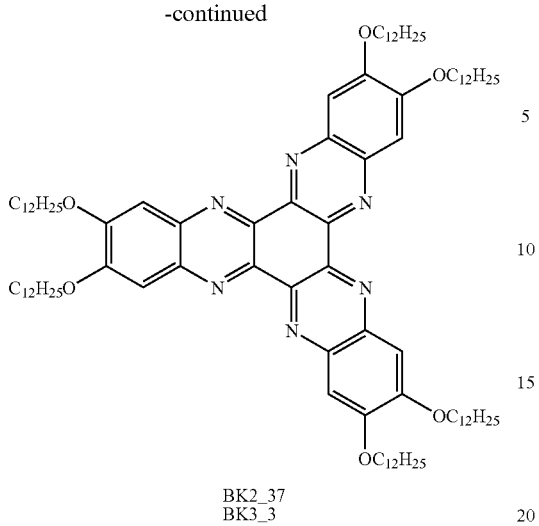

BK2_37
BK3_3

TABLE 4

Mesophase assignment, transition temperatures (° C.),
and transient enthalpies (kJ/mol).[a]

| BK3_3G HATNA_(OC$_{12}$H$_{25}$)$_6$ | 1st cycle | X $\xrightarrow{50\ (2.5)}$ X$_1$ $\xrightarrow{69\ (6.4)}$ LC $\xrightarrow{203\ (2.2)}$ I |
| --- | --- | --- |
| | | X $\xleftarrow{39\ (-6.8)}$ LC $\xleftarrow{192\ (-1.0)}$ I |
| | 2nd cycle | X $\xrightarrow{37\ (5.7)}$ LC $\xrightarrow{200\ (1.1)}$ I |
| | | X $\xleftarrow{42\ (-4.2)}$ LC |

[a]X is unknown phase; LC = liquid crystalline; I = isotropic (liquid).

Oxadiazole Based HATNA

Figure 26:
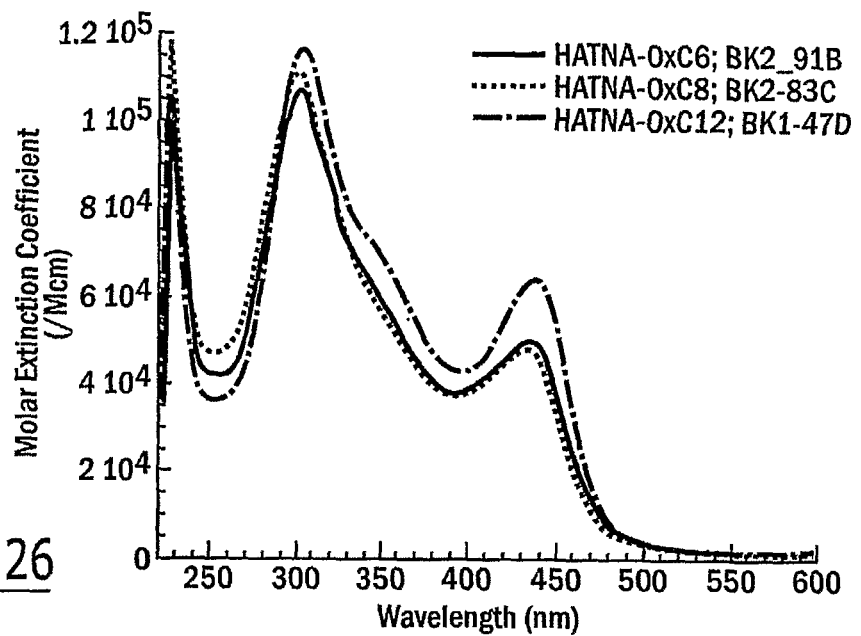
FIG. 26 illustrates the absorbance of HATNA_OxC$_6$, BK2__91B, HATNA_OxC$_8$, BK2__83C, HATNA_OxC$_{12}$, BK1__47D, in CH$_2$Cl$_2$.
Figure 27:
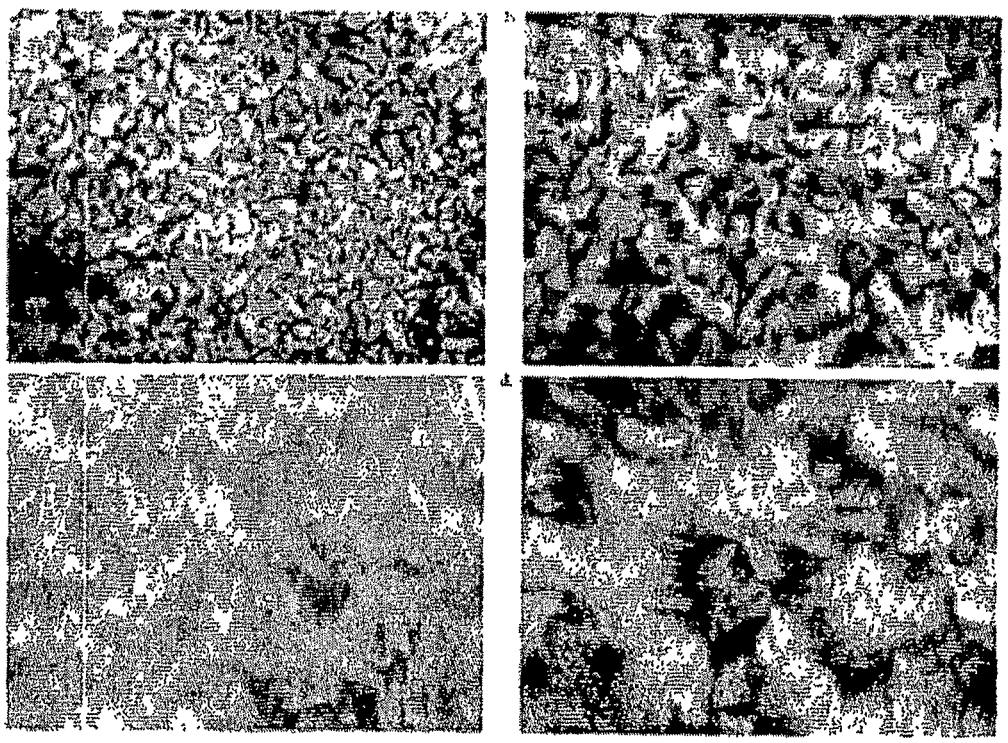
FIG. 27 illustrates the polarized optical photos of BK1__47D between cross-polarizers; (a) 10× magnification; (b) 20× magnification; (c) & (d) 50× magnification.
Figure 28A:
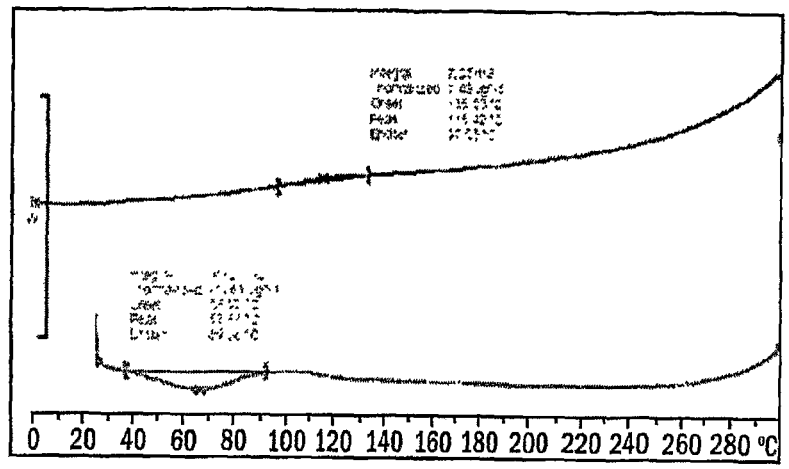
FIG. 28A illustrates the DSC of HATNA_[Ox(PhOC$_{12}$H$_{25}$)$_3$]$_3$, BK2__27B; the first cycle of heating and cooling.
Figure 28B:
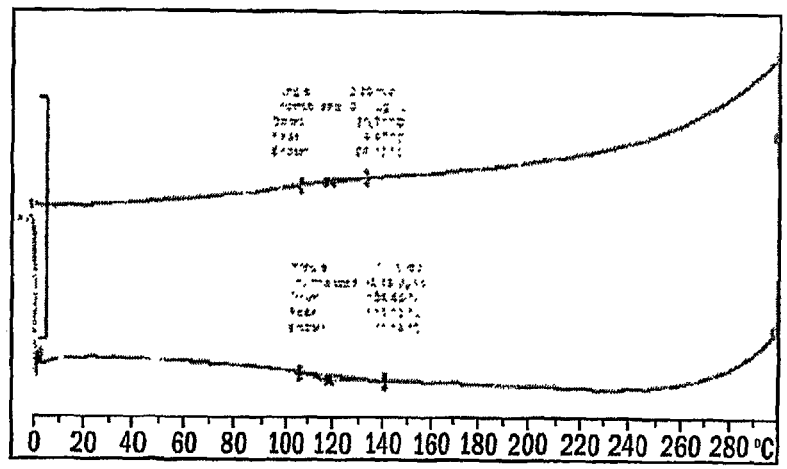
FIG. 28B illustrates the DSC of HATNA_[Ox(PhOC$_{12}$H$_{25}$)$_3$]$_3$, BK2__27B; the second cycle of heating and cooling.
Figure 29A:
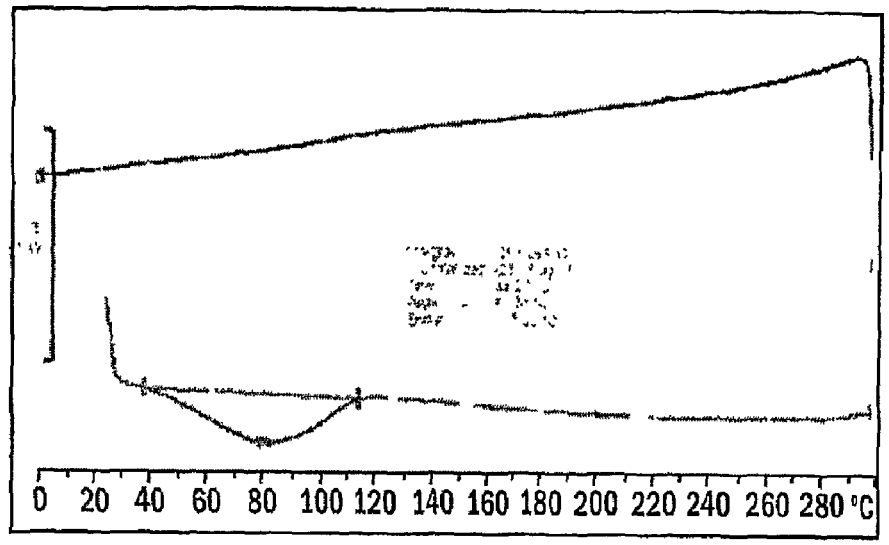
FIG. 29A illustrates the DSC of HATNA_[Ox(PhOC$_8$H$_{17}$)$_3$]$_3$, BK2__83D; the first cycle of heating and cooling.
Figure 29B:
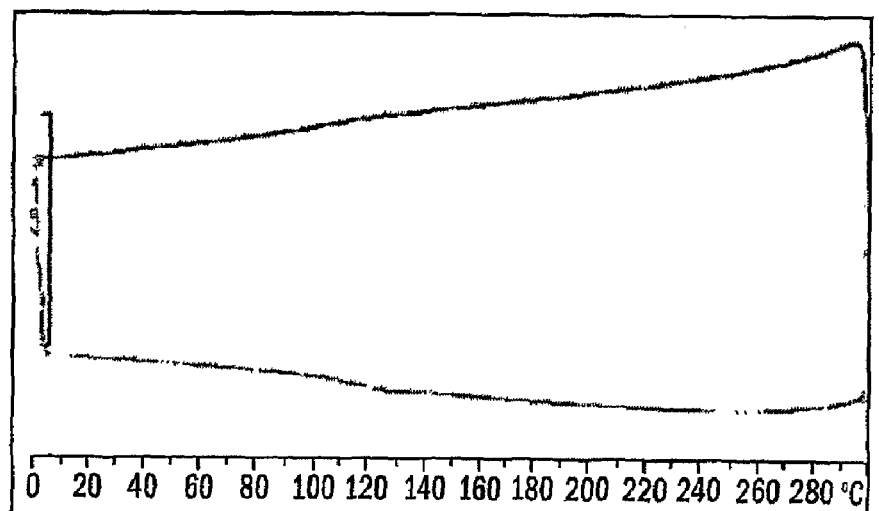
FIG. 29B illustrates the DSC of HATNA_[Ox(PhOC$_8$H$_{17}$)$_3$]$_3$, BK2__83D; the second cycle of heating and cooling.
Figure 30:
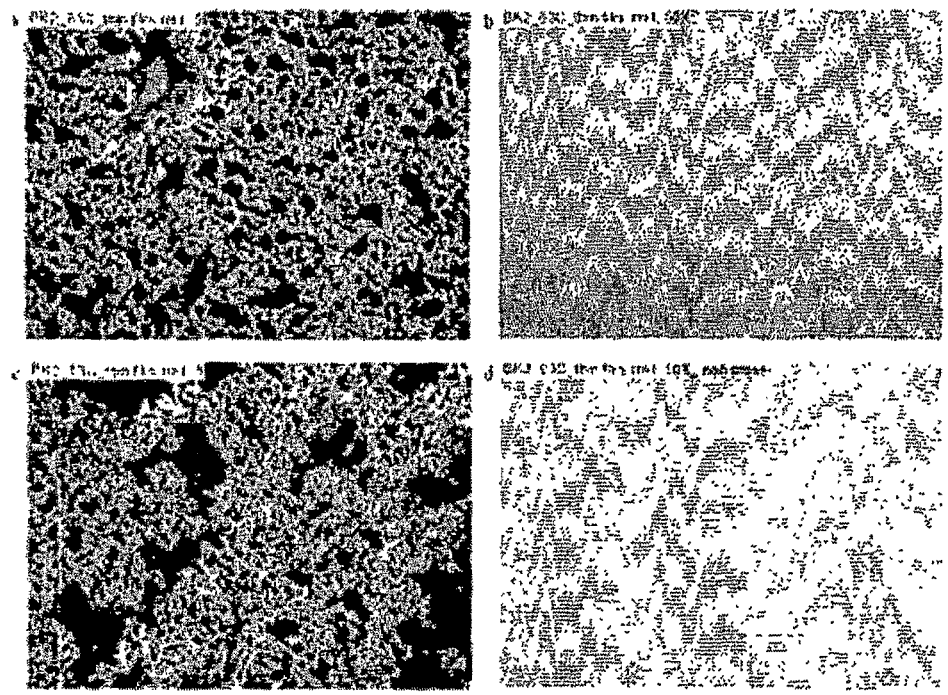
FIG. 30 illustrates the textures of BK2__83C; (a) & (c) between cross-polarizers; (b) and (d) between non-cross-polarizers.
Figure 31:
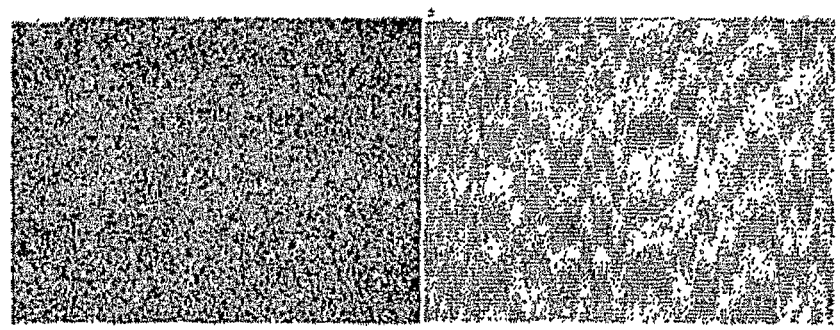
FIG. 31 illustrates the textures of BK1__91D; (a) between cross-polarizers; (b) between non-cross-polarizers.

Organic electron-transport materials based on 1,3,4-oxadiazoles,[9] having mobilities as high as ca. $10^{-3}$ cm$^2$V$^{-1}$s$^{-1}$, have been reported.[27] Furthermore, 1,3,4-oxadiazoles have been proven to be effective as electron-transport agents in organic light-emitting diodes.[28] A series of columnar discotic liquid-crystalline (LC) oxadiazoles with benzene core were synthesized and their mobility was studied for potential applications in electron-transport materials.[29] Since HATNA core is larger in size than the benzene core, the oxadiazole-based HATNA is anticipated to show higher mobility. Oxadiazole-based HATNA's are synthesized according to Scheme 5. Upon refluxing the hydrazide in POCl$_3$, excess POCl$_3$ was distilled off till ca. 20 ml remained. The reaction mixture is then slowly added to a large volume of ice-water. This step results in the formation of a solid, which can be filtered off. The first purification step involves dissolving the solid in minimum amount of CH$_2$Cl$_2$ (or CHCl$_3$) and subsequent precipitation in methanol. This step is followed by flashing the compound over a bed of silica using hexanes as an eluent (these compounds do not run on TLC using solvents of wide range of polarity). Evaporating the solvent results in a black sticky solid that can be reprecipitated into methanol, resulting in brown powder suspended in the solution. This process is reproducible and reversible. It was observed that recrystallizing these compounds from toluene/ethanol results in dark reddish solid. The UV-vis absorption data of BK1_47, BK2_83, and BK2_91 are shown in FIG. 26. These compounds have two distinctive absorption bands at 302 and 437 nm. The difference in molar extinction coefficient of BK1_47 from BK2_83 and BK2_91 might be due to inaccuracy of the concentration of BK1_47 solution. However, preliminary polarized optical microscope investigation of BK1_47D showed discotic columnar-like texture, FIG. 23. The sample was melted and was then cooled down to room temperature. Textures of BK2-83 and BK2_91 are shown in FIGS. 30 and 31, respectively.

Scheme 5. Synthetic Scheme of HATNA_[OxPh(OC$_8$H$_{17}$)$_3$]$_3$, BK2_83, HATNA_[OxPh(OC$_{12}$H$_{25}$)$_3$]$_3$, BK2_91, and HATNA_[OxPh(OC$_{12}$H$_{25}$)$_3$]$_3$, BK1_47.

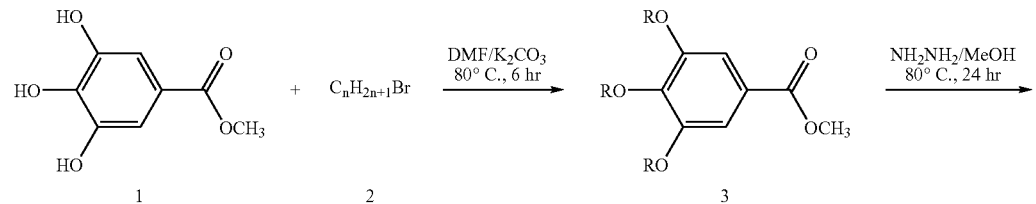

-continued
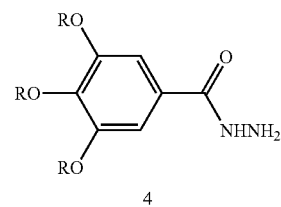
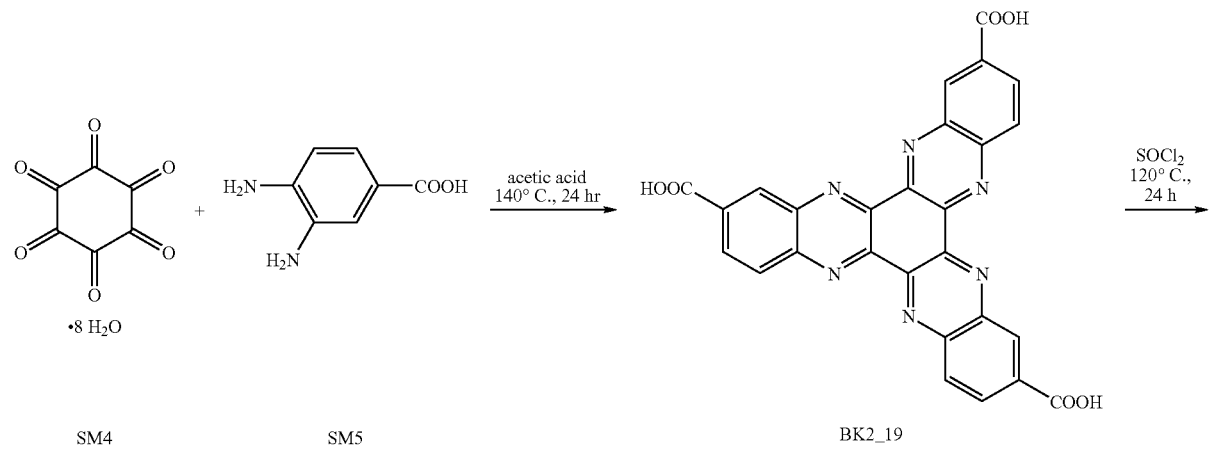
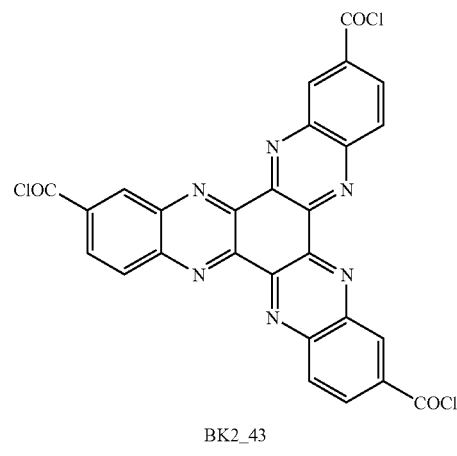
4 + BK2_43 $\xrightarrow{\text{THF/Pyr} \atop {0° \text{C.}, 3 \text{ h} \atop \text{r.t. 8 h}}}$
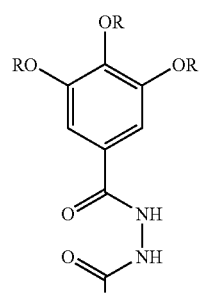

-continued

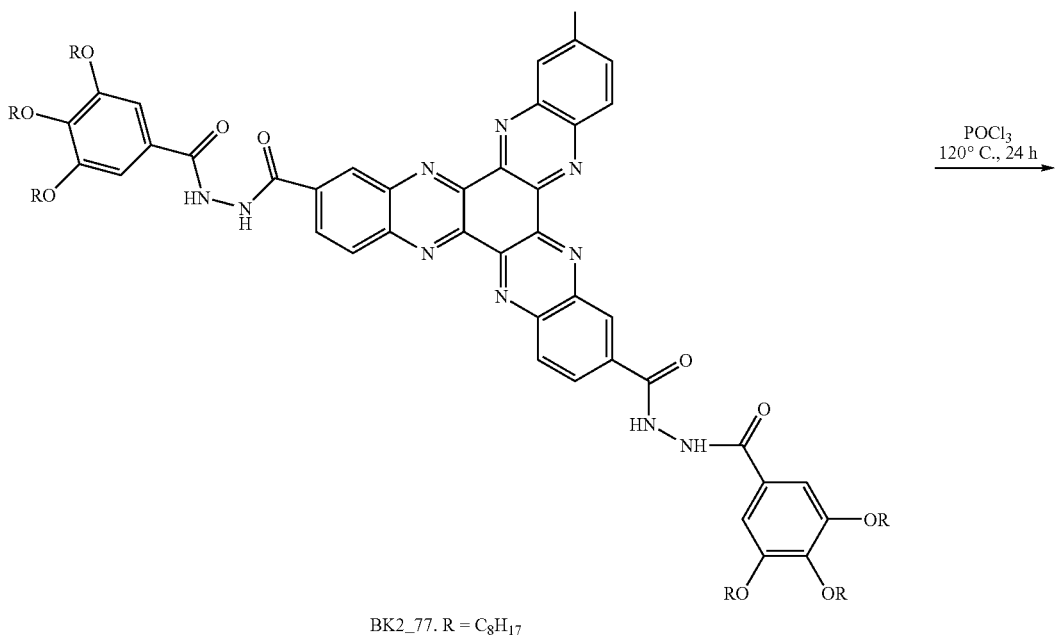

BK2_77. R = C$_8$H$_{17}$
BK2_87. R = C$_6$H$_{13}$
BK1_43. R = C$_{12}$H$_{25}$

POCl$_3$
120° C., 24 h

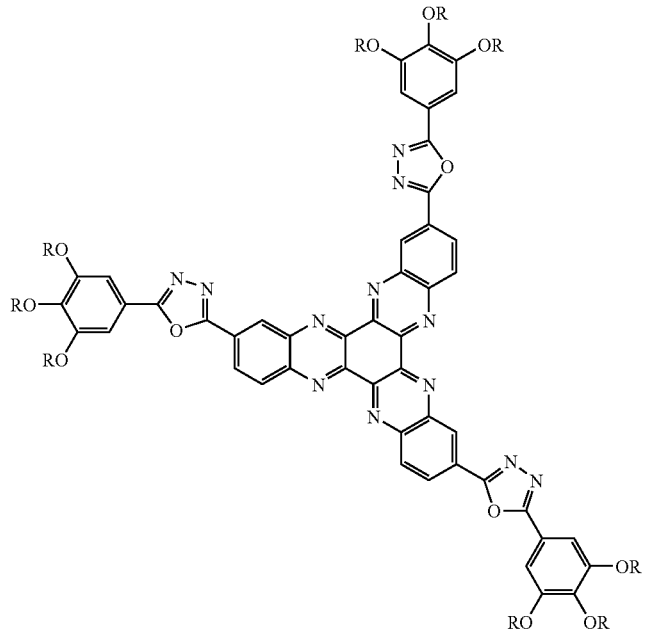

Figure 32:
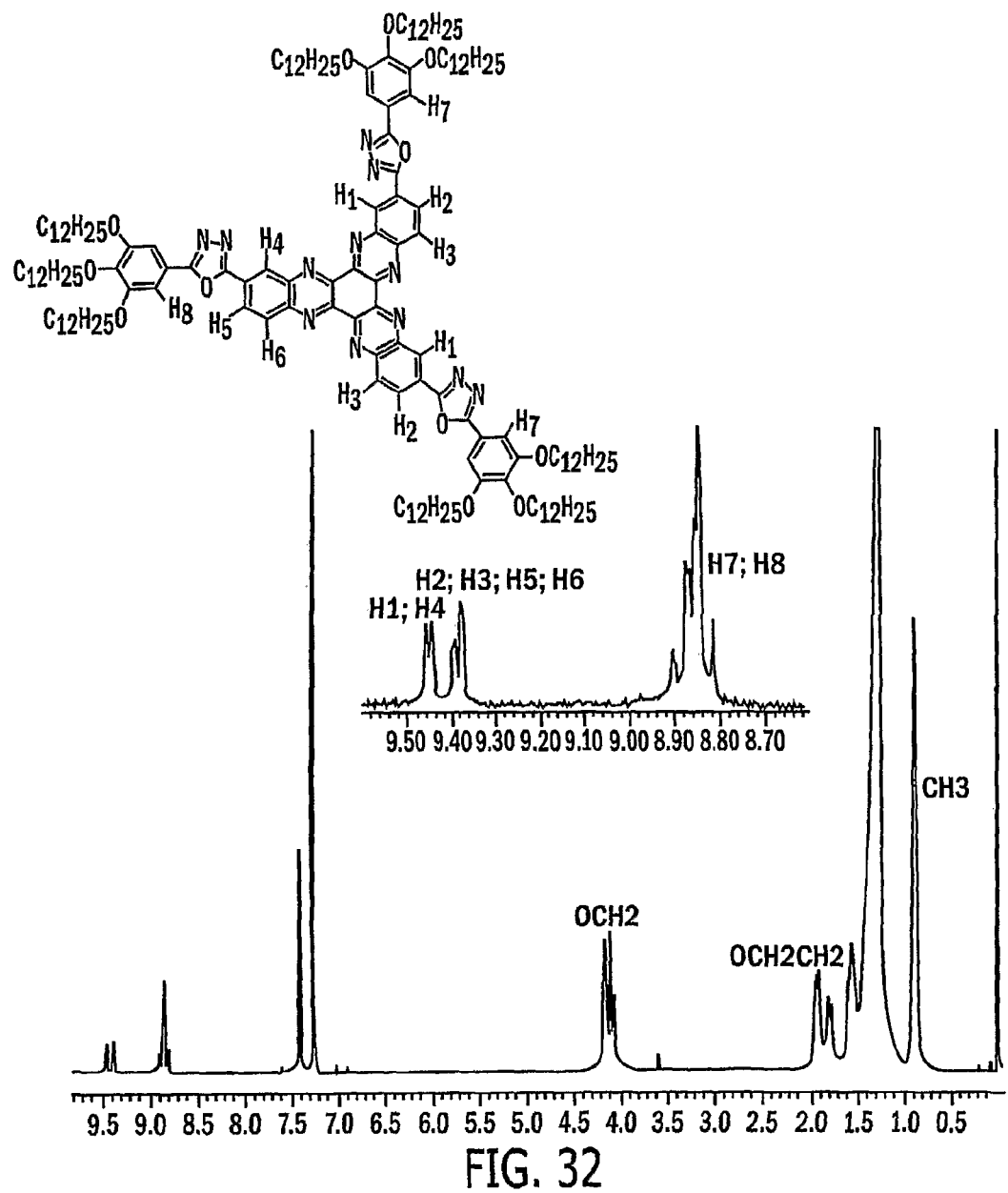
FIG. 32 illustrates the 300 $^1$H MHz of HATNA_[Ox(PhOC$_{12}$H$_{25}$)$_3$]$_3$, BK1__47D.
Figure 33:
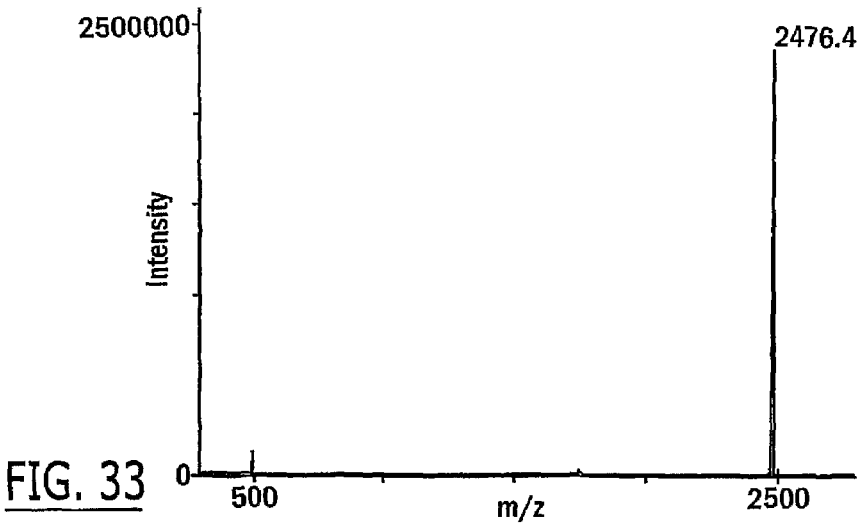
FIG. 33 illustrates the MALDI-TOF of HATNA_[Ox(PhOC$_{12}$H$_{25}$)$_3$]$_3$, BK1__47D.

BK2_83. R = C$_8$H$_{17}$
BK2_99. R = C$_6$H$_{13}$
BK1_45. R = C$_{12}$H$_{25}$ $^1$H NMR (CDCl$_3$, 300 MHz) of BK1_47D shows the distinctive aromatic peaks as well as those of the elongated chains, FIG. 32. MALDI-TOF MS measurement indicated the presence of BK1_47D as the only large MW (2476) compound, FIG. 33. The MALDI showed that the compound is relatively pure.

Figure 34:
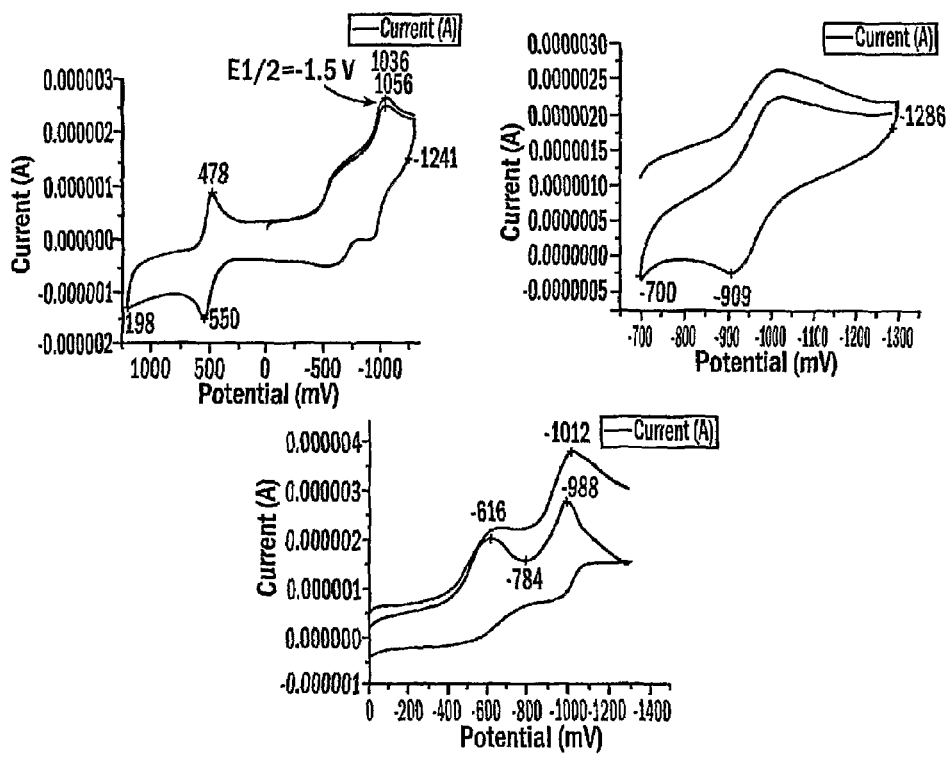
FIG. 34 illustrates the cyclic DC and AC (OSWV) voltammograms of BK1__21H in dichloromethane with 0.1 M $^n$BuN$^+$PF$_6^-$ (relative to ferrocenium/ferrocene).

Cyclic voltammetry studies of BK1_21H (BK1_47D) in CH$_2$Cl$_2$/0.1 M $^n$BuN$^+$PF$_6^-$ showed reversible reduction with $E_{1/2}$=−1.5 V and a nonreversible reduction with $E_{1/2}$=−1.1 V (vs Ferrocene in CH$_2$Cl$_2$), FIG. 34.

Figure 35:
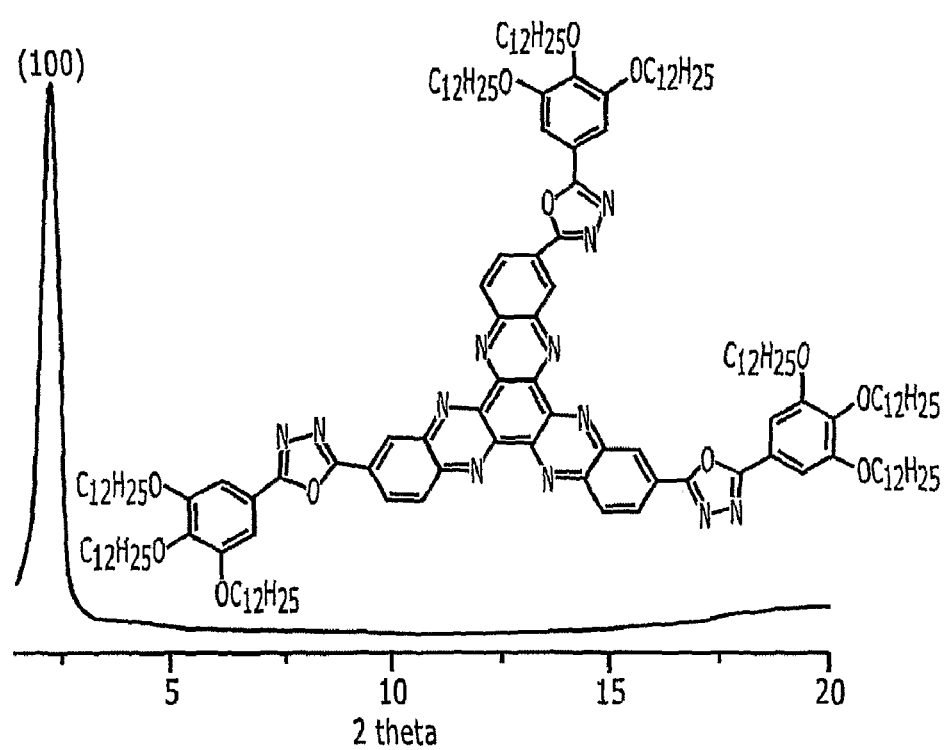
FIG. 35 illustrates the powder XRD pattern for BK3__27B assumed to be in the Col$_{hd}$ phase at room temperature.

The HATNA molecules with oxadiazole side-chains were heated to 250° C. and cooled to room temperature before recording the PXRD patterns. All showed only one low-angle reflection; this was assigned to the (100) reflection of a COl$_{hd}$ phase by analogy with compounds based on the same core for which only one reflection was observed.[23] The PXRD pattern for the dodecyloxy-substituted material (BK3-27B) is shown in FIG. 35 and the data obtained for all the liquid-crystalline materials is collated in Table 5.

TABLE 5

PXRD data for (assumed) $Col_{hd}$ phases of oxadiazole-HATNAs at room temperature.

| Compound | $a_o$ (assuming $Col_{hd}$)/ | wide-angle halos/ |
|---|---|---|
| BK2__91F1 (R = hexyl) | 40.6 | 4.3 |
| BK2__83D (R = octyl) | 41.8 | 3.4, 4.4 |
| BK3__27B (R = dodecyl) | 48.6 | 3.5, 4.4 |
| BK2__9F (oxadiazole-phenyl-oxadiazole-dodecyl) | 56.1 | 3.4, 4.5 |

The unit cell parameter increases with increasing substituent size, as might be expected. The values for $a_0$ are larger than observed for $Col_{hd}$ phases of phenazine complexes in the literature,[23] consistent with a bigger molecule due to the oxadiazole spacer; the wide-angle halos are similar, however, presumably reflecting comparable intrachain π-stacking distances, although with no significant long-range order.

MALDI-TOF measurement of BK1__31 showed its MW (2908), FIG. 36. However, the $^1$H NMR showed broad peaks; this may be attributed to aggregation of the compound in solution.

HATNA Based Esters

A series of esters having the HATNA core, Scheme 6, have been synthesized. A wide range of R groups have been selected to examine the substitution effect on their mobility and mesophase behavior.

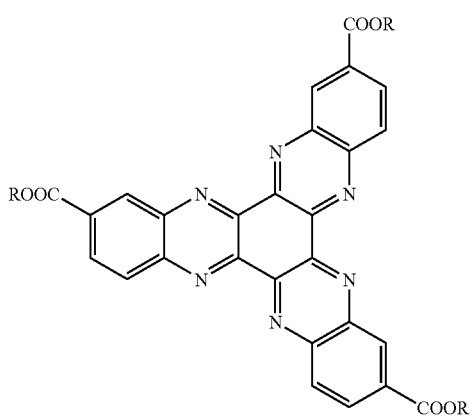

Scheme 6. HATNA esters.

DD1_39. R = $C_2H_5$
DD1_43. R = $C_{12}H_{25}$
DD1_45. R = $CH_2CF_2CF_2CF_3$

DD1_49. R =

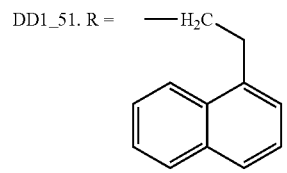

DD1_51. R =

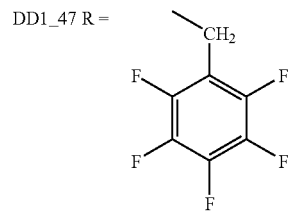

DD1_47 R =

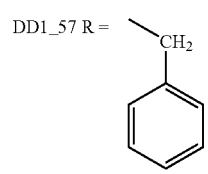

DD1_57 R =

Perfluorophenyl-phenyl interactions have been discussed and upon mixing DD1__47 and DD1__57 their stacking interactions are anticipated, between the pentafluorophenyl arms of DD1__47 and the phenyl arms of DD1__57. Such stacking would tend to align the cores of the two compounds. Accordingly, stacking of DD1__47 and DD1__57 can be studied by mixing different molar ratios of these two compounds and can determined by DSC and $^1$H NMR measurements. The mobility along the aromatic core can be affected if such stacking occurs.

Bock et al.[30] reported that that three fold condensation of SM4 and SM5 lead exclusively to the isomer 3,4,15- rather than the 3,4,14-isomer or the statistical isomer mixture (3:1; 3,4,15-isomer:3,4,14-isomer), Scheme 7. The authors made this conclusion based on the 2:1 ratio of the aromatic peaks, which is consistent with the 3,4,15-isomer.

Figure 37:
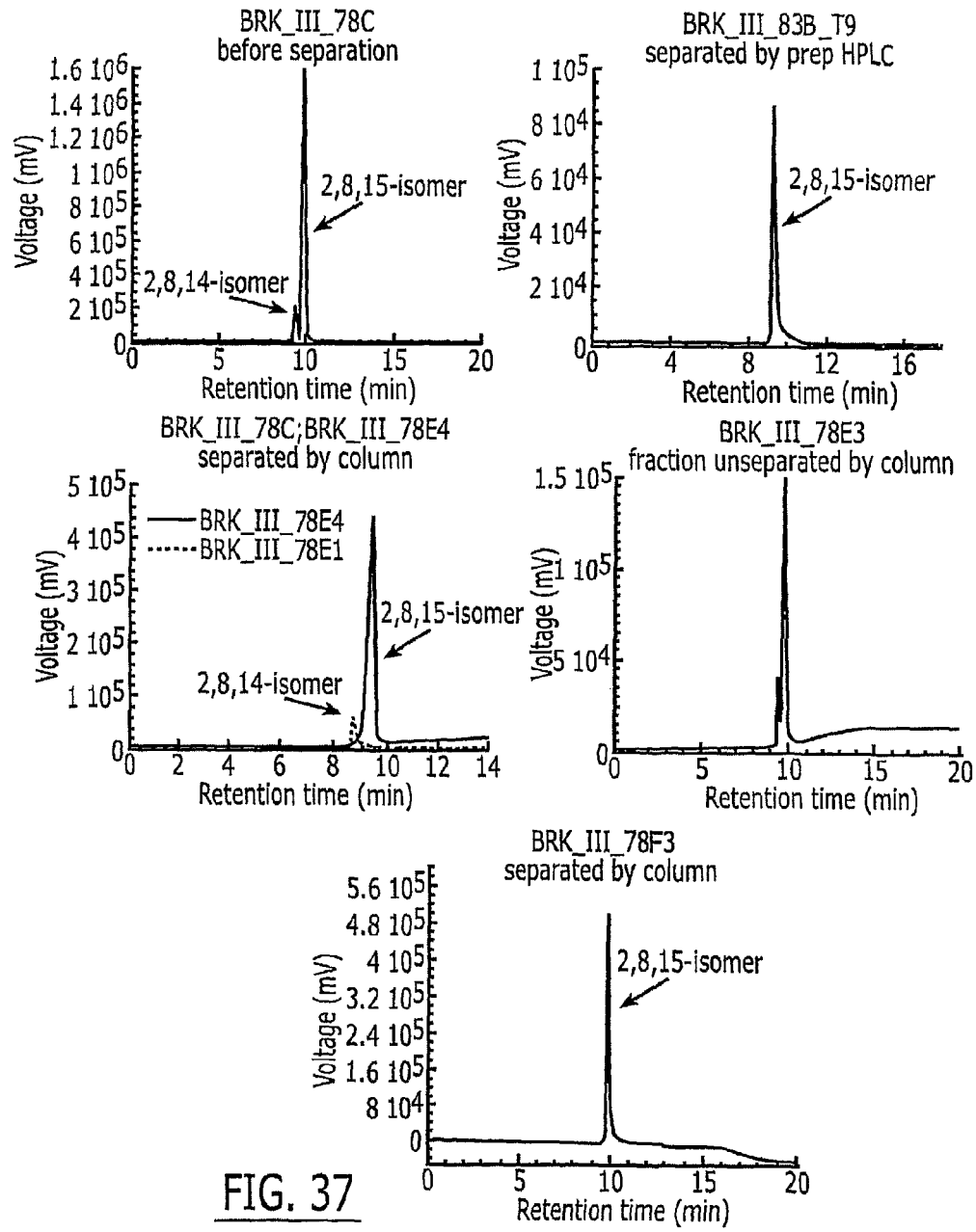
FIG. 37 illustrates the HPLC traces of HATNA_[CO$_2$CH$_2$PhF$_5$]$_3$, BRK_III__78C, BRK_III__83B_T9, BRK_III__78E1, BRK_III__78E4, BRK_III__78E3, and BRK_III__78F2.
Figure 37A:
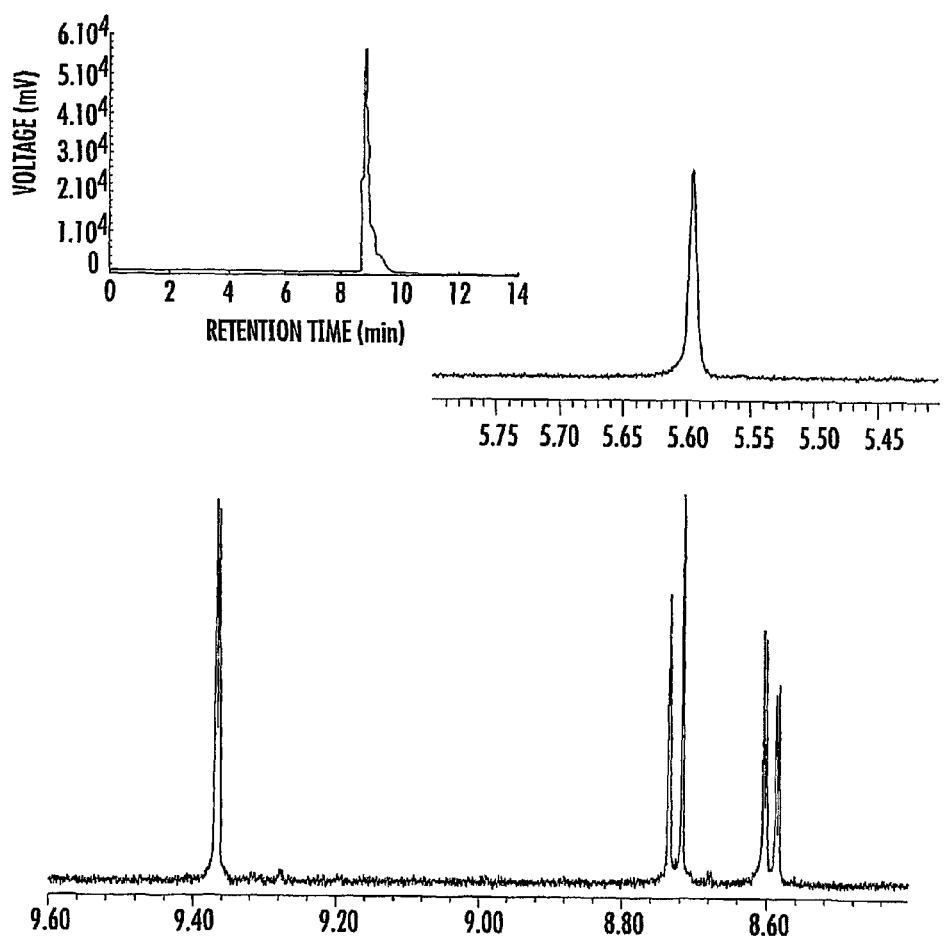
FIG. 37A illustrates the $^1$H 500 MHz NMR of BRK_III__78E1 in CDCl$_3$. The inset is the corresponding analytical HPLC traces analysis.
Figure 37B:
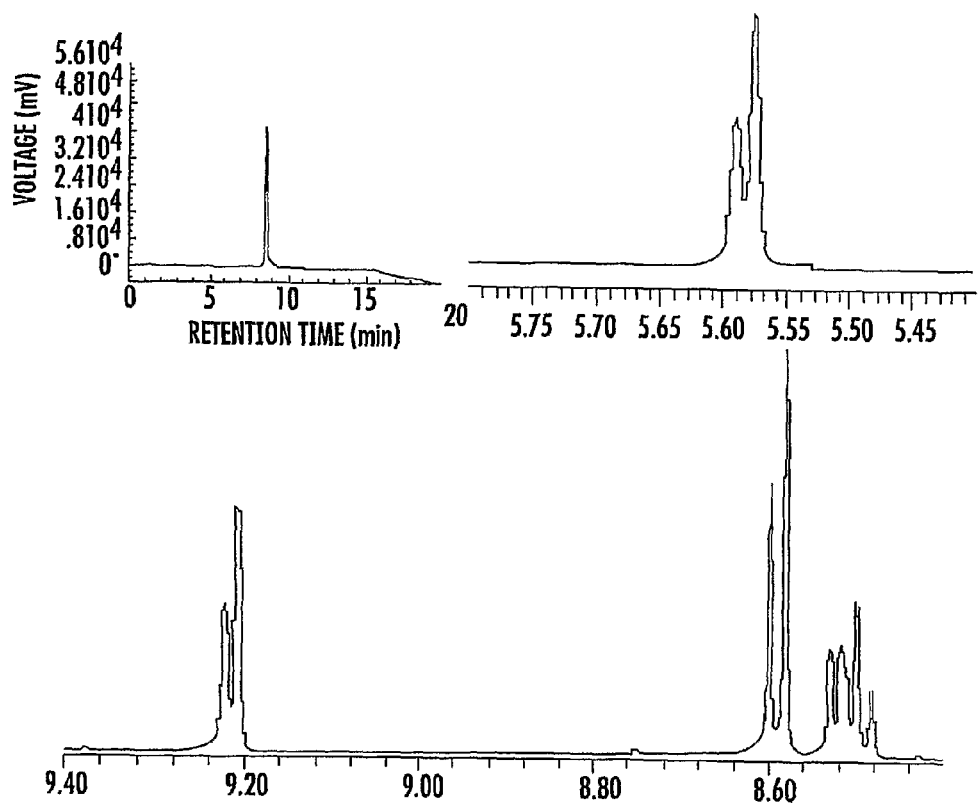
FIG. 37B illustrates the $^1$H 500 MHz NMR of BRK_III__78F2 in CDCl$_3$. The inset is the corresponding analytical HPLC traces analysis.
Figure 37C:
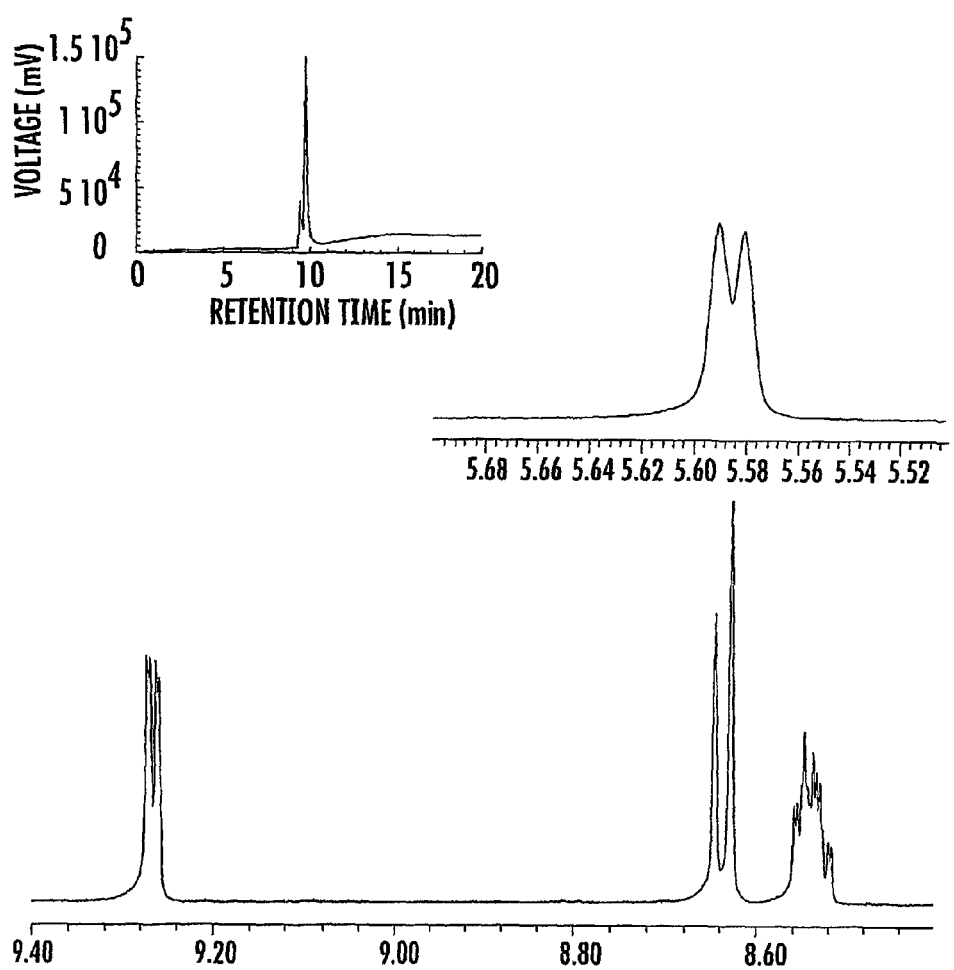
FIG. 37C illustrates the $^1$H 500 MHz NMR of BRK_III__78E3 in CDCl$_3$. The inset is the corresponding analytical HPLC traces analysis.
Figure 37D:
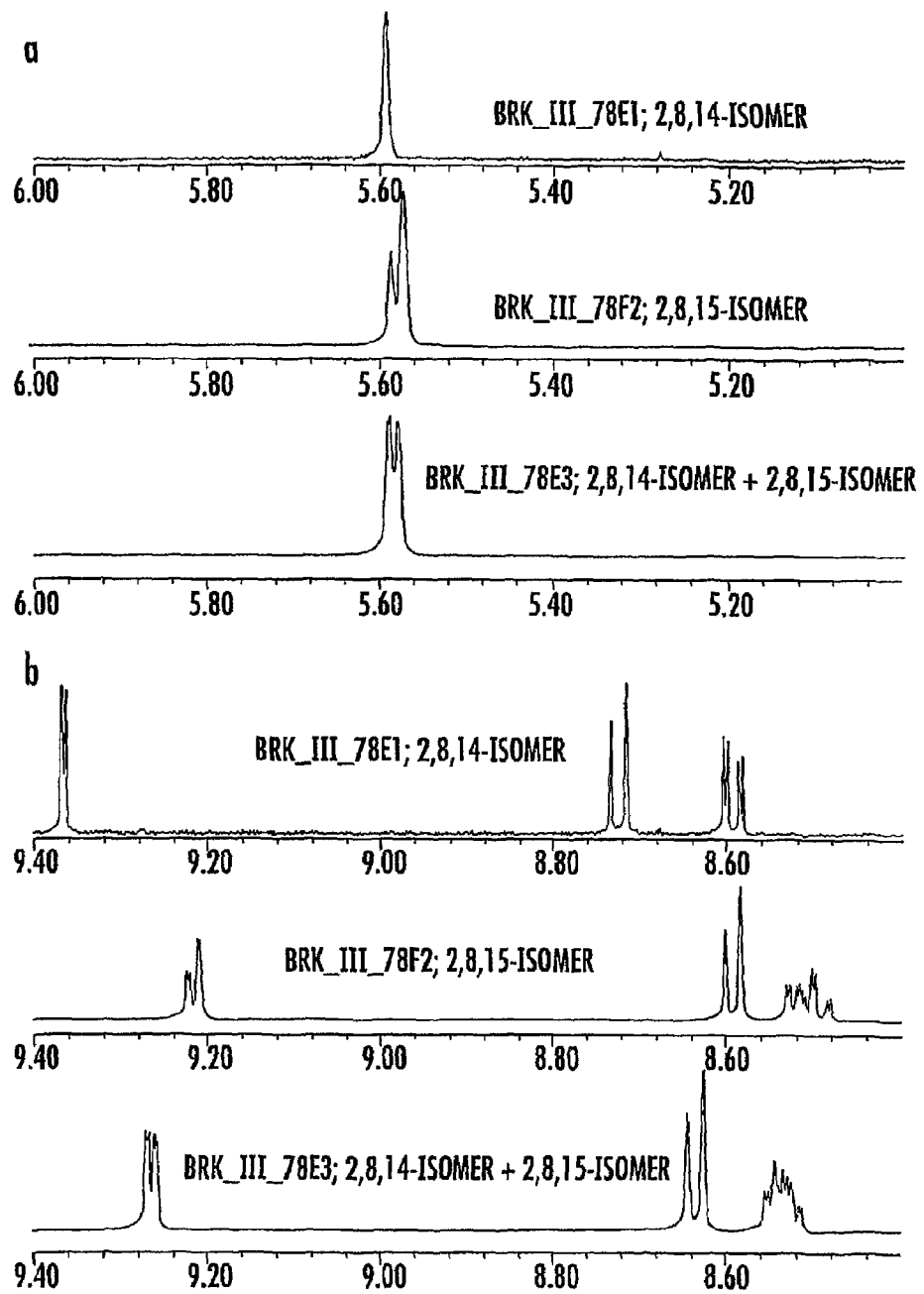
FIG. 37D illustrates the $^1$H 500 MHz NMR of BRK_III__78F2, BRK_III__78F2, and BRK_III__78F2 in CDCl$_3$; (a) aliphatic region; (b) aromatic region.
Figure 37E:
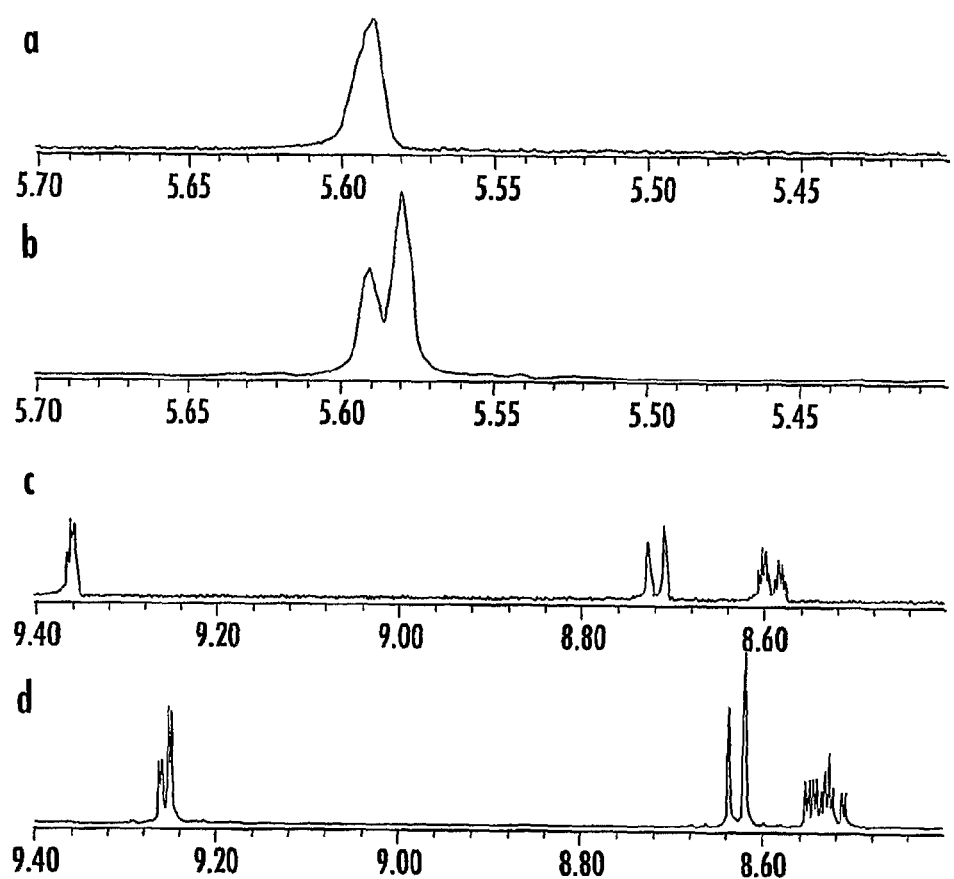
FIG. 37E illustrates the $^1$H NMR (CDCl$_3$, 500 MHz) of concentrated (24.03 mg/0.8 ml) and dilute (3.93 mg/0.8 ml) solutions of BRK_III__78E4-2,8,15 isomer ((a) and (c) $^1$H NMR of concentrated solution of aliphatic and aromatic regions, respectively; and (b) and (d) $^1$H NMR of dilute solution of aliphatic and aromatic regions, respectively.
Figure 37F:
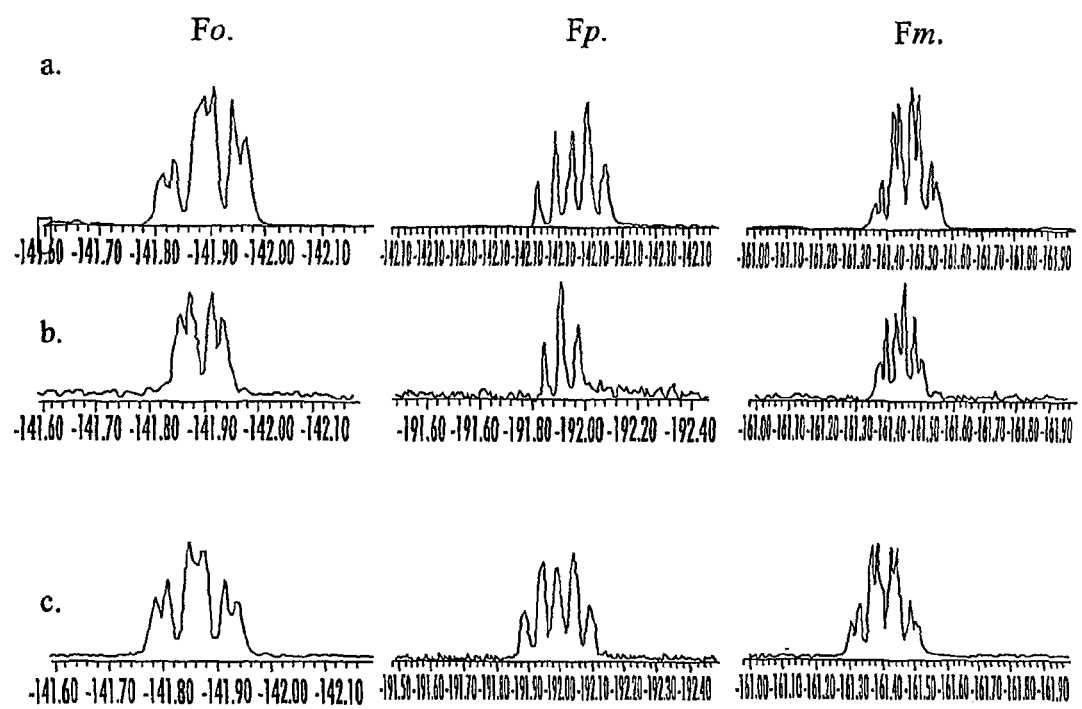
FIG. 37F illustrates the $^{19}$F (CDCl$_3$, 376 MHz) of the isomers of HATNA_[CO$_2$CH$_2$PhF$_5$]$_3$. (a) 2,8,15-isomer, BRK_III__78F2; (b) 2,8,14-isomer, BRK_III__78E1; (c) mixture of isomers, BRK_III__78E3. F$_o$:F$_m$:F$_p$=2:2:1 for all three spectra. The chemical shifts are relative to trifluoromethylbenzene, which was used as an external standard.

The results reported here, however, suggest that condensation of SM4 and SM5 lead to a mixture of approximate 3:1 ratio of 3,4,15-isomer:3,4,14-isomer. HPLC traces of HATNA_$[Z_1]_3$ compounds, Scheme 7, showed two peaks of approximate relative area 3:1, which may be attributed to the statistical isomer mixture-cyano normal phase column was used for both analytical and preparative HPLC; HPLC grade $CH_2Cl_2$ and hexanes were used; the initial % flow of $CH_2Cl_2$ was 20% till 2 min; at 15 min the % flow of $CH_2Cl_2$ was 100%. Both peaks have identical UV-vis spectra. The 2,8,15-isomer of HATNA-$[Z_1]_3$ has been isolated by preparative HPLC. It was discovered that the 2,8,14 and 2,8,15 isomers of HATNA_$CO_2CH_2PhF_5]_3$ could be separated by column chromatography using $CH_2Cl_2$:ethyl acetate (9:1) as eluent. FIG. 37 shows the HPLC traces of HATNA_$[CO_2CH_2PhF_5]_3$ before separation, BRK_III__78C, the 2,8,15-isomer separated by HPLC, BRK_III__83B_T9, and the two isomers separated by column chromatography, BRK_III__78E1 and BRK_III__78E4. BRK_III__78E3 is the fraction where the two isomers eluted together. BRK_III_78E4 was then run through a column using $CH_2Cl_2$: ethyl acetate (9:1) as eluent and was dissolved in small amount of $CHCl_3$ and was reprecipitated in ethanol, BRK_III_78F2. The $^1$H NMR (500 MHz, $CDCl_3$) of BRK_III_78E1, BRK_III_78F2, and BRK_III_78E3 along with their corresponding analytical HPLC traces are shown in FIGS. 37A, 37B, and 37C, respectively. Comparison of the $^1$H NMR (500 MHz, $CDCl_3$) of BRK_III_78E1, BRK_III_78F2, and BRK_III_78E3 is shown in FIG. 37D. The methylene group in the symmetrical 2,8,14-isomer BRK_III_78E1, FIG. 37Da, is a singlet. In the unsymmetrical 2,8,15-isomer BRK_III_78F2, FIG. 37Da, the three methylene groups appear as two singlets of approximate ratio 2:1. In the mixture of isomers BRK_III_78E3, FIG. 37Da, the three methylene groups overlap. Whilst the methylene groups have the same chemical shift in the mixture as that in the pure isomer, the aromatic region appears at a different chemical shift. This may be attributed to intermolecular interactions between the two isomers in the mixture BRK_III_78E3. $^1$H NMR (500 MHz, $CDCl_3$) of different concentrations (24.03 mg and 3.93 mg in 0.8 ml of $CDCl_3$) of BRK_III_78E4, FIG. 37E, shows possible intermolecular interactions in this compound. The $^{13}$C NMR (125 MHz, $CDCl_3$) of BRK_III_78F2—2,8,15-isomer—shows only one methylene peak at 54.68 ppm whilst that of BRK_III_78E3—mixture of isomers—shows two methylene peaks at 58.69 and 58.45 ppm ($^{13}$C NMR were not acquired on BRK_III_78E1—2,8,14-isomer—solution was dilute). $^{19}$F NMR ($CDCl_3$, 376 MHz) of BRK_III_78F2, BRK_III_78E1, and BRK_III_78E3 are shown in FIG. 37F. In the 2,8,14-isomer, BRK_III_78E1, the $F_p$'s appear as triplets because they are coupled to two $F_m$, whilst $F_o$ appear as doublet of doublets. In the 2,8,15-isomer, BRK_III_78F2, the $F_p$ appear as two overlapped triplets of approximate ratio 2:1 corresponding to two different set of fluorinated aromatic rings. The NMR data is consistent with the assignment of the HPLC traces to the corresponding isomer, i.e. the more dominant compound is the unsymmetrical 2,8,15-isomer.

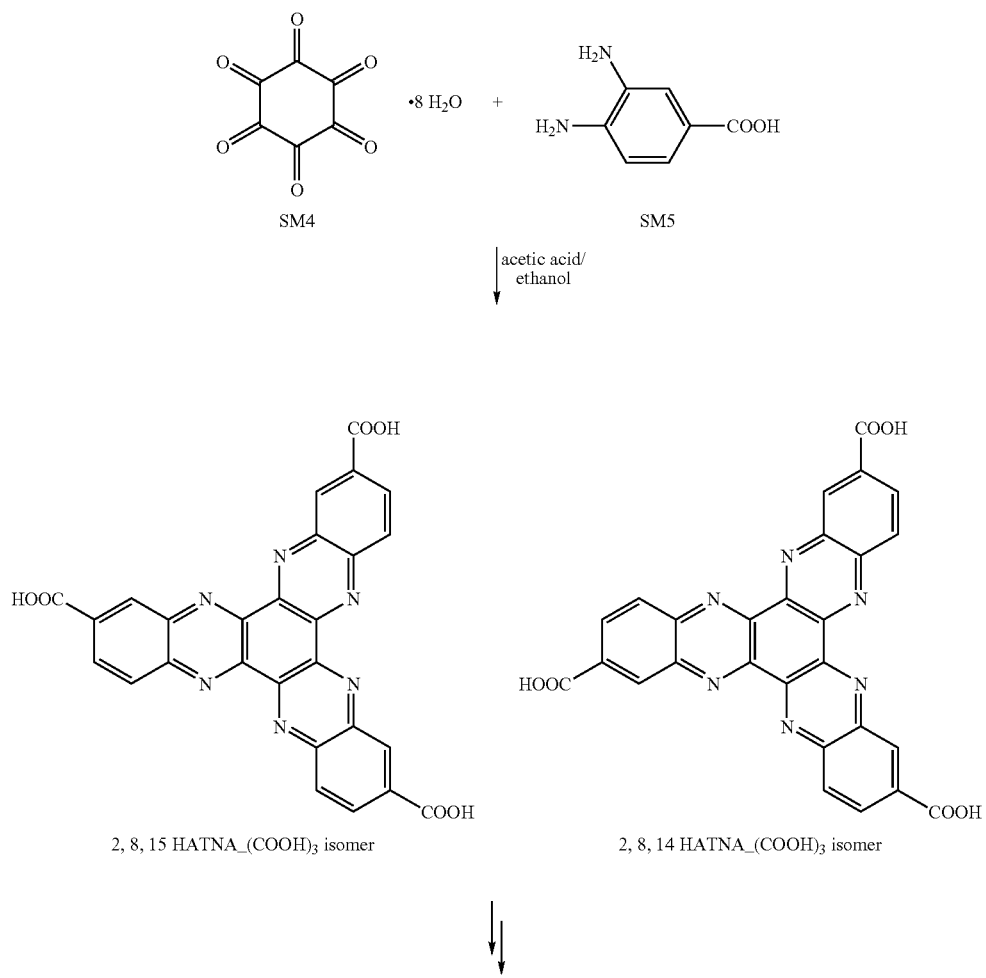

Scheme 7. Isomers of HATNA_[Z]$_3$ upon condensation of SM4 and SM5.

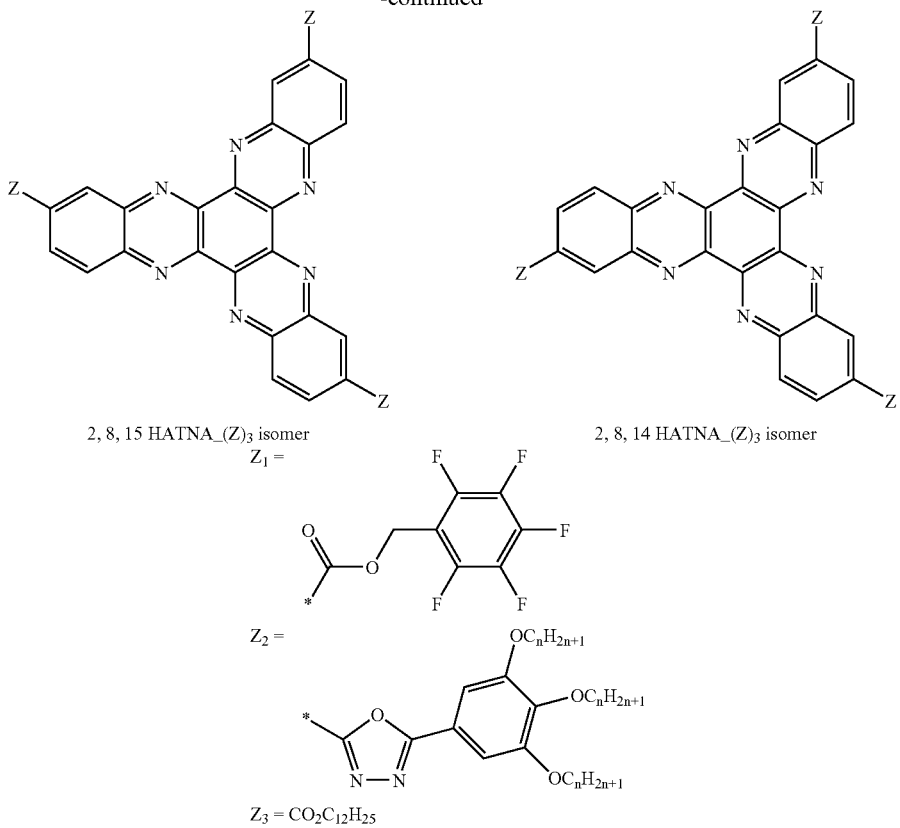

2, 8, 15 HATNA_(Z)₃ isomer 2, 8, 14 HATNA_(Z)₃ isomer $Z_1 =$ $Z_2 =$ $Z_3 = CO_2C_{12}H_{25}$ To isolate the pure isomers of oxadiazole substituted HAT-NA's, the synthesis of the appropriate ester HATNA_[CO₂R]₃ was proposed, where the two isomers can easily be separated by sublimation, recrystallization, or chromatography-HATNA_[CO₂CH₂PhF₅]₃ isomers were separated by column chromatography as shown above. A subsequent saponification can lead to the isomer pure HATNA-[COOH]₃ which can be used to get to isomer pure HATNA-[Z]₃.

Figure 38:
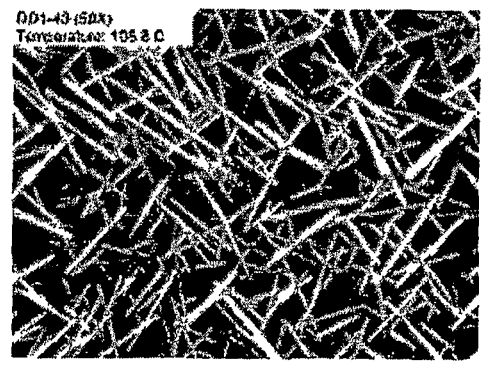
FIG. 38 illustrates the POM micrograph of DD1__43 at t=108.8° C. upon heating.

MALDI-TOF measurements confirmed the presence of all HATNA esters (DD1__39, DD1__41, DD1__43, DD1__45, DD1__47, DD1__49, DD1__51, and DD1__57). Differential scanning calorimetry (DSC) measurements showed for the ester DD1__43 two phase transitions at 35 and 98° C. Polarized optical microscope (POM) investigation suggests that this compound is polycrystalline (FIG. 38).

Figure 39:
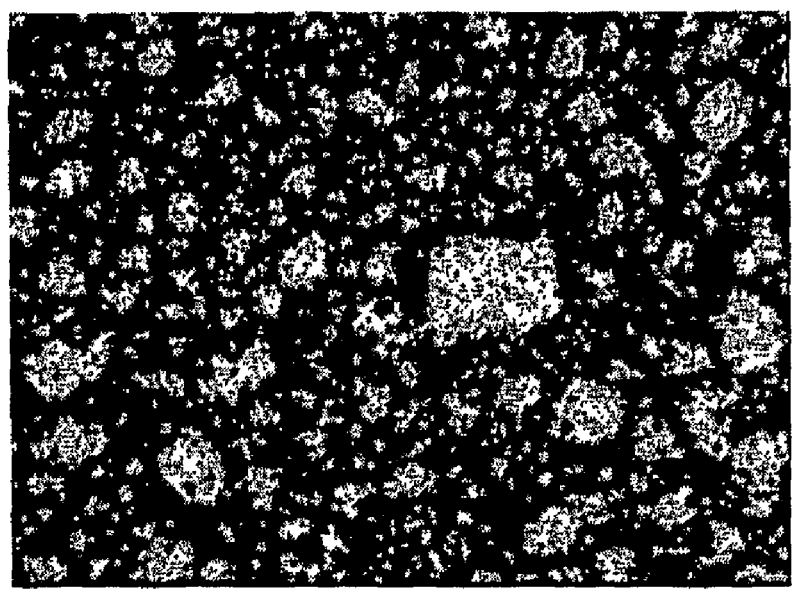
FIG. 39 illustrates the POM micrograph of DD1__45 ester at t=62° C. upon cooling.

The DD1__45 thermogram showed (in the second heating) two transitions at 220 and 265° C.; this ester showed two different phase-transitions upon cooling. POM investigations confirmed that the 220° C. transition is a solid-liquid crystalline first order phase transition while the 265° C. transition is the liquid crystalline-isotropic phase transition (FIG. 39).

The DD1__47 thermogram showed a single transition at 240° C. and no phase-transition was observed upon cooling; this behaviour is characteristic of metastable glassy materials. The DD1__49 thermogram showed a single transition at 180° C. as well as upon cooling. The DD1__51 thermogram showed two phase-transitions at 110 and 180° C. and only one on cooling. POM studies on DD1__51 have not been performed yet. The thermal behaviour of the HATNA esters is summarized in Table 6.

TABLE 6

First order phase transitions according to DSC observation

| Ester | Middle phase-transition T/° C. | Melting point T/° C. |
|---|---|---|
| DD1__39[a] | 290, 325 | 340 |
| DD1__43 | 35 | 98 |
| DD1__45 | 220 | 265 |
| DD1__47 |  | 240 |
| DD1__49 |  | 180 |
| DD1__51 | 110 | 180 |
| DD1__57 |  | 280 |

[a]The DD1__39 thermal data are from the literature.[30]

Figure 40:
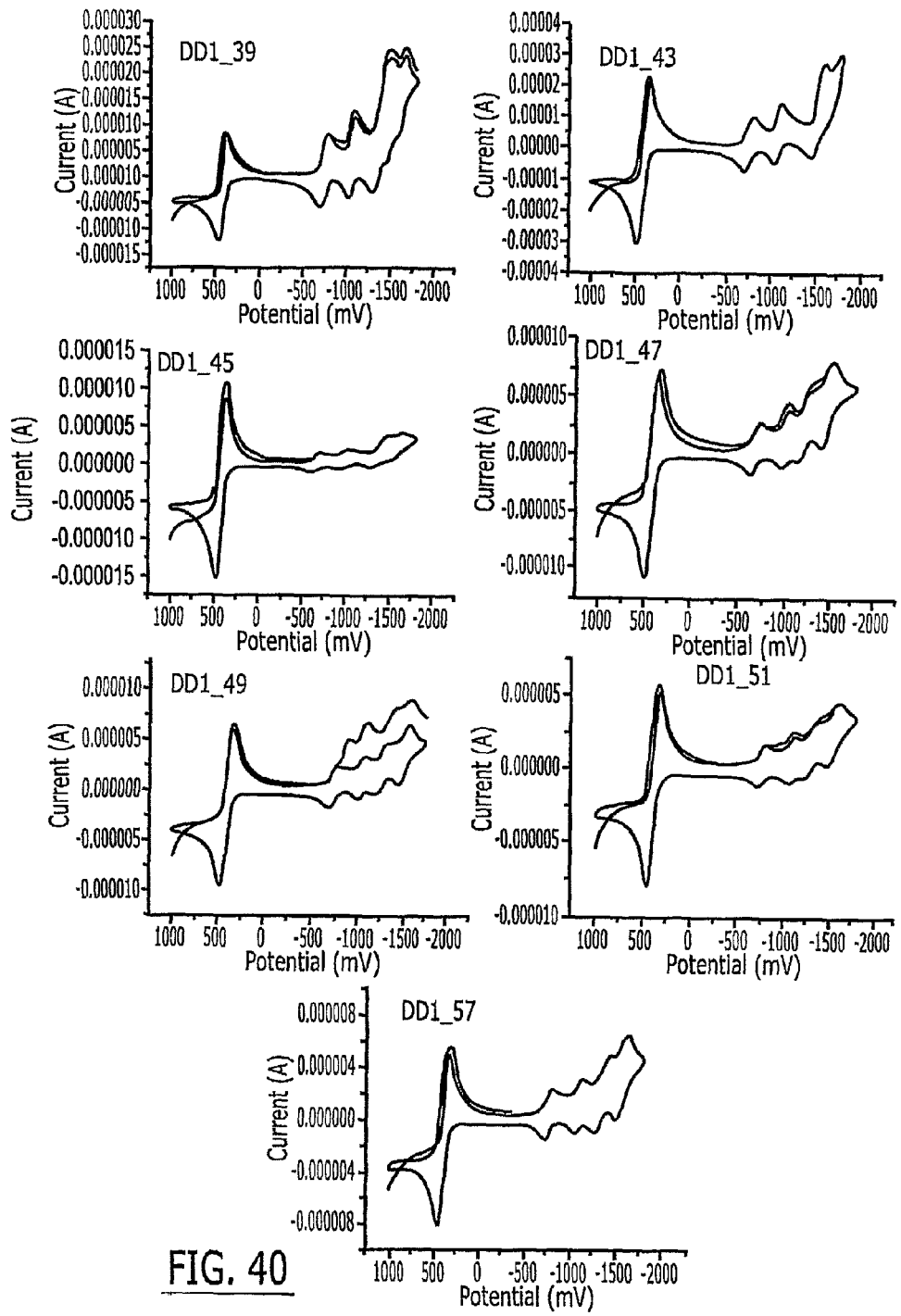
FIG. 40 illustrates the CV graphs of HATNA esters in CH$_2$Cl$_2$/0.1 M $^n$BuN$^+$PF$_6^-$ (relative to ferrocenium/ferrocene).

The electrochemistry studies showed two well-structured reversible reduction peaks at approximately −1.2 eV and −1.4 eV (relative to ferrocene). Two more reductions were observed (except for the DD 1__43 ester where we observed only one reduction). Detailed overview of the CV's graphs of the HATNP esters are presented in FIG. 40. The results are summarized in Table 7.

TABLE 7

Summary of CV data of HATNA esters.

| Compound | $E_1$(V) Δp (mV)[a] | $E_2$ Δp (mV)[a] | $E_3$ Δp (mV)[a] | $E_4$ Δp (mV)[a] |
|---|---|---|---|---|
| DD1__39 | −1.17 Δp = 106 | −1.48 Δp = 74 | −1.88 Δp = 228 | −1.98 Δp = 218 |
| DD1__43 | −1.17 Δp = 100 | −1.50 Δp = 80 | — | −1.95 Δp = 154 |

TABLE 7-continued

Summary of CV data of HATNA esters.

| Compound | $E_1(V)$<br>$\Delta p\ (mV)^a$ | $E_2$<br>$\Delta p\ (mV)^a$ | $E_3$<br>$\Delta p\ (mV)^a$ | $E_4$<br>$\Delta p\ (mV)^a$ |
|---|---|---|---|---|
| DD1_45 | −1.08 | −1.41 | −1.82 | −1.08 |
|  | $\Delta p = 76$ | $\Delta p = 58$ | $\Delta p = 157$ | $\Delta p = 76$ |
| DD1_47 | −1.05 | −1.45 | −1.66 | −1.05 |
|  | $\Delta p = 96$ | $\Delta p = 74$ | $\Delta p = 143$ | $\Delta p = 96$ |
| DD1_49 | −1.18 | −1.50 | −1.71 | −1.95 |
|  | $\Delta p = 104$ | $\Delta p = 74$ | $\Delta p = 134$ | $\Delta p = 72$ |
| DD1_51 | −1.17 | −1.49 | −1.71 | −1.94 |
|  | $\Delta p = 88$ | $\Delta p = 74$ | $\Delta p = 174$ | $\Delta p = 132$ |
| DD1_57 | −1.13 | −1.48 | −1.75 | −1.81 |
|  | $\Delta p = 88$ | $\Delta p = 66$ | $\Delta p = 150$ | $\Delta p = 133$ |

$^a\Delta p$ is the difference between the anodic and cathodic peaks for a given redox process.

Figure 41:
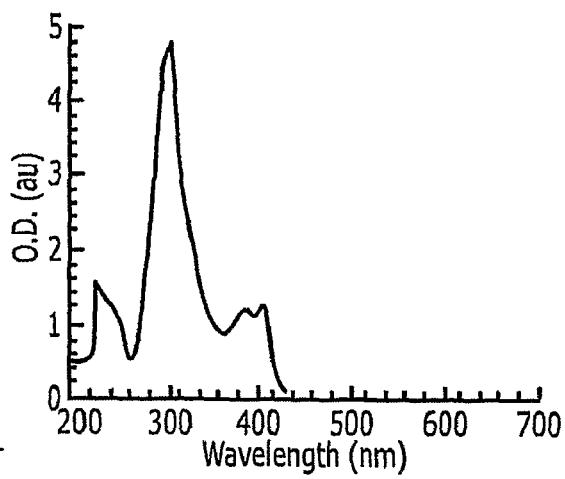
FIG. 41 illustrates the UV-vis spectrum of DD1__43 in CH$_2$Cl$_2$.

The UV spectra of HATNA esters were collected in dichloromethane. The shapes and the frequencies of the UV-vis spectra are the same for all the esters. The UV spectrum of DD1_43, FIG. 41, is a representative for all the esters.

Sonogashira[31] couplings of HATNA_Br$_6$, BK2_31 or more preferably with HATNA_I$_6$, with the appropriate acetylene should to lead to the corresponding HATNA_[CCU]$_6$, Scheme 8. Synthesis of HATNA_[CCU]$_6$ whilst U$_1$=Si(iPr)$_3$ and U$_2$=tBu could be accomplished with of HATNA_Br$_6$.

Scheme 8. Proposed synthetic Scheme of HATNA-[CCU]$_6$.

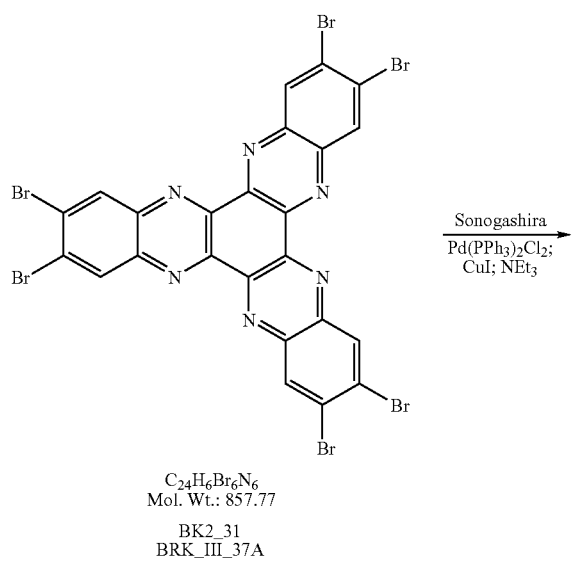

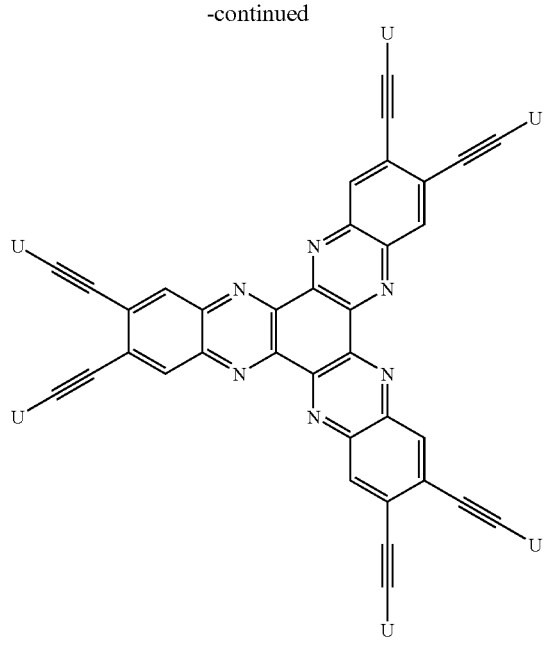

HATNA[CCU]$_6$ $U_1$ = Si(iPr)$_3$
$U_2$ = tBu
$U_3$ =

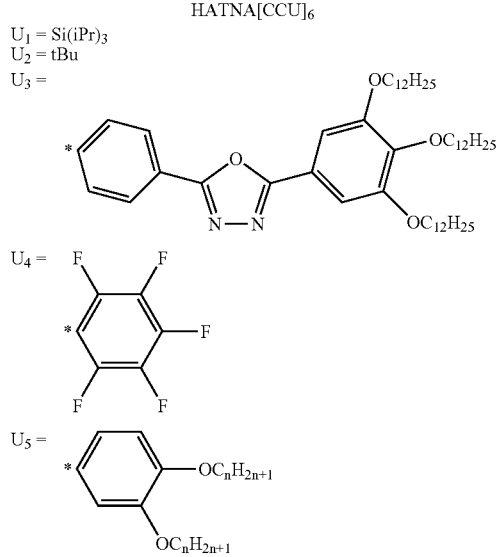

Figure 42:
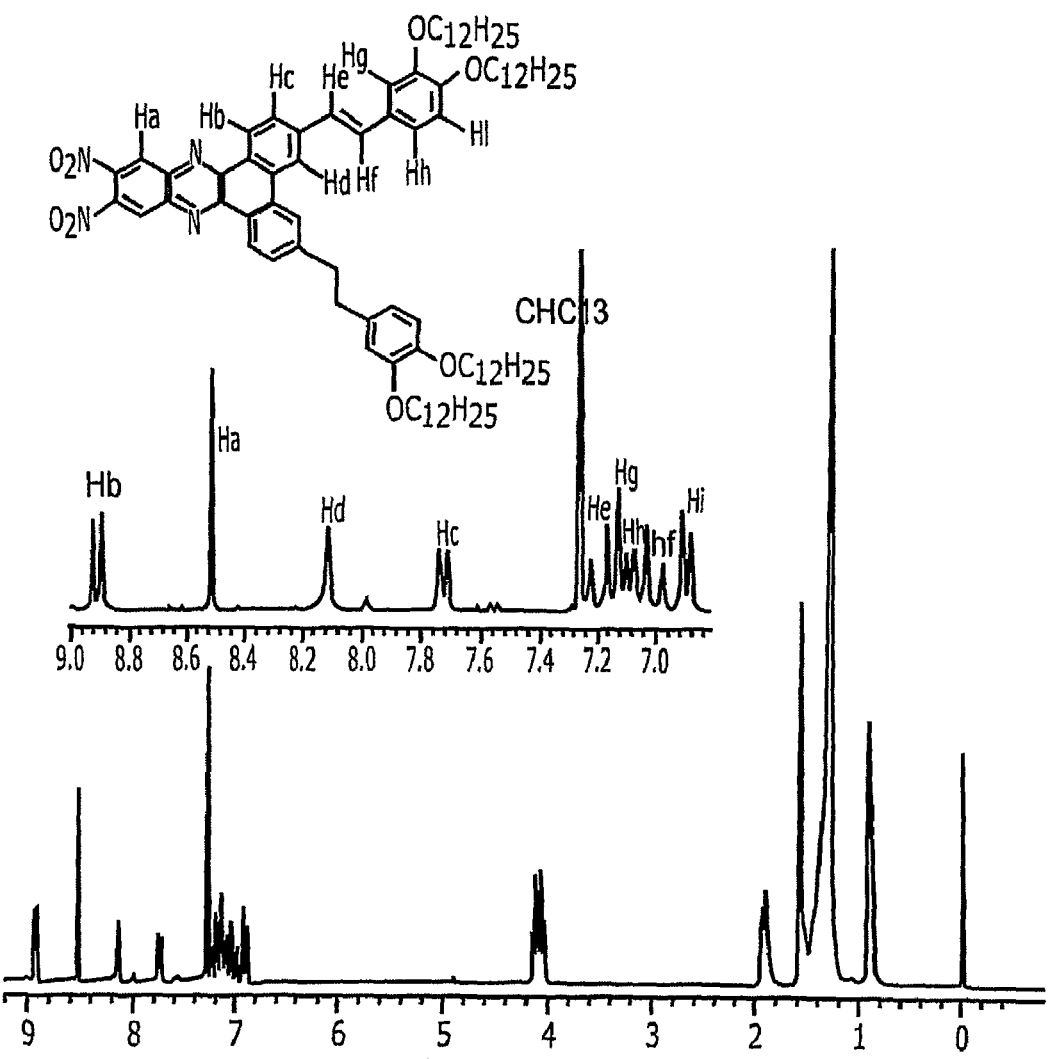
FIG. 42 illustrates the $^1$H NMR (300 MHz, CDCl$_3$) of BRK_III__63A.
Figure 43:
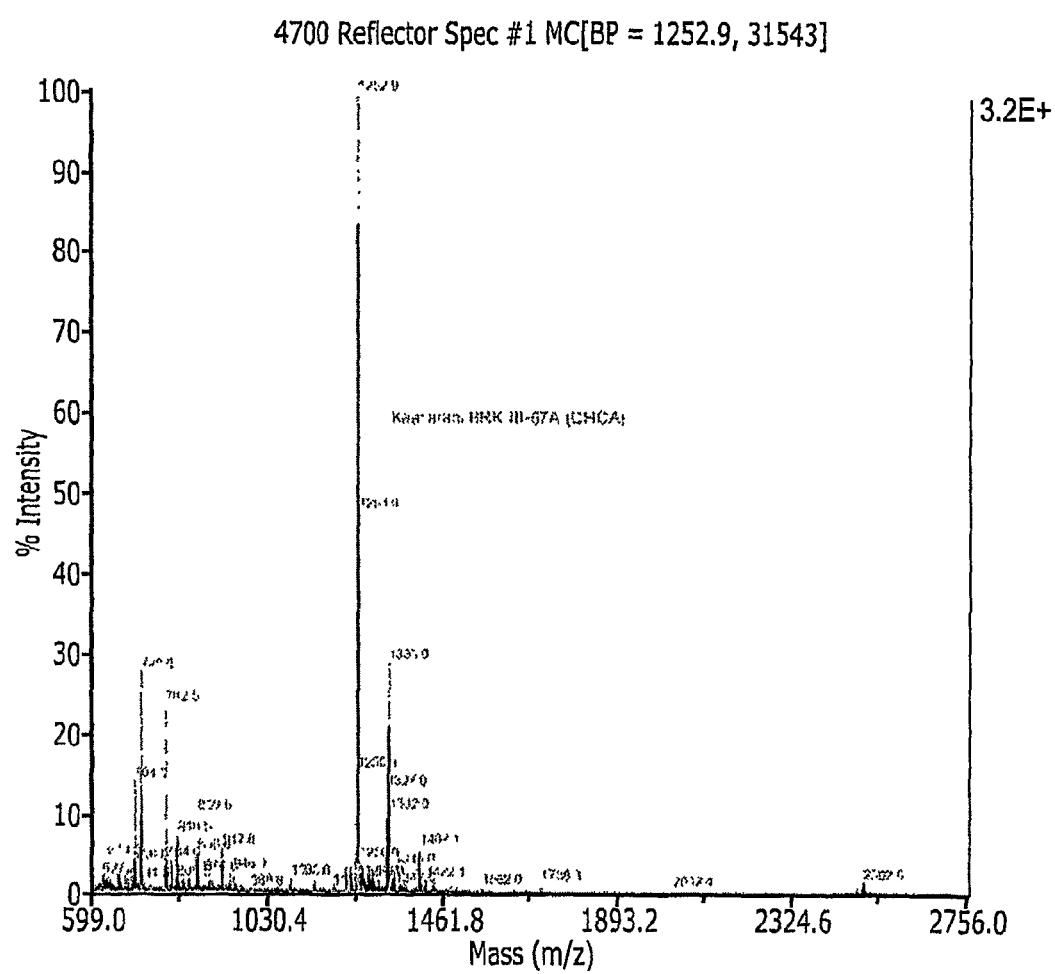
FIG. 43 illustrates the MALDI-TOF of BRK_III__67A.
Figure 44:
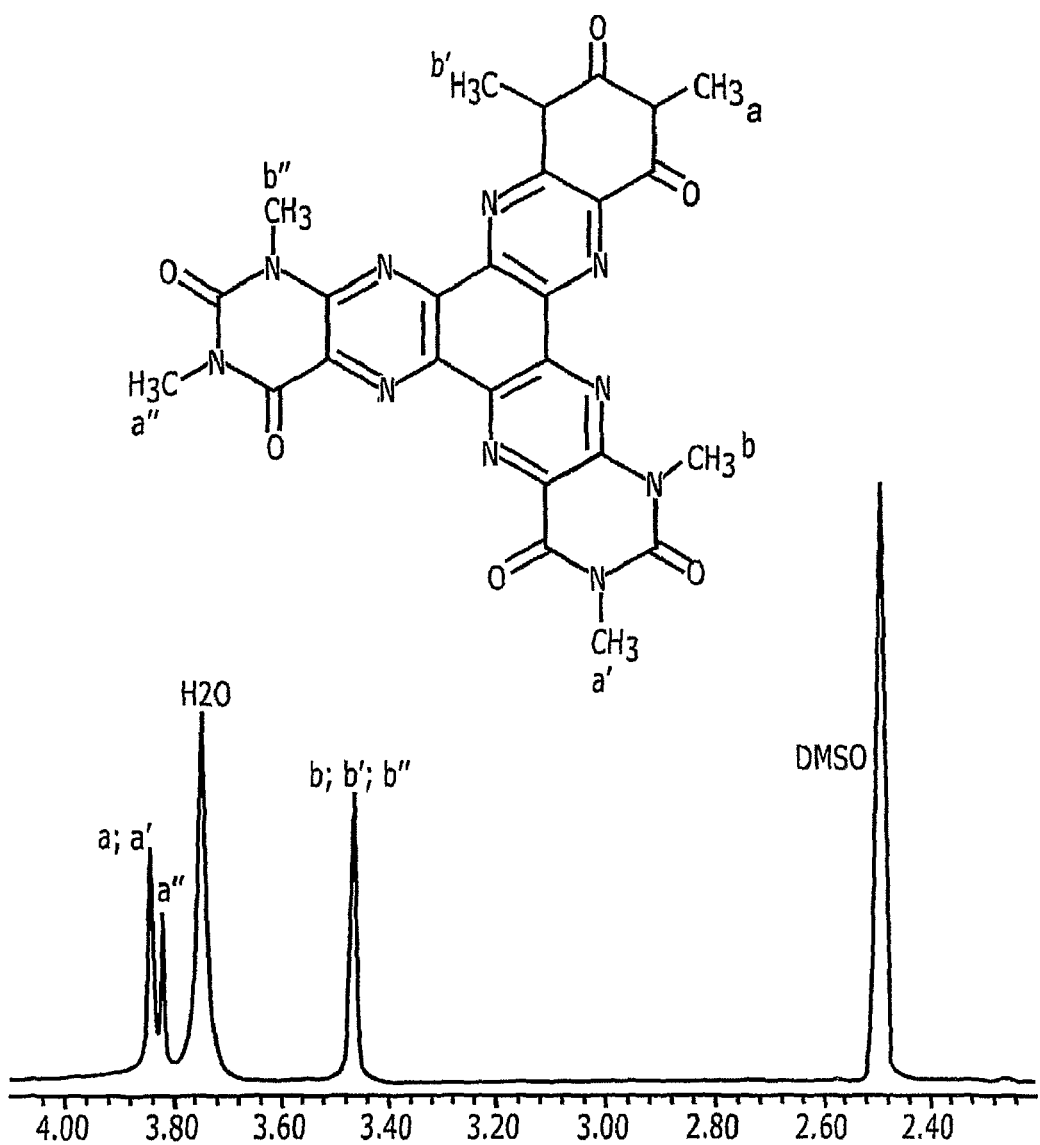
FIG. 44 illustrates the 300 MHz $^1$H NMR of BRK_III__41A in DMSO.

Three fold condensations of SM4 and diamine SM39 proceeded in low yield (9%) to lead to the unsymmetric isomer BRK_III_41A, Scheme 9, which was confirmed by $^1$H NMR as shown in FIG. 42. MALDI TOF measurement showed the MW 571.2 (M+1) but it also showed high MW peak 1196.2, which does not correspond to the dimer of BRK_III_41A.

Scheme 9. Synthesis of BRK_III_41A.

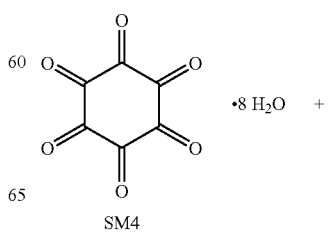

SM4

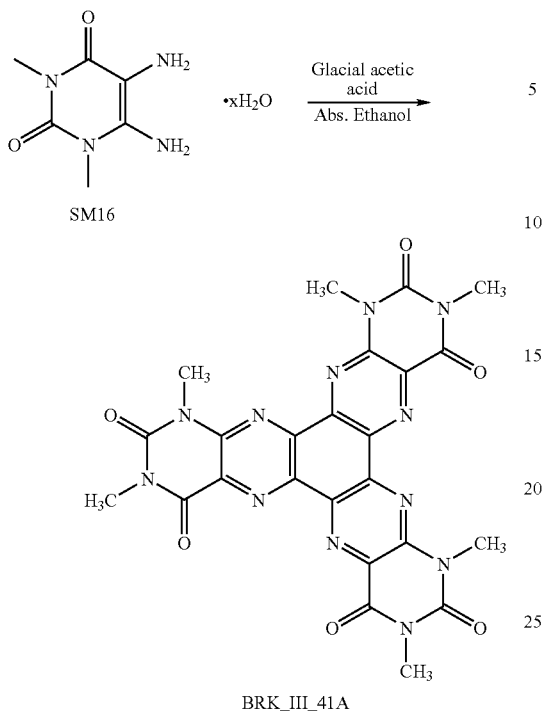
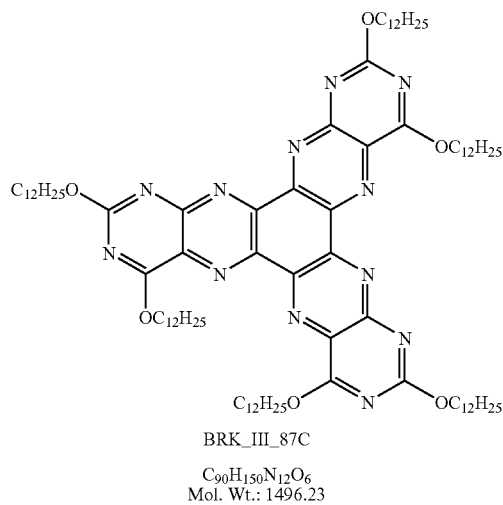

BRK_III_87C

C₉₀H₁₅₀N₁₂O₆
Mol. Wt.: 1496.23

HATNA_Cl₆ was converted to HATNA_[SR]₆ by its reaction with HSR. Microwave synthesis was used for this conversion, Scheme 11. The reaction to BRK_III_45 was successfully carried out in 30 min in 59% yield.

Figure 45:
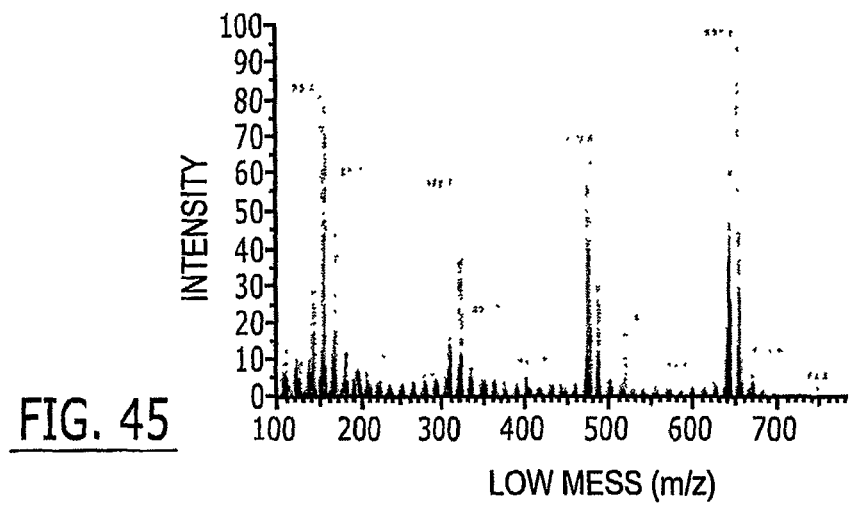
FIG. 45 illustrates the FAB of BRK_III__57B.
Figure 46:
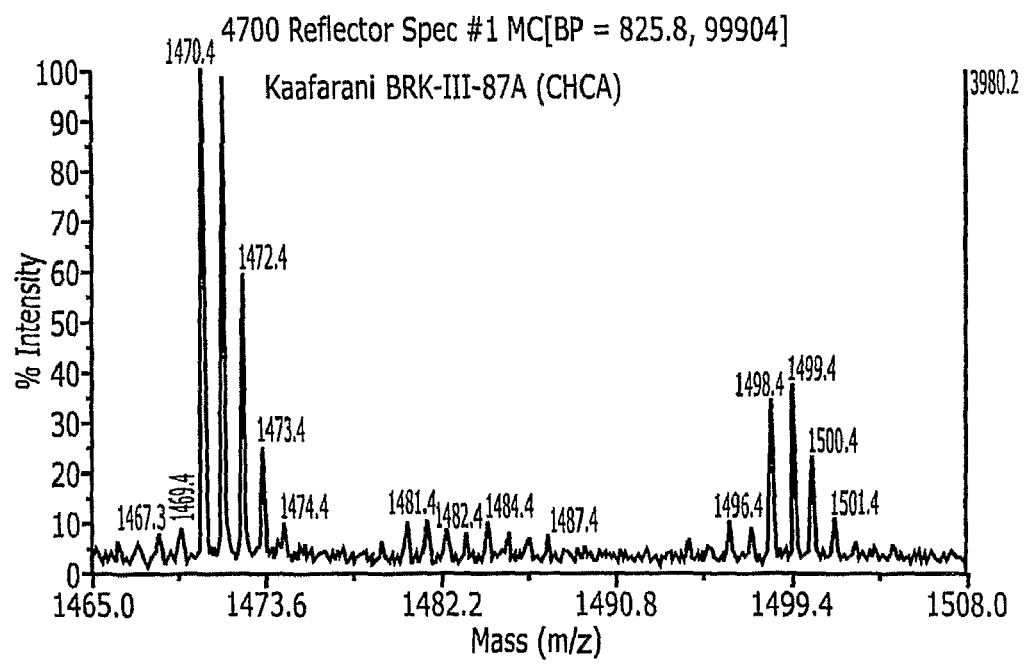
FIG. 46 illustrates the MALDI-TOF of DATNA BRK_III__87C.

The synthesis of BRK_III_75 was performed as shown in Scheme 10. Three-fold condensation of BRK_III_57. FAB of BRK_III_57B shows M+1 of the compound, FIG. 45, with SM4 was performed to lead to 2,4,8,10,13,15-hexakis-dodecyloxy-1,3,5,6,7,9,11,12,14,16,17,18-dodecaazatri-naphthylene DATNA BRK_III_75. DATNA is anticipated to be of higher electron deficiency than HATNA due to the presence of six extra N's. MALDI-TOF indicated the presence of BRK_III_75, FIG. 46.

Scheme 11. Microwave synthesis of HATNA_X₆.

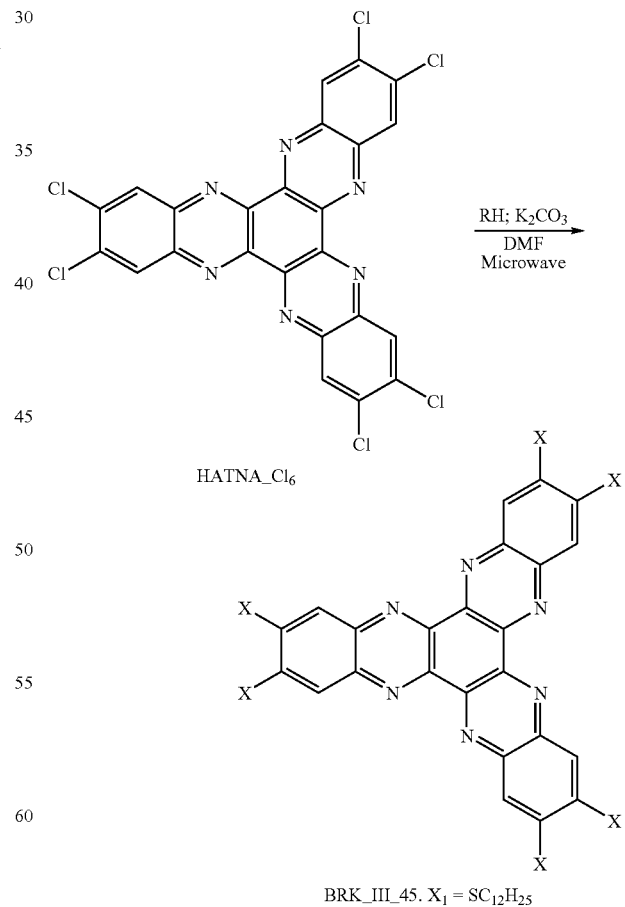

BRK_III_45. X₁ = SC₁₂H₂₅
BRK_III_51. X₂ = OC₁₂H₂₅
BRK_III_47. X₃ = SF₅Ph

Scheme 10. Synthesis of DATNA BRK_III_87C.

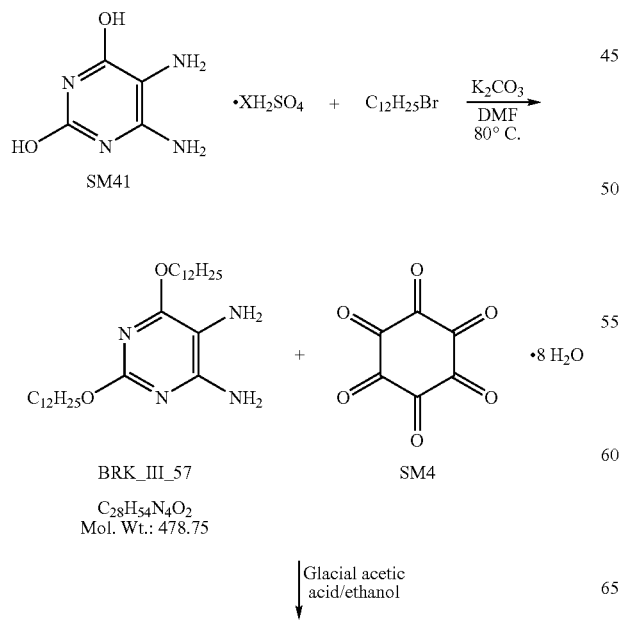

Mobility Measurements

HATNA_[CO$_2$CH$_2$PhF$_5$]$_3$

Figure 47:
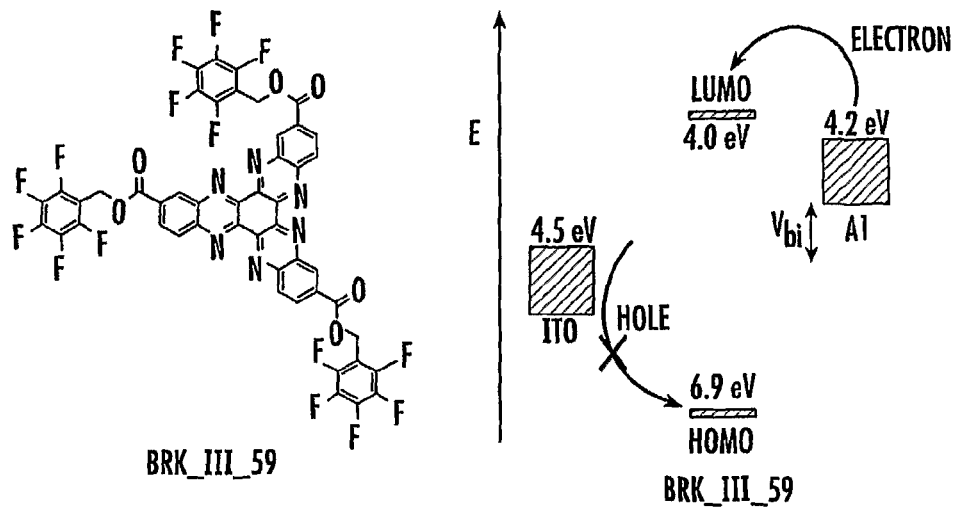
FIG. 47 illustrates the energy levels of the ITO-BRK_III__59-A1 device.

Current amorphous organic molecular glasses and doped polymers have low mobility ($10^{-8}$ to $10^{-2}$ cm$^2$/Vs).[40] Electron mobility in organic materials is generally orders of magnitude lower than hole mobility. Very few useful materials with high electron mobilities have been developed. There is paucity for developing new organic materials with high charge mobility, and particularly with high electron mobility. Charge transport in disordered molecular solids occurs by "hopping," which is essentially a one-electron oxidation-reduction process between neutral molecules and their charged derivatives.[41,42] The mobility is known to be influenced by the effects of disorder on the charge transporting sites. Thus, enhanced molecular order or reduction in disorder represents a possible way of enhancing mobility. Among the transporting materials, HATNA esters are good transport materials candidates; furthermore, due to their high electron deficiency they may show electron transport properties. Conventional time-of-flight measurements were performed but no signal was detected. The current-voltage characteristic of HATNA esters-based devices was investigated at room temperature and as a function of temperature. The occurrence of space-charge limited current (SCLC) enables a direct determination of the electron mobility.[43] A bulk heterojunction, consisted of a three dimensional interpenetrating donor-acceptor network, sandwiched between two electrodes with different work functions, was used. The relative energetic diagram and molecular structure of the three work functions of the electrodes and the organic material BRK_III__59 in the device are shown in FIG. 47.

Figure 48:
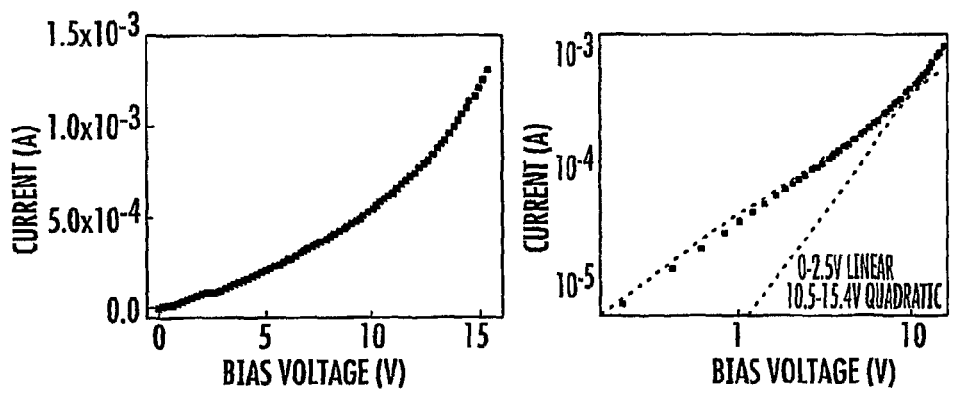
FIG. 48 illustrates the linear (left) and log-log (right) plots of I-V curve for 5-μm thick HATNA-[CO$_2$CH$_2$PhF$_5$]$_3$, BRK_III__59, device at room temperature, the dotted red lines are the linear and quadratic fitting at different voltage range.
Figure 49:
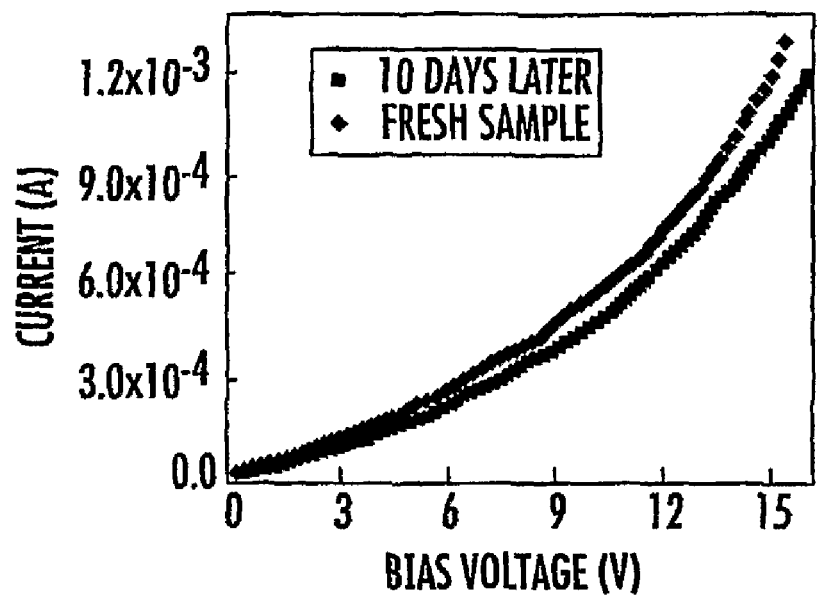
FIG. 49 illustrates the I-V curve for 51n) thick HATNA-[CO$_2$CH$_2$PhF$_5$]$_3$ device at room temperature after 10 days storage, the dotted red line is I-V curve is that of the fresh sample.

The SCLC method was used to determine the electron mobility of this compound. The current-bias voltage (I-V) curve of the 5 μm thick film between two ITO electrodes is shown in FIGS. 48 and 49.

By combining the SCLC with the field-dependent charge mobility expressed by Eq. (1) and numerical fitting the experimental results of the I-V curve, the I-V characteristics could be described by the modified SCLC equation.

$$\mu(E) = \mu(E=0)\exp(\gamma\sqrt{E}) \qquad (1)$$

$$I = \frac{9}{8}C\mu(E=0)\exp\left(0.8495\gamma\sqrt{\frac{V}{d}}\right)\frac{V^2}{d^2} \qquad (2)$$

where μ(E=0) is the charge mobility at zero electric field, and coefficient γ is comparable to the Poole-Frenkel effect.[44] A prefactor 0.8495 instead of 0.891 was obtained,[45] since the simulation was performed further on the modified equation and found that a prefactor 0.8495 fits the experimental data better. Fitting of this curve according to the procedure described above yields an electron mobility of $$\mu = 0.01124\exp(0.001718\sqrt{E}) \qquad (3)$$

The unit for μ in this Eq. is cm$^2$/Vs, in other Eqs in this report the unit is mKs if not pointed out. Assuming an the electric field of $2.8\times10^4$ and $10^5$ V/cm, the electron mobility for HATNA-[CO$_2$CH$_2$PhF$_5$]$_3$ could attain to 0.016 and 0.021 cm$^2$/Vs, respectively. To the best of our knowledge, the mobility of HATNA-[CO$_2$CH$_2$PhF$_5$]$_3$ (at the same electric field) is among the highest reported electron transport mobility for amorphous molecular materials in the range of this electric field at room temperature. This result was reproducible. In order to obtain further information concerning the stability of this material, the I-V curve of this device was measured after 10 days storage in air. The I-V curve characteristic after 10 days is shown FIG. 38, whilst the initial I-V curve of the same fresh sample was also included for comparison.

The current of the HATNA-[CO$_2$CH$_2$PhF$_5$]$_3$ device has slightly decreased after 10 days storage in air. The HATNA-[CO$_2$CH$_2$PhF$_5$]$_3$ device is, therefore, stable and reproducible after storage in air. The I-V curve, after 10 days storage, was also measured of a 5 μm HATNA-[CO$_2$CH$_2$PhF$_5$]$_3$ device between 293 K and 338 K. The zero-field electron mobility and the coefficient γ are shown in Table 8.

TABLE 8

Zero-field electron mobility and the coefficient γ at different temperature of 5 μm HATNA-(COOCH$_2$PhF$_5$)$_3$ device.

| | 293 K | 318 K | 328 K | 338 K |
|---|---|---|---|---|
| μ (E = 0) (cm$^2$/Vs) | $1.05 \times 10^{-2}$ | $1.217 \times 10^{-2}$ | $1.254 \times 10^{-2}$ | $1.34 \times 10^{-2}$ |
| γ (cm/V)$^{1/2}$ | $1.823 \times 10^{-3}$ | $1.004 \times 10^{-3}$ | $6.5 \times 10^{-4}$ | $1.78 \times 10^{-4}$ |

Figure 50:
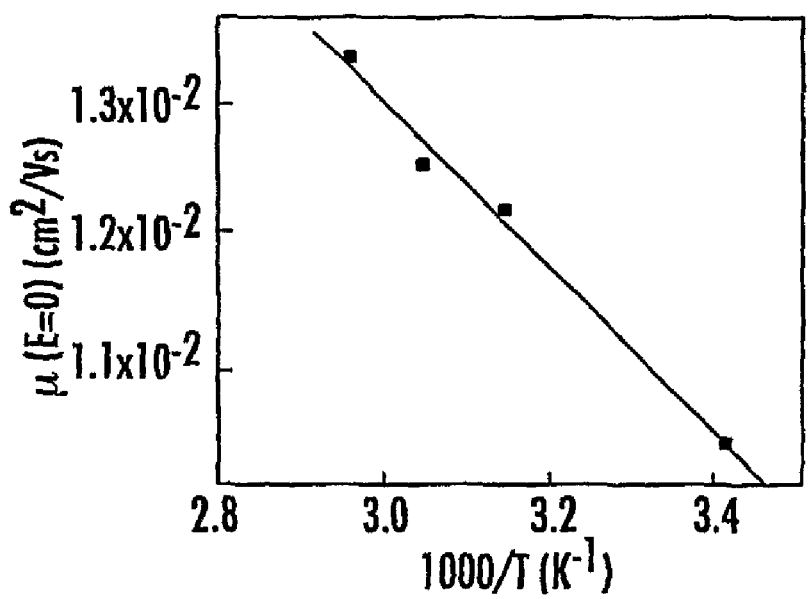
FIG. 50 illustrates the Arrhenius plot of the zero-field mobility versus temperature. The solid line is according to Eq. (3).

The zero-filed electron mobility is shown in FIG. 50 in an Arrhenius plot between 293 K and 338K. It exhibits a thermally dependent behavior as depicted in Eq. 3 with activation energy $\Delta=0.045$ eV and prefactor $\mu_0=0.062$ cm$^2$/Vs as a function of temperature. Such a phenomenon was previously observed in molecular doped polymers[44,46] and in PPV polymer.[47]

$$\mu(E=0) = \mu_0 \exp\left(-\frac{\Delta}{\kappa_B T}\right) \qquad (3)$$

Figure 51:
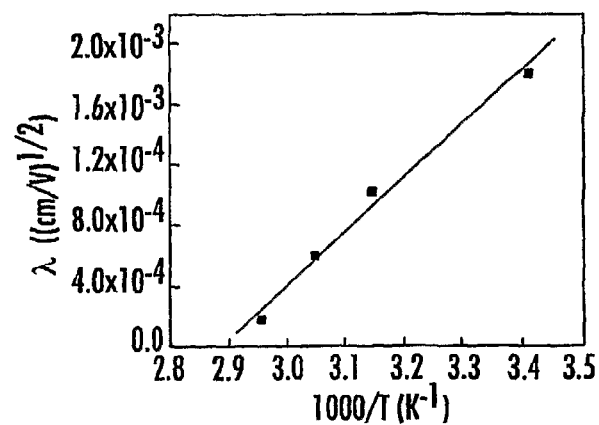
FIG. 51 illustrates the relation of coefficient γ and temperature T. The solid line was obtained from Eq. (3). This empirical dependence of γ and T was initially suggested by Gill for PVK system.[46]

The relation of γ and 1/T has linear dependence, FIG. 51, according to Eq. 4 whilst $B=3.05\times10^{-4}$ eV(cm/V)$^{1/2}$ and $T_0=346$ K. The experimental I-V characteristics as a function of temperature can be expressed by Eqs (1), (3) and (4) using the following parameters: $\Delta=0.045$ eV and prefactor $\mu_0=0.062$ cm$^2$/Vs, $B=3.05\times10^{-4}$ eV(cm/V)$^{1/2}$ and $T_0=346$ K.

$$\gamma = B\left(\frac{1}{\kappa_B T} - \frac{1}{\kappa_B T_0}\right) \qquad (4)$$

HATNA_[SC$_{12}$H$_{25}$]$_6$

Figure 52:
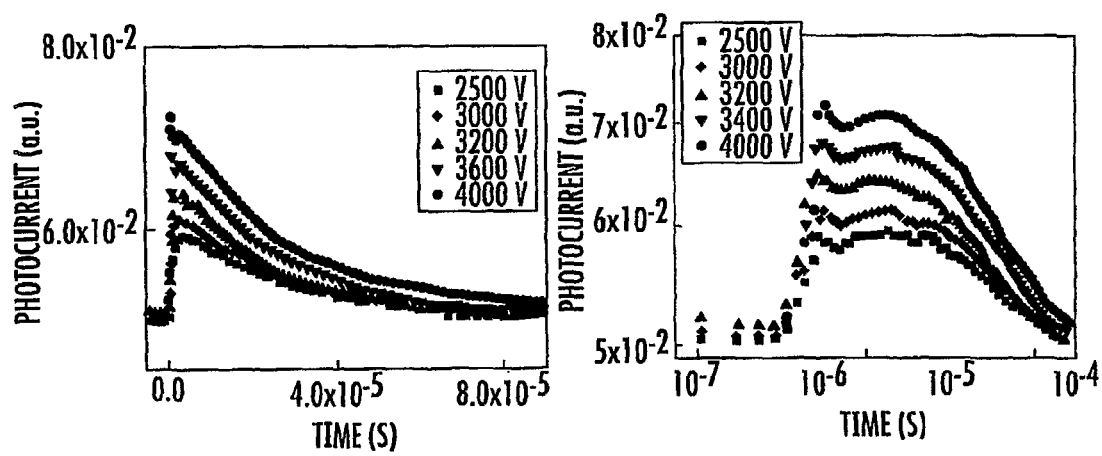
FIG. 52 illustrates the linear (left) and log-log (right) plots of the transient photocurrents for 104 μm thick HATNA_[SC$_{12}$H$_{25}$]$_6$ device at room temperature.
Figure 53:
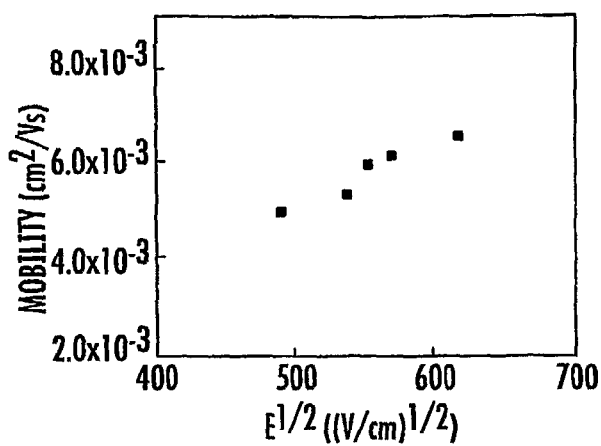
FIG. 53 illustrates the field dependence of the electron mobility of HATNA_[SC$_{12}$H$_{25}$]$_6$ film at room temperature.

The mobility of HATNA_[SC$_{12}$H$_{25}$]$_6$ was determined using time of flight (TOF) method. The transient photocurrents for 104 μm thick HATNA_[SC$_{12}$H$_{25}$]$_6$ sample were measured as a function of time at room temperature for different values of the electric field, FIG. 52. The transient time and charge mobility at different electric field of HATNA_[SC$_{12}$H$_{25}$]$_6$, BK2__71E, at room temperature, are summarized in Table 9. The electron mobility of HATNA_[SC$_{12}$H$_{25}$]$_6$ is in the order of $10^{-3}$ cm$^2$/Vs at the electric field from $2.4\times10^5$ to $4\times10^5$ V/cm, which is consistent with the results obtained for the 20 μm thick sample. The field dependence of the electron mobility for 104 μm thick HATNA_[SC$_{12}$H$_{25}$]$_6$ sample is shown in FIG. 53.

TABLE 9

Summary of the Transient time and electron mobility of 104 μm thick HATNA_[SC$_{12}$H$_{25}$]$_6$ device at different bias voltages.

| Bias Voltage (V) | Transient time (μs) | Electron mobility (cm$^2$/Vs) |
|---|---|---|
| 2500 | 8.71 | 0.0050 |
| 3000 | 6.45 | 0.0054 |
| 3200 | 5.67 | 0.0060 |
| 3400 | 5.15 | 0.0062 |
| 4000 | 4.2  | 0.0066 |

The electron mobility increases with the increasing electric field, i.e., in Eq. (5), γ is positive, FIG. 62. The reason for this phenomenon is unclear until now.

$$\mu(E) = \mu(E=0)\exp(\gamma\sqrt{E}) \quad (5)$$

where μ(E=0) is the charge mobility at zero electric field, and coefficient γ is comparable to the Poole-Frenkel effect.[44]

Figure 54:
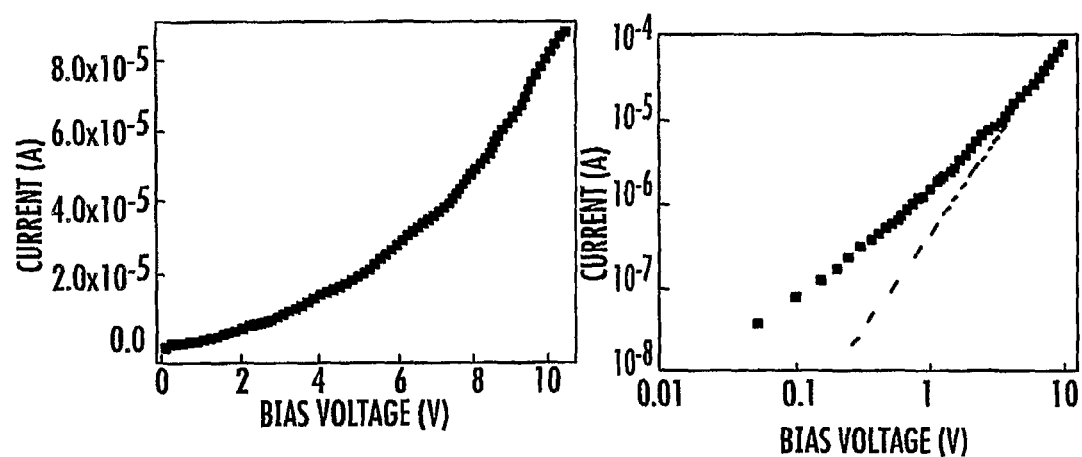
FIG. 54 illustrates the linear (left) and log-log (right) plots of I-V curve for 5 μm thick HATNA_[SC$_{12}$H$_{25}$]$_6$ device at room temperature, the dotted red line is quadratic fitting at 6.5-10.3V range.

The most widely used method to measure the carrier mobility of organic materials included liquid crystal (LC), amorphous, and crystalline films is time of flight (TOF) technique. However, TOF is generally applied to thick samples (in the order of several μm or thicker) and this is disadvantageous. However, OLEDs and OFETs are comprised of films that have a thickness of around 100 nm. In many cases, carrier mobility in thick films may be different from that in thin films due to different morphologies that can result from different film preparation techniques. TOF experiments are particularly difficult to carry out in thin films when significant charge gets injected into the films under bias. Therefore, different methods such as the space-charge-limited conduction (SCLC) technique should be applied to such films. Here, the mobility values obtained in the same materials using the TOF and SCLC methods are compared. The purpose of this is that the mobility values that are extracted from two independent measurements are in good agreement. The current-bias voltage (I-V) curve of the 5 μm thick HATNA_[SC$_{12}$H$_{25}$]$_6$ film between two ITO electrodes is shown in FIG. 54. By combining the conventional SCLC equation with the field-dependent charge mobility and numerical fitting the experimental results of the I-V curve, the I-V characteristics could be described by the modified SCLC Eq. 6.

$$I = \frac{9}{8}\mu_0 C\left(1 + 0.00628\gamma^2 \frac{V}{d}\right)\exp\left(0.846\frac{\gamma}{\sqrt{d}}\right)\frac{V^2}{d^2} \quad (6)$$

Upon simulation studies, a modified equation was used to fit the experimental data in the broader bias voltage range. The electron mobility can be calculated according to Eq. 7.

$$\mu = 1.169 \times 10^{-3} \exp(4.3 \times 10^{-3}\sqrt{E}) \quad (7)$$

The unit for p in Eq. (7) is cm$^2$/Vs. Assuming at the electric field of $2 \times 10^4$ and $10^5$ V/cm, the electron mobility for HATNA [SC$_{12}$H$_{25}$]$_6$ could attain to $2.15 \times 10^{-3}$ and $4.5 \times 10^{-3}$ cm$^2$/Vs, respectively. Comparison of the electron mobility using TOF and SCLC of HATNA_[SC$_{12}$H$_{25}$]$_6$, BK2_71E, is shown in Table 10.

TABLE 10

Comparison of electron mobility of HATNA_[SC$_{12}$H$_{25}$]$_6$ using TOF and SCLC.

| E (V/cm) | μ$_e$(TOF) (cm$^2$/Vs) | μ$_e$ (SCLC) (cm$^2$/Vs) |
|---|---|---|
| $2.40 \times 10^5$ | $4.98 \times 10^{-3}$ | $3.26 \times 10^{-3}$ |
| $2.88 \times 10^5$ | $5.37 \times 10^{-3}$ | $3.47 \times 10^{-3}$ |
| $3.07 \times 10^5$ | $5.97 \times 10^{-3}$ | $3.57 \times 10^{-3}$ |
| $3.27 \times 10^5$ | $6.19 \times 10^{-3}$ | $3.67 \times 10^{-3}$ |
| $3.84 \times 10^5$ | $6.57 \times 10^{-3}$ | $3.95 \times 10^{-3}$ |

Figure 55:
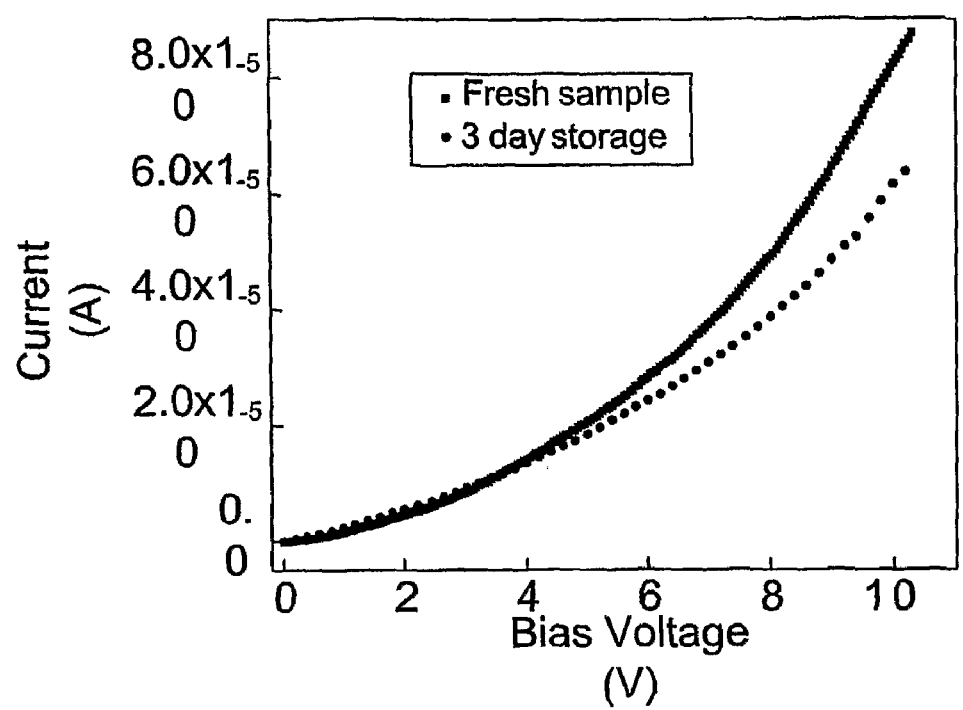
FIG. 55 illustrates the I-V curve for 5 μm thick HATNA_[SC$_{12}$H$_{25}$]$_6$ device at room temperature after three days storage, the solid black line is that of the I-V curve of the fresh sample.

The stability of HATNA_[SC$_{12}$H$_{25}$]$_6$ was tested by measuring the I-V curve of the same device after 3 days storage in air (the stability measurement is still under way). The comparison of the I-V curves of a fresh sample and that of the sample stored for three-days are shown in FIG. 55. This indicates that the current of the HATNA_[SC$_{12}$H$_{25}$]$_6$ device has decreased after three-days storage in air. The reason for this phenomenon is still unclear. One of the tentative explanations could be the different interfacial property of the ITO and organic layer, which are hydrophilic and hydrophobic, respectively. This causes the organic layer to delaminate from the ITO electrodes and the current to decrease.

The preliminary results, therefore, show good agreement between the TOF technique and the SCLC method. This also verifies that both TOF and SCLC are reliable for the characterization of the carrier mobility.

SYNTHESIS 2,3,8,9,14,15-Hexamethyl-5,6,11,12,17,18-hexaazatrinaphthylene [BK2_25]. This compound was synthesized according to a modified literature procedure, which incorporated herein by reference.[30] Cyclohexane octahydrate SM4 (7.64 g, 24.5 mmol), 4,5-dimethyl benzene-1,2-diamine SM27 (10.0 g, 73.4 mmol) were refluxed in 200 ml of glacial acetic acid for 24 hours at 140° C. The solution was then filtered and the obtained green powder was washed with 200 ml of hot glacial acetic acid and was then refluxed in 200 ml of 30% nitric acid for 2 hours. The solution was filtered to yield 9.71 g (84%) of orange powder. $^1$H (300 MHz, DMSO-d$_6$) δ 8.12 (s, 6H), 2.56 (s, 18H). HRMS-EI (m/z): [M]$^+$ calcd. for C$_{30}$H$_{24}$N$_6$, 468.20624. found, 468.20630.

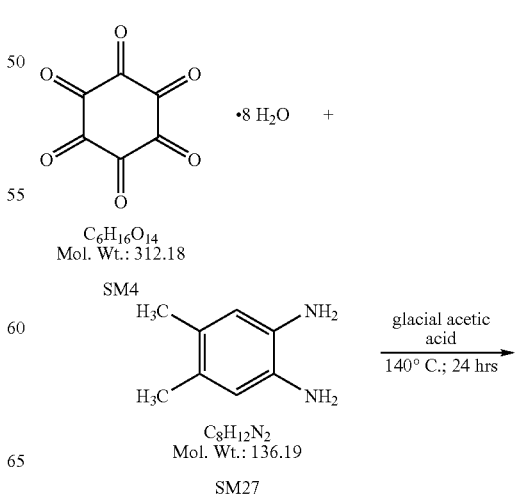

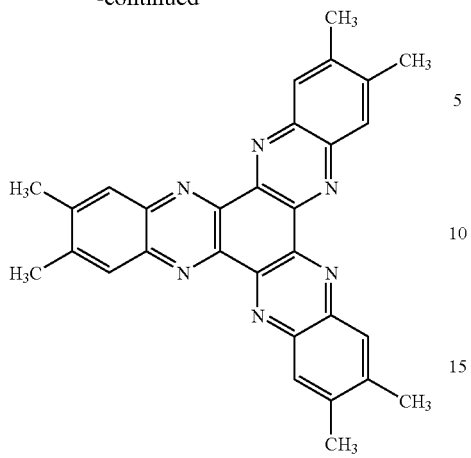

C30H24N6
Mol. Wt.: 468.55
BK2_25

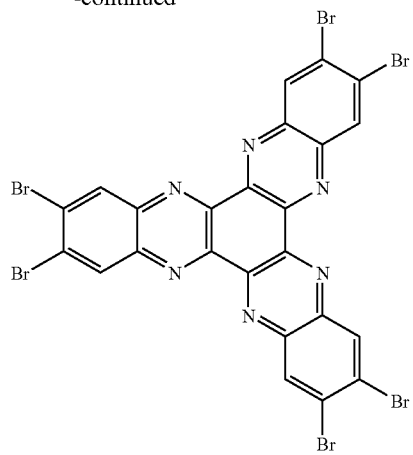

C24H6Br6N6
Mol. Wt.: 857.77
BK2_31

2,3,8,9,14,15-Hexabromo-5,6,11,12,17,18-hexaazatrinaphthylene [BK2_31]. This compound was synthesized according to a modified literature procedure.[30] Cylcohexane octahydrate SM4 (1.17 g, 3.76 mmol), 4,5-dibromo benzene-1,2-diamine QZ-IB-8 (3.00 g, 11.3 mmol) were refluxed in 450 ml of glacial acetic acid (additional volume of glacial acetic acid was added because the solution was hard to stir), for 24 hours at 140° C. The solution was then filtered and the obtained powder was washed with 120 ml of hot glacial acetic acid and was then refluxed in 200 ml of 30% nitric acid for 23 hours. The solution was filtered to yield 3.06 g (95%) of greenish powder. $^1$H (300 MHz, DMSO-d$_6$) δ 8.97 (s, 6H). MALDI-TOF MS (MH+H): m/z 853.5, 855.5, 857.5, 859.5, 861.5, 863.5; calcd for C$_{24}$H$_7$Br$_6$N$_6$, 858.8. An amount of 1 g was sublimed under high vacuum (ca. $10^{-6}$ torr) at ca. 400° C. An amount of 252 mg of yellow solid was isolated. Anal. Calcd. for C$_{24}$H$_6$Br$_6$N$_6$: C, 33.61; H, 0.71; Br, 55.89; N, 9.80. Found: C, 33.74; H, 0.75; Br, 55.66; N, 9.55.

4-Nitro-benzoic acid N'-{4-[5-(3,4,5-tris-dodecyloxy-phenyl)-[1,3,4]oxadiazol-2-yl]-benzoyl}-hydrazide [BK2_23]. This compound was synthesized according to a modified literature procedure.[29] 4-nitro-benzoyl chloride SM22 (941 mg, 5.07 mmol) was dissolved in 75 ml of freshly dried THF (over Na) and was placed in a three-neck round bottom flask. 4-[5-(3,4,5-Tris-dodecyloxy-phenyl)-[1,3,4]oxadiazol-2-yl]-benzoic acid hydrazide SM9 (4.23 g, 5.07 mmol) was dissolved in 150 ml dry THF and was placed in a dropping funnel. The set-up was placed in an ice-water bath and was degassed with argon. SM9 solution was dropped slowly. The reaction mixture was stirred at 0° C. for 2.5 hrs. Pyridine (10 ml) was then added and the reaction mixture was stirred at room temperature for 20 hrs. The reaction mixture was then poured over 500 ml of water and the white solid was filtered and was washed with 750 ml of water to yield 3.25 g of white powder (65%). This compound was used for next step without further purification.

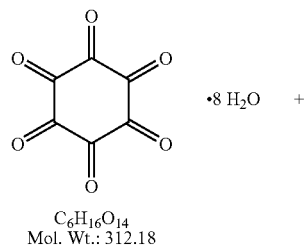

C6H16O14
Mol. Wt.: 312.18
SM4

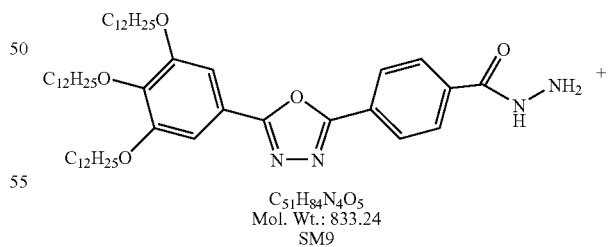

C51H84N4O5
Mol. Wt.: 833.24
SM9

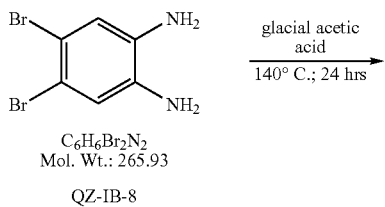

C6H6Br2N2
Mol. Wt.: 265.93
QZ-IB-8

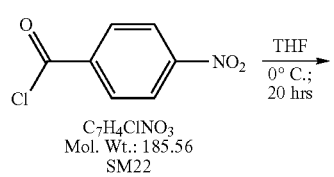

C7H4ClNO3
Mol. Wt.: 185.56
SM22

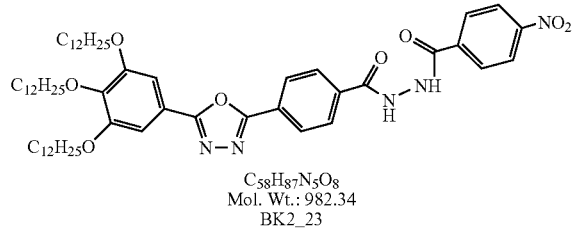

[BK2__27]. This compound was synthesized according to a modified literature procedure.[29] 4-Nitro-benzoic acid N'-{4-[5-(3,4,5-tris-dodecyloxy-phenyl)-[1,3,4]oxadiazol-2-yl]-benzoyl}-hydrazide BK2_23 (3.25 g, 3.31 mmol) was heated in 140 ml of POCl$_3$ at 120° C. overnight. Excess POCl$_3$ was distilled off till around 25 ml are left (the complete distillation of POCl$_3$ lead to tarr and no product was detected, experiment BK2-5). The solution was then poured slowly over 1 L of ice-water (excess POCl$_3$ reacts with water). The greenish solid was filtered off and was recrystallized from CHCl$_3$/ethanol to yield 2.92 g (92%) of greenish solid. $^1$H (300 MHz, CDCl$_3$) δ 8.44-8.34 (m, 4H), 8.32 (s, 4H), 7.33 (s, 2H), 4.10-4.058 (t, J=12.6 Hz, 4H), 4.06-4.02 (t, J=12 Hz, 2H), 1.89-1.80 (pentet, J=7.8 Hz, 4H), 1.78-1.71 (pentet, J=6.9 Hz, 2H), 1.54-1.43 (m, 6H), 1.39-1.19 (m, 48H), 0.88-0.84 (t, J=6 Hz, 9H). $^{13}$C (CDCl$_3$, 75 MHz), δ 165.16, 164.51, 163.17, 163.11, 153.52, 149.56, 141.61, 128.96, 127.85, 127.62, 127.49, 127.11, 125.72, 124.40, 117.91, 105.49, 73.66, 69.44, 32.00, 30.42, 29.78, 29.73, 29.66, 29.40, 29.45, 29.40, 26.18, 22.78, 14.22 ppm. MALDI-TOF MS (M): m/z 964.5; calcd for C$_{58}$H$_{85}$N$_5$O$_7$, 964.3.

of water. The formed yellow solid was filtered off and was then refluxed in 200 ml of hexanes and hot filtration was then performed. White solid formed upon filtration. The solution was put in the freezer and was then filtered off to yield 2.23 g (43%) of white solid. $^1$H (300 MHz, CDCl$_3$) showed a singlet at 8.19 (s, 2H) which is consistent with literature. However, other peaks were present. Attempts to purify this compound by column chromatography failed. This compound may be used for the next step with no further purification.

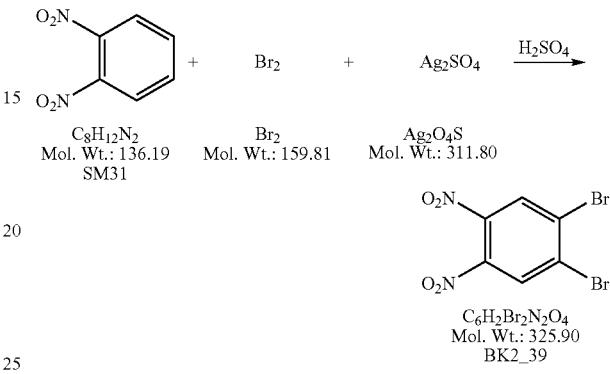

5,6,11,12,17,18-Hexaazatrinaphthylene [BK2__73]. The title compound was synthesized according to a modified literature procedure.[30] Hexaketocyclohexane octahydrate (10.0 g, 32.0 mmol) and 1,2-phenylenediamine SM17 (10.4 g, 96.0 mmol) were refluxed in 500 ml of glacial acetic acid:ethanol (1:1) at 140° C. for 24 hours. The reaction mixture was then

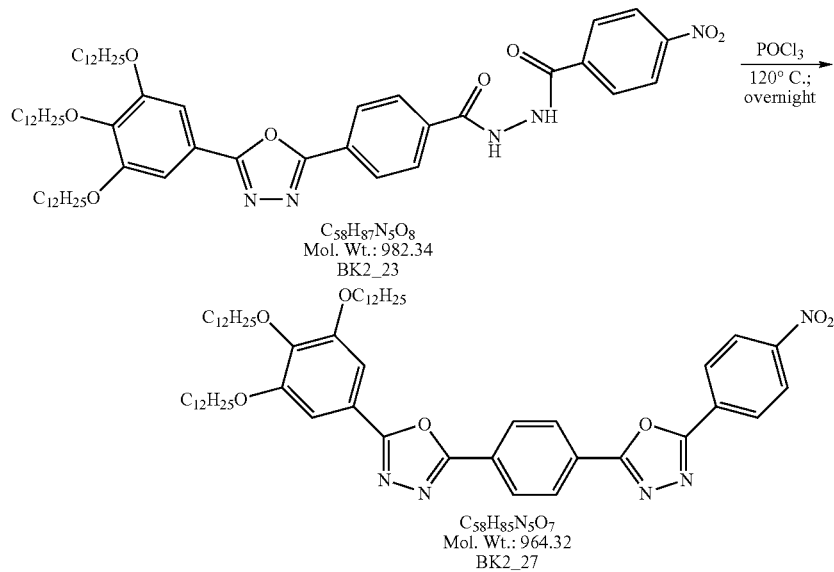

1,2-Dibromo-4,5-dinitro benzene [BK2-39]. This compound was synthesized according to a literature procedure.[51] 1,2-Dinitrobenzene SM31 (2.17 g, 16.0 mmol), bromine (7.66 g, 47.9 mmol), silver sulfate (10.0 g, 32.1 mmol), 24 ml of concentrated sulfuric acid were placed in a 200 ml round bottom flask equipped with a condenser and magnetic stirrer. The reaction mixture was heated to 155° C. and was kept at this temperature for 15 min. The solution was left to cool down to room temperature and was then dropped over 500 ml filtered and washed with ca. 200 ml of hot glacial acid. The solid was then refluxed with 200 ml of 30% nitric acid for 3 hours at 140° C. The yellow solid (12.6 g) was filtered and dried under vacuum. An amount 2.0 g was sublimed at high vacuum (3.2×10$^{-6}$ torr and t=350° C.) to yield 0.77 g (estimated extrapolated yield=40%) of yellow solid. The yield could be increased with prolonged sublimation time. This compound is slightly soluble in CHCl$_3$. $^1$H NMR (CDCl$_3$, 300 MHz) δ 8.73-8.69 (dd, J=6.6 Hz; J$_2$=3.6 Hz, 6H), 8.08-

8.043 (m, 6H). $^{13}$C NMR (CDCl$_3$, 75 MHz), 143.57, 132.30, 130.65, 119.05, 98.58. Anal. Calcd. for C$_{24}$H$_{12}$N$_6$: C, 74.99; H, 3.15; N, 21.86. Found: C, 74.76; H, 3.11; N, 21.66.

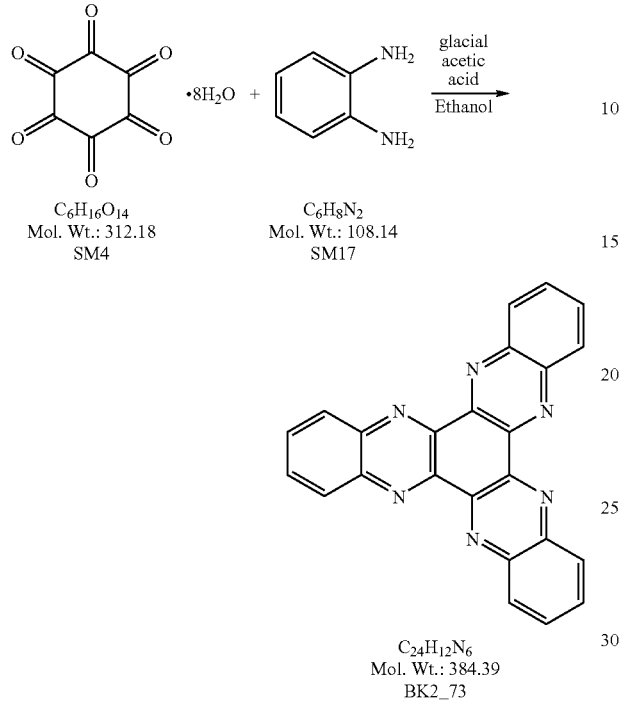

2,3,8,9,14,15-Hexachloro-5,6,11,12,17,18-hexaazatrinaphthylene [BK2_67]. The title compound was synthesized according to a modified literature procedure.[30] Hexaketocyclohexane octahydrate (5.29 g, 17.0 mmol) and 4,5-dichloro-1,2-phenylenediamine SM11 (9.00 g, 50.8 mmol) were refluxed in 110 ml of glacial acetic acid:ethanol (1:1) at 140° C. for 24 hours. The reaction mixture was then filtered and washed with ca. 150 ml of hot glacial acetic acid. The solid was then refluxed with 150 ml of 30% nitric acid for 3 hours at 140° C. The yellow solid (10 g, 100%) was filtered and dried under vacuum. This compound can be used without further purification for further synthesis. An amount of 2.37 g was sublimed under high pressure (P=2×10$^{-6}$ torr and t=450° C.) to yield 1.40 g of pure yellow shining crystals (estimated extrapolated yield=59%). This compound has low solubility in most organic solvents. $^1$H NMR (CDCl$_3$, 300 MHz) δ (s, 6H). Anal. Calcd. for C$_{24}$H$_6$Cl$_6$N$_6$: C, 48.77; H, 1.02; Cl, 35.99; N, 14.22. Found: C, 48.80; H, 1.00; Cl, 36.12; N, 14.24.

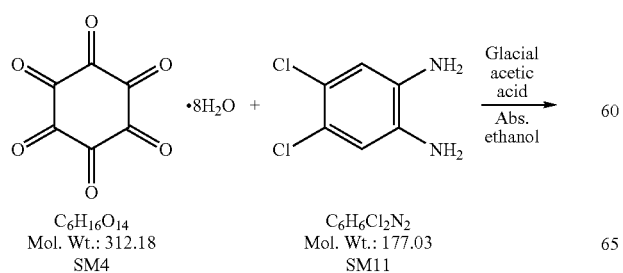

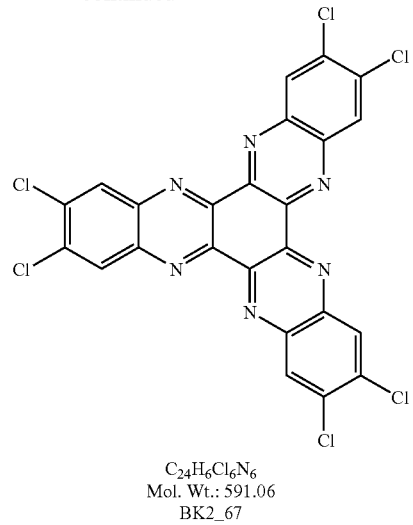

2,3,8,9,14,15-Hexanitro-5,6,11,12,17,18-hexaazatrinaphthylene [BK2_93]. The title compound was synthesized according to a modified literature procedure.[30] Hexaketocyclohexane octahydrate (2.63 g, 8.41 mmol) and 4,5-dinitro-1,2-phenylenediamine SM29 (5.00 g, 25.2 mmol) were refluxed in 150 ml of glacial acetic acid:ethanol (1:1) at 140° C. for 24 hours. The reaction mixture was then filtered and washed with ca. 150 ml of hot glacial acid. The solid was then refluxed with 145 ml of 30% nitric acid for 1.5 hours at 140° C. The yellow solid (4.62 g, 84%) was filtered and dried under vacuum. This compound has very low solubility in most organic solvents. $^1$H NMR (DMSO-d$_6$, 300 MHz), 9.47 (s, 6H). MALDI-TOF MS (M+H): m/z 655.1; calcd for C$_{24}$H$_7$N$_{12}$O$_{12}$, 655.5.

2,3,8,9,14,15-Hezaazatristriphenylene [BK2_97]. The title compound was synthesized according to a modified literature procedure.[30] Hexaketocyclohexane octahydrate (422 mg, 1.35 mmol) and [9,10]-diaminophenanthrene SM7 (845 mg, 4.06 mmol) were placed in a Sclenck tube. The system was degassed with nitrogen. Free-$O_2$ 100 ml of glacial acetic acid was transferred to the Sclenck tube under nitrogen. The reaction mixture was refluxed at 140° C. for 24 hours. The reaction mixture was then filtered and washed with ca. 50 ml of ethanol. An amount of 922 mg (99%) of yellow-orange solid was collected. This compound has very low solubility in most organic solvents. Attempts to purify this compound by high vacuum train sublimation have yet failed. MALDI-TOF shows the presence of the compound. MALDI-TOF MS (M+H): m/z 686.2, calcd for $C_{48}H_{26}N_6$, 686.7.

mixture was transferred to a 300 ml round bottom flask and 80 ml of DMF were added. The reaction mixture was then poured over 1 L of water. The solution was neutralized with concentrated HCl (15 ml) and was then filtered. The obtained green sold was washed with copious amount of water. The obtained solid was dried and was then recrystallized twice from toluene/ethanol to yield 4.18 g (77%) of yellow solid. An amount of 1.57 g was run through a column of silica using $CH_2Cl_2$ as eluent. An amount of 1.23 g was isolated (estimated extrapolated yield: 61%). $^1$H (300 MHz, $CDCl_3$) δ 8.22 (s, 6H), 3.26-3.21 (t, J=7.5 Hz, 12H), 1.94-1.84 (pentet, J=7.5 Hz, 12H), 1.64-1.54 (m, 12H), 1.46-1.26 (m, 96H), 0.89-0.85 (t, J=6.3 Hz, 18H). $^{13}$C ($CDCl_3$, 75 MHz) δ 144.38, 142.21, 141.36, 123.10, 33.24, 31.98, 29.72, 29.60, 29.43, 29.31, 28.20, 22.77, 14.21 ppm. MALDI-TOF MS (M+H): m/z 1587.2, calcd for $C_{96}H_{157}N_6S_6$, 1587.7. Anal. Calcd. for $C_{96}H_{156}N_6S_6$: C, 72.67; H, 9.91; N, 5.30; S, 12.13. Found: C, 72.59; H, 9.77; N, 5.33; S, 12.02.

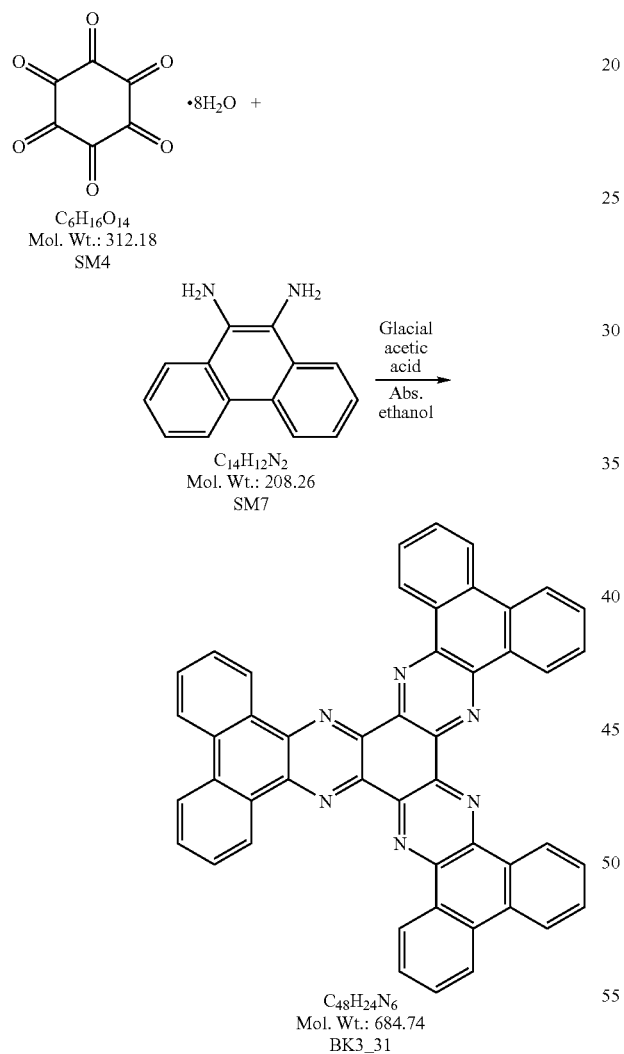

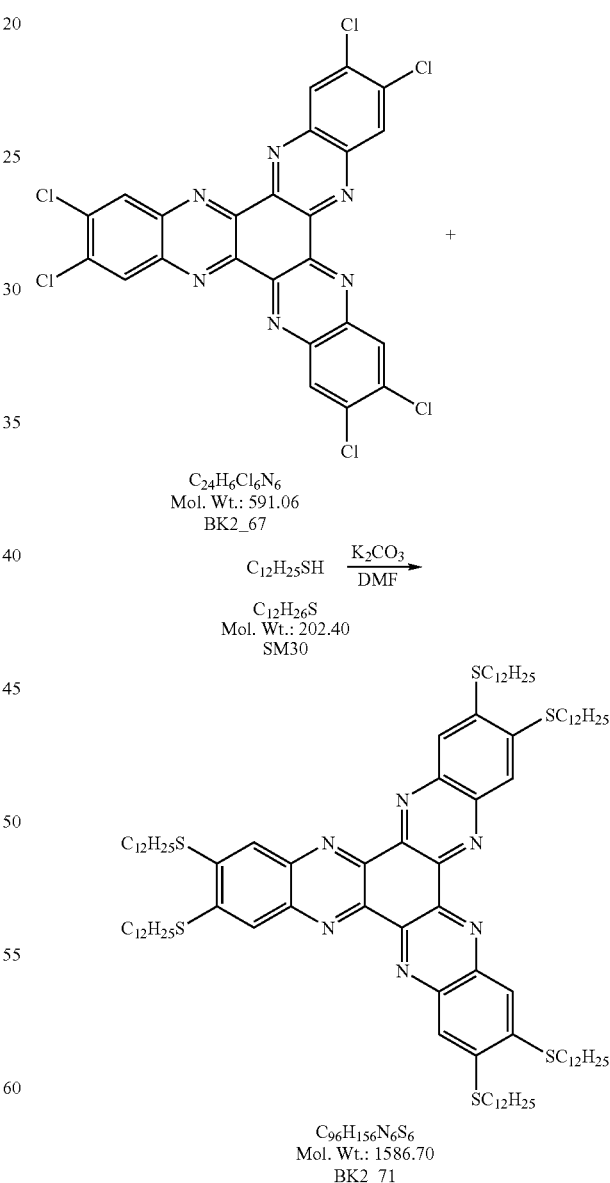

2,3,8,9,14,15-Hexakis-dodecylsulfanyl-5,6,11,12,17,18-hexaazatrinaphthylene [BK2 71]. This compound was synthesized according to a literature procedure.[21] In a Schlenk tube, 2,3,8,9,14,15-hexachloro-5,6,11,12,17,18-hexaazatrinaphthylene BK2_67 (2.00 g, 3.38 mmol), 1-dodecanethiol SM30 (9.00 g, 44.4 mmol), $K_2CO_3$ (17.0 g, 123 mmol) were placed. The tube was degassed with argon under which ca. 60 ml of DMF were transferred. After 72 hours of heating at 80° C., the reaction was dense and hardly stirring. The reaction 2,3,8,9,14,15-Hexakis-dodecylsulfanyl-5,6,11,12,17,18-hexaazatrinaphthylene [BK2_99]. This compound was synthesized according to a literature procedure, which is incorporated herein by reference. In a Schlenk tube, 2,3,8,9,14,15-Hexachloro-5,6,11,12,17,18-hexaazatrinaphthylene BK2_67 (2.00 g, 3.38 mmol), 1-octanethiol SM35 (7.00 ml, 40.3 mmol), $K_2CO_3$ (16.7 g, 121 mmol) were placed. The tube was degassed with argon under which ca. 120 ml of DMF were transferred. The reaction mixture was stirred at 80° C. for a week. The reaction mixture was then poured over 1 L of water. The solution was neutralized with concentrated HCl (ca. 20 ml) and was then filtered. The obtained green solid was washed with copious amount of water. The obtained solid was dried and was then recrystallized twice from toluene/ethanol to yield 3.01 g (71%) of yellow solid. $^1$H (300 MHz, $CDCl_3$) δ 8.27 (s, 6H), 3.28-3.23 (t, J=7.2 Hz, 12H), 1.97-1.86 (pentet, J=7.2 Hz, 12H), 1.64-1.55 (pentet, J=7.5 Hz, 12H), 1.46-1.26 (m, 48H), 0.93-0.89 (m, 18H). $^{13}$C ($CDCl_3$, 75 MHz) δ 144.87, 141.81, 141.25, 122.83, 33.27, 31.90, 29.31, 29.25, 28.19, 22.75, 14.22 ppm. MALDI-TOF MS (M+H): m/z 1251.7, calcd for $C_{72}H_{109}N_6S_6$, 1251.1. Anal. Calcd. for $C_{72}H_{108}N_6S_6$: C, 69.18; H, 8.71; N, 6.72; S, 15.39. Found: C, 69.24; H, 8.61; N, 6.67; S, 15.50.

echol SM23 (10.0 g, 90.1 mmol), 1-bromododecane (45.3 g, 182 mmol), and potassium carbonate (25.0 g, 182 mmol) were heated in 300 ml DMF at 80° C. for 6 days. The reaction mixture was added to 600 ml water, and was extracted with chloroform. The chloroform extracts were combined and were washed with water, brine solution, dried over $MgSO_4$, and the solution was then filtered. The solvent was evaporated, and the obtained solid was recrystallized from ethanol to yield 18.0 g (44.4%) of grayish solid. E1 (m/z): [M]$^+$ calcd. for $C_{30}H_{54}O_2$, 446.8. found, 446.5. This compound was used for the next step with no further purification.

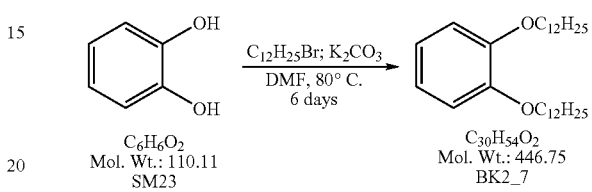

1,2-Bis-dodecyloxy-4,5-dinitro benzene [BK2_13]. This compound was synthesized according to a literature procedure, which is incorporated herein by reference.$^{24}$ To 1,2-Bis-dodecyloxy benzene BK2_7 (5.00 g, 11.2 mmol) in a 500 ml round bottom flask placed in an ice bath, 80 ml of $CH_2Cl_2$ and 80 ml of acetic acid were added. Concentrated $HNO_3$ (50 ml) was added slowly. The color changed from orange-brown to green then back to orange-brown. The solution was stirred at 0° C. for 10 min then at room temperature for 30 min. The setup was placed again in the ice bath and 100 ml of concentrated $HNO_3$ were added. The reaction mixture was stirred at 0° C. for 10 min then at room temperature for 6 days. The solution was poured over 500 ml of ice-water and was then extracted with $CH_2Cl_2$, dried over $MgSO_4$, filtered. The solvent was evaporated. The obtained solid was recrystallized from acetone to yield 4.21 g (70%) of yellow solid. $^1$H (300 MHz, $CDCl_3$) δ 7.27 (s, 2H), 4.10-4.05 (t, J=6.3 Hz, 4H), 1.90-1.80 (pentet, J=7.2 Hz, 4H), 1.50-1.41 (pentet, J=7.2 Hz, 4H), 1.40-1.20 (m, 32H), 0.88-0.83 (t, J=6.3 Hz, 6H). $^{13}$C ($CDCl_3$, 75 MHz) δ 143.20, 128.20, 106.69, 70.67, 32.00, 29.78, 29.73, 29.67, 29.55, 29.45, 26.17, 22.78, 14.22 ppm. HRMS-E1 (m/z): [M]$^+$ calcd. for $C_{30}H_{52}N_2O_6$, 536.38254. found, 536.38397.

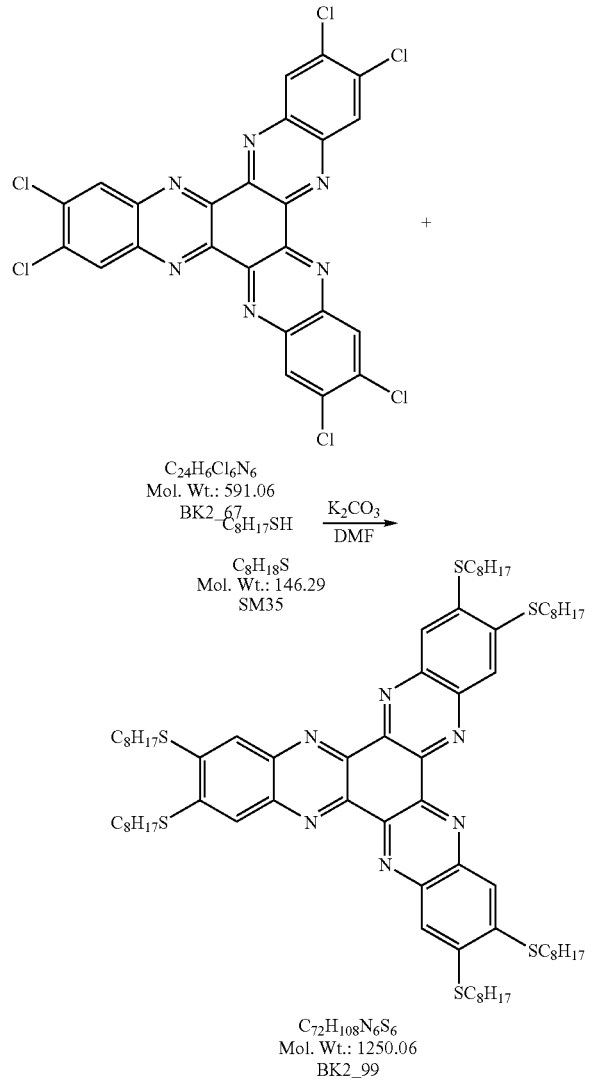

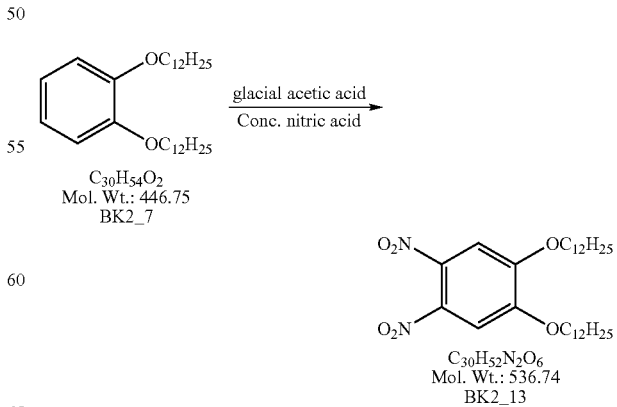

1,2-Bis-dodecyloxy benzene [BK2_7]. This compound was synthesized according to a literature procedure.$^{24}$ Cat- 4,5-Bis-dodecyloxy benzene-1,2-diamine [BK2_13; BK3_1]. This compound was synthesized according to a literature procedure.[24] In a Schlenk tube, 1,2-Bis-dodecyloxy-4,5-dinitro benzene BK2_13 (2.36 g, 4.39 mmol), hydrazine monohydrate (8.25 ml, 48.5 mmol), 131 mg of Pd/C, and 65 ml of absolute ethanol were placed. The reaction mixture was refluxed under argon for 22 hours. Hot filtration under argon was then performed. Upon cooling, a white solid formed. The solid was washed with $O_2$-free methanol and was dried overnight under nitrogen to yield 1.57 g (75%) of white solid. $^1$H (300 MHz, $CDCl_3$) δ 6.353 (s, 2H), 3.880-3.835 (t, J=6.6 Hz, 4H), 3.062 (br s, 4H, $NH_2$), 1.767-1.673 (pentet, J=7.2 Hz, 4H), 1.43-1.36 (m, 4H), 1.358-1.080 (m, 32H), 0.878-0.833 (t, J=7.2 Hz, 6H).$^{13}$C ($CDCl_3$, 75 MHz) δ 143.20, 128.20, 106.69, 70.67, 32.00, 29.78, 29.73, 29.67, 29.55, 29.45, 26.17, 22.78, 14.22 ppm. HRMS-E1 (m/z): [M]$^+$ calcd. for $C_{30}H_{56}N_2O_2$, 476.43418. found 476.43449.

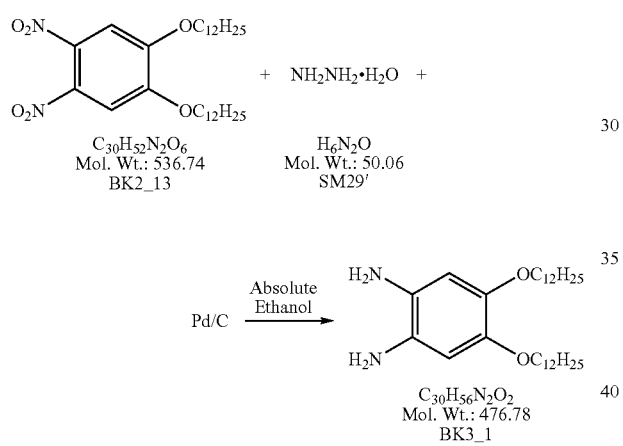

2,3,8,9,14,15-Hexakis-dodecyloxy-5,6,11,12,17,18-hexaazatrinaphthylene [BK2-37; BK3-3]. This compound was synthesized according to a modified literature procedure.[30] Cylcohexane octahydrate SM4 (347 mg, 1.11 mmol), 4,5-Bis-dodecyloxy benzene-1,2-diamine BK3_1 (1.57 g, 3.29 mmol) were refluxed in 150 ml of glacial acetic acid: ethanol (1:1) at 140° C. for 24 hours. The solvent was then evaporated. The dark solid was recrystallized from toluene/ethanol to yield 1.50 g (92%) of reddish solid. The compound was flashed over a column of silica using $CH_2Cl_2$ as eluent. The solvent was evaporated and the obtained solid was recrystallized three times from toluene/ethanol to yield 811 mg (49%). $^1$H (300 MHz, $CDCl_3$) δ 7.95 (s, 6H), 4.32-4.28 (t, J=12.3 Hz, 12H), 2.02-1.93 (pentet, J=7.2 Hz, 12H), 1.61-1.51 (pentet, J=7.2 Hz, 12H), 1.43-1.22 (m, 98H), 0.88-0.84 (m, 18H). $^{13}$C ($CDCl_3$, 75 MHz) δ 154.91, 140.98, 107.15, 69.68, 32.00, 29.75, 29.72, 29.49, 29.46, 28.85, 26.15, 22.78, 14.22 ppm. MALDI-TOF MS (M+H): m/z 1492.3, calcd for $C_{96}H_{158}N_6O_6$, 1492.3. Anal. Calcd. for $C_{96}H_{158}N_6O_6$: C, 77.37; H, 10.55; N, 5.64. Found: C, 76.88; H, 10.72; N, 5.67.

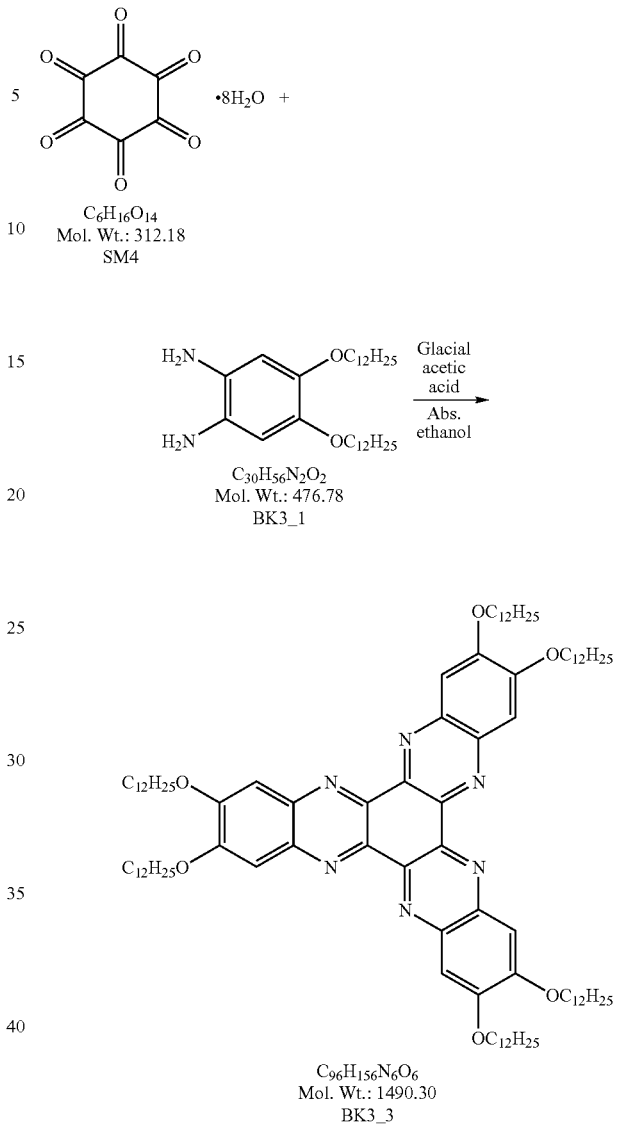

9,14-Bis-[N'-(3,4,5-tris-octyloxy-benzoyl)-hydrazinocarbonyl]-5,6,11,12,17,18-hexaazatrinaphthylene-2-carboxylic acid N'-(3,4,5-tris-octyloxy-benzoyl)-hydrazide [BK2_77]. The title compound was synthesized according to a modified literature procedure.[29] It should be noted that a mixture of the 2,8,14 and 2,8,15 isomers are formed. BK2_43 (3.00 g, 5.43 mmol) was dissolved in 80 ml dry THF and placed in a 500 ml three neck round bottom flask. 3,4,5-Tris-octyloxy-benzoic acid hydrazide SM21 (8.47 g, 16.3 mmol), dissolved in 150 ml THF, was placed in a dropping funnel. The setup was placed in an ice-bath (ice+$H_2O$). The setup was degassed with argon. At a steady rate, SM21 solution was added slowly dropwise. The reaction mixture was stirred at 0° C. for 5 hours, after which 15 ml of pyridine were added and the solution was further stirred at room temperature overnight. Water (500 ml) was added to the reaction mixture upon, which a green solid formed (9.80 g, 92%). This solid was filtered and dried. This compound was used with no further purification.

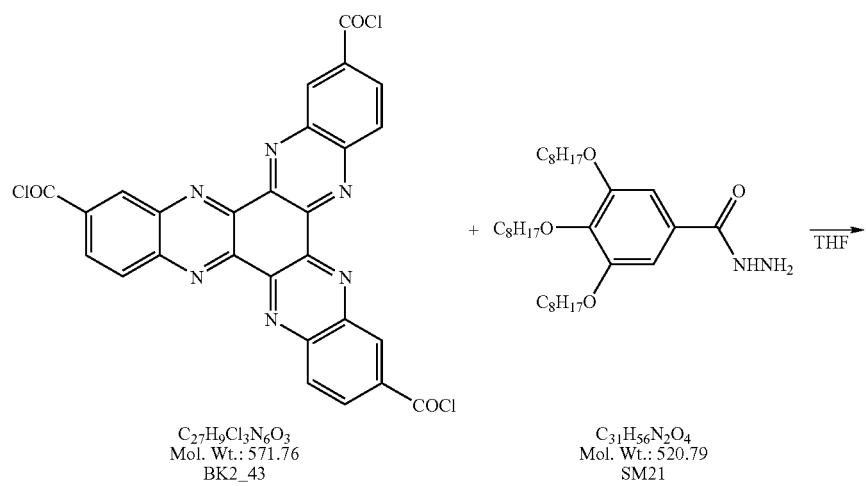
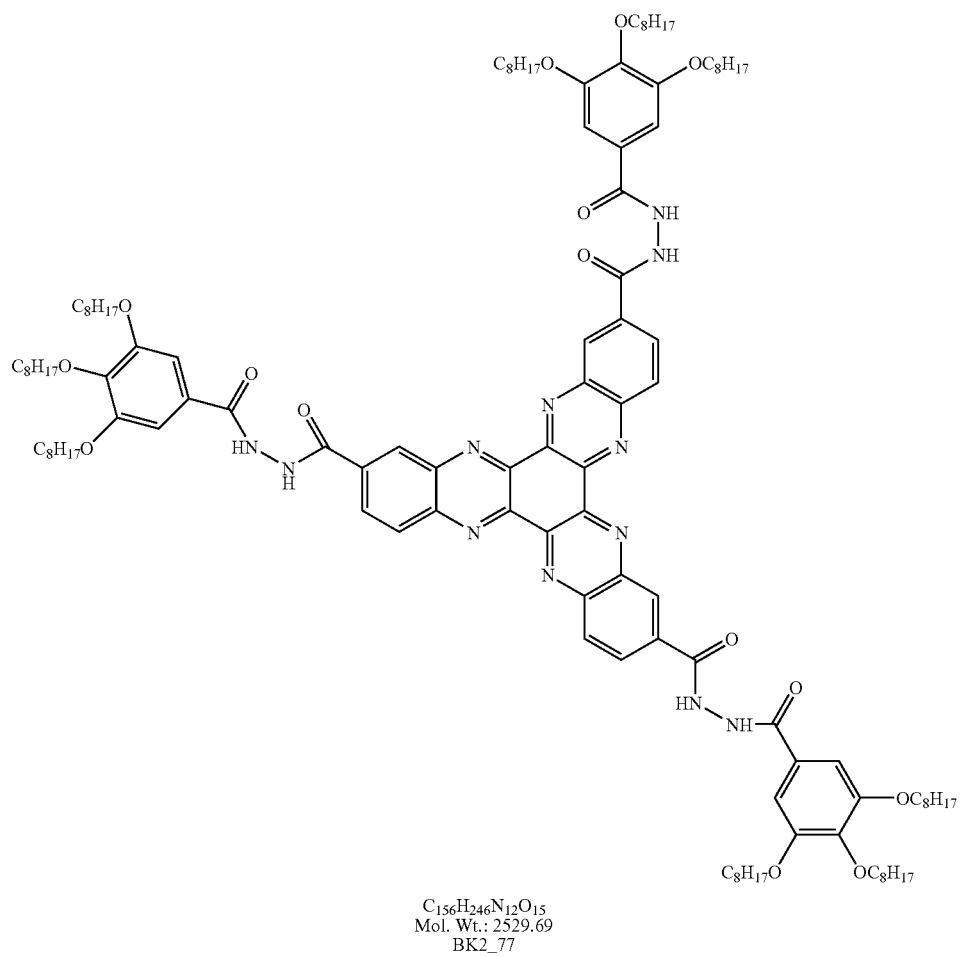

2,8,15-Tris-[5-(3,4,5-tris-octyloxyl-phenyl)-[1,3,4]oxadiazol-2-yl]-5,6,11,12,17,18-hexaazatrinaphthylene [BK2_83]. The title compound was synthesized according to a modified literature procedure.[29] It should be noted that a mixture of the 2,8,14 and 2,8,15 isomers are formed. BK2_77 (9.80 g, 8.84 mmol) was refluxed in 150 ml of $POCl_3$ at 110° C. for 12 hours. The excess $POCl_3$ (100 ml) was distilled off. The remaining solution was added to 600 ml of water and ice, upon which a brown solid forms. This latter was filtered and dried. The dark brown solid was passed through a column of silica using hexanes as eluent. The solvent was evaporated to yield 5.49 g of black shining crystals, which were dissolved in minimum amount of $CHCl_3$ and were precipitated with 200 ml of methanol. The brown solid was filtered off and was then recrystallized from toluene/ethanol to yield 2.82 g (30%) of brown solid. $^1H$ (300 MHz, $CDCl_3$) δ 9.41-9.40 (m, 1H), 9.34 (d, J=1.2 Hz, 1H), 9.32-9.31 (d, J=1.5 Hz, 1H), 8.87-8.76 (m, 6H), 7.40-7.39 (m, 6H), 4.18-4.07 (m, 18H), 1.98-1.87 (pentet, J=6.3 Hz, 12H), 1.85-1.76 (pentet, J=7.5 Hz, 6H), 1.62-1.49 (m, 18H), 1.48-1.15 (m, 72H), 0.98-0.85 (m, 27H). $^{13}C$ ($CDCl_3$, 75 MHz) δ 153.59, 144.03, 143.18, 141.59, 127.42, 117.68, 105.26, 73.68, 69.43, 32.01, 31.95, 31.92, 30.49, 29.64, 29.52, 29.43, 26.27, 26.20, 22.81, 22.77, 14.24 ppm. MALDI-TOF MS (MH+H): m/z 1972.4, calcd for $C_{120}H_{170}N_{12}O_{12}$, 1972.7. Anal. Calcd. for $C_{120}H_{168}N_{12}O_{12}$: C, 73.14; H, 8.59; N, 8.53. Found: C, 72.28; H, 8.63; N, 8.53.

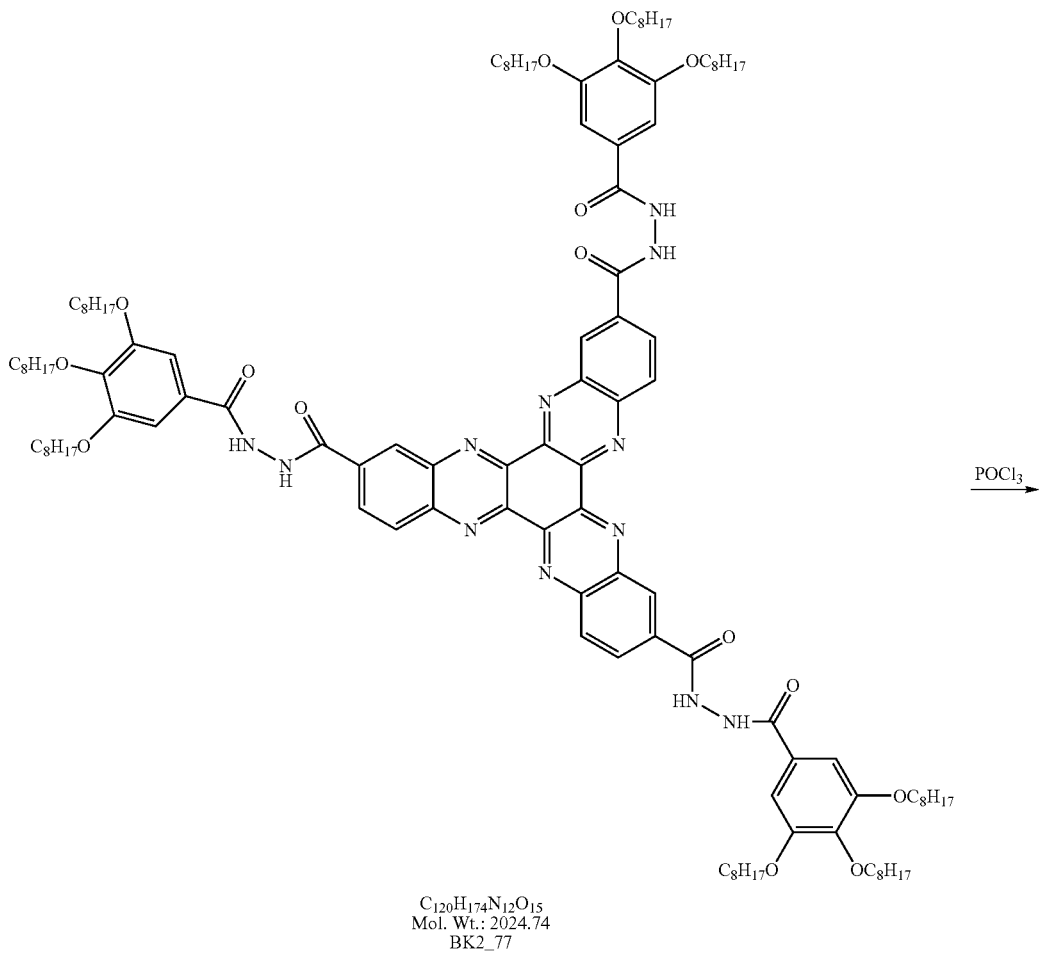

$C_{120}H_{174}N_{12}O_{15}$
Mol. Wt.: 2024.74
BK2_77

-continued

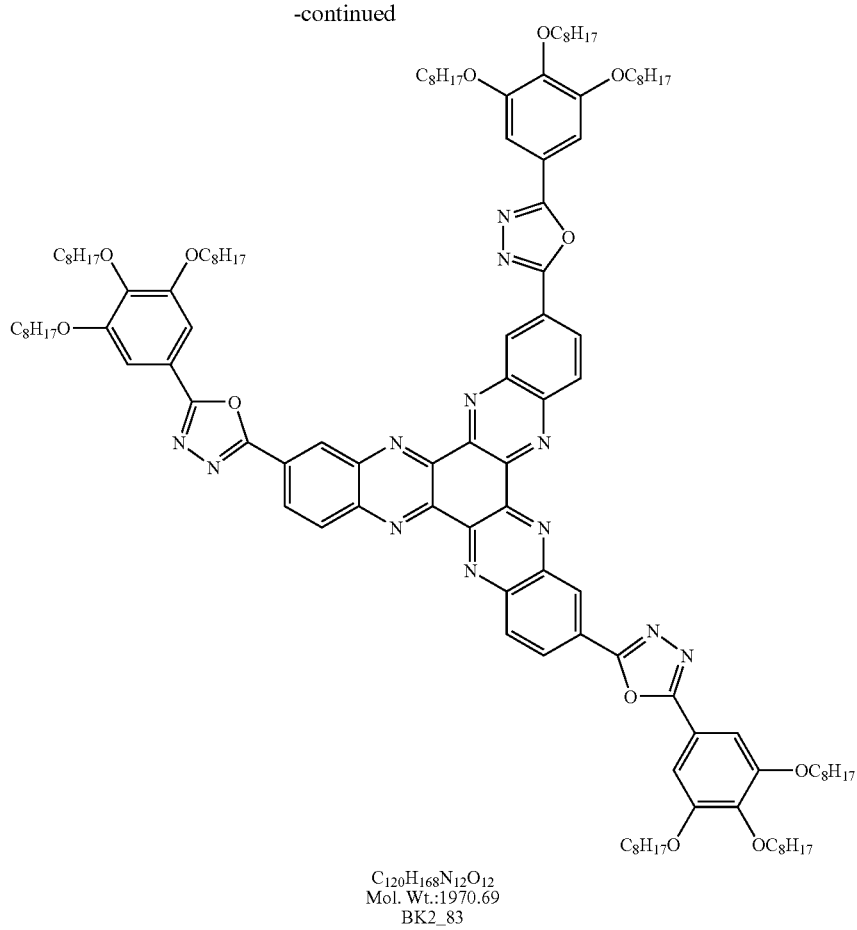

C₁₂₀H₁₆₈N₁₂O₁₂
Mol. Wt.:1970.69
BK2_83

9,14-Bis-[N'-(3,4,5-tris-hexyloxy-benzoyl)-hydrazinocarbonyl]-5,6,11,12,17,18-hexaaza-trinaphthylene-2-carboxylic acid N'-(3,4,5-tris-hexyloxy-benzoyl)-hydrazide [BK2-87]. The title compound was synthesized according to a modified literature procedure, which is incorporated herein by reference. It should be noted that a mixture of the 2,8,14 and 2,8,15 isomers are formed. BK2-43 (3.00 g, 5.25 mmol) was dissolved in 100 ml dry THF and placed in a 500 ml three neck round bottom flask. 3,4,5-Tris-hexyloxybenzoic acid hydrazide SM35 (7.10 g, 16.3 mmol), dissolved in 150 ml THF, was placed in a dropping funnel. The setup was placed in an ice-bath (ice+H₂O). The setup was degassed with argon. At a steady rate, SM35 solution was slowly added dropwise. The reaction mixture was stirred at 0° C. for 7.5 hours, after which 15 ml of pyridine were added and the solution was further stirred at room temperature overnight. Water (1 L) was added to the reaction mixture upon which a green solid formed (9.1 g, 98%). This solid was filtered and dried. This compound was used with no further purification.

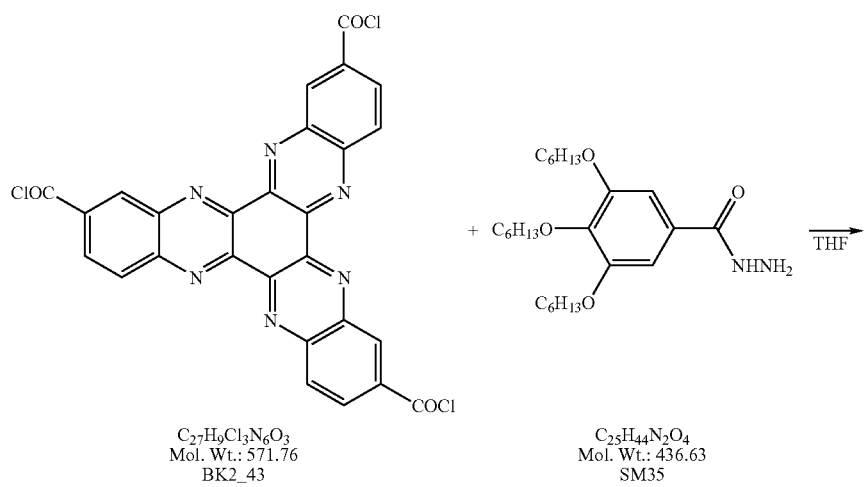

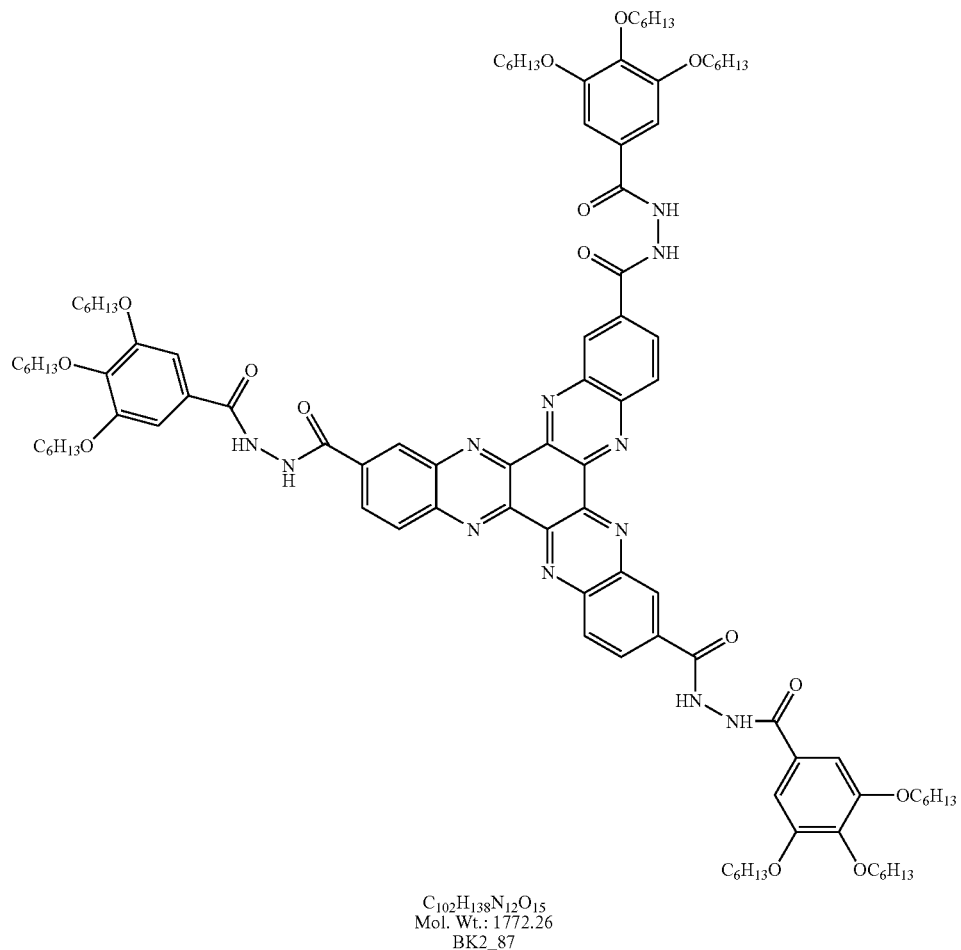

C₁₀₂H₁₃₈N₁₂O₁₅
Mol. Wt.: 1772.26
BK2_87

2,8,15-Tris-[5-(3,4,5-tris-hexyloxyl-phenyl)-[1,3,4]oxa-diazol-2-yl]-5,6,11,12,17,18-hexaazatrinaphthylene [BK2-91]. The title compound was synthesized according to a modified literature procedure.[29] It should be noted that a mixture of the 2,8,14 and 2,8,15 isomers are formed. BK2_77 (9.10 g, 5.14 mmol) was refluxed in 150 ml of POCl₃ at 120° C. for 24 hours. The excess POCl₃ (ca. 120 ml) was distilled off. The remaining solution was added to 1 L of water and ice, upon which a brown solid forms. This solid was filtered and dried. The dark brown solid was passed through a column of silica using hexanes as eluent. The solvent was evaporated to yield 1.09 g (12%) of black shining crystals. Recrystallization from toluene/ethanol led to 640 mg (7%) of brown powder. MALDI-TOF MS (MH+H): m/z 1720.2, calcd for $C_{102}H_{134}N_{12}O_{12}$, 1720.2. Anal. Calcd. for $C_{102}H_{132}N_{12}O_{12}$: C, 71.30; H, 7.74; N, 9.78. Found: C, 70.15; H, 7.78; N, 9.79.

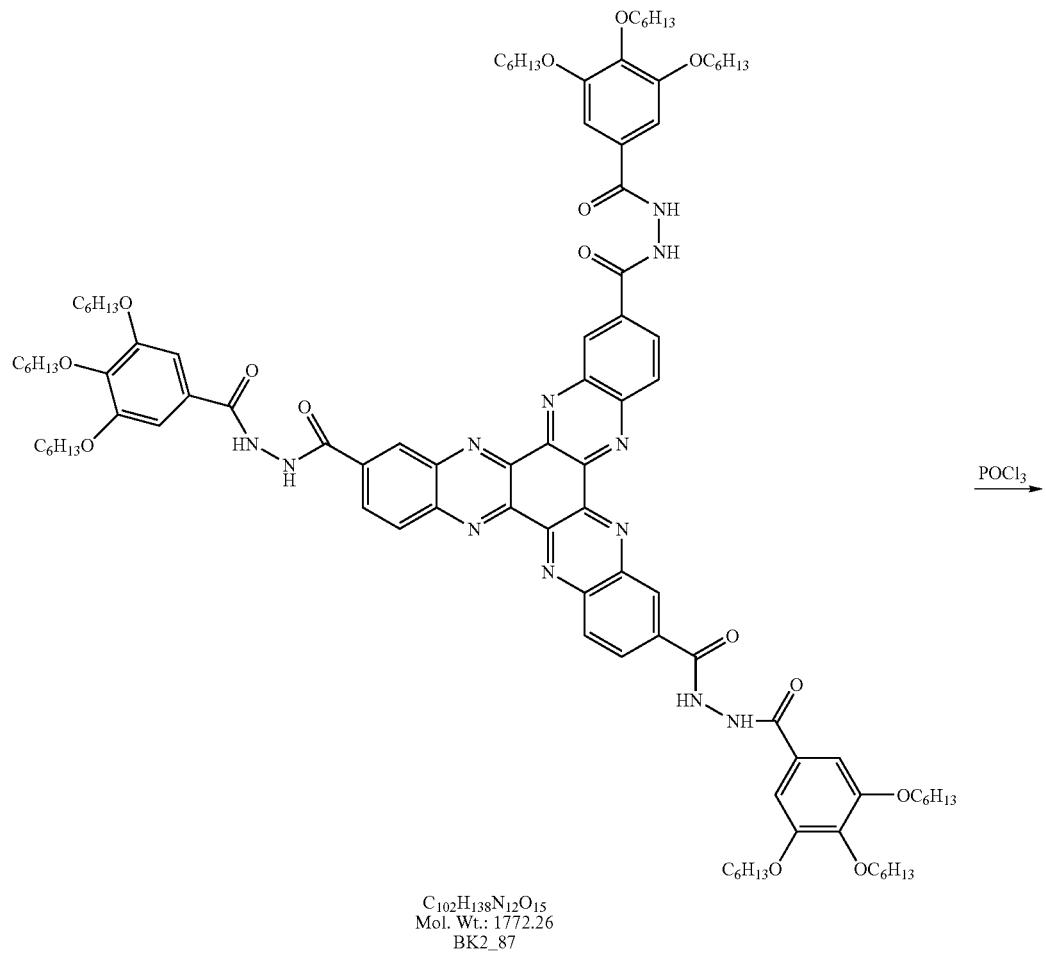

-continued

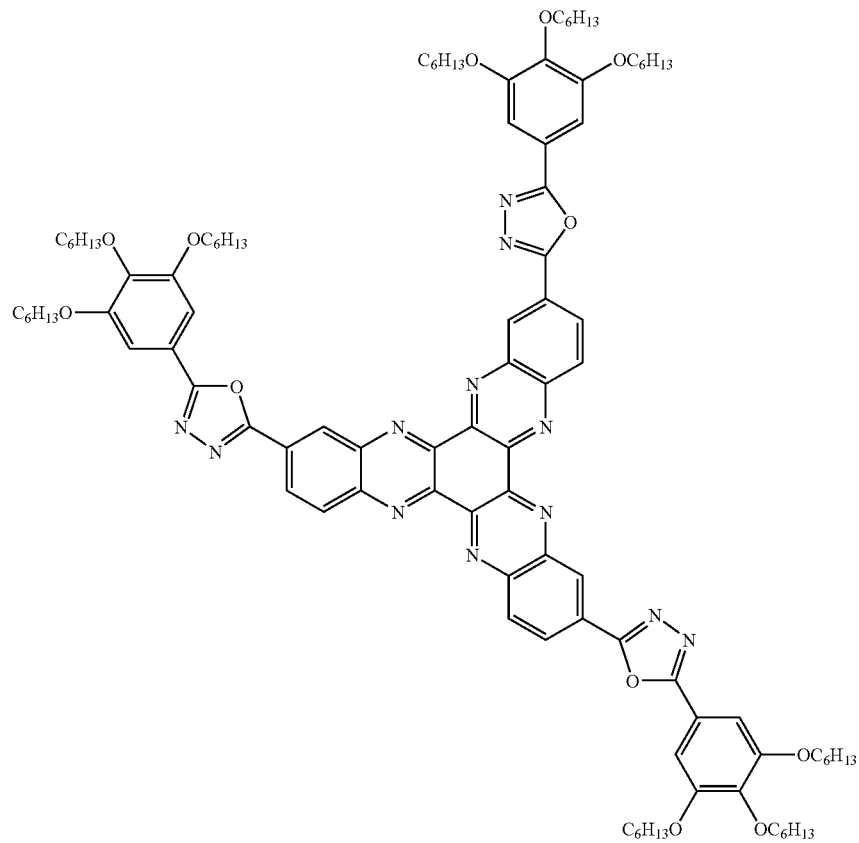

$C_{102}H_{132}N_{12}O_{12}$
Mol. Wt.:1718.21
BK2_91

$N^2,N^8,N^{14}$-Tris[3,4,5-tris(dodecyloxy)benzoyl]diquinoxalino[2,3-a:2',3'-c]phenazine-2,8,14-tricarbohydrazide [BK1_17]. The title compound was synthesized according to a modified literature procedure.[29] It should be noted that a mixture of the 2,8,14 and 2,8,15 isomers are formed. 5,6,11,12,17,18-Hexaazatrinaphthylene 2,8,14-tricarbonyl trichloride BK1_17 (2.28 g, 3.99 mmol) was dissolved in 80 ml dry THF and placed in a 100 ml three neck round bottom flask. 3,4,5-Tris(dodecanyloxy)benzoichydrazide SM6 (9.07 g, 13.2 mmol), dissolved in 200 ml THF, was placed in a dropping funnel. The apparatus was placed in a dewar flask (ice+$H_2O$). The apparatus was degassed with argon. At a steady rate, SM6 solution was slowly added dropwise. The reaction mixture was stirred at 0° C. for two hours, after which 3 ml of pyridine were added and the solution was further stirred at room temperature overnight. Water (200 ml) was added to the reaction mixture upon which a dark solid formed. This solid (10.0 g, 99%) was filtered and dried. This compound was used with no further purification.

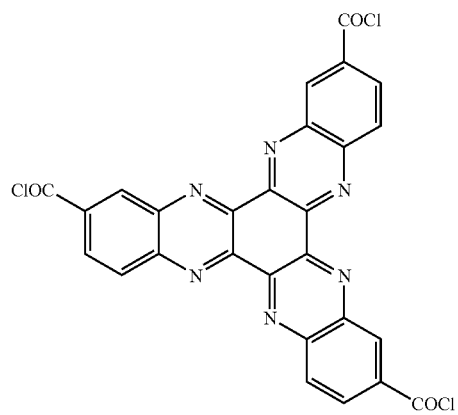

C$_{27}$H$_9$Cl$_3$N$_6$O$_3$
Mol. Wt.: 571.76
BK1_17

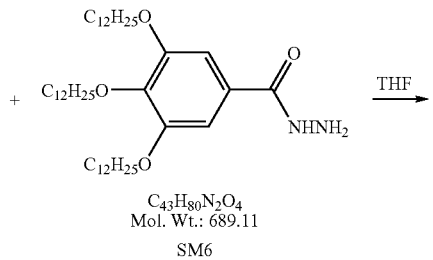

C$_{43}$H$_{80}$N$_2$O$_4$
Mol. Wt.: 689.11
SM6

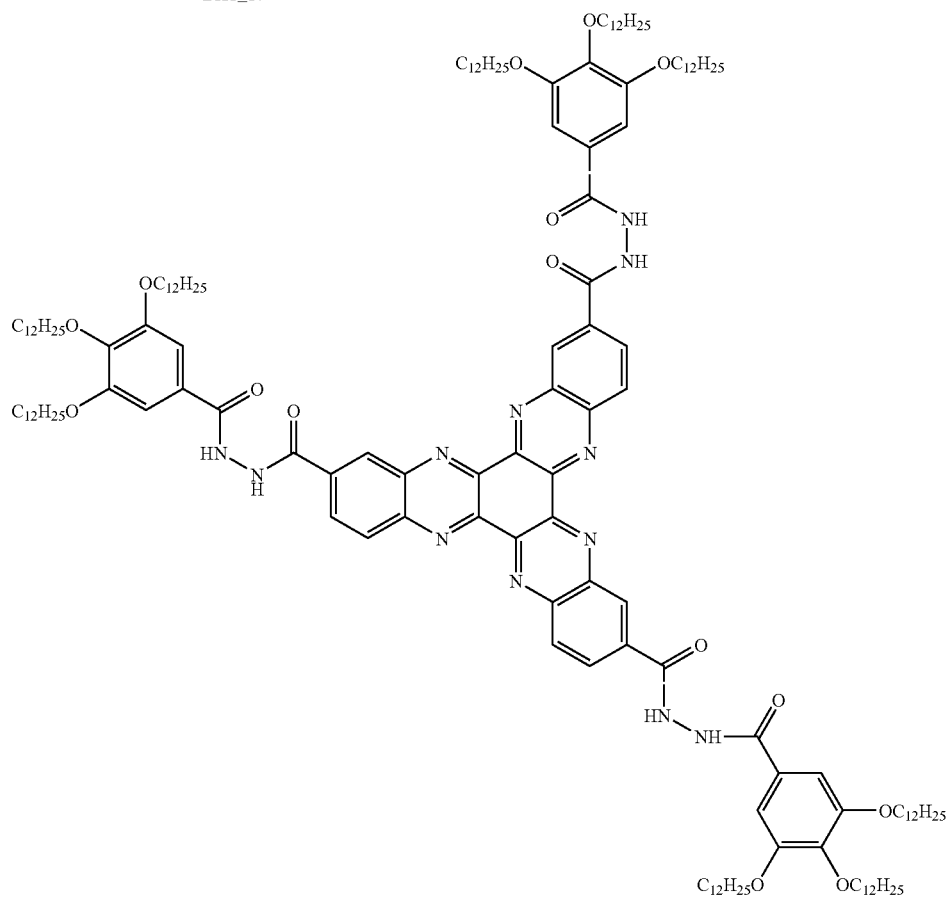

C$_{156}$H$_{246}$N$_{12}$O$_{15}$
Mol. Wt.: 2529.69
BK1_19

2,8,14-Tris{5-[3,4,5-tris(dodecyloxy)phenyl]-1,3,4-oxadiazol-2-yl}diquinoxalino[2,3-a:2',3'-c]phenazine [BK1_21]. The title compound was synthesized according to a modified literature procedure. It should be noted that a mixture of the 2,8,14 and 2,8,15 isomers are formed. N$^2$,N$^8$,N$^{14}$-Tris[3,4,5-tris(dodecyloxy)benzoyl]diquino-xalino[2,3-a:2',3'-c]phenazine-2,8,14-tricarbohydrazide BK1_19 (10.0 g, 3.95 mmol) was heated in 120 ml of POCl$_3$ at 120° C. for 10 hours. The excess POCl$_3$ was distilled off. Water (200 ml) was added and repetitive extraction from CH$_2$Cl$_2$ (3×100 ml) was performed. The extract solutions were combined, dried over MgSO$_4$, and the solvent was then evaporated. The product was then dissolved in minimum amount of CH$_2$Cl$_2$ and precipitated in 600 ml MeOH to yield 6.04 g (61.7%) of yellow-brown solid. A small sample of the solid was further purified by column chromatography on silica, using hexanes as eluent. $^1$H NMR (CDCl$_3$, 300 MHz) δ 9.45-9.37 (m, 3H), 8.91-8.81 (m, 6H), 7.42 (s, 6H), 4.17-4.07 (m, 18H), 1.96-1.49 (m, 18H), 1.59-1.24 (m, 162H), 0.89-0.84 (m, 27H). $^{13}$C NMR (CDCl$_3$, 75 MHz) δ 165.74, 163.01, 153.71, 144.54, 144.14, 143.28, 141.77, 130.01, 128.61, 127.48, 117.75, 105.23, 73.65, 69.38, 31.94, 30.43, 29.80, 29.71, 29.53, 29.43, 29.39, 26.19, 26.14, 22.69, 14.12. MALDI-TOF MS (MH+): m/z 2477.34, calcd for C$_{156}$H$_{241}$N$_{12}$O$_{12}$, 2477.67. Anal. Calcd for C$_{156}$H$_{240}$N$_{12}$O$_{12}$: C, 75.68; H, 9.77; N, 6.79. Found: C, 75.34; H, 9.78; N, 6.72.
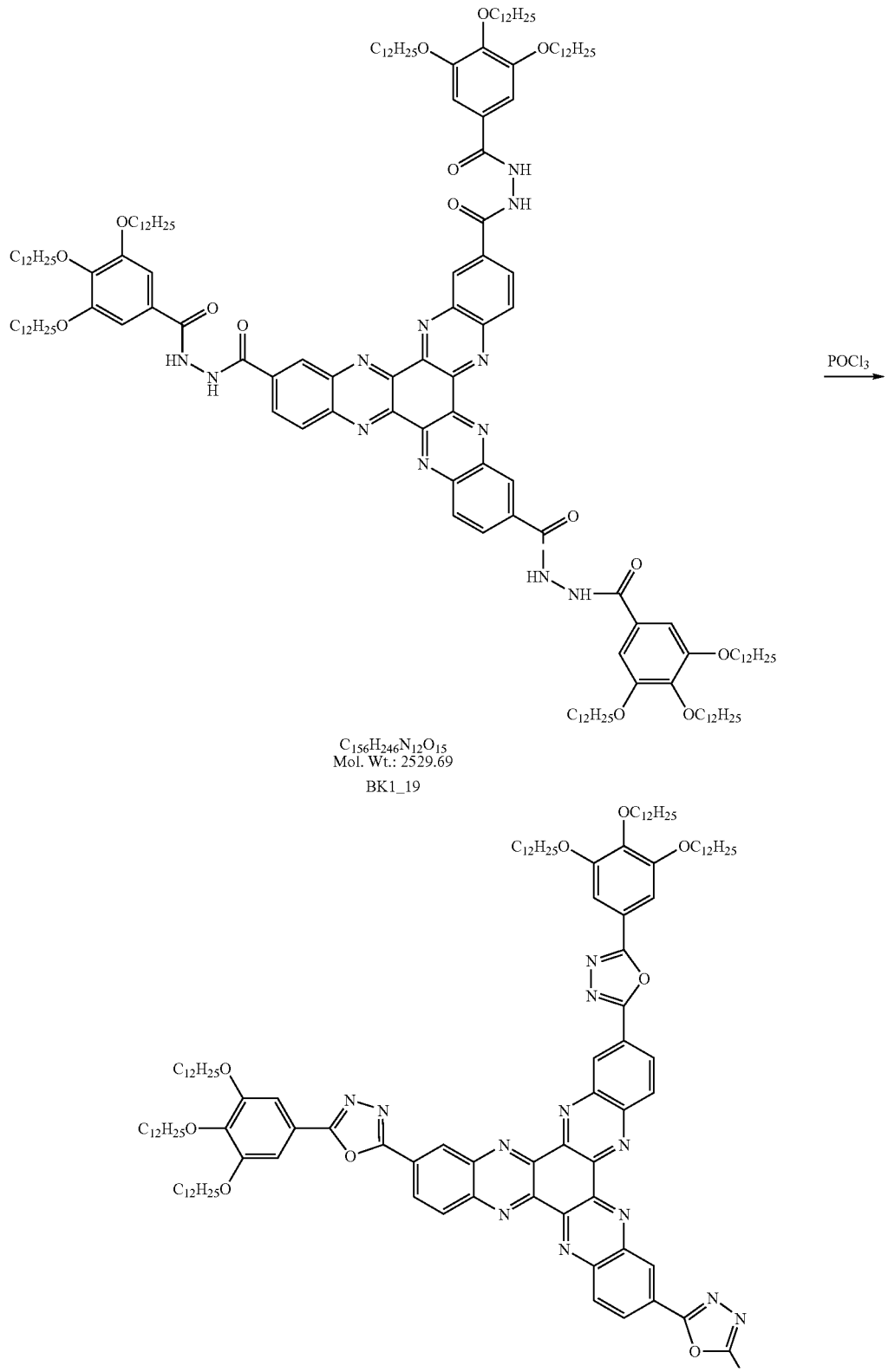

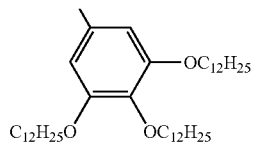

C₁₅₆H₂₄₀N₁₂O₁₂
Mol. Wt.: 2475.65
BK1_21

Patch: BK1_47D 8,14-Bis-(N'-{4-[5-(3,4,5-tris(dodecyloxy))-phenyl)-[1,3,4]oxadiazol-2-yl]-benzoyl}-hydrazinocarbonyl)-5,6,11,12,17,18-hexaaza-trinaphthylene-2-carboxylic acid N'-{4-[5-(3,4,5-tris(dodecyloxy))-phenyl)-[1,3,4]oxadiazol-2-yl]-benzoyl}-hydrazide [BK1_29]. The title compound was synthesized according to a modified literature procedure.[29] It should be noted that a mixture of the 2,8,14 and 2,8,15 isomers are formed. 5,6,11,12,17,18-Hexaazatrinaphthylene 2,8,14-tricarbonyl trichloride BK1_17 (2.00 g, 3.50 mmol) was dissolved in 50 ml dry THF and placed in a 500 ml three neck round bottom flask. 3',4',5'-tris-dodecyloxy-biphenyl-4-carboxylic acid hydrazide SM9 (8.74 g, 11.4 mmol), dissolved in 150 ml THF, was placed in a dropping funnel. The setup was placed in a dewar flask (ice+$H_2O$). The setup was degassed with argon. At a steady rate, SM9 solution was dropped slowly. The reaction mixture was stirred at 0° C. for 2.5 hours, after which 5 ml of pyridine were added and the solution was further stirred at room temperature overnight. Water (300 ml) was added to the reaction mixture upon which a green solid formed. This solid was filtered and dried. This compound was used with no further purification.

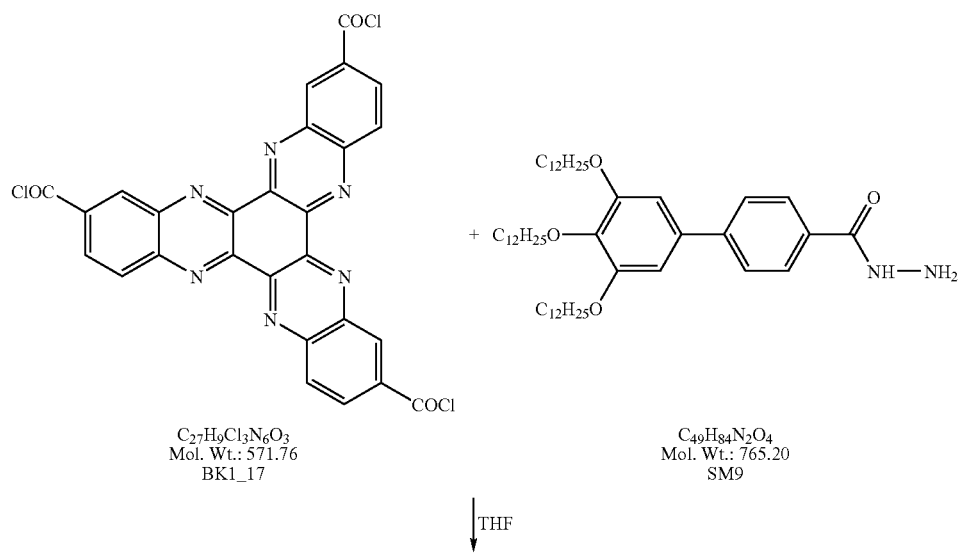

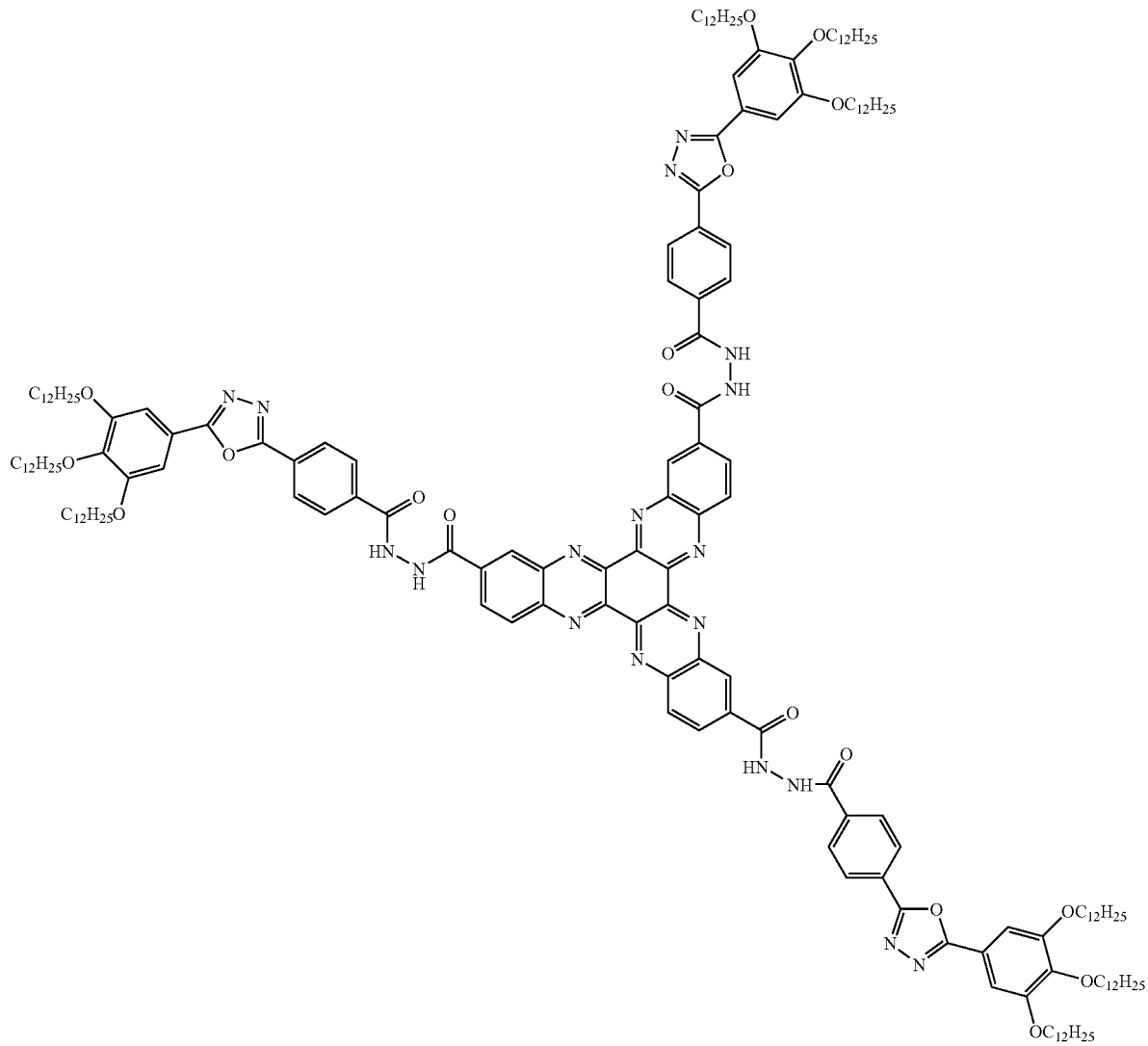

2,8,14-Tris-(5-{4-[5-(3,4,5-tris(dodecyloxy))-phenyl]-[1,3,4]oxadiazol-2-yl]-phenyl}-[1,3,4]oxadiazol-2-yl)-5,6,11,12,17,18-hexaaza-trinaphthylene [BK1_31]. The title compound was synthesized according to a modified literature procedure.[29] It should be noted that a mixture of the 2,8,14 and 2,8,15 isomers are formed. BK1_29 (9.56 g, 3.23 mmol) was heated in 150 ml of $POCl_3$ at 120° C. for 24 hours. The excess $POCl_3$ was distilled off. Water (200 ml) was added and repetitive extraction from $CHCl_3$ was performed. The extract solutions were combined, and the solvent was then evaporated. The solid formed was dissolved in minimum amount of $CHCl_3$ and precipitated in 600 ml of MeOH to yield 6.13 g (65.3%) of green solid. MALDI-TOF MS (MH+H): m/z 2909.49, calcd for $C_{180}H_{253}N_{18}O_{15}$, 2908.97.

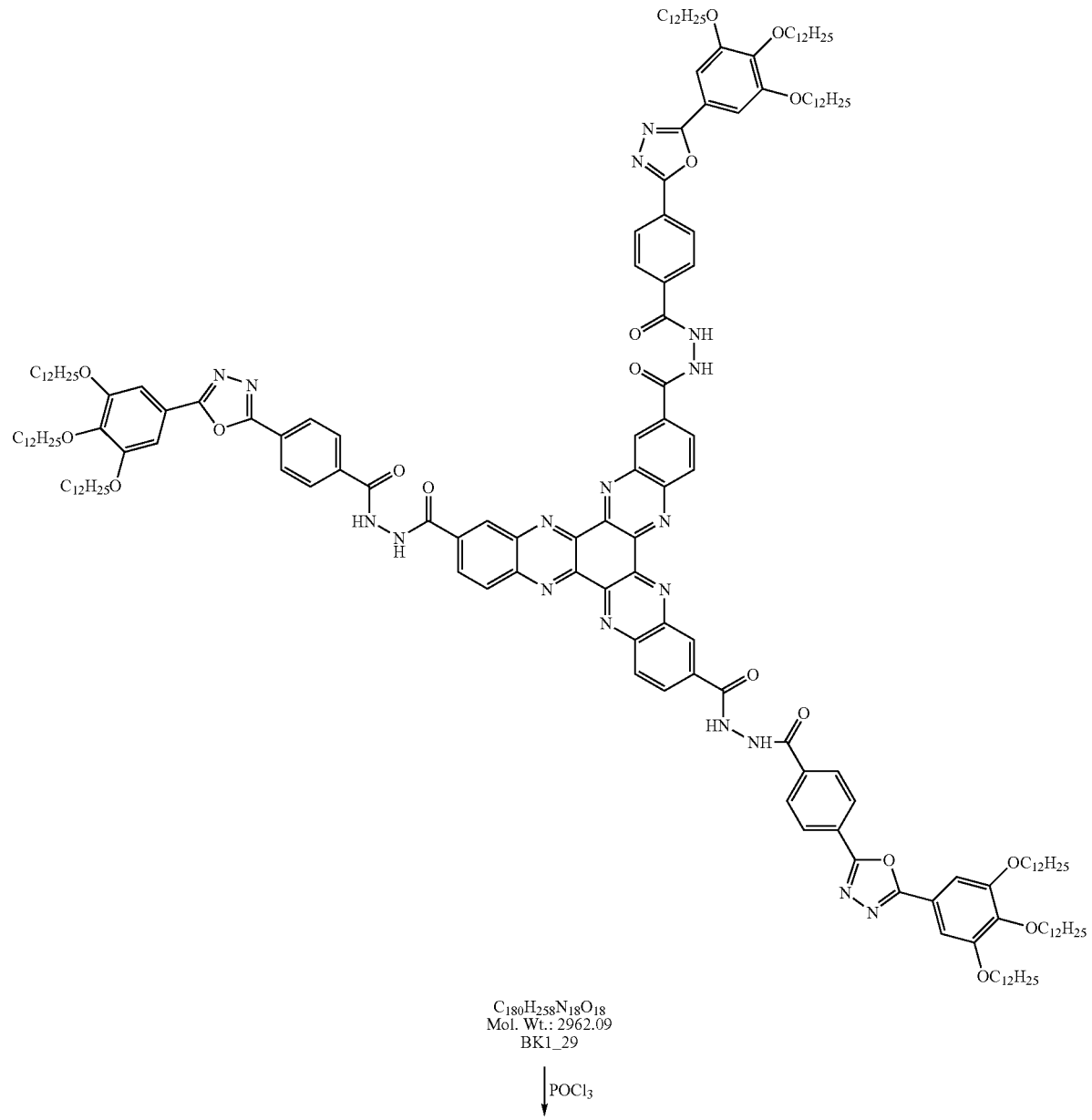

-continued

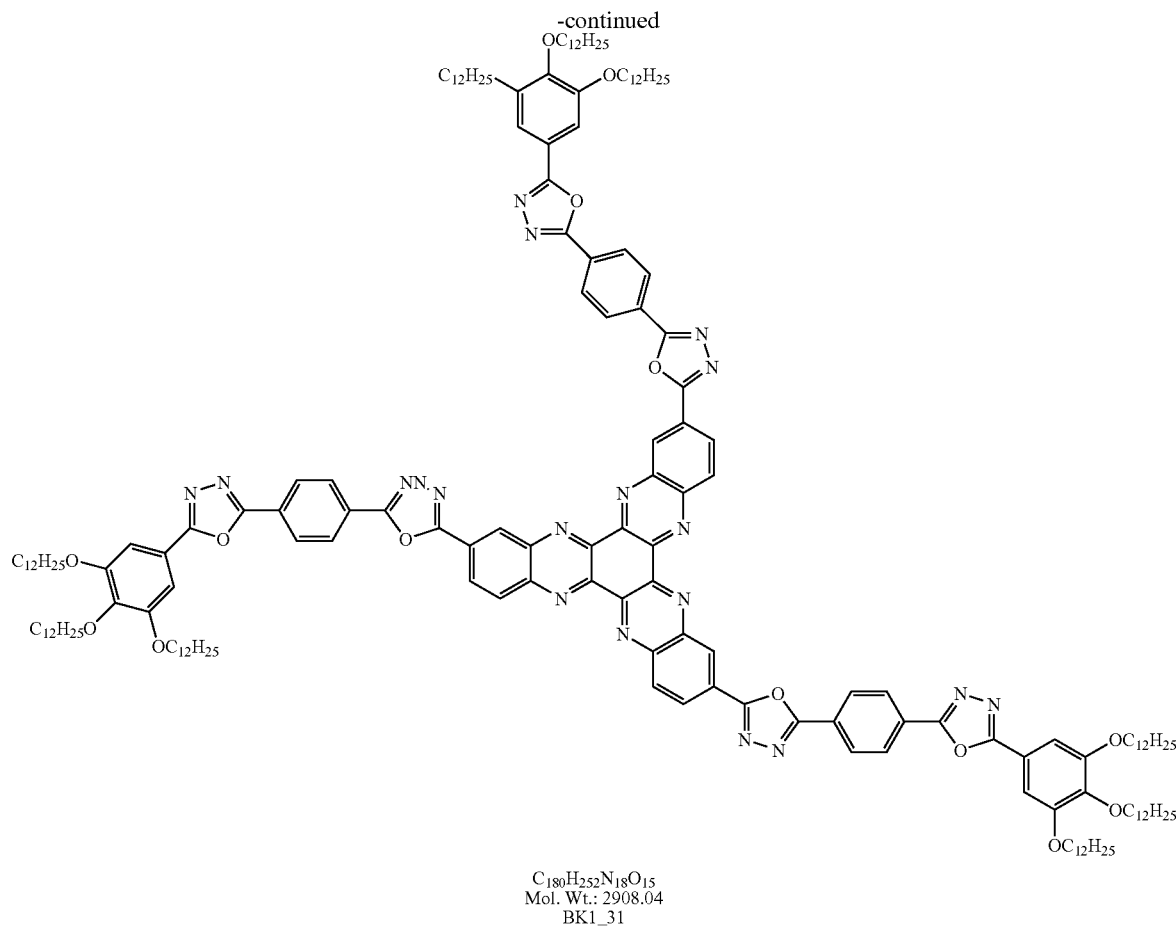

$C_{180}H_{252}N_{18}O_{15}$
Mol. Wt.: 2908.04
BK1_31

3,6-Bis-[2-(3,4-bis-dodecyloxy-phenyl)-vinyl]-11,12-dinitro-dibenzo[a,c]phenazine [BRK_III_63A; BRK_III_71A]. This compound was synthesized according to a modified literature procedure.[30] 4,5-Dinitro-1,2-phenylenediamine SM29 (689 mg, 3.48 mmol), 3,6-bis-[2-(3,4-bis-dodecyloxy-phenyl)-vinyl]-phenanthrene-9,10-dione JYC_III_067-A (4.00 g, 3.48 mmol) were refluxed in 200 ml of glacial acetic acid/absolute ethanol (1:1) in a 500 ml round bottom flask at 130° C. for 24 hours. The solution was then cooled down to room temperature and was then filtered to yield 4.31 g (94%) of red powder. This compound was used for next step with no further purification. $^1$H (300 MHz, $CDCl_3$) δ 8.92-8.90 (d, J=8.7 Hz, 2H), 8.52 (s, 2H), 8.81 (s, 2H), 7.74-7.71 (d, J=8.7 Hz, 2H), 7.22-7.17 (d, J=16.2 Hz, 2H), 7.13 (s, 2H), 7.10-7.07 (d, J=8.4 Hz, 2H), 7.03-6.98 (d, J=16.2 Hz, 2H), 6.91-6.88 (d, J=8.4 Hz, 2H), 4.14-4.09 (t, J=6.6 Hz, 4H), 4.08-4.04 (t, J=6.6 Hz, 4H), 1.96-1.84 (sextet, 8H), 1.60-1.48 (m, 8H), 1.47-1.20 (m, 72H), 0.92-0.86 (two overlapped triplets, 12H). $^{13}$C ($CDCl_3$, 75 MHz) δ 149.98, 149.18, 144.91, 141.39, 141.15, 140.98, 132.42, 131.64, 129.20, 126.79, 125.09, 124.80, 120.73, 113.23, 111.59, 69.46, 69.18, 32.03, 29.84, 29.79, 29.69, 29.61, 29.57, 29.49, 29.43, 26.29, 26.20, 22.81, 14.24 ppm.

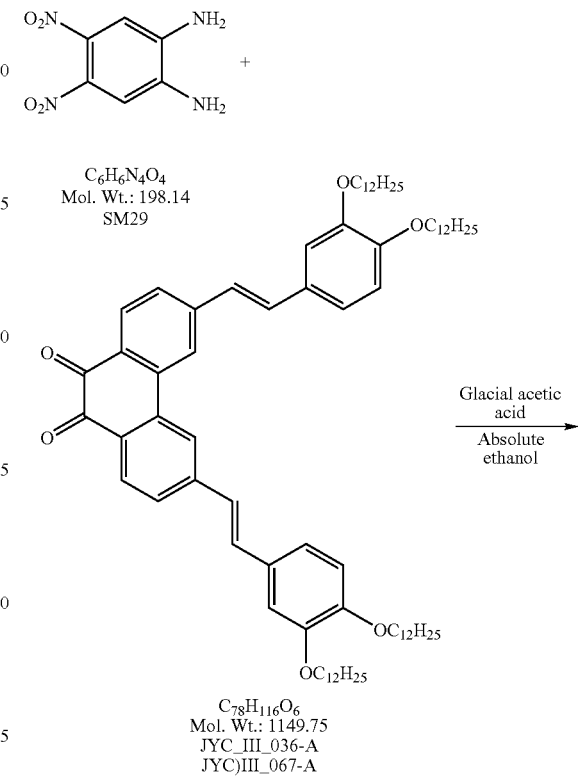

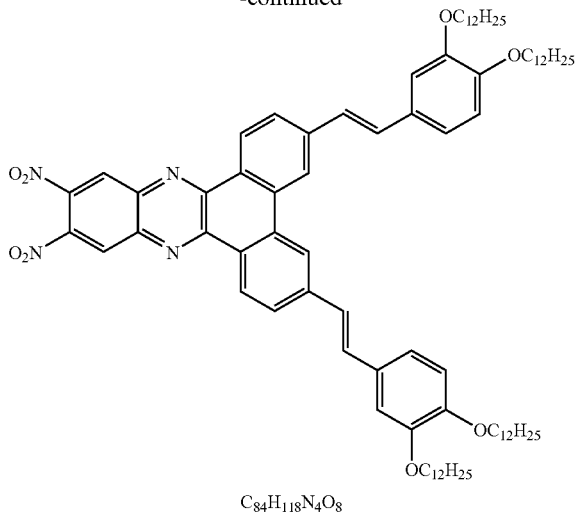

C<sub>84</sub>H<sub>118</sub>N<sub>4</sub>O<sub>8</sub>
Mol. Wt.: 1311.86
BRK_III_63A
BRK_III_71A 3,6-Bis-[2-(3,4-bis-dodecyloxy-phenyl)-vinyl]-dibenzo[a,c]phenazine-11,12-diamine [BRK_III_67A]. This compound was synthesized according to a modified literature procedure.[52] A Schlenk tube was charged with 3,6-Bis-[2-(3,4-bis-dodecyloxy-phenyl)-vinyl]-11,12-dinitro-dibenzo[a,c]-phenazine BRK_III_63A (564 mg, 0.43 mmol) and (970 mg, 4.30 mmol) of SnCl$_2$·2H$_2$O and was subjected to vacuum. Under N$_2$, 30 ml of O$_2$-free ethanol was transferred to the reaction mixture, which was heated at 70° C. The color of the reaction mixture did not change after one hour and TLC did not show the conversion of the starting material. Additional 50 ml of O$_2$-free ethanol was added and the mixture was refluxed for 23 hours. The reaction was allowed to cool down to room temperature and was then dropped over ice. The solution was extracted with 3×150 ml of ether. The ether extracts were combined and were dried over MgSO$_4$ and was filtered. The solvent (solution is blue fluorescent) was evaporated under vacuum to yield 122 mg (23% yield) of brown solid. HRMS-MALDI-TOF (M+H): m/z 1251.9535; calcd for C$_{84}$H$_{123}$N$_4$O$_4$, 1251.9539.

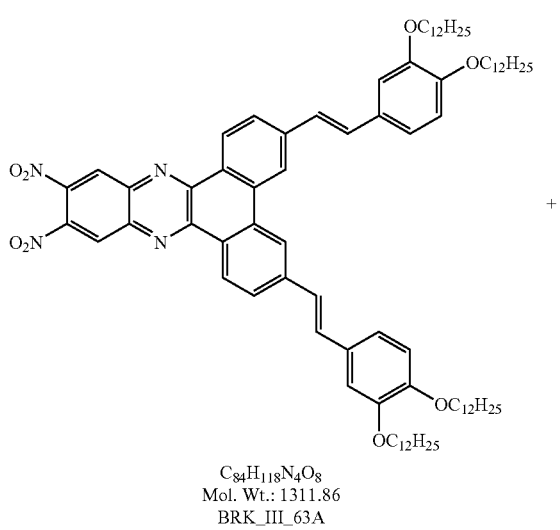

C<sub>84</sub>H<sub>118</sub>N<sub>4</sub>O<sub>8</sub>
Mol. Wt.: 1311.86
BRK_III_63A

+

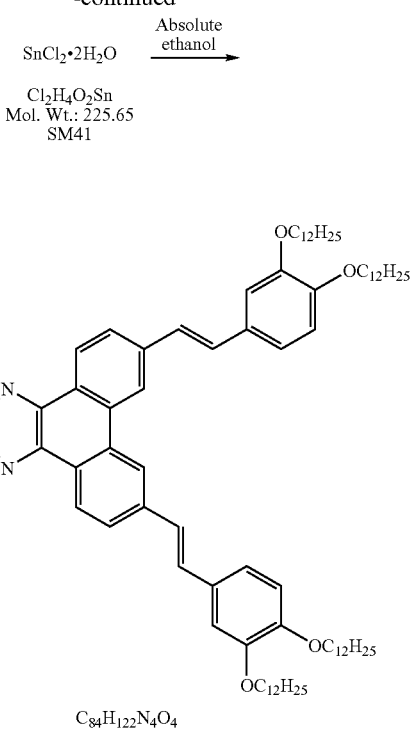

5,6,11,12,17,18-Hexaazatrinaphthylene 2,8,14-tricarboxylic acid [BK1_5; BK1_11]. The title compound was synthesized according to a literature procedure.[30] It should be noted that a mixture of the 2,8,14 and 2,8,15 isomers are formed. Hexaketocyclohexane octahydrate (5.00 g, 16.0 mmol) and 3,4-diaminobenzoic acid (18.0 g, 118 mmol) were refluxed in 600 ml of glacial acetic acid at 150° C. for 5 hours. The reaction mixture was then filtered and washed with 5×60 ml of hot glacial acid. The solid was then refluxed with 100 ml of 30% nitric acid for 3 hours at 120° C. (this step was done for BK1_11 but not BK1_5). The yellow solid (6.07 g, 73.4%) was filtered and dried under vacuum (the solid BK1_11 turns green after 3 days storage in a vial; BK1_5 was originally green). Mp>390° C. This compound was used with no further purification. $^1$H NMR (DMSO-d$_6$, 300 MHz) δ 8.76 (s, 2H), 8.67 (s, 1H), 8.48-8.32 (m, 6H). MALDI-TOF MS (M+H): m/z 518.175, calcd for C$_{27}$H$_{13}$N$_6$O$_6$, 517.428.

-continued

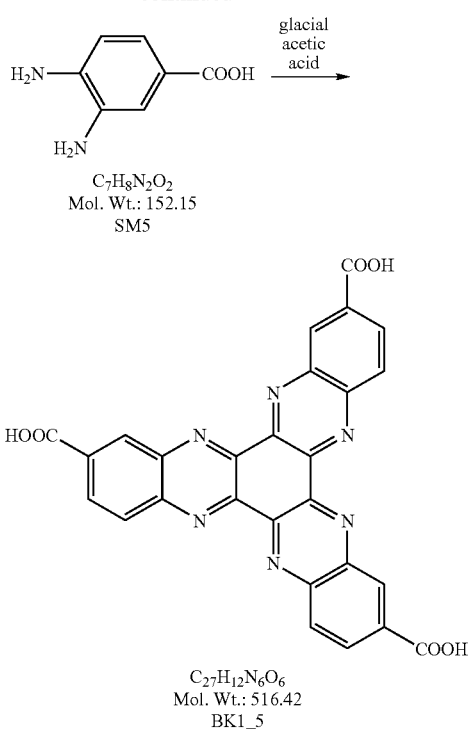

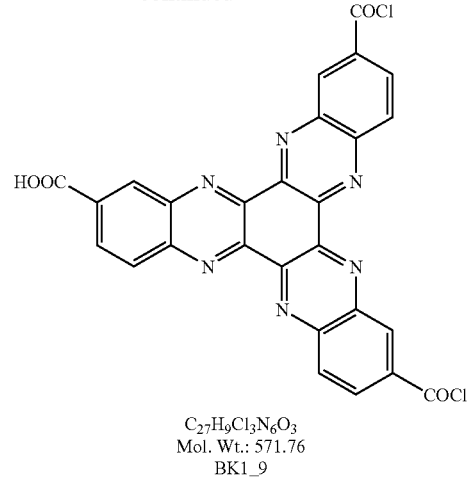

5,6,11,12,17,18-Hexaazatrinaphthylene 2,8,14-tricarbonyl trichloride [BK1_9; BK1_17]. The title compound was synthesized according to a literature procedure.[30] It should be noted that a mixture of the 2,8,14 and 2,8,15 isomers are formed. 5,6,11,12,17,18-Hexaazatrinaphthylene 2,8,14-tricarboxylic acid BK1_5 (1.7 g, 3.29 mmoles) was refluxed in 30 ml $SOCl_2$ at 115° C. for 24 hours. Excess $SOCl_2$ was evaporated to yield 1.76 g (93.6%) of brownish powder. Mp>390° C. This compound was used with no further purification. $^1$H NMR (CDCl$_3$, 200 MHz), 9.52-9.49 (m, 3H), 8.74-8.73 (d, J=1.6 Hz, 1H), 8.71-8.70 (d, J=1.4 Hz, 2H), 8.63-8.56 (m, 3H). MALDI-TOF MS: m/z 570.898, calcd for $C_{27}H_9Cl_3N_6O_6$, 571.76.

5,6,11,12,17,18-Hexaaza-trinaphthylene-2,8,15-tricarboxylic acid triethyl ester [DD1_39]. The title compound was synthesized according to a literature procedure.[30] It should be noted that a mixture of the 2,8,14 and 2,8,15 isomers are formed. 5,6,11,12,17,18-Hexaaza-trinaphthylene-2, 8,14-tricarbonyl trichloride DD1_21 (1.00 g, 1.75 mmol) was suspended in 15 ml of ethanol. Pyridine (15.0 ml) was slowly added to the reaction mixture, which was stirred at room temperature for 24 hours. Dichloromethane was then added and the resulting solution was passed through a short silica column using dichloromethane as eluent. The solvent was evaporated and the yellow solid was boiled in ethanol and filtered. The yellow solid was further purified by column chromatography using dichloromethane:ethyl acetate (1:1) as the eluent mixture. The obtained yellow solid was dissolved in the minimum amount of dichloromethane and precipitated with 30 ml of ethanol to yield 60 mg (5.7% yield) of yellow solid. $^1$H NMR (CDCl$_3$, 300 MHz) δ 9.36-9.35 (d, J=1.80 Hz, 3H), 8.69-8.66 (d, J=9.00 Hz, 3H), 8.61-8.58 (dd, $J_o$=8.59 Hz, $J_m$=1.50 Hz, 1H), 4.59-4.52 (quartet, J=7.2 Hz, 6H), 1.56-1.51 (t, J=6.9 Hz, 9H). $^{13}$C NMR (CDCl$_3$, 75 MHz) δ 165.33, 145.24, 144.61, 143.94, 142.96, 133.99, 133.30, 132.03, 130.91, 62.23, 14.56. MALDI-TOF MS (M+H): m/z 601.22, calcd for $C_{33}H_{25}N_6O_6$, 601.59.

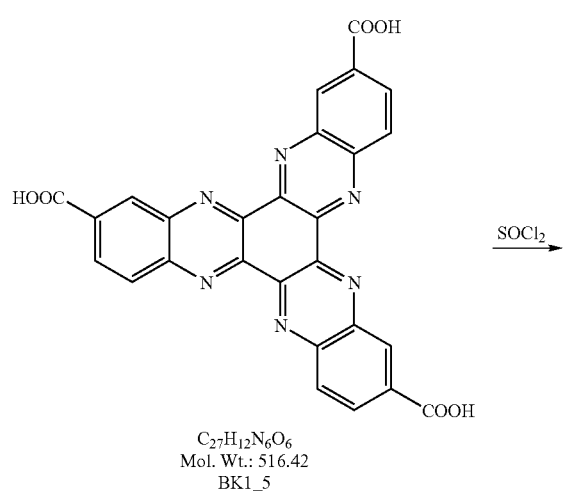 SOCl$_2$ → 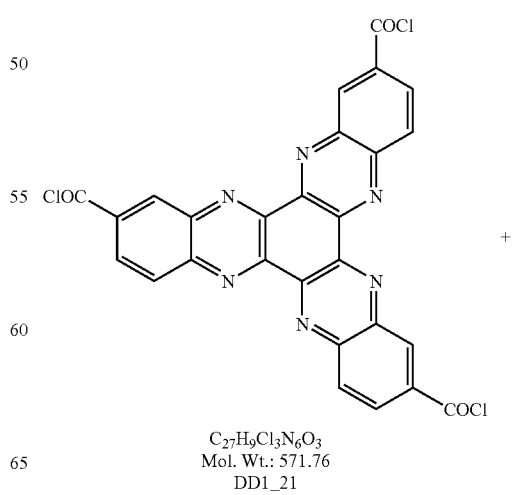 +

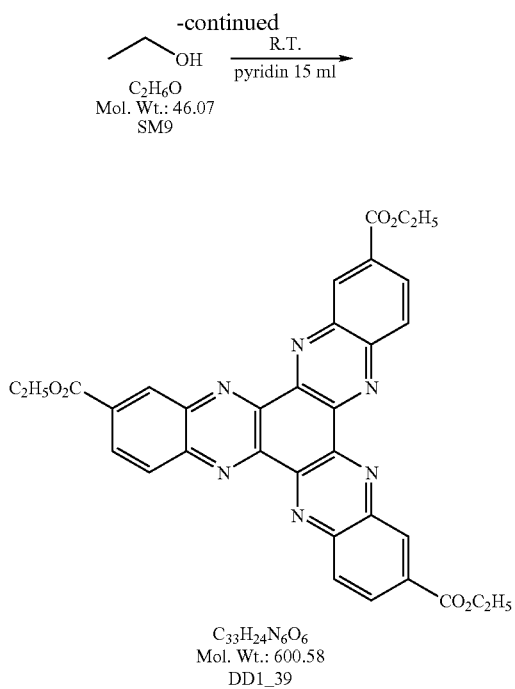
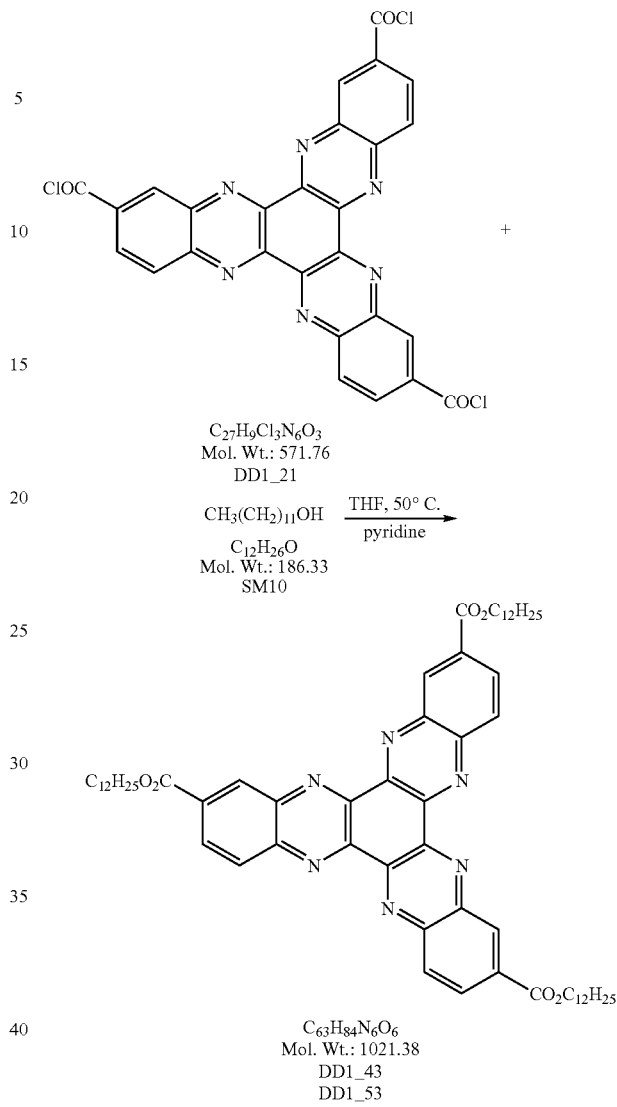

5,6,11,12,17,18-Hexaaza-trinaphthylene-2,8,15-tricarboxylic acid tridodecyl ester [DD1_43, DD1_53]. The title compound was synthesized according to a modified literature procedure.[30] It should be noted that a mixture of the 2,8,14 and 2,8,15 isomers are formed. 5,6,11,12,17,18-Hexaaza-trinaphthylene-2,8,14-tricarbonyl trichloride DD1_21 (2.00 g, 3.50 mmol) was suspended in 15 ml of THF and 1-dodecanol SM 10 (15.0 g, 80.5 mmol) was added. Pyridine (15.0 ml) was slowly added to the reaction mixture, which was stirred at 50° C. for 72 hours. Dichloromethane was added to the suspension and the resulting solution was passed through a short silica column using dichloromethane as eluent. The solvent was evaporated and the green solid was dissolved in the minimum amount of dichloromethane and precipitated with 40 ml of ethanol. The resulting green solid was further purified by column chromatography using dichloromethane:ethyl acetate (1:1) as eluent mixture. The obtained green solid was dissolved in the minimum amount of dichloromethane and precipitated with 60 ml of ethanol to yield 1.58 g (44% yield) of green solid. $^1$H NMR (CDCl$_3$, 300 MHz) δ 9.36-9.34 (m, 3H), 8.70-8.67 (d, J=9.3 Hz, 1H), 8.68-8.65 (d, J=9.3 Hz, 2H), 8.62-8.56 (m, 3H), 4.51-4.45 (t, J=6.9 Hz, 6H), 1.92-1.82 (m, 6H), 1.88-1.16 (m, 45H), 0.90-0.84 (m, 9H). $^{13}$C NMR (CDCl$_3$, 75 MHz) 165.83, 145.11, 145.06, 144.45, 144.40, 144.27, 144.23, 143.98, 143.94, 143.74, 143.7, 142.75, 142.80, 142.86, 142.89, 134.04, 134.00, 133.99, 133.90, 133.14, 133.06, 132.00, 131.91, 130.91, 130.85, 66.41, 32.12, 29.90, 29.88 (m), 29.83, 29.61, 29.57, 29.00, 26.36, 22.89, 14.32. MALDI-TOF MS (M+H): m/z 1022.75, calcd for $C_{63}H_{85}N_6O_6$, 1022.37. Anal. Calcd for $C_{63}H_{84}N_6O_6$: C, 74.08; H, 8.29; N, 8.23; O, 9.40. Found: C, 74.01; H, 8.28; N, 8.26, O, 9.45.

5,6,11,12,17,18-Hexaaza-trinaphthylene-2,8,15-tricarboxylic acid tris-(2,2,3,3,4,4,4-heptafluoro-butyl) ester [DD1_45]. The compound was synthesized according to a literature procedure.[30] It should be noted that a mixture of the 2,8,14 and 2,8,15 isomers are formed. 5,6,11,12,17,18-Hexaaza-trinaphthylene-2,8,14-tricarbonyl trichloride DD1_21 (2.00 g, 3.50 mmol) was suspended in 15 ml of 2,2,3,3,4,4,4-heptafluoro-butan-1-ol SM 11. Pyridine (15.0 ml) was slowly added to the reaction mixture, which was stirred at room temperature for 72 hours. Dichloromethane was added to the suspension and the resulting solution was passed through a short silica column using dichloromethane as eluent. The resulting solution was evaporated and the yellow-green solid was boiled in ethanol and filtered. The resulting yellow-green solid was further purified by column chromatography using dichloromethane:ethyl acetate (1:1) as an eluent mixture. The obtained yellow-green solid was dissolved in a minimum amount of dichloromethane and was precipitated with 50 ml of ethanol to yield 120 mg (yield 3%) of yellow green solid. $^1$H NMR (CDCl$_3$, 300 MHz) δ 9.461-9.431 (m, 3H), 8.79-8.76 (d, J=8.7 Hz, 1H), 8.77-8.74 (d, J=8.7 Hz, 2H), 8.65-8.61 (m, 3H), 5.09-4.95 (t, J=13.2 Hz, 6H). MALDI-TOF MS (MH+H): m/z 1064.44, calcd for $C_{39}H_{17}F_{21}N_6O_6$, 1064.56.

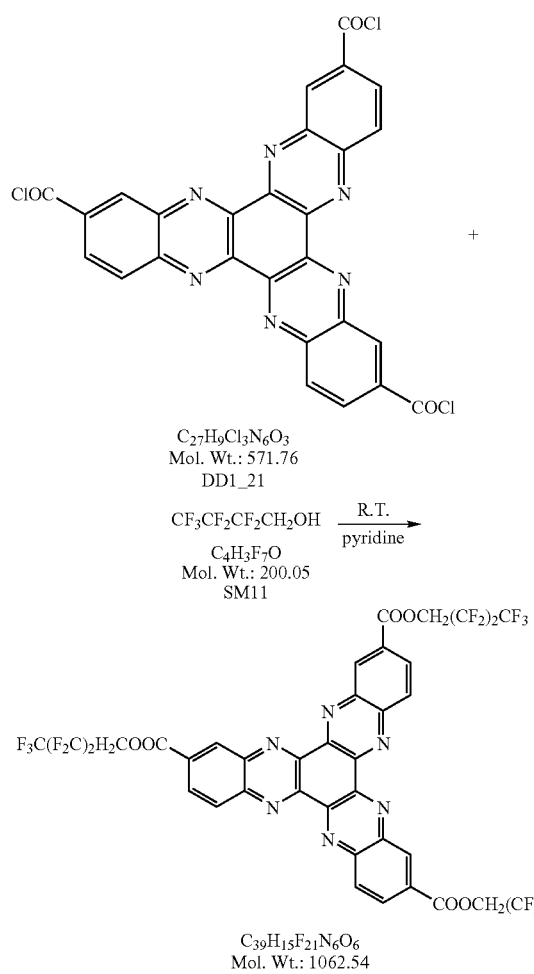

5,6,11,12,17,18-Hexaaza-trinaphthylene-2,8,15-tricarboxylic acid tripentafluoro-phenylmethyl ester [DD1_47]. The title compound was synthesized according to a modified literature procedure.[30] It should be noted that a mixture of the 2,8,14 and 2,8,15 isomers are formed. 5,6,11,12,17,18-Hexaaza-trinaphthylene-2,8,14-tricarbonyl trichloride DD1_21 (2.00 g, 3.5 mmol) was suspended in 15 ml of THF and pentafluorophenyl-methanol (15.0 g, 75.7 mmol) SM 12 was added. Pyridine (15.0 ml) was slowly added to the reaction mixture, which was stirred at 50° C. for 72 hours. Dichloromethane was added to the suspension and the resulting solution was passed through a short silica column using dichloromethane:ethyl acetate (1:1) as eluent. The solvent was evaporated and the green solid was dissolved in the minimum amount of chloroform and precipitated with 30 ml of ethanol. The resulting green-solid was further purified by column chromatography using dichloromethane:ethyl acetate (1:1) as eluent. The obtained green solid was dissolved in the minimum amount of dichloromethane and was precipitated with 60 ml of ethanol to yield 1.29 g of green solid (yield 35%). $^1$H NMR (CDCl$_3$, 300 MHz) δ 9.29-9.27 (m, 3H), 8.67-8.64 (d, J=9.30 Hz, 3H), 8.58-8.55 (m, 3H), 5.60 (s, 6H). $^{13}$C NMR (CDCl$_3$, 75 MHz) δ 164.53, 147.75 (m), 145.29, 144.66, 144.46, 144.08, 143.89, 142.76, 139.64 (m), 136.23 (m), 133.70, 133.55, 132.86, 132.82, 132.76, 132.70, 131.87, 131.74, 131.20, 131.14, 119.28, 109.21 (m), 54.90. $^{19}$F NMR (CDCl$_3$, 282 MHz) δ (−142.32)-(−142.49) (m, 6F), (−152.37)-(−152.62) (quartet, J=27.4 Hz, 3F), (−161.74)-(−161.98) (m, 6F). MALDI-TOF MS (MH+H): m/z 1058.22, calcd for C$_{48}$H$_{17}$F$_{15}$N$_6$O$_6$, 1058.67. Anal. calcd. for C$_{48}$H$_{15}$F$_{15}$N$_6$O$_6$: C, 54.56; H, 1.43; F, 26.97; N, 7.95. Found: C, 54.28; H, 1.43; F, 26.92; N, 7.95.

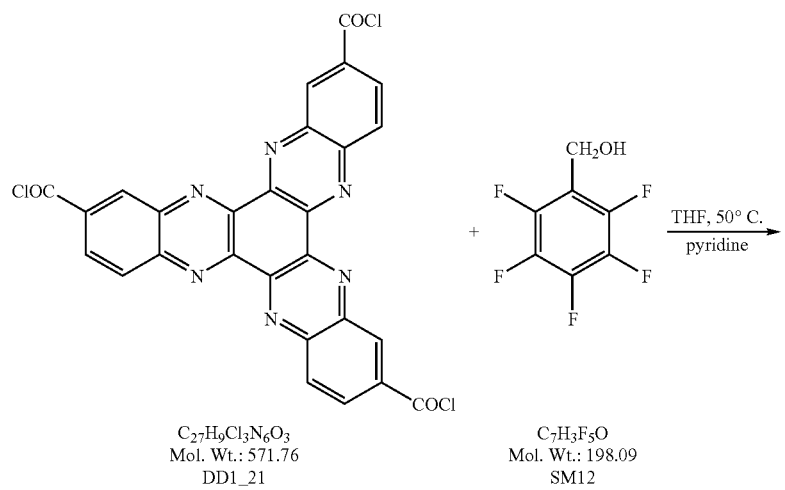

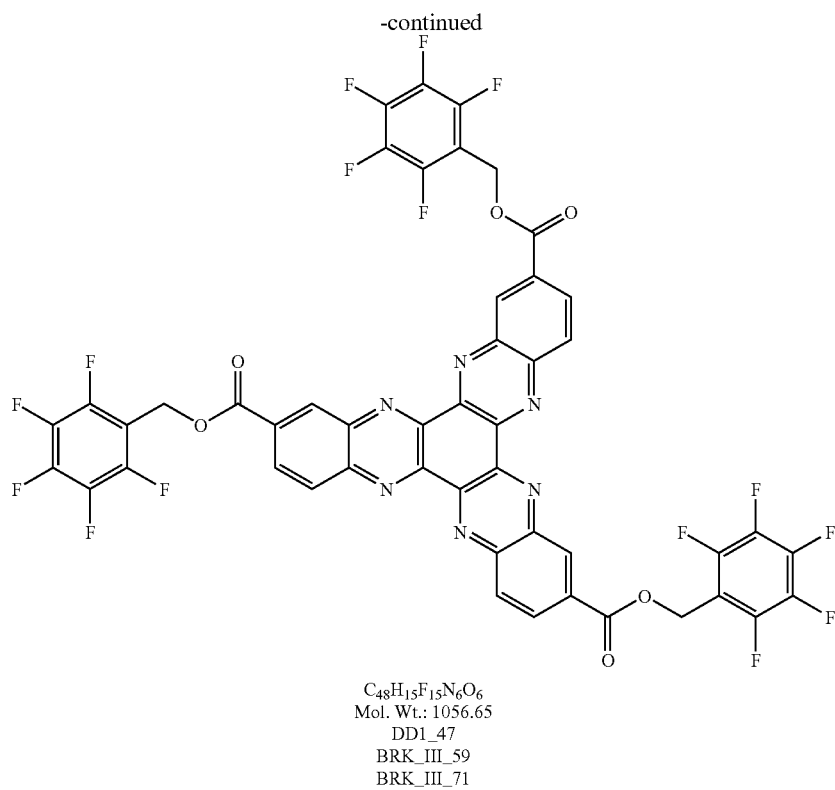

C<sub>48</sub>H<sub>15</sub>F<sub>15</sub>N<sub>6</sub>O<sub>6</sub>
Mol. Wt.: 1056.65
DD1_47
BRK_III_59
BRK_III_71

5,6,11,12,17,18-Hexaaza-trinaphthylene-2,8,15-tricarboxylic acid tripentafluoro-phenylmethyl ester [BRK_III_78]. Modified Procedure. The title compound was synthesized according to a modified literature procedure.[30] It should be noted that a mixture of the 2,8,14 and 2,8,15 isomers are formed. 5,6,11,12,17,18-Hexaaza-trinaphthylene-2,8,14-tricarbonyl trichloride BRK_III_56D (11.6 g, 20.2 mmol) was suspended in 100 ml of THF and pentafluorophenyl-methanol (75.0 g, 379 mmol) SM12 was added. Pyridine (20.0 ml) was slowly added to the reaction mixture, which was stirred at 50° C. for 72 hours. Solvent was evaporated. Dichloromethane:ethyl:acetate (1:1) was added to the suspension and the resulting solution was passed through a short alumina column using dichloromethane:ethyl acetate (1:1) as eluent. The solvent was evaporated and the green solid was dissolved in the minimum amount of chloroform and precipitated with 300 ml of ethanol. The resulting green solid was further purified by column chromatography using dichloromethane:ethyl acetate (1:1) as eluent. The obtained green solid was dissolved in the minimum amount of dichloromethane and was precipitated with 300 ml of ethanol to yield 4.76 g of green solid (yield 22% over two steps). The compound was then recrystallized from CHCl$_3$/EtOH. To separate the 2,8,14- and 2,8,15-isomers, the compound was run through a column of silica using DCM:ethyl acetate (9:1). Amounts of 45 mg of the 2,8,14-isomer, BRK_III_78E1, 2.417 g of 2,8,15-isomer, BRK_III_78E4, 534 mg and 1.246 g of mixture of isomers, BRK_III_78E2 and BRK_III_78E3, respectively, were isolated. BRK_III_78E4 was run again through a column of silica using DCM:ethyl acetate (9:1). After solvent evaporation, the compound was dissolved in 10 ml of CHCl$_3$ and was then reprecipitated in 300 ml MeOH. An amount of 2.389 g of BRK_III_78F2 was isolated.

[BRK_III_78F2]. $^1$H NMR (500 MHz, CDCl$_3$) δ 9.23-9.21 (two quasi-doublets, J=1.5 Hz, 3H), 8.60 & 8.59 (two br singlets, 3H), 8.53-8.48 (m, 3H), 5.59 & 5.58 (two br singlets, 6H). $^{13}$C NMR (CDCl$_3$, 125 MHz) δ 164.32, 146.88 (m), 145.17, 144.87 (m), 144.54, 144.37, 144.35, 143.99, 143.80, 143.09 (m), 142.67, 142.62, 141.15 (m), 138.69 (m), 136.71 (m), 136.57, 133.55, 133.51, 132.68, 132.64, 132.52, 131.71, 131.59, 131.02, 130.96, 109.09, 108.96, 54.68 ppm. $^{19}$F NMR (CDCl$_3$, 376 MHz) δ (−141.86)-(−142.01) (m, 6F), (−152.02)-(−152.18) (quartet, J=19.6 Hz, 3F), (−161.41)-(−161.59) (m, 6F). $^{19}$F NMR Chemical shifts are relative to trifluoromethylbenzene which was used as an external standard. MALDI-TOF MS (M+H): m/z 1057.0983, calcd for C$_{48}$H$_{16}$F$_{15}$N$_6$O$_6$, 1057.0886. Anal. calcd. for C$_{48}$H$_{15}$F$_{15}$N$_6$O$_6$: C, 54.56; H, 1.43; F, 26.97; N, 7.95. Found: C, 53.81; H, 1.46; F, 26.83; N, 7.73.

[BRK_III_78E1]. $^1$H NMR (500 MHz, CDCl$_3$) δ 9.42-9.41 (m, 3H), 8.78 & 8.76 (two br singlets, 3H), 8.66-8.65 (quartet, J=2 Hz, 2H), 8.64-8.63 (quartet, J=1.5 Hz, 1H), 5.59 & 5.58 (two br singlets, 6H). $^{19}$F NMR (CDCl$_3$, 376 MHz) δ (−141.86)-(−141.93) (dd, J$_1$=21.4 Hz, J$_2$=6 Hz, 6F), (−151.95)-(−152.06) (t, J=21.4 Hz, 3F), (−161.37)-(−161.48) (sextet, J=9.0 Hz, 6F). $^{19}$F NMR Chemical shifts are relative to trifluoromethylbenzene which was used as an external standard. MALDI-TOF MS (M+H): m/z 1057.0643, calcd for C$_{48}$H$_{16}$F$_{15}$N$_6$O$_6$, 1057.0886. Anal. calcd. for C$_{48}$H$_{15}$F$_{15}$N$_6$O$_6$: C, 54.56; H, 1.43; N, 7.95. Found: C, 53.65; H, 1.48; F, N, 7.77.

[BRK_III_78E3]. $^1$H NMR (500 MHz, CDCl$_3$) (9.272-9.269 (d, J=1.5 Hz, 1.5H), 9.259-9.262 (d, J=1.5 Hz, 1.5H), 8.65 & 8.63 (two br singlets, 3H), 8.56-8.52 (m, 3H), 5.59 & 5.58 (two br singlets, 6H). $^{13}$C NMR (CDCl$_3$, 125 MHz) δ 164.37, 146.87 (m), 145.26, 145.23, 144.87 (m), 144.65, 144.62, 144.46, 144.43, 144.08, 143.89, 142.74 (m), 142.69, 138.71 (m), 136.67 (m), 133.57, 133.71, 132.68, 132.60, 132.57, 131.75, 131.63, 131.05, 131.01, 108.97, 58.45, 54.69 ppm. $^{19}$F NMR (CDCl$_3$, 376 MHz) δ (−141.78)-(−141.93) (m, 6F), (−151.89)-(−152.10) (m, 3F), (−161.31)-(−161.52) (m, 6F). $^{19}$F NMR Chemical shifts are relative to trifluoromethylbenzene which was used as an external standard. MALDI-TOF MS (M+H): m/z 1057.0850, calcd for C$_{48}$H$_{16}$F$_{15}$N$_6$O$_6$, 1057.0886.
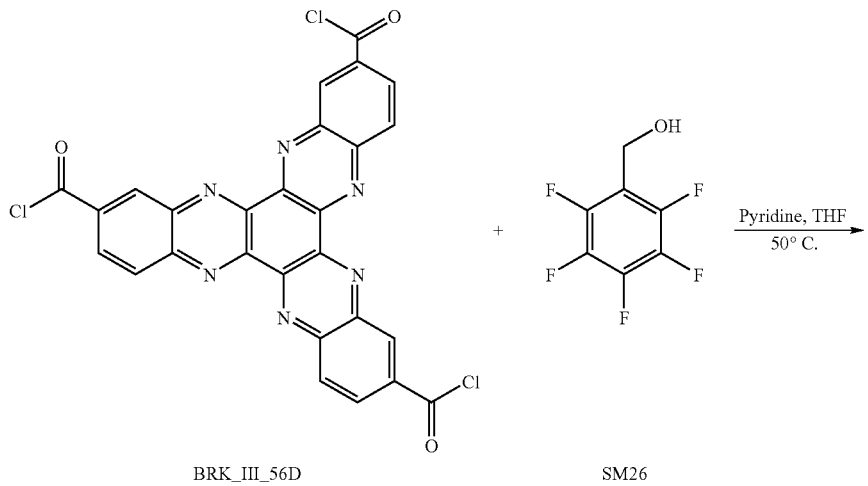
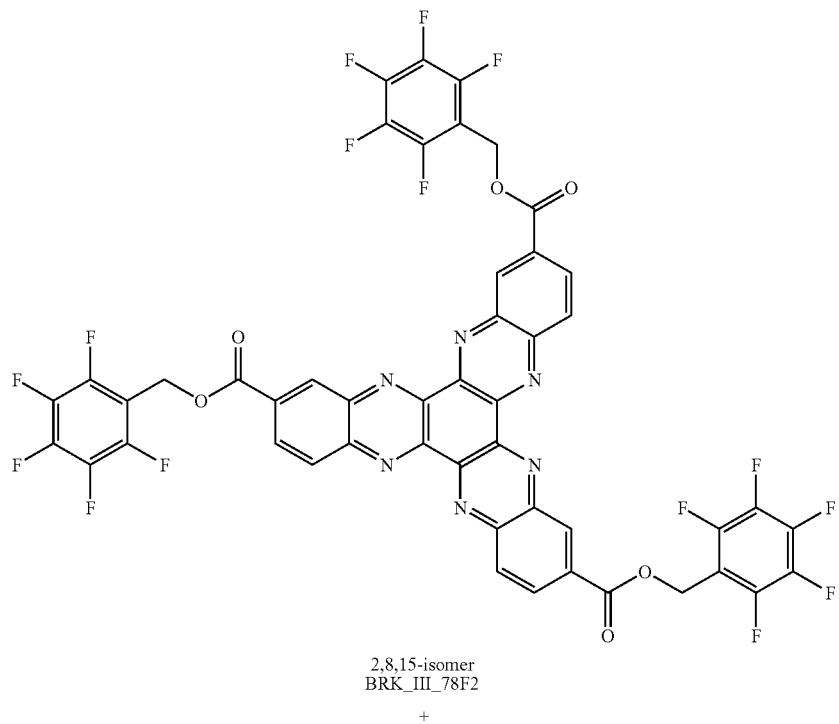

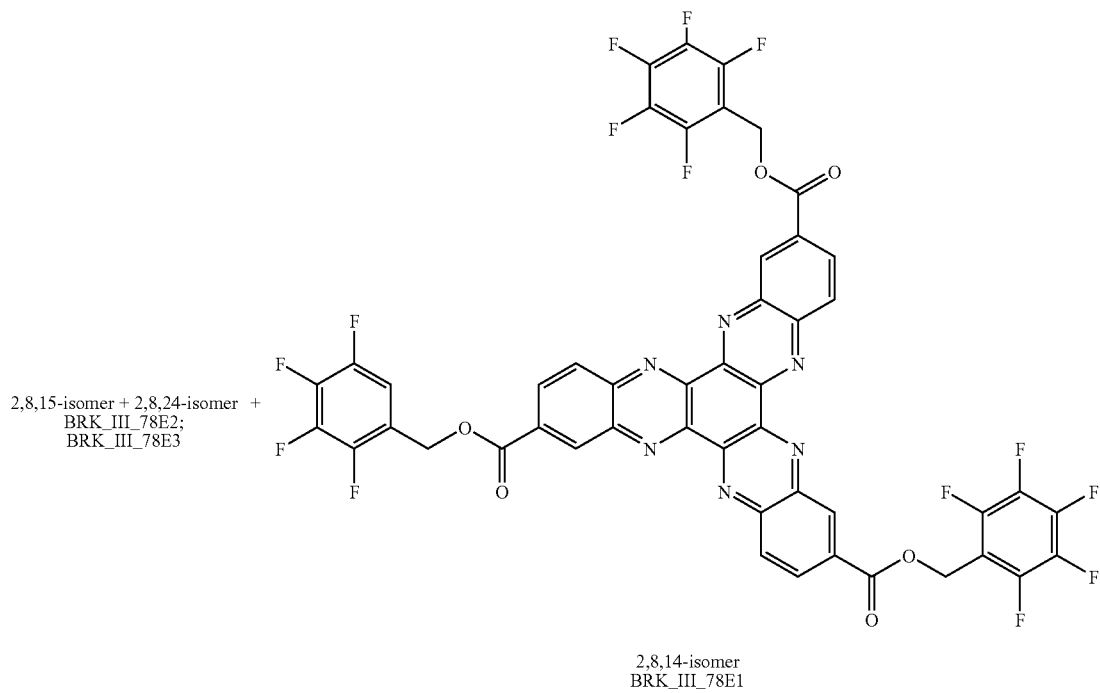

2,8,15-isomer + 2,8,24-isomer +
BRK_III_78E2;
BRK_III_78E3

2,8,14-isomer
BRK_III_78E1

5,6,11,12,17,18-Hexaaza-trinaphthylene-2,8,15-tricarboxylic acid tris-(2-methyl-butyl) ester [DD1_49]. The title compound was synthesized according to a literature procedure.[30] It should be noted that a mixture of the 2,8,14 and 2,8,15 isomers are formed. 5,6,11,12,17,18-Hexaaza-trinaphthylene-2,8,14-tricarbonyl trichloride DD1_21 (2.00 g, 3.50 mmol) was suspended in 15 ml of 2-Methyl-butan-1-ol SM 13. Pyridine (15.0 ml) was slowly added to the reaction mixture, which was at room temperature for 72 hours. Dichloromethane was added to the suspension and the resulting solution was passed through a short silica column using dichloromethane:ethyl acetate (1:1) as eluent mixture. The solvent was evaporated and the yellow-green solid was dissolved in the minimum amount of dichloromethane and precipitated with 30 ml of ethanol. The resulting yellow-green solid was further purified by column chromatography using dichloromethane:ethyl acetate 1:1 (as eluent mixture). The obtained yellow-green solid was dissolved in the minimum amount of dichloromethane and precipitated with 50 ml of ethanol to yield 407 mg (yield 16%) of yellow green solid. $^1$H NMR (CDCl$_3$, 300 MHz) δ 9.36-9.35 (m, 3H), 8.72-8.69 (d, J=8.7 Hz, 1H), 8.70-8.67 (d, J=8.9 Hz, 2H), 8.62-8.56 (m, 3H), 8.64-8.60 (dd, J$_o$=8.70 Hz, J$_m$=2.1 Hz, 1H), 4.42-4.36 (dd, J$_v$=10.8 Hz, J$_g$=6.3 Hz, 3H), 4.33-4.28 (dd, J$_v$=10.8 Hz, J$_g$=6.9 Hz, 3H), 2.03-1.96 (sextet, J=6.9 Hz, 3H), 1.72-1.64 (m, 3H), 1.46-1.36 (m, 3H), 1.16-1.03 (m, 18H). $^{13}$C NMR (CDCl$_3$, 75 MHz) δ 165.26, 133.99, 133.96, 133.91, 133.88, 132.98, 132.95, 131.98, 131.91, 130.82, 130.5, 145.01, 144.98, 144.33, 144.27, 144.19, 144.13, 143.88, 143.83, 143.73, 143.69, 141.90, 142.02, 142.79, 142.50, 70.81, 34.51, 26.35, 16.75, 11.53 ppm. MALDI-TOF MS (MH+H): m/z 728.46, calcd for C$_{42}$H$_{44}$N$_6$O$_6$, 728.84.

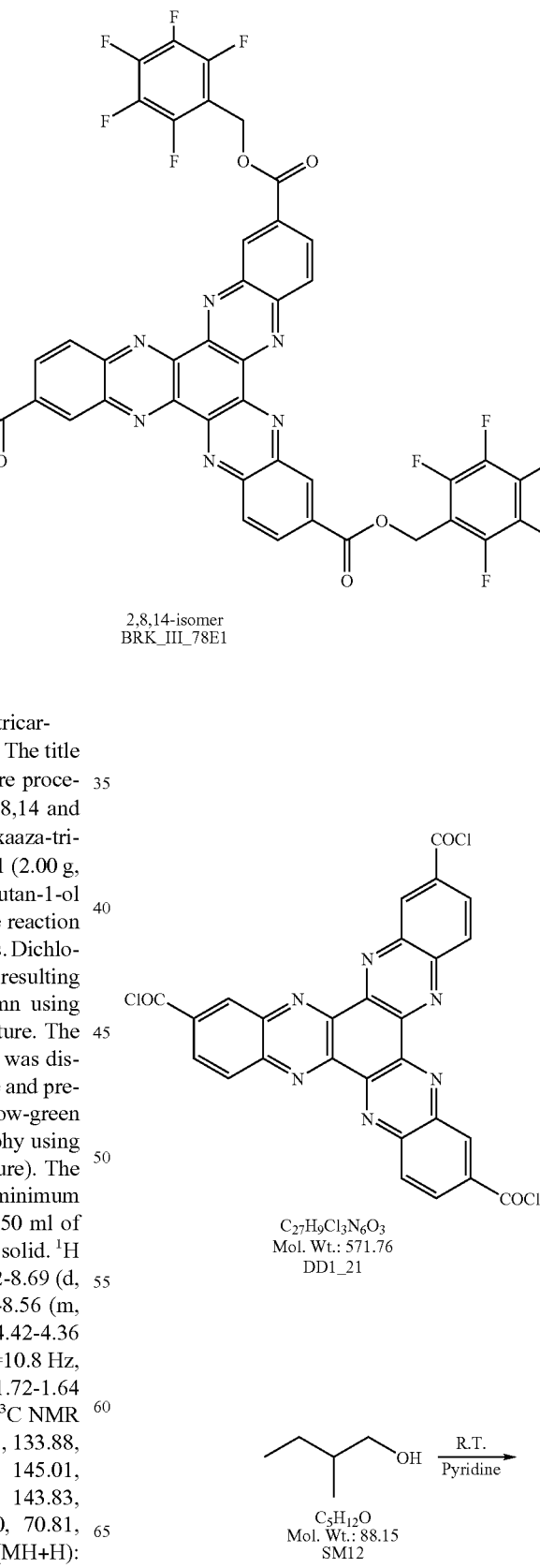

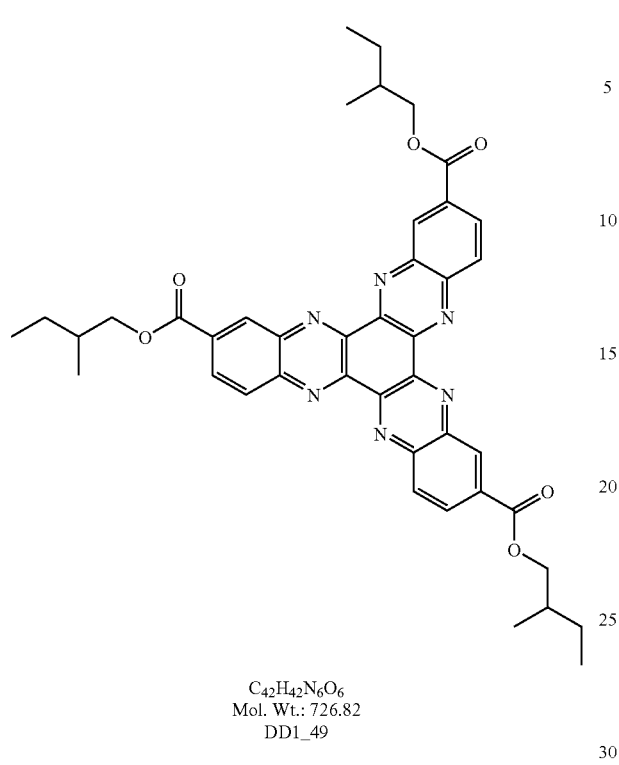

C₄₂H₄₂N₆O₆
Mol. Wt.: 726.82
DD1_49

5,6,11,12,17,18-Hexaaza-trinaphthylene-2,8,15-tricarboxylic acid tris-(2-naphthalen-1-yl-ethyl) ester [DD1__51]. The title compound was synthesized according to a modified literature procedure.[30] It should be noted that a mixture of the 2,8,14 and 2,8,15 isomers are formed. 5,6,11,12,17,18-Hexaaza-trinaphthylene-2,8,14-tricarbonyl trichloride DD1__21 (2.00 g, 3.50 mmol) was suspended in 15 ml of THF. 2-Naphthalen-1-yl-ethanol (15.0 g, 87.1 mmol) SM 14 was added. Pyridine (15.0 ml) was slowly added to the reaction mixture, which was stirred at 75° C. for 24 hours. Dichloromethane was added to the suspension and the resulting solution was passed through a short silica column using dichloromethane:ethyl acetate (1:10) as eluent. The solvent was evaporated and the dark green solid was dissolved in the minimum amount of chloroform and was precipitated with 30 ml of ethanol. The resulting green solid was further purified by column chromatography using dichloromethane-ethyl acetate 1:1 as eluent. The obtained dark green solid was dissolved in the minimum amount of dichloromethane and was precipitated with 40 ml of ethanol. Yield 14%. NMR (CDCl₃, 300 MHz) δ 9.30-9.35 (m, 3H), 8.64-8.61 (d, J=8.7 Hz, 1H), 8.62-8.59 (d, J=8.7 Hz, 2H), 8.53-8.49 (m, 3H), 8.20-8.17 (d, J=8.1 Hz, 3H), 7.88-7.85 (d, J=7.8 Hz, 3H), 7.79-7.76 (d, J=7.8 Hz, 3H), 7.61-7.42 (m, 12H), 4.82-4.78 (t, J=7.5 Hz, 6H), 3.66-3.61 (t; J=7.5 Hz, 6H). ¹³C NMR (CDCl₃, 75 MHz) δ 165.33, 145.30, 144.70, 144.01, 142.95, 142.98, 134.13, 133.89, 133.80, 133.51, 133.4, 132.24, 132.04, 131.00, 129.15, 127.90, 127.28, 126.61, 126.00, 125.82, 123.71, 66.11, 32.49. MALDI-TOF MS (M+H): m/z 980.52, calcd for C₆₃H₄₃N₆O₆, 980.05.

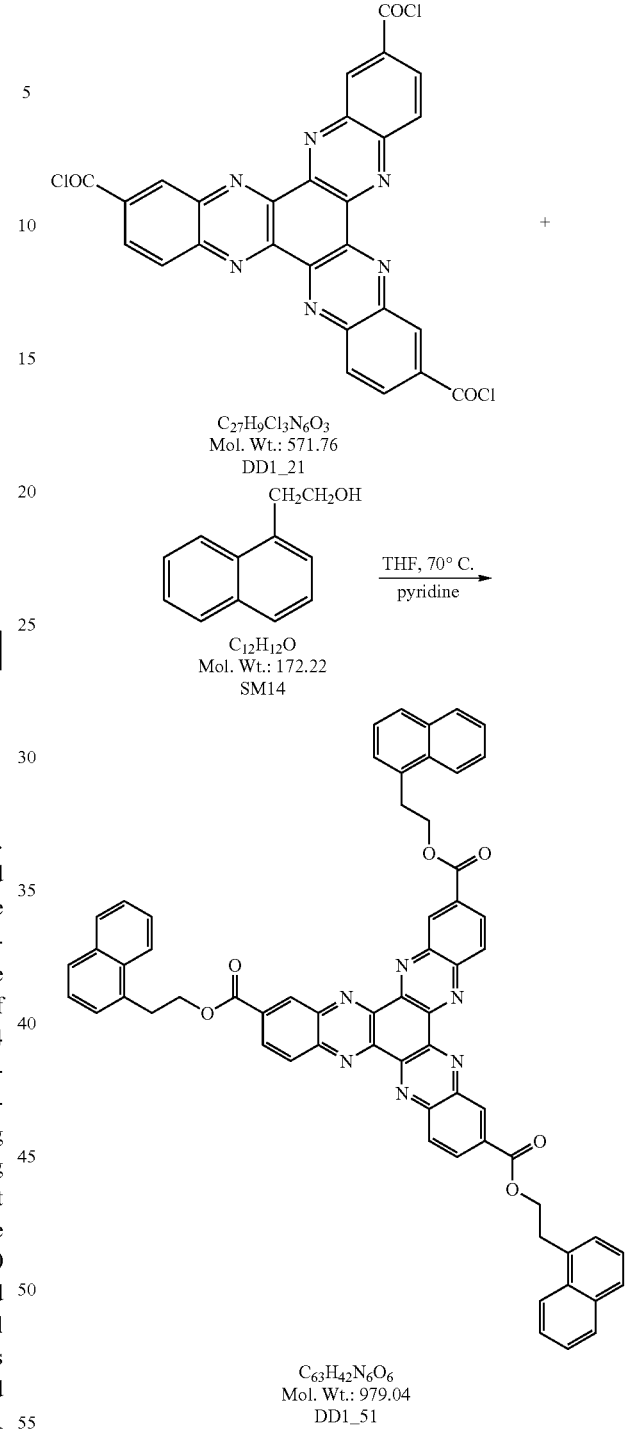

C₂₇H₉Cl₃N₆O₃
Mol. Wt.: 571.76
DD1_21

C₁₂H₁₂O
Mol. Wt.: 172.22
SM14

THF, 70° C.
pyridine

C₆₃H₄₂N₆O₆
Mol. Wt.: 979.04
DD1_51

5,6,11,12,17,18-Hexaaza-trinaphthylene-2,8,15-tricarboxylic acid tribenzyl ester [DD1__57]. The title compound was synthesized according to a literature procedure.[30] It should be noted that a mixture of the 2,8,14 and 2,8,15 isomers are formed. 5,6,11,12,17,18-Hexaaza-trinaphthylene-2,8,14-tricarbonyl trichloride DD1__21 (2.00 g, 3.50 mmol) was suspended in 15 ml of phenyl-methanol SM 16. Pyridine (15.0 ml) was slowly added to the reaction mixture, which was stirred at room temperature for 24 hours. Dichloromethane was added to the suspension and the resulting solution was passed through a short silica column using dichloromethane:ethyl acetate (1:1) as eluent. The solvent was evaporated and the green solid was dissolved in the minimum amount of dichloromethane and precipitated with 30 ml of ethanol. The resulting yellow-green solid was further purified by column chromatography using dichloromethane:ethyl acetate (1:1). The obtained green solid was dissolved in the minimum amount of dichloromethane and was precipitated in 50 ml of ethanol. Only traces of product were recovered. $^1$H NMR (CDCl$_3$, 300 MHz) δ 9.38-9.40 (m, 3H), 8.70-8.67 (d, J=8.7 Hz, 3H), 7.57-7.41 (m, 15H), 5.51 (s, 6H). MALDI-TOF MS (M+H): m/z 787.28, calcd for $C_{48}H_{31}N_6O_6$, 787.80 (other peaks were present).

Benzo[i]bisbenzo[6,7]quinoxalino[2,3-a:2',3'-c]phenazine [BK1_49]. The title compound was synthesized according to a literature procedure.[30] Hexaketocyclohexane octahydrate (534 mg, 1.71 mmoles) and 2,3-diaminonaphthalene SM13 (1.00 g, 5.65 mmoles) were refluxed in 200 ml of glacial acetic acid at 140° C. overnight. The reaction mixture was then filtered and washed with 6×50 ml of hot glacial acetic acid. The solid was then refluxed with 200 ml of 30% nitric acid for 3 hours at 120° C. The dark brown solid (1.55 g, theoretical yield is 915 mg; therefore, impurities present) was filtered and dried under vacuum. This compound is insoluble in most organic solvents. MALDI-TOF MS (M+H): m/z 535.16, calcd for $C_{36}H_{19}N_6$, 535.58.

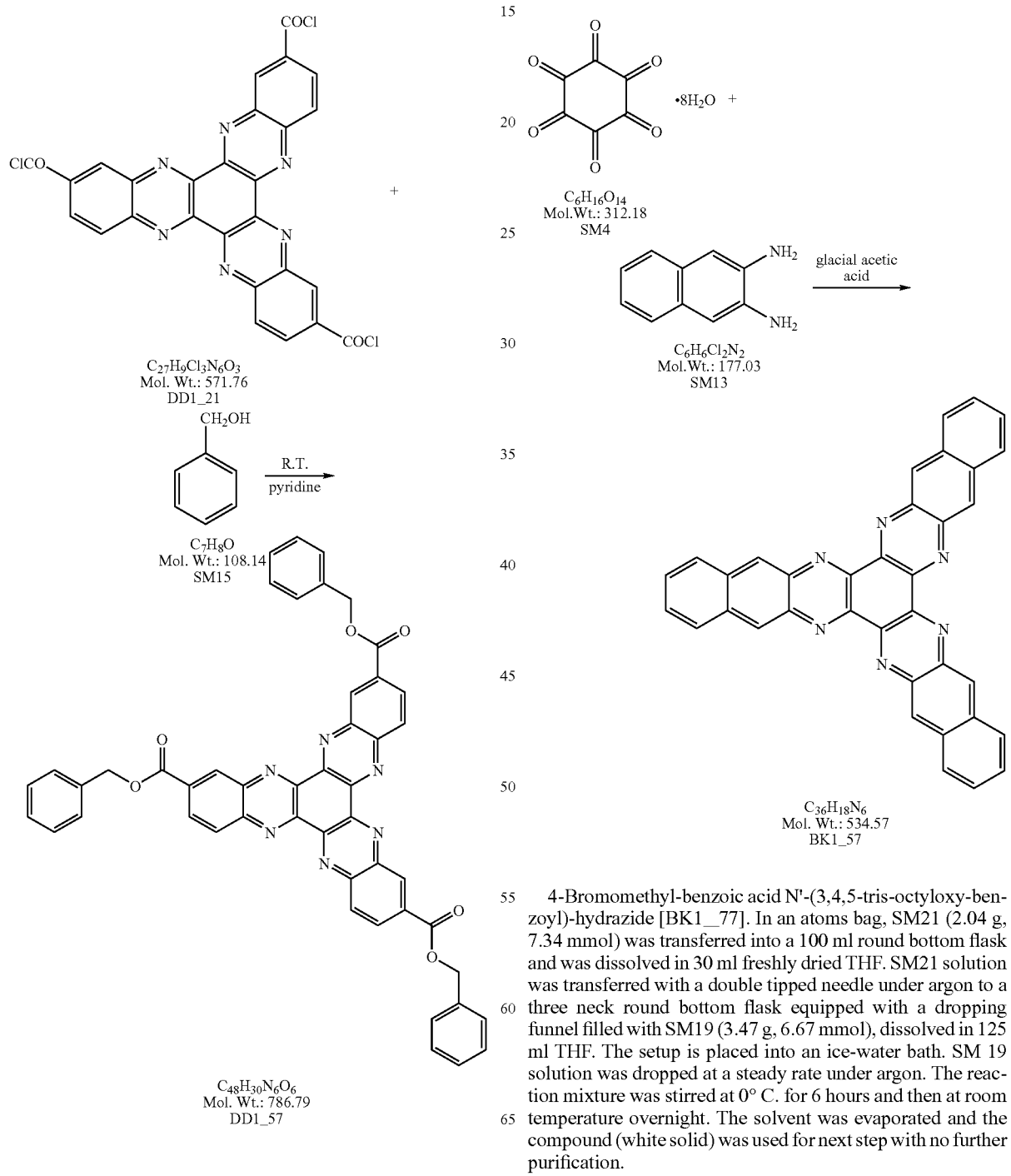

4-Bromomethyl-benzoic acid N'-(3,4,5-tris-octyloxy-benzoyl)-hydrazide [BK1_77]. In an atoms bag, SM21 (2.04 g, 7.34 mmol) was transferred into a 100 ml round bottom flask and was dissolved in 30 ml freshly dried THF. SM21 solution was transferred with a double tipped needle under argon to a three neck round bottom flask equipped with a dropping funnel filled with SM19 (3.47 g, 6.67 mmol), dissolved in 125 ml THF. The setup is placed into an ice-water bath. SM 19 solution was dropped at a steady rate under argon. The reaction mixture was stirred at 0° C. for 6 hours and then at room temperature overnight. The solvent was evaporated and the compound (white solid) was used for next step with no further purification.

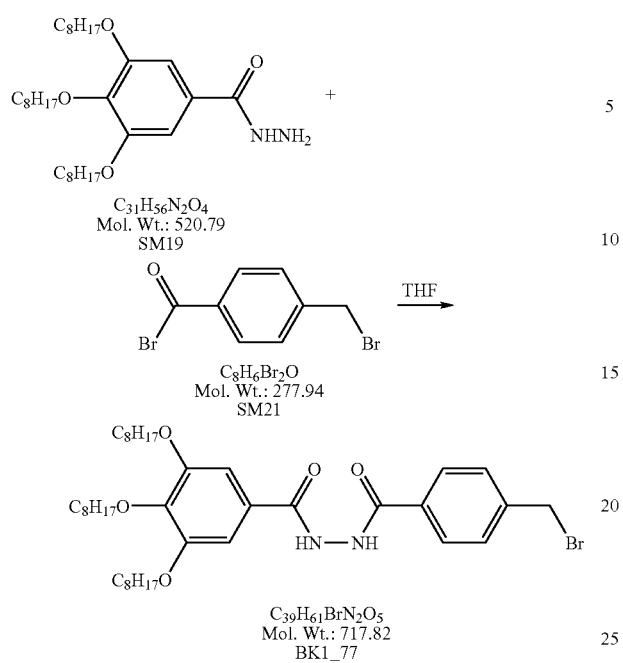

2-(4-Bromomethyl-phenyl)-5-(3,4,5-tris-octyloxy-phenyl)-[1,3,4]oxadiazole [BK1_79]. BK1_77 was refluxed in 125 ml POCl₃ at 130° C. for 24 hours. The excess POCl₃ (100 ml) was distilled off. The remaining solution was added to 600 ml of water and ice, upon which a white-brown oily solid forms. The solid was run through a column of silica using hexanes:ethyl acetate (10:1) as eluent to yield 2.08 g (45%) of white solid. $^1$H NMR (CDCl₃, 300 MHz) δ 8.065-8.038 (d, 2H, J₁=8.1 Hz), 7.491-7.463 (d, 2H, J=8.4 Hz), 7.25 (s, 2H), 4.57 (s, 2H), 4.04-3.97 (m, 6H), 1.85-1.68 (m, 6H), 1.56-1.43 (m, 6H), 1.40-1.05 (m, 24H), 0.86-0.82 (t, J=6.6 Hz, 9H). $^{13}$C NMR (CDCl₃, 75 MHz) δ 164.71, 163.78, 153.49, 141.35, 140.84, 129.03, 127.09, 123.80, 118.26, 105.31, 77.42, 76.99, 76.57, 73.50, 69.26, 45.28, 31.80, 31.73, 30.25, 29.42, 29.27, 29.19, 25.99, 22.57, 13.99.

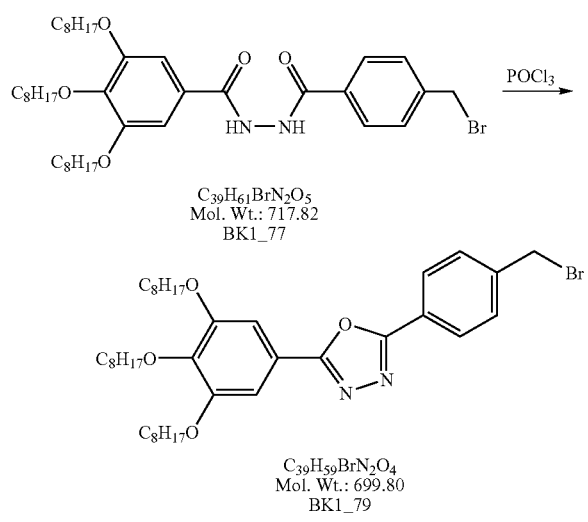

2-(4-Hydroxymethyl-phenyl)-5-(3,4,5-tris-octyloxy-phenyl)-[1,3,4]oxadiazole [BK1_81]. This reaction was done on a preparatory scale. BK1_79 (45 mg, 64.1×10⁻³ mmol) was stirred in 20 ml of water at room temperature for 96 hours. The reaction mixture was extracted in 3×30 ml of CHCl₃ and the combined solvent was dried over MgSO₄ and was then filtered. The solvent was evaporated to yield a yellowish solid. $^1$H NMR (CDCl₃, 300 MHz) δ 8.15-8.11 (d, J=8.4 Hz, 2H), 7.58-7.55 (d, J=8.4 Hz, 2H), 7.32 (s, 2H), 4.65 (s, 2H), 4.11-4.03 (m, 6H), 1.90-1.73 (m, 6H), 1.62 (s, 1H), 1.56-1.48 (m, 6H), 1.41-1.32 (m, 24H), 1.30-0.87 (t, J=6.6 Hz, 9H).

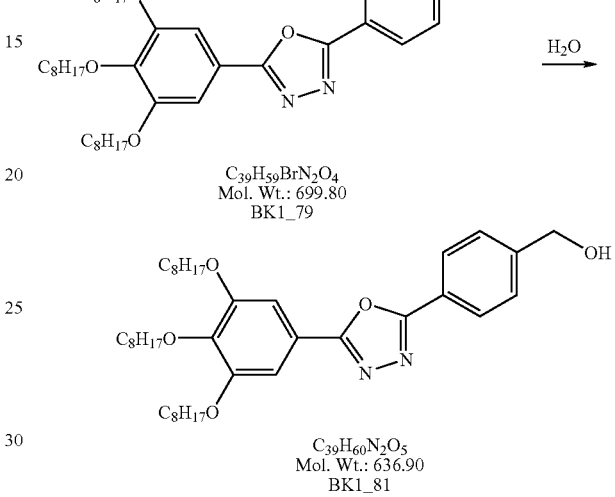

The following references are all incorporated herein by reference.
(1) Adam, D.; Closs, F.; Frey, T.; Funhoff, D.; Haarer, D.; Ringsdorf, H.; Schumacher, P.; Siemensmeyer, K. *Phys. Rev. Lett.* 1993, 70, 457-460.
(2) Boden, N.; Bushby, R. J.; Clements, J.; Movghar, B.; Donovan, K. J.; Kreouzis, T. *Phys. Rev.* 1995, B52, 13274-113280.
(3) Simmerer, J.; Gluesen, B.; Paulus, W.; Kettner, A.; Schuhmacher, P.; Adam, D.; Etzbach, K. H.; Siemensmeyer, K.; Wendorff, J. H. *Adv. Mater.* 1996, 8, 815-819.
(4) Schmidt-Mende, L.; Fechtenkötter, A.; Müllen, K.; Moons, E.; Friend, R. H.; MacKenzie, J. D. *Science* 2001, 293, 1119-1122.
(5) Tang, C. W.; VanSlyke, S. A. *Appl. Phys. Lett.* 1987, 51, 913.
(6) Dodabalapur, A.; Torsi, L.; Katz, H. E. *Science* 1995, 268, 270-271.
(7) Comil, J.; Lemaur, V.; Calbert, J.-P.; Bredas, J.-L. *Adv. Mater.* 2002, 14, 726-729.
(8) Magin, E. H.; Borsenberger, P. M. *J. Appl. Phys.* 1993, 73, 787.
(9) Tokuhisa, H.; Era, M.; Tsutsui, T.; Saito, S. *Appl. Phys. Lett.* 1995, 66, 3433-3435.
(10) Alfonso, M.; Stoeckli-Evans, H. *Acta Crystallogr.* 2001, E57, o242-o244.
(11) Du, M.; Bu, X.-H.; Biradha, K. *Acta Crystallogr.* 2001, C57, 199-200.
(12) Bu, X.-H.; Biradha, K.; Yamaguchi, T.; Nishimura, M.; Ito, T.; Tanaka, K.; Shionoya, M. *Chem. Commun.* 2000, 1953-1954.
(13) Cheesman, G.; Cookson, R.; John Wiley and Sons: New York, 1979.

(14) Aumiller, W. D.; Dalton, C. R.; Czarnik, A. W. *J. Org. Chem.* 1995, 60, 728-729.

(15) Sakamoto, Y.; Suzuki, T.; Kobayashi, M.; Gao, Y.; Fukai, Y.; Inoue, Y.; Sato, F.; Tokito, S. *J. Am. Chem. Soc.* 2004, 126, 8138-8140.

(16) Heaton, A.; Hill, M.; Drakesmith, F. *Journal of Fluorine Chemistry* 1997, 81, 133-138.

(17) Coates, G. W.; Dunn, A. R.; Henling, L. M.; Ziller, J. W.; Lobkovsky, E. B.; Grubbs, R. H. *J. Am. Chem. Soc.* 1998, 120, 3641-3649.

(18) Coates, G. W.; Dunn, A. R.; Henling, L. M.; Dougherty, D. A.; Grubbs, R. H. *Angew. Chem., Int. Ed. Engl.* 1997, 36, 248-251.

(19) Kaafarani, B. R.; Pinkerton, A. A.; Neckers, D. C. *Tetrahedron Lett.* 2001, 42, 8137-8139.

(20) Dierking, I. *Textures of Liquid Crystals*; Wiley-VCH: Manchester, 2003.

(21) Kestemont, G.; de Halleux, V.; Lehmann, M.; Ivanov, D. A.; Watson, M.; Geerts, Y. H. *Chemical Commun.* 2001, 2074-2075.

(22) Weck, M.; Dunn, A. R.; Matsumoto, K.; Coates, G. W.; Lobkovsky, E. B.; Grubbs, R. H. *Angew. Chem., Int. Ed. Engl.* 1999, 38, 2741-2745.

(23) Ong, C. W.; Liao, S.-C.; Chang, T. H.; Hsu, H.-F. *J. Org. Chem.* 2004, 69, 3181-3185.

(24) Antonisse, M. M. G.; Snellink-Ruel, B. H. M.; Yigit, I.; Engbersen, J. F. J.; Reinhoudt, D. N. *J. Org. Chem.* 1997, 62, 9034-9038.

(25) Craats, A. M. v. d.; Warman, J. H. *Adv. Mater.* 2001, 13, 130-133.

(26) Lemaur, V.; Filho, D. A. d. S.; Coropceanu, V.; Lehmann, M.; Geerts, Y.; Piris, J.; Debije, M. G.; Craats, A. M. v. d.; Senthilkumar, K.; Siebbeles, L. D. A.; Warman, J. H.; Bredas, J.-L.; Comil, J. *J. Am. Chem. Soc.* 2004, 126, 3271-3279.

(27) Tokuhisa, H.; Era, M.; Tsutsui, T. *Adv. Mater.* 1998, 10, 404-407.

(28) Adachi, C.; Tsutsui, T.; Saito, S. *Appl. Phys. Lett.* 1989, 55, 1489-1491.

(29) Zhang, Y.-D.; Jespersen, K. G.; Kempe, M.; Kornfield, J. A.; Barlow, S.; Kippelen, B.; Marder, S. R. *Langmuir* 2003, 19, 6534-6536.

(30) Bock, H.; Babeau, A.; Seguy, I.; Jolinet, P.; Destruel, P. *CHEMPHYSCHEM* 2002, 532-535.

(31) Sonogashira, K.; Tohda, Y.; Hagihara, N. *Tetrahedron Lett.* 1975, 4467-4470.

(32) Ong, C. W.; Liao, S.-C.; Chang, T. H.; Hsu, H.-F. *Tetrahedron Lett.* 2003, 44, 1477-1480.

(33) Becke, A. D. *Phys. Rev.* 1988, A38, 3098-3100.

(34) Becke, A. D. *J. Chem. Phys.* 1993, 98, 5648-5652.

(35) Frisch, M. J.; A. II ed.; Gaussian Inc.: Pittsburgh, 2001.

(36) Frisch, M. J.; Trucks, G. W.; Schlegel, H. B.; Gill, P. M. W.; Johnson, B. G.; Robb, M. A.; Cheeseman, J. R.; Keith, T.; Petersson, G. A.; Montgomery, J. A.; Raghavachari, K.; Al-Laham, M. A.; Zakrzewski, V. G.; Ortiz, J. V.; Foresman, J. B.; Cioslowski, J.; Stefanov, B. B.; Nanayakkara, A.; Challacombe, M.; Peng, C. Y.; P. Y. Ayala; Chen, W.; Wong, M. W.; Andres, J. L.; Replogle, E. S.; Gomperts, R.; Martin, R. L.; Fox, D. J.; Binkley, J. S.; Defrees, D. J.; Baker, J.; Stewart, J. P.; Head-Gordon, M.; Gonzalez, C.; Pople, J. A.; Gaussian Inc.: Pittsburgh Pa., 1995.

(37) Gruhn, N. E.; da Silva, D. A.; Bill, T. G.; Malagoli, M.; Coropceanu, V.; Kahn, A.; Bredas, J.-L. *J. Am. Chem. Soc.* 2002, 126, 3271-3279.

(38) Malagoli, M.; Brédas, J.-L. *Chem. Phys. Lett.* 2000, 327, 13.

(39) Lin, B. C.; Cheng, C. P.; Lao, Z. P. M. *J. Phys. Chem. A* 2003, 107, 5241-5251.

(40) Borsenberger, P. M.; Weiss, D. S. *Organic photoreceptors for imaging systems*; Marcell Dekker: New York, 1993.

(41) Bässler, H. *Phys. Stat. Sol.* 1993, B175, 15-56.

(42) Abkowitz, M. A. *Philos. Mag. B* 1992, 65, 817.

(43) Meyer, E. M.; Gambarotta, S.; Floriani, C.; Chiesi-Villa, A.; Guastini, C. *Organometallics* 1989, 8, 1067-1079.

(44) Pai, D. M. *J. Chem. Phys.* 1970, 52, 2285.

(45) Murray, M. M.; Kaszynski, P.; Kaisaki, D. A.; Chang, W. H.; Dougherty, D. A. *J. Am. Chem. Soc.* 1994, 116, 8152-8161.

(46) Gill, W. D. *J. Appl. Phys.* 1972, 43, 5033.

(47) Byers, B. P.; Hall, M. B. *Inorg. Chem.* 1987, 26, 2186-2188.

(48) Rumi, M.; Ehrlich, J. E.; Heikal, A. A.; Perry, J. W.; Barlow, S.; Hu, Z.; McCord-Maughon, D.; Röckel, H.; Thayumanavan, S.; Marder, S. R.; Beljonne, D.; Brédas, J.-L. *J. Am. Chem. Soc.* 2000, 122, 9500-9510.

(49) Rapta, P.; Hatermann, H. *Electrochim. Acta* 1994, 39, 2251.

(50) Goerlitz, G.; Hartmass, H. *Heteroatom Chem.* 1997, 8, 147.

(51) Ma, L.; Hu, Q.-S.; Vitharana, D.; Wu, C.; Kwan, C. M. S.; Pu, L. *Macromolecules* 1997, 30, 204-218.

(52) Bellany, F. D.; Ou, K. *Tetrahedron Lett.* 1984, 25, 839-842.

Synthesis of 2,3,8,9,14,15-Hexafluoro-5,6,11,12,17, 18-hexaaza-trinaphthylene [(HATNA)F$_6$]

4,5-Difluoro-2-nitro-phenylamine is a known compound.[8] It was reduced with tin (II) chloride dihydrate in ethanol to give the 4,5-difluoro-benzene-1,2-diamine. The diamine was reacted with hexaketocyclohexane octahydrate to give [(HATNA)F$_6$]. The product was purified by train purification (sublimation). The compound is yellow needle like crystal. It is slightly soluble in chloroform. It is very soluble in chloroform/TFA (3:1) mixture.

Synthesis of 2,3,8,9,14,15-Hexafluoro-5,6,11,12,17, 18-hexaaza-trinaphthylene [(HATNA)(CF$_3$)$_3$]

2-Nitro-4-trifluoromethyl-phenylamine was purchased from Aldrich. It was reduced with tin (11) chloride dihydrate in ethanol to give 4-trifluoromethyl-benzene-1,2-diamine (Scheme 3). The diamine was reacted with hexaketocyclohexane octahydrate to give [(HATNA)(CF$_3$)$_3$]. The product contains two isomers (from HPLC). The product is a yellow solid. It is soluble in common organic solvent including dichloromethane, THF and hot methanol. It was purified by flash chromatography on silica gel eluting with dichloromethane.

Synthesis of 2,3,8,9,14,15-Hexaiodo-5,6,11,12,17, 18-hexaaza-trinaphthylene [(HATNA)I$_6$]

1,2-di-iodo-4,5-dinitrobenzene was prepared by the literature procedure.[7] It was reduced with tin (II) chloride dihydrate in ethanol to give 4,5-Diiodo-benzene-1,2-diamine. The diamine was reacted with hexaketocyclohexane octahydrate to give [(HATNA)I$_6$]. The compound is a green solid. The structure was confirmed by MALDI-TOF MS and NMR.

Synthesis of [(HATNA)I₃]2,8,14 and 2,8,15 isomer mixture

4-Iodo-benzene-1,2-diamine was prepared by the literature procedure.[10] The diamine was reacted with hexaketocyclohexane octahydrate to give [(HATNA)I₃]. The compound is a green colored solid. It is slightly soluble in a mixture of chloroform/TFA. The structure was confirmed by MALDI-TOF MS.

Synthesis of Hexaazatriisothianaphthene Compound A 2,5-Bis-(3,5-bis-trifluoromethyl-phenyl)-3,4-dinitro-thiophene was made by Stille coupling reaction of 2,5-dibromo-3,4-dinitro-thiophene and 3,5-bis-trifluoromethyl-phenyl-tributyl-stannane. It was reduced with tin (II) chloride dihydrate in ethanol to give 2,5-bis-(3,5-bis-trifluoromethyl-phenyl)-thiophene-3,4-diamine. The diamine was reacted with hexaketocyclohexane octahydrate to give compound A. The product is a red-brown solid. It is soluble in common organic solvents such as dichloromethane and THF. It was purified by flash chromatography on silica gel and crystallization in ethanol. The purified product had elemental analysis data consistent with the formula for the desired compound.

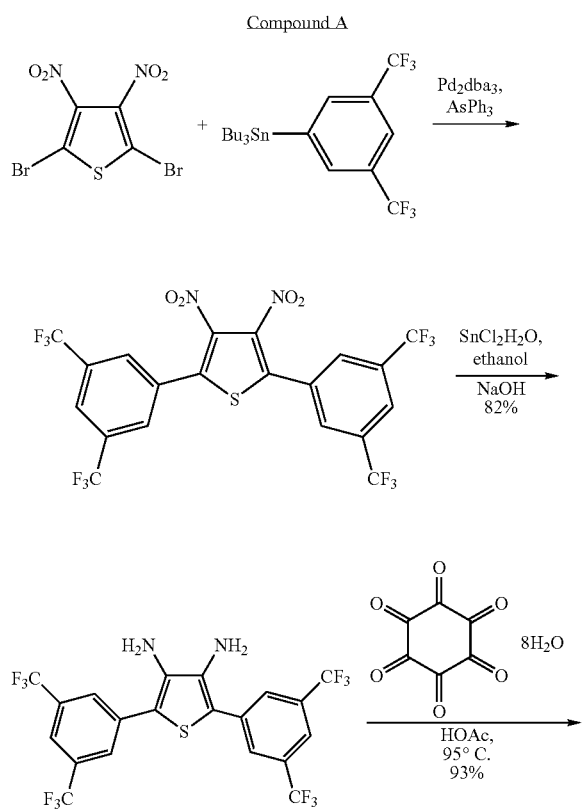

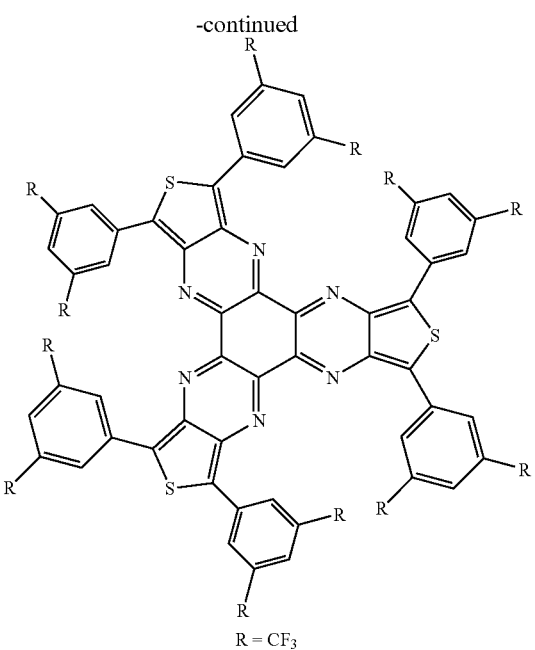

Synthesis of 2,3,8,9,14,15-Hexakis-decylsulfanyl-5,6,11,12,17,18-hexaaza-trinaphthylene [(HATNA)(SC₁₀H₂₁)₆]

2,3,8,9,14,15-hexakis-decylsulfanyl-5,6,11,12,17,18-hexaazatrinaphthylene HATNA(SC₁₀H₂₁)₆ can be synthesized analogously to other related compounds.[11] We teach that these kinds compounds could be purified easily by washing them in a Soxhlet extraction apparatus with acetone for 12 hrs. In general the compounds are soluble in hexane but not in acetone.

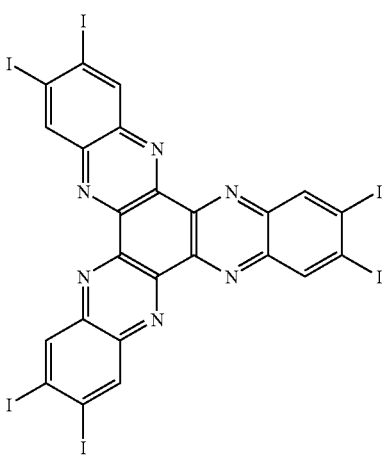

2,3,8,9,14,15-[HATNA]I₆, A mixture of hexaketocyclohexane octahydrate (2.17 g, 6.95 mmol) and 4,5-Diiodo-benzene-1,2-diamine (7.50 g, 20.84 mmol) was added to a degassed acetic acid (175 mL). The mixture was heated to 99° C. for 12 hrs under nitrogen. After cooled to room temperature, the solid was collected by filtration and was washed with acetic acid to give a green solid (7.39 g, 93% yield). ¹H (300 MHz, CD₃Cl/CF₃COOD) δ 9.11 (s, 6H). HRMS MALDI- TOF (with CHCA as matrix), 1140.5066; calcd. For $C_{24}H_7N_6I_6$ (M+H), 1140.4995.

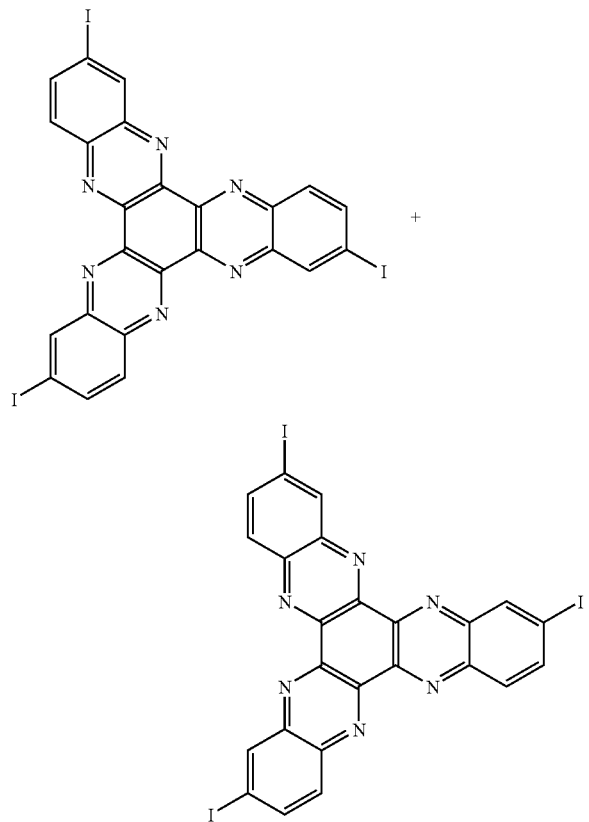

[HATNA]I$_3$, 2,8,14 and 2,8,15 isomer mixture. A mixture of hexaketocyclohexane octahydrate (2.21 g, 7.08 mmol) and 4-Iodo-benzene-1,2-diamine (4.97 g, 21.24 mmol) was added to a degassed acetic acid (140 mL). The mixture was heated to 110° C. for 3 hrs under nitrogen. After cooled to room temperature, the solid was collected by filtration and was washed with acetic acid to give a green solid (5.35 g, 99% yield). $^1$H (300 MHz, CD$_3$Cl/CF$_3$COOD) δ 9.11 (br, 3H), 8.54 (br, 3H), 8.32 (br, 3H). HRMS E1: m/z calcd for $C_{24}H_9I_3N_6$ 761.8023. Found 761.8087.

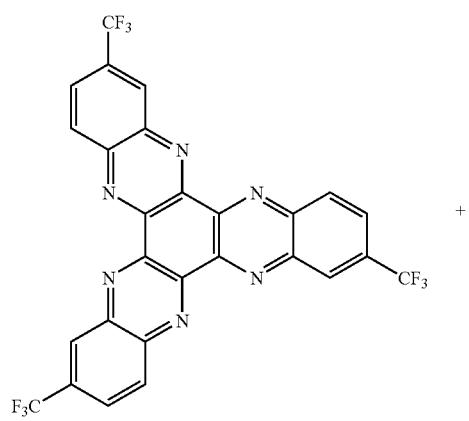

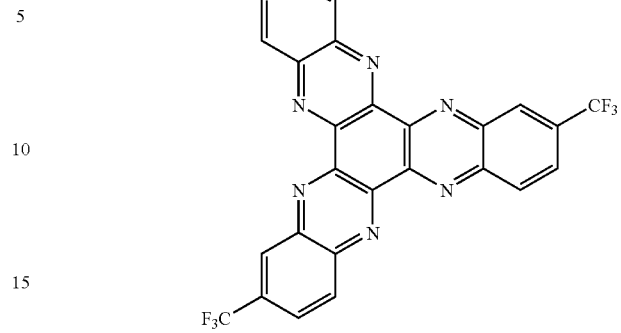

HATNA(CF$_3$)$_3$, mixture of 2,8,14 and 2,8,15 isomers. A mixture of hexaketocyclohexane octahydrate (1.39 g, 8.90 mmol) and 3,4-Diaminobenzotrifluoride (4.70 g, 26.71 mmol) was added to a degassed acetic acid (250 mL). The mixture was refluxed for 15 hrs under nitrogen. After the mixture cooled down to room temperature, solvent was removed under reduced pressure. The solid was purified by flash chromatography on silica gel eluting with dichloromethane to give a yellow solid (3.66 g, 70% yield). The product was washed with hexane in Soxhlet for 3 hrs before sending for elemental analysis. $^1$H (300 MHz, CD$_3$Cl) δ 8.95 (d, J=0.82 Hz, 3H), 8.72 (dd, J=9.0, 0.82 Hz, 3H), 8.19 (m, 3H); $^{13}$C NMR (75 MHz, CD$_2$Cl$_2$): 144.45, 144.32, 144.13, 143.99, 143.85, 142.43, 142.39, 134.92, 134.50, 134.43, 134.03, 133.99, 133.58, 131.90, 128.74, 128.68, 128.32, 125.13, 121.52, 117.91. $^{19}$F NMR (376.3 MHz, CDCl$_3$): δ-89.18. HRMS E1: m/z calcd for $C_{27}H_9F_9N_6$ 588.0745. Found 588.0734. Anal. Calcd. For $C_{27}H_9F_9N_6$: C, 55.11; H, 1.54; N, 14.28. Found: C, 54.92; H, 1.49; N, 14.09.

2,3,8,9,14,15-Hexakis-decylsulfanyl-5,6,11,12,17,18-hexaazatrinaphthylene. A mixture of 2,3,8,9,14,15-hexachloro-5,6,11,12,17,18-hexaazatrinaphthylene (3.00 g, 5.08 mmol), 1-decanethiol (13.74 mL, 66.75 mmol) and K$_2$CO$_3$ (25.55 g, 185.00 mmol) in DMF (250 mL) was stirred at 80° C. for 72 hrs under nitrogen. After cooled down to room temperature, solvent was removed in vacuo. To the solid residue, water and dichloromethane was added. The organic layer was separated and the aqueous layer was extracted with dichloromethane (100 mL) twice. The combined organic layer was dried over magnesium sulfate and filtered. Solvent was evaporated under reduced pressure to give a yellow solid. The yellow solid was purified by flash chromatography on silica gel eluting with hexane:dichloromethane (1:1) to give a solid (4.00 g, 56% yield). The yellow product was washed with hot acetone in a Soxhlet extractor for 12 hrs before sending for elemental analysis. $^1$H (300 MHz, CD$_2$Cl$_2$) δ 7.49 (s, 6H), 2.81 (t, J=6.8 Hz, 12H), 1.55 (p, J=6.6 Hz, 12H), 1.50-1.25 (m, 84H), 0.93 (t, J=6.3 Hz, 18H). $^{13}$C NMR (75 MHz, CD$_2$Cl$_2$): 143.36, 141.84, 140.42, 122.26, 33.22, 32.36, 30.14, 30.07, 29.91, 29.82, 28.24, 23.13, 14.32. HRMS MALDI-TOF (with CHCA as matrix), 1417.8975; calcd. For $C_{84}H_{133}N_6S_6$ (M+H), 1417.8911. Anal. Calcd. For $C_{84}H_{132}N_6S_6$: C, 71.13; H, 9.38; N, 5.93. Found: C, 70.92; H, 9.38; N, 5.90.

1,2,3,4,7,8,9,10,13,14,15,16-Dodecafluoro-5,6,11,12,17,18-hexaaza-trinaphthylene. A mixture of hexaketocyclohexane octahydrate (2.50 g, 9.25 mmol) and 3,4,5,6-Tetrafluoro-benzene-1,2-diamine (5.00 g, 27.76 mmol) was added to a degassed acetic acid (150 mL). The mixture was refluxed for 12 hrs under nitrogen. After cooled down to room temperature, the solid was collected by filtration and was washed with acetic acid to give a yellow solid (4.05 g, 73% yield). $^{19}$F NMR (376.3 MHz, CDCl$_3$): δ-123.53, -138.35. HRMS E1: m/z calcd for C$_{24}$F$_{12}$N$_6$: 599.9993. Found 599.9981. Anal. Calcd. C$_{24}$F$_{12}$N$_6$: C, 48.02; H, 14.00. Found: C, 48.03; H, 14.10.

2,3,8,9,14,15-Hexafluoro-5,6,11,12,17,18-hexaaza-trinaphthylene. A mixture of hexaketocyclohexane octahydrate (2.78 g, 8.90 mmol) and 4,5-Difluoro-benzene-1,2-diamine (3.85 g, 26.71 mmol) was added to a degassed acetic acid (250 mL). The mixture was refluxed for 16 hrs. The solid was collected by filtration and was washed with acetic acid to give a yellow solid (2.88 g, 58% yield).$^1$H (300 MHz, CDCl$_3$) δ 8.42 (t, J=8.5 Hz, 6H). $^{19}$F NMR (376.3 MHz, CDCl$_3$): δ-121.26 (t, J=8.5 Hz). HRMS E1: m/z calcd for C$_{24}$H$_6$F$_6$N$_6$ 492.0558. Found 492.0585. Anal. Calcd. For C$_{24}$H$_6$F$_6$N$_6$: C, 58.55; H, 1.23; N, 17.07; F, 22.34. Found: C, 56.98; H, 1.39; N, 16.81; F, 22.36.

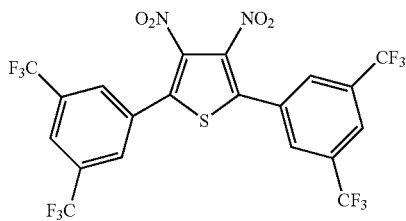

Compound B. A mixture of 2,5-dibromo-3,4-dinitrothiophene (6.00 g, 18.08 mmol), (3,5-Bis-trifluoromethyl-phenyl)-tributyl-stannane (16.52 g, 36.15 mmol), tris(dibenzylideneacetone) dipalladium (0.66 g, 0.72 mmol) and triphenylarsine in toluene (100 mL) was heated to 80° C. for 12 hrs under nitrogen. The mixture was cooled down to room temperature, and then a solution of potassium fluoride (30 mL, 2.0 M) was added. The mixture was stirred for one hour. The organic layer was collected and aqueous layer was extracted with ether. The combined organic layer was dried over magnesium sulfate and filtered. Solvent was removed under reduced pressure. The residue was crystallized in methanol to give a yellow solid (7.25 g, 67% yield).$^1$H (300 MHz, CDCl$_3$) δ 8.08 (br, 2H), 8.01 (br, 4H). $^{13}$C NMR (75 MHz, CD$_2$Cl$_2$): 138.41, 133.90, 133.45, 132.99, 132.54, 129.91, 129.64, 128.09, 125.21, 125.16, 124.48, 120.87. HRMS E1: m/z calcd for C$_{20}$H$_6$F$_{12}$N$_2$O$_4$S 597.9857. Found 597.9843. Anal. Calcd. For C$_{20}$H$_6$F$_{12}$N$_2$O$_4$S, C, 40.15; H, 1.01; N, 4.68. Found: C, 39.95; H, 0.88; N, 4.72.

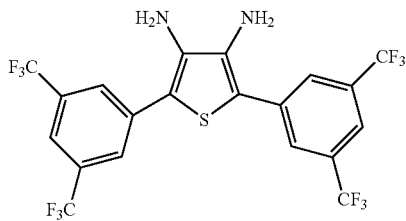

Compound C. A mixture of 2,5-bis-(3,5-bis-trifluoromethyl-phenyl)-3,4-dinitro-thiophene (2.22 g, 5.00 mmol) and tin (II) chloride dihydrate (11.28 g, 50.00 mmol) in ethanol (50 mL) was heated to reflux for 30 min under nitrogen atmosphere. After the mixture cooled down to room temperature, it was poured onto ice. The pH of the solution was made slight basic by addition of 5% of sodium hydroxide solution. The solution was extracted with ethyl acetate 3×. The combined organic layer was dried over magnesium sulfate. Solvent was removed under reduced pressure to give a solid. The solid was purified by flash chromatography on silica gel eluting with hexane:ethyl acetate (10:1) to give 1.60 g of product in 59% yield. $^1$H (300 MHz, benzene-d$_6$) δ 7.72 (brs, 4H), 7.59 (brs, 2H), 7.12 (brs, 4H), 2.62 (brs, 4H). $^{13}$C NMR (75 MHz, CD$_2$Cl$_2$): 136.61, 135.01, 133.19, 132.75, 132.31, 131.87, 129.00, 127.03, 127.06, 125.39, 121.78, 120.12, 120.08, 120.02, 118.16, 114.52. HRMS E1: m/z calcd for C$_{20}$H$_{10}$F$_{12}$N$_2$S 538.0373 Found 538.0379.

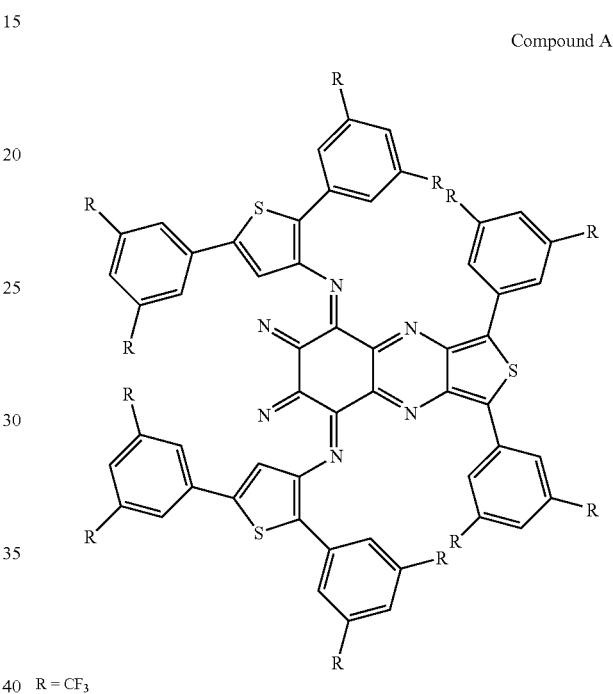

Compound A

R = CF$_3$

Compound A. A mixture of hexaketocyclohexane octahydrate (0.296 g, 0.95 mmol) and 2,5-bis-(3,5-bis-trifluoromethyl-phenyl)-thiophene-3,4-diamine (1.58 g, 2.85 mmol) was added to a degassed acetic acid (50 mL). The mixture was heated to 99° C. for 12 hrs under nitrogen atmosphere. After cooled down to room temperature, the solid was collected by filtration and was washed with acetic acid to give the product. The product was purified by flash chromatography on silica gel eluting with hexane:ethyl acetate (10:2) to give 1.00 g of purified product in 63% yield. $^1$H (300 MHz, CD$_2$Cl$_2$) δ 8.81 (br, 12H), 7.96 (br, 6H). HRMS MALDI-TOF (with CHCA as matrix): 1674.0167; calcd. For C$_{66}$H$_{18}$F$_{36}$N$_6$S$_3$, 1674.0180. Anal. Calcd. For C$_{66}$H$_{18}$F$_{36}$N$_6$S$_3$: C, 47.32; H, 1.08; N, 5.02. Found: C, 47.35; H, 0.99; N, 5.14.

2,3,8,9,14,15-Hexabromo-5,6,11,12,17,18-hexaaza-trinaphthylene. QZ-IB-51. A mixture of hexaketocyclohexane octahydrate (1.00 g, 3.20 mmol) and 4,5-dibromo-benzene-1,2-diamine (2.56 g, 9.61 mmol) was added to a degassed acetic acid (50 mL). The mixture was heated to 140° C. for 12 hrs under nitrogen atmosphere. After cooled down to room temperature, the solid was collected by filtration and was washed with acetic acid to give a green product (2.09 g, 76% yield).

3,4,5,6-Tetrafluoro-benzene-1,2-diamine[2]. A mixture of 2,3,4,5-tetrafluoro-6-nitro-phenylamine (9.72 g, 46.26 mmol) and tin(II) chloride dihydrate (52.00 g, 231.30 mmol) in ethanol (100 mL) was heated to reflux under nitrogen atmosphere for 30 min. After mixture was cooled down to room temperature, it was poured into a $K_2CO_3$ solution. The solution was extracted with ethyl acetate. The combined organic layer was dried over magnesium sulfate. Solvent was removed under reduced pressure and the residue was crystallized in hexane to give a white solid (5.20 g, 62%). $^1$H (300 MHz, $CD_2Cl_2$) δ 3.12 (s, 4H). $^{13}$C NMR (75 MHz, $CD_2Cl_2$): 139.55, 136.30, 133.02, 120.71, 100.12. HRMS E1: m/z calcd for $C_6H_4F_4N_2$ 180.0311 Found 180.0318.

2,3,4,5-Tetrafluoro-6-nitro-phenylamine.[2] Dry ammonia gas was passed slowly through a diethyl ether (500 mL) solution of 1,2,3,4,5-pentafluoro-6-nitro-benzene (25.00 g, 117.33 mmol) at room temperature for 3 hrs. The reaction was stirred for another 18 hrs. The mixture was filtered to remove white solid ammonia fluoride. Solvent was removed under reduced pressure. Residue was purified by flash chromatography on silica gel eluting with hexane: diethyl ether (10:1) to give 16.00 g of orange solid in 65% yield. $^1$H (300 MHz, $CD_3Cl$) δ 5.80 (s, 2H). [A yellow solid was also isolated as 2,3,5,6,-tetrafluoro-4-nitroaniline.]

4,5-Difluoro-benzene-1,2-diamine, QZ-IIIB-94. A mixture of 4,5-difluoro-2-nitro-phenylamine (10.00 g, 57.46 mmol) and tin(II) chloride dihydrate (64.83 g, 287.32 mmol) in ethanol (100 mL) was heated to reflux under nitrogen atmosphere for 30 min. After mixture was cooled down to room temperature, the pH of the solution was made basic (10 to 12) by addition of 5% of sodium hydroxide solution. The solution was extracted with ethyl acetate. The combined organic layer was dried over magnesium sulfate. Solvent was removed under reduced pressure and the residue was crystallized in hexane to give a white solid (6.05 g, 62%). $^1$H NMR (300 MHz, $CDCl_3$): δ 6.53 (t, J=8.5 Hz, 2H), 3.38 (br, 4H). HRMS: Calcd. For $C_6H_6F_2N_2$ 144.0499. Found 144.0500.

4,5-Difluoro-2-nitro-phenylamine. 4,5-Difluoro-2-nitrophenylacetamide (51.00 g, 235.96 mmol) was added to a solution of hydrochloric acid (100 mL) in ethanol (300 mL). The mixture was refluxed for 2 hrs. After the mixture was cooled down to room temperature, it was poured onto ice (1000 g). The precipitate was filtered and was washed with cold water to give a solid. $^1$H NMR (300 MHz, $CDCl_3$): δ 8.02-7.96 (m, 1H), 6.70-6.64 (m, 1H), 6.15 (br, 2H).

4,5-Difluoro-2-nitro-phenylacetamide. Nitric acid (56 mL) was added dropwise to a solution of N-(3,4-difluoro-phenyl)-acetamide (48.00 g, 282.28 mmol) in sulfuric acid in ice bath. The temperature of the solution was controlled at 1 to 3° C. After the addition, the mixture was stirred for 1.5 hrs at 0 to 16° C., and was poured onto ice (1000 g). The precipitate was filtered and washed with cold water to give a solid (51.00 g, 84% yield).

N-(3,4-Difluoro-phenyl)-acetamide.[1] Acetyl chloride (82.61 mL, 774.50 mmol) was added slowly to a solution of 3,4-Difluoro-phenylamine (100 g, 774.50 mmol) in pyridine (250 mL) in ice bath. The mixture was stirred at 0° C. for 45 min then was kept at room temperature for 3 hrs. Solvent was removed under reduced pressure. The residue was crystallized in acetone/water to give a solid. $^1$H NMR (300 MHz, $CDCl_3$): δ 7.86 (br, 1H), 7.62-7.55 (m, 1H), 7.07 (m, 2H), 2.16 (s, 3H).

The following references are all incorporated herein by reference.
(1) Christopher R. Newman, C. R.; Frisbie, C. D.; Silva Filho, D. A.; Bredas, J. L.; Ewbank, P. C.; Mann, K. R. *Chem. Mater.* 2004, 16, 4436-4451
(2) Dimitrakopoulos, C. D.; Malenfant, P. R. L. *Adv. Mater.* 2002, 14, 99
(3) Katz, H. E.; Johnson, J.; Lovinger, A. J.; Li, W. *J. Am. Chem. Soc.* 2000, 122, 7787
(4) Heaton, A.; Hill, M.; Drakesmitrh, F. *J. Fluorine Chem.* 1997, 81, 129
(5) Bock, H.; Babeau, A.; Seguy, I.; Jolinat, P.; Destruel, P. *CHEMPHYSCHEM.* 2002, 6,
(6) Rademacher, J. T.; Kanakarajan, K.; Czarnik, A. W. *Synthesis*, 1994, 378
(7) Arotsky, J.; Butler, R.; Darby, A. C. *J. Chem. Soc.* 1970, 1480
(8) Kotovskaya, S. K.; Charushin, V. N.; Chupakhin, O. N.; Kozhevnikova, E. O. *Russ. J. Org. Chem.* 1998, 34, 369
(9) Mitzel, F.; FitzGerald, S.; Beeby, A.; Faust, Rudiger *Chem. Commun.* 2001, 2596
(10) Dirk, S. M.; Tour, J. M.; *Tetrahedron* 2003, 59, 287
(11) Kestemont, G.; Halleux, V. D.; Lehmann, M.; Ivanov, D. A.; Watson, M.; Geert, Y. H. *Chem. Commun.* 2001, 2074

Example 2

The HATNA and/or DATAN charge-transport materials can be used in organic electronic devices, including, but not limited to, organic light-emitting diodes, lasers, photovoltaic cells, photodetectors, active and passive electronic devices, and memories. Active electronic devices include, but are not limited to, diodes and transistors. Passive electronic devices include, but are not limited to, resistors, capacitors, and inductors. Active and passive electronic devices can be combined to form electrical circuits with properties tailored to the need of specific applications. For example, transistors can be combined to form inverters and ring oscillators. Likewise, passive elements can be combined to form resonant circuits and various filters. Electronic devices and circuits are the foundation of modern electronics and are well known in the art. Examples of applications can be found for instance in P. Horowitz and W. Hill, The Art of Electronics, Cambridge University Press, Cambridge, 1989.

Organic electronic devices typically include one or several organic semiconductors that can conduct electrical charge. In devices, such as organic light-emitting diodes, transistors and memories, charges are injected into the organic semiconductor through electrical contacts formed with conductive electrodes such as metals and conductive oxides. In photovoltaic cells and photodetectors, electrical charges are produced by the optical absorption of light. These charges are then collected through electrical contacts formed with conductive electrodes such as metals and conductive oxides. In some devices and circuits it is important to combine two different organic semiconductors, one of which conducts electrons, and the other of which conducts holes. Preferably, the two semiconductors should have hole and electron mobilities that are comparable. Interfaces formed between such semiconductors are often called heterojunctions.

Figure 56:
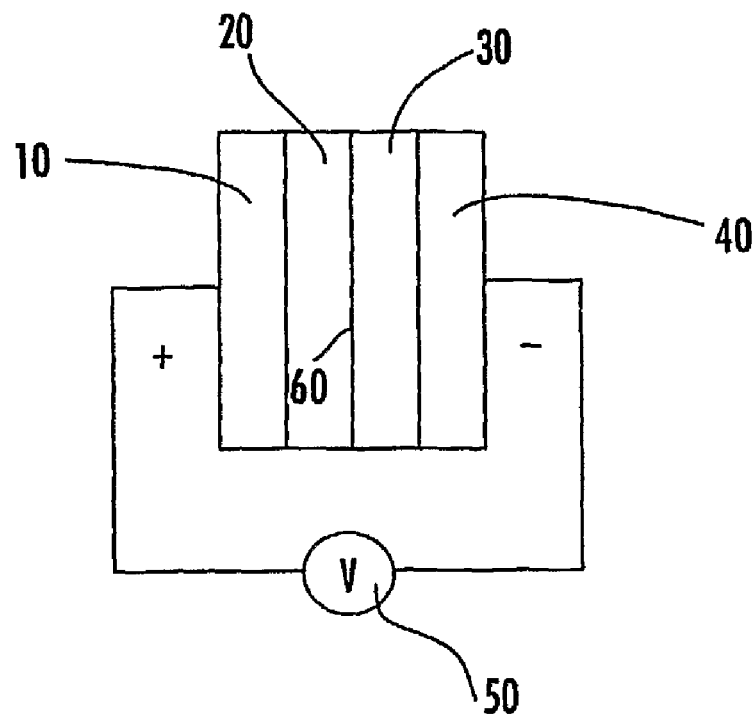
FIG. 56 is a schematic of an organic light-emitting diode.

In an embodiment, the HATNA and/or DATAN charge-transport materials are used as electron-transport materials in organic light-emitting devices. An example of a geometry structure for such a device is shown in FIG. 56. In this device a hole transport organic semiconductor 20 and an electron transport organic semiconductor 30 are sandwiched between an anode 10 and a cathode 40. When a voltage is applied by a power supply 50 with positive electrode applied to anode 10 and negative electrode applied to cathode 40, holes get injected into hole transport semiconductor 20 and electrons get injected into electron transport semiconductor 30. Holes and electrons form excited states at the heterojunction 60, the recombination of which leads to emission of light through at least one of the electrodes (10 or 40) that is semitransparent.

The hole transport semiconductor 20 can be a triphenyldiamine (TPD) derivative thin film or other hole transport materials known in the art, the anode 10 can be indium tin oxide (ITO), the electron-transport semiconductor 30 can include of one or more of the HATNA and/or DATAN charge-transport materials described herein, and the cathode 40 can be a metal including, but limited to, Ca, Ag, Mg, Al, Au, or mixtures thereof.

Figure 57:
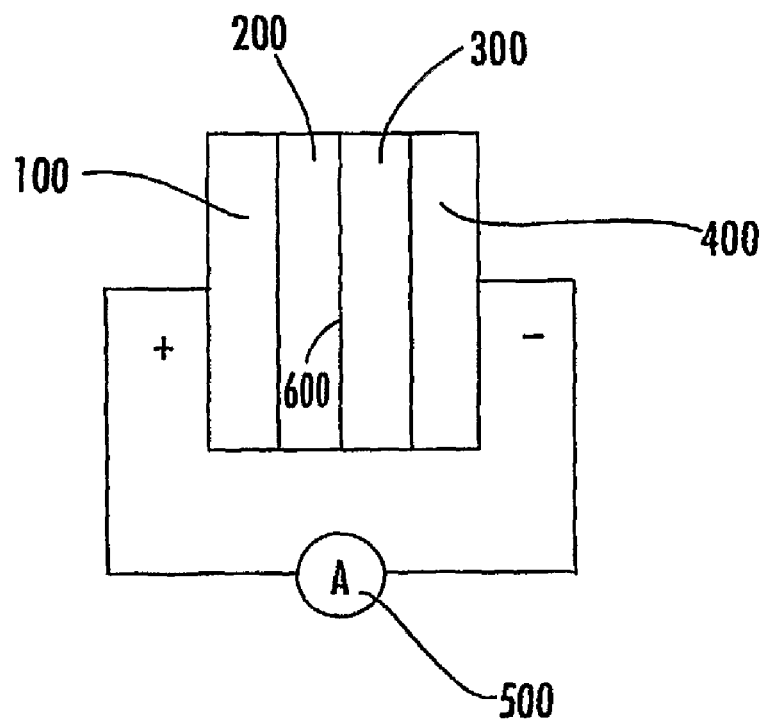
FIG. 57 is a schematic of an organic photovoltaic cell.

In another embodiment, the HATNA and/or DATAN charge-transport materials are used as electron transport materials in photovoltaic cells. In an embodiment, a possible geometry for such a device is shown in FIG. 57. In this device a hole-transport organic semiconductor 200 and an electron-transport organic semiconductor 300 are sandwiched between a first electrode 100 and a second electrode 400. When the device is exposed to light, optical absorption in the organic semiconductors 200 and 300 leads to the formation of excited states that diffuse to the heterojunction 600 where they separate into electron-hole pairs. Holes are transported in the semiconductor layer 200 and get collected by the electrode 100. Electrons are transported in the layer 300 and are collected by the electrode 400. The transport of the charges created optically leads to a current that can be measured by an ampmeter 500.

The hole transport semiconductor 200 can be a thin film of triphenyldiamine (TPD), a phthalocyanine, an oligoacene, an oligothiophene or any other organic hole transport material with high hole mobility known in the art. The electrode 100 can be indium tin oxide (ITO) or any other conducting oxide known in the art, the electron transport semiconductor 300 can be comprised of one or more of the HATNA and/or DATAN charge-transport materials described herein. The second electrode 400 can be a metal including, but limited to, Ca, Ag, Mg, Al, Au, or mixtures thereof. In some cases, an additional layer can be added between 300 and 400 to prevent the dissociation of excited states (also referred to as excitons) near the electrode 400. This layer may be called an exciton blocking layer.

Figure 58:
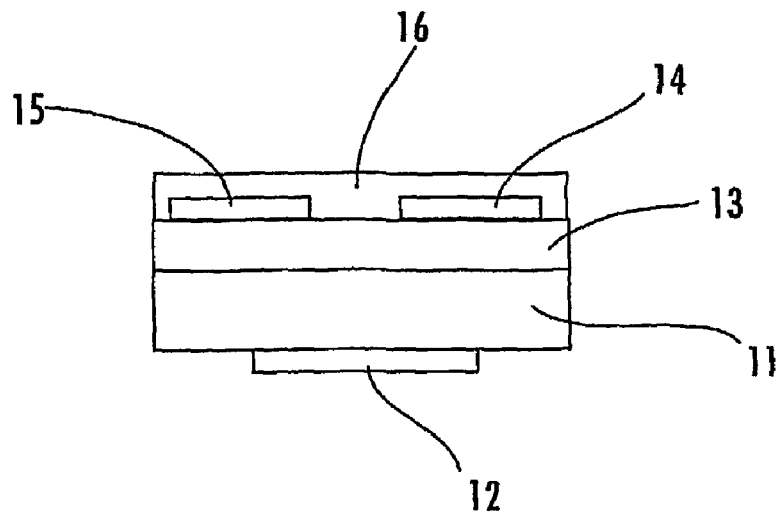
FIG. 58 is a schematic of an organic field-effect transistor with bottom electrodes.
Figure 59:
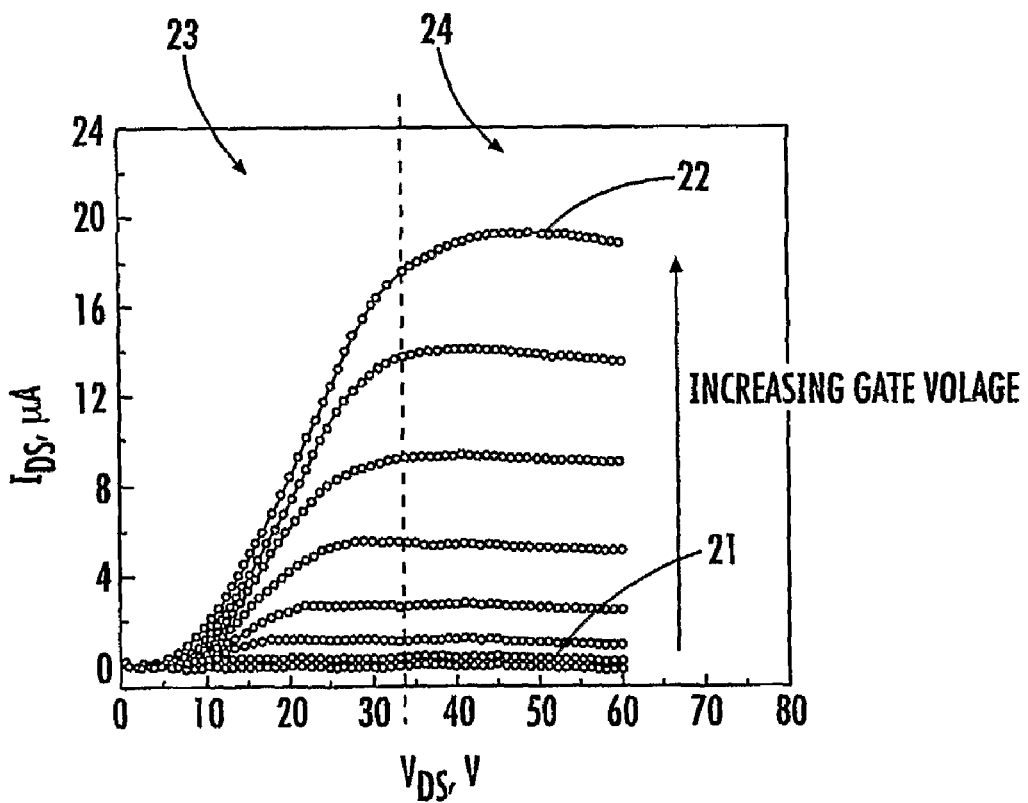
FIG. 59 is a schematic of the electrical output characteristic of an organic field-effect transistor. The curves show the current measured between source and drain electrodes as a function of the voltage between source and drain electrodes.

In another embodiment, the HATNA and/or DATAN charge-transport materials are used as electron transport materials in organic field-effect transistors. In an embodiment, a possible structure for such a device is shown in FIG. 58. The organic electron-transport semiconductor 16 is deposited on top of a structure that is comprised of a conductive substrate 11 such as highly doped silicon, an insulator layer 13 such as a thermally grown silicon oxide layer, a gate electrode 12, a source electrode 15 and a drain electrode 14. A positive voltage applied to the gate electrode changes the density of electrons in the organic semiconductor 16 and will influence the current voltage characteristics measured between the source electrode 15 and the drain electrode 14. The typical electrical output characteristic of a field-effect transistor is shown in FIG. 59. When a low voltage is applied between the source electrode 15 and the drain electrode 14 a small current is measured, as shown by curve 21. In contrast, when a larger gate voltage is applied between the source electrode 15 and the drain electrode 14, a large current is measured, as shown by curve 22. For a given gate voltage, the electrical characteristics 21 and 22 have a linear regime 23 and a saturation regime 24. These electrical characteristics are similar to those measured for MOSFET transistors including inorganic semiconductors including silicon and germanium.

At low drain voltage where the response is linear (as shown by region 23 in FIG. 59), the current-voltage response is given by:

$$I_D = \frac{WC_{ox}\mu}{L}\left(V_G - V_T - \frac{V_D}{2}\right)V_D \tag{1}$$

Where W is the channel width, L the distance between source and drain electrodes (channel length), $C_{ox}$ is the capacitance per unit area of the insulator, $V_T$ is the threshold voltage and $\mu$ is the "effective" field-effect mobility, which can be calculated in this regime from the transconductance g, defined by:

$$g_m = \frac{\partial I_D}{\partial V_G}\bigg|_{V_D=const.} = \frac{WC_{ox}}{L}\mu V_D \tag{2}$$

For large drain voltages (as shown by region 24 in FIG. 59), the saturated drain current $I_{Dsat}$ is given by the so-called "square-law":

$$I_{Dsat} = \frac{WC_{ox}\mu}{2L}(V_G - V_T)^2 \tag{3}$$

In this regime, mobility can be extracted from the slope of the plot of the square root of the drain current versus gate voltage. Such a curve is called a transfer curve.

Figure 60:
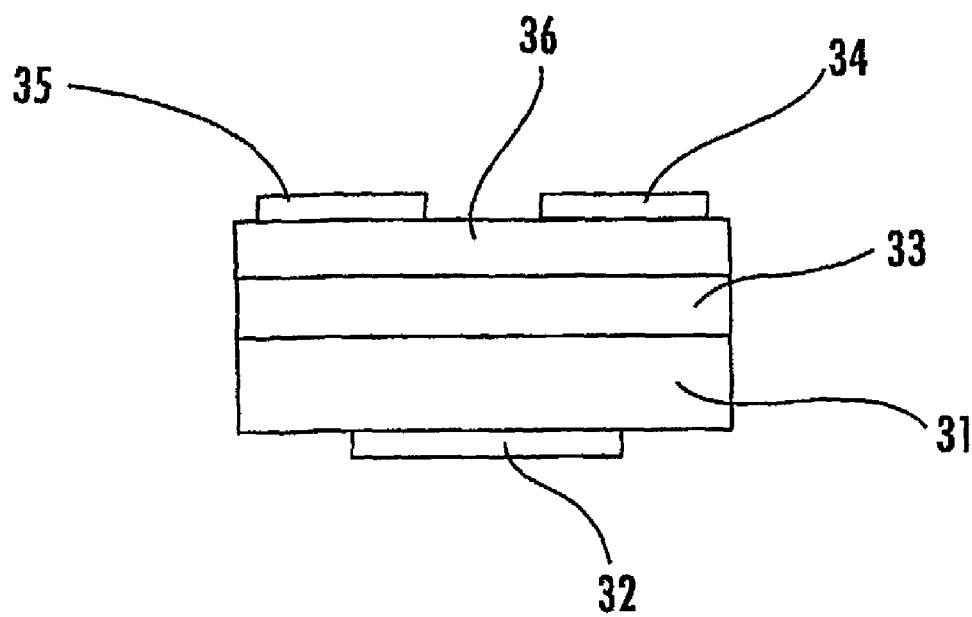
FIG. 60 is a schematic of an organic field-effect transistor with top electrodes.

Another geometry for an organic field-effect transistor is shown in FIG. 60. The organic electron-transport semiconductor 36 is deposited on top of a structure that includes a conductive substrate 31 such as highly doped silicon, an insulator layer 33 such as a thermally grown silicon oxide layer, and a gate electrode 32. In this geometry, source electrode 35 and a drain electrode 34 are deposited on top of the semiconductor layer 36.

Figure 61A:
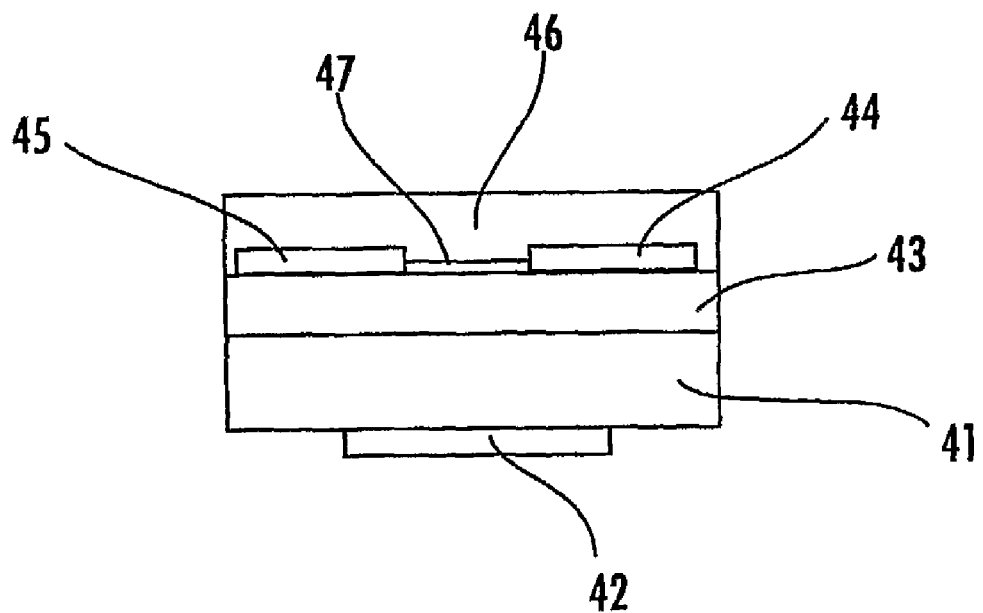
FIG. 61A is a schematic of an organic field-effect transistor with a surface modifier and with bottom electrodes.
Figure 61B:
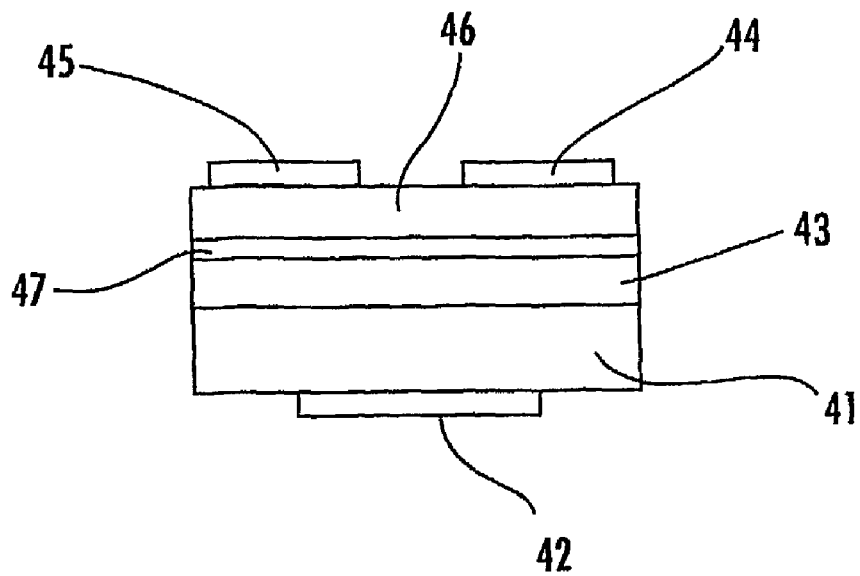
FIG. 61B is a schematic of an organic field-effect transistor with a surface modifier and top electrodes.

Another geometry for an organic field-effect transistor is shown in FIGS. 61A and 61B. In this geometry, an additional layer is introduced between the gate insulator 43 and the organic semiconductor 46. This layer modifies the properties of the surface of the gate insulator and improves its compatibility with the organic semiconductors. The surface modifier 47 can be a self-assembled monolayer leading to a thin layer. It can be deposited on top of the gate insulator 43 after the deposition of the source and drain electrodes, 45 and 44, respectively, and before the deposition of the organic semiconductor 46, as shown in FIG. 61A. Alternatively, layer 47 can be deposited on top of the gate insulator 43 before deposition of the organic semiconductor 46, as shown in FIG. 61B.

Figure 62A:
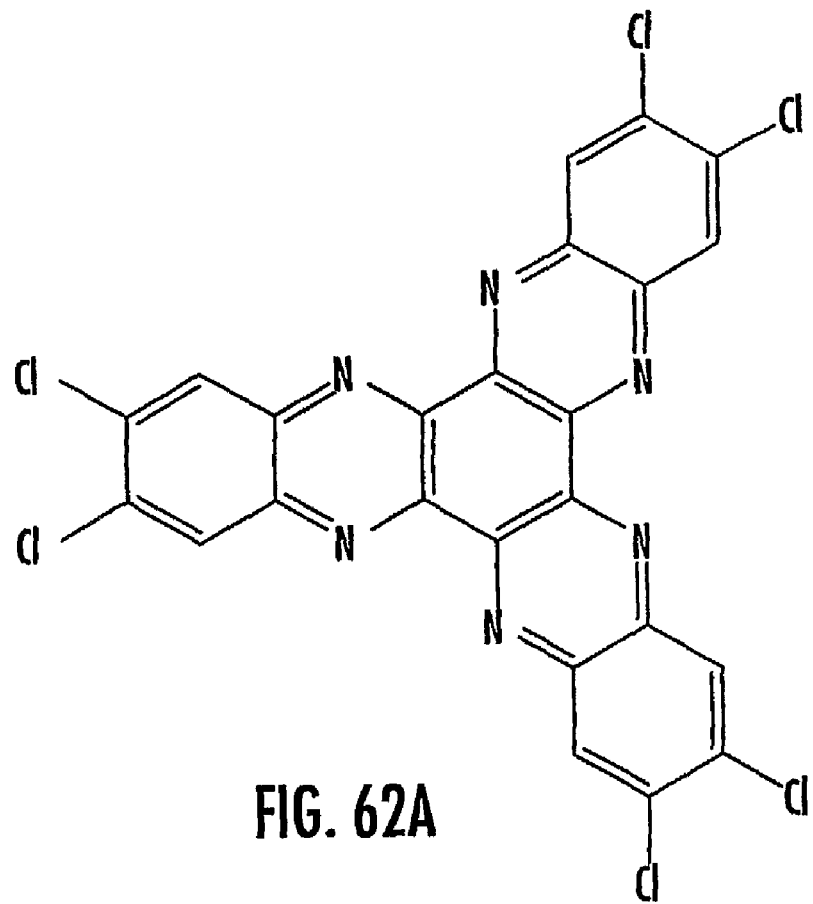
FIG. 62A illustrates the chemical structure of HATNA-Cl$_6$.
Figure 62B:
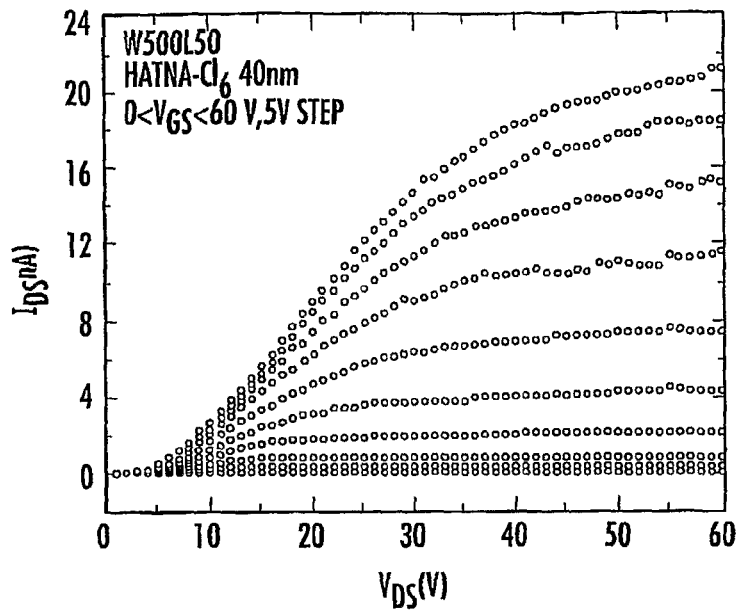
FIG. 62B illustrates the output characteristic of a transistor comprised of HATNA-$Cl_6$ as the organic semiconductor.
Figure 62C:
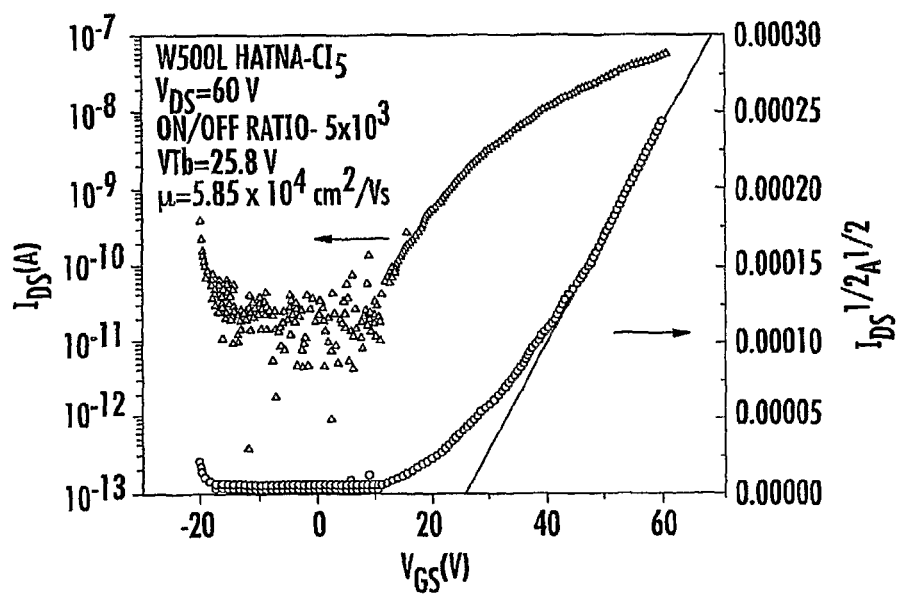
FIG. 62C illustrates the transfer curve of a transistor comprised of HATNA-$Cl_6$ as the organic semiconductor.

An example of the performance of an organic field-effect transistor in which the organic electron transport semiconductor was a HATNA compound is shown in FIG. 62A. The chemical structure of the HATNA molecule used in this device is shown in FIG. 62A. The geometry of this device is similar to that described in FIG. 61A. The HATNA compound was purified by thermal gradient zone sublimation prior to device fabrication. Following the device structure of FIG. 61A, the substrate 41 was doped silicon and the gate insulator 43 was a 200 nm-thick thermally grown $SiO_2$ layer. The back gate electrode 42 was formed by evaporating a thin layer of titanium followed by gold on the back side of the silicon substrate that was previously etched to remove the thermal oxide. The source and drain electrodes, 45 and 44 were formed by depositing a thin layer of titanium followed by gold on top of the gate insulator 43. The width W of the electrodes and the length L of the channel formed between the source and drain electrodes was 500 μm and 50 μm, respectively. These electrodes were defined by standard photolithography after the deposition of gold. The surface modifier 47 used was diphenyldimethoxysilane (DPMS). This material was processed into a film by implementing the following steps: first, the hydroxyl derivative of the silane compound was formed by dispersing 0.1 wt. % of DPMS into an acidic solution of 1:1 EtOH $H_2O$ (pH=4 to 5); then, the $SiO_2$ dielectric surface was activated using an atmospheric plasma treatment (60 s, 750 W) to produce hydroxyl groups at the interface; finally, the wafer was dipped into the solution and upon heating (120° C., 20 min) the silane compound reacted with the hydroxyl groups of the surface and formed a thin layer that covered the surface of the gate insulator 43. The HATNA derivative (HATNA-$Cl_6$ shown in FIG. 62A) was deposited by physical vapor deposition under a vacuum below $10^{-7}$ Torr. The thickness of the HATNA semiconductor film was controlled by crystal quartz monitors and evaluated to be 40 nm. The electrical output characteristics and the transfer curves of these devices are shown in FIGS. 62B and 62C, respectively. From the transfer curve shown in FIG. 62C, a field-effect mobility of $5.85 \times 10^{-4}$ $cm^2/Vs$ can be extracted.

Figure 63A:
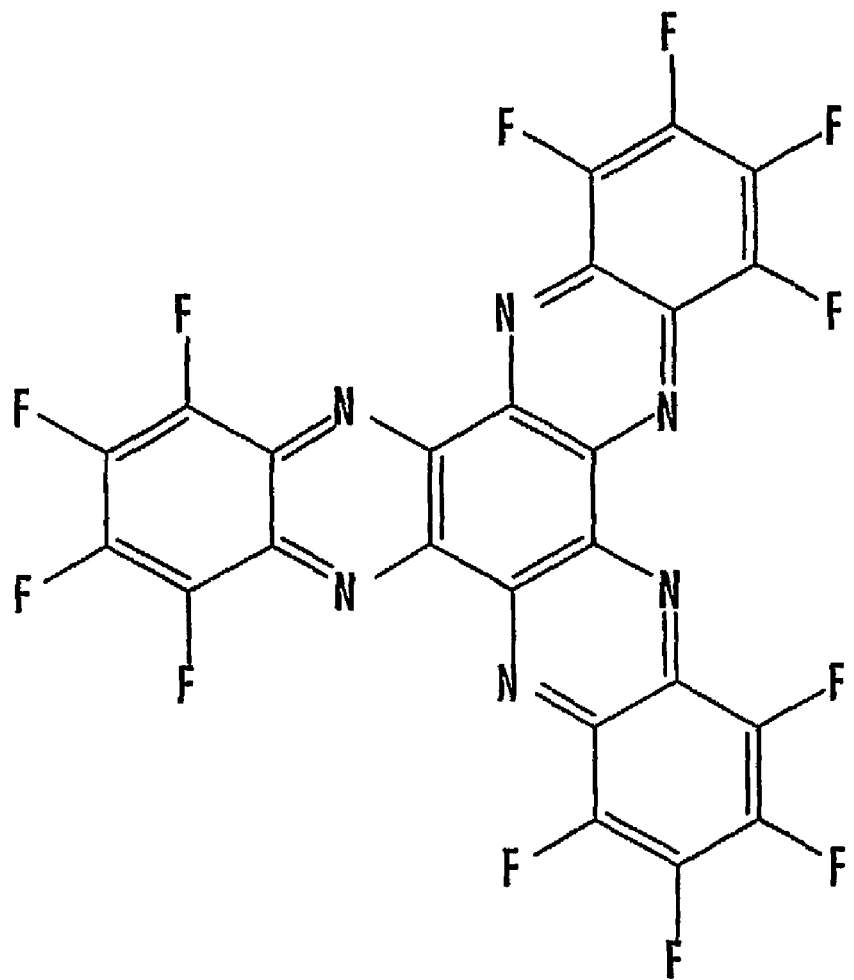
FIG. 63A illustrates the chemical structure of HATNA-$F_{12}$.
Figure 63B:
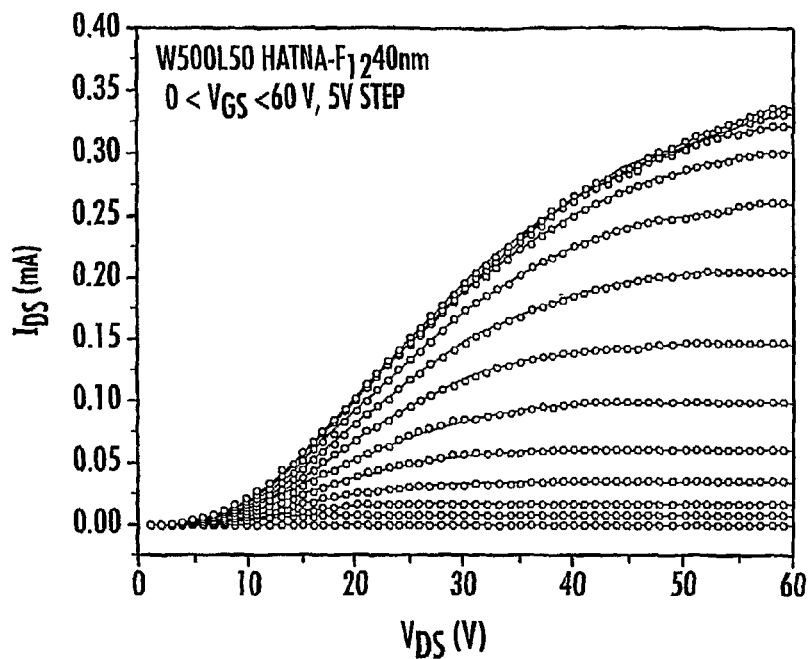
FIG. 63B illustrates the output characteristic of a transistor comprised of HATNA-$F_{12}$ as the organic semiconductor.
Figure 63C:
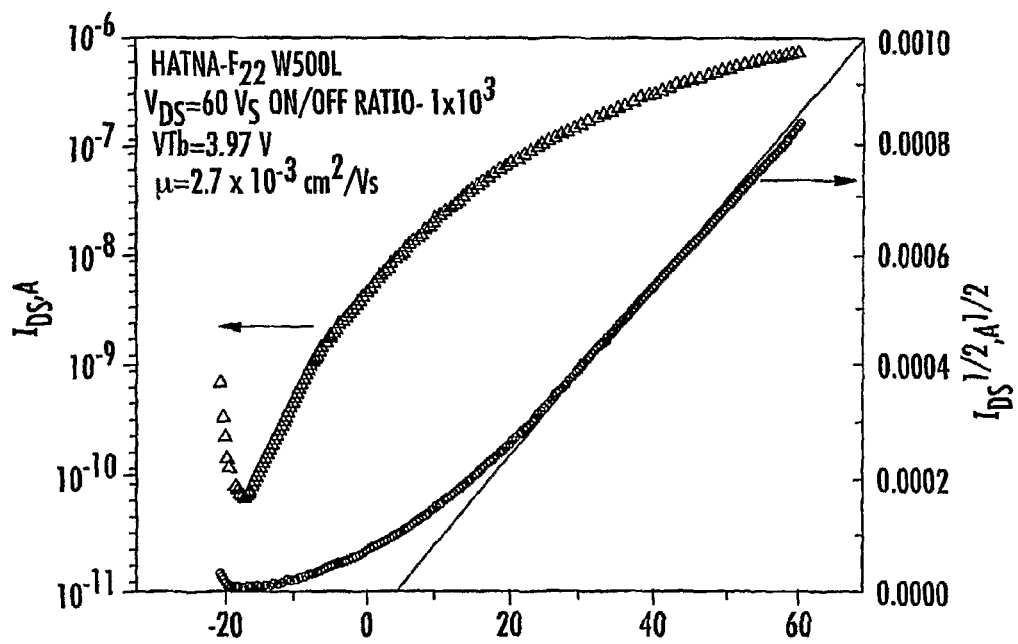
FIG. 63C illustrates the transfer curve of a transistor comprised of HATNA-$F_{12}$ as the organic semiconductor.

Another example of a HATNA compound that can be used in an organic field-effect transistor is shown in FIG. 63A: The geometry of this device is similar to that of the device described in FIG. 62A, except that the organic semiconductor (46 in FIG. 61A) includes HATNA-$F_{12}$ (see FIG. 63A). The device fabrication procedures are identical to those used in the fabrication of the device described in the example above. The electrical output characteristics and the transfer curves of these devices are shown in FIGS. 63B and 63C, respectively. From the transfer curve shown in FIG. 63C, a field-effect mobility of $2.7 \times 10^{-3}$ $cm^2/Vs$ can be extracted.

Example 3

5,6,11,12,17,18-Hexaaza-trinaphthylene-2,8,15-tricarboxylic acid tripentafluoro-phenylmethyl ester (1a) and 5,6,11,12,17,18-Hexaaza-trinaphthylene-2,8,15-tricarboxylic acid tripentafluoro-phenylmethyl ester (1b) 5,6,11,12,17,18-Hexaaza-trinaphthylene-2,8,14-tricarbonyl trichloride 3 (2.0 g, 3.5 mmol) was suspended in 15 ml of THF and pentafluorophenyl-methanol (15.0 g, 75.7 mmol) was added. Pyridine (15.0 ml) was slowly added to the reaction mixture, which was stirred at 50° C. for 72 hours. Solvent was evaporated. The clued solid was passed through a short column chromatography by used dichloromethane as eluent. The solvent was evaporated and the resulting solid was further purified by column chromatography using dichloromethane: ethyl acetate (9:1) as eluent, and then solvent was evaporated completely. To isolate the 2,8,14-isomers from the crude product, recrystallizations were carried out three times by using dichloromethane and cooling the sample in a freezer to yield the yellow solid 1a. The filtrate of the first recrystallization was evaporated, and then the solid that was obtained was dissolved in the minimum amount of chloroform and was precipitated with 300 mL of MeOH to yield the yellow solid (1a/b). An amount of 0.7 g of 1a, 0.9 g of 1a/b were obtained.

To obtain pure 1b', column chromatography was performed on the crude product of another reaction prepared according the procedure above batch using dichloromethane: ethyl acetate (9:1) as eluent by using the crude product of another reaction batch. After solvent evaporation, the compound was dissolved in 10 ml of $CHCl_3$ and was then reprecipitated in 300 ml MeOH. In this manner the 2,8,15-isomer, late fraction 1b', was isolated from the crude product.

[1a]. $^1$H NMR (300 MHz, $CDCl_3$) δ 9.38-9.40 (two quasi-doublets, J=1.5 Hz, 3H), 8.73 & 8.76 (two br singlets, 3H), 8.59-8.62 (m, 3H), 5.61-5.63 (two br singlets, 6H). $^{13}$C NMR ($CDCl_3$, 125 MHz) δ 164.35, 146.89 (m), 145.17, 144.87 (m), 144.54, 144.37, 144.35, 143.99, 143.80, 143.09 (m), 142.67, 142.62, 141.15 (m), 138.69 (m), 136.71 (m), 136.57, 133.55, 133.51, 132.68, 132.64, 132.52, 131.61, 131.49, 131.11, 130.89, 109.15, 108.94, 54.65 ppm. $^{19}$F NMR ($CDCl_3$, 376 MHz) δ (−141.71)-(−141.90) (dd, J=21.4 Hz, $J_2$=6 Hz, 6F), (−151.86)-(−152.02) (t, J=21.4 Hz, 3F), (−161.26)-(−161.44) (sextet, J=9.0 Hz, 6F). $^{19}$F NMR Chemical shifts are relative to trifluoromethylbenzene, which was used as an external standard. MALDI-TOF MS (M+H): m/z 1058.1.

[1a/b]. $^1$H NMR (300 MHz, $CDCl_3$) (9.42-9.41 (m, 3H), 8.78 & 8.76 (two br singlets, 3H), 8.66-8.65 (quartet, J=2 Hz, 2H), 8.64-8.63 (quartet, J=1.5 Hz, 1H), 5.59 & 5.58 (two br singlets, 6H). $^{19}$F NMR ($CDCl_3$, 376 MHz) δ (−141.72)-(−141.92) (m, 6F), (−151.82)-(−152.12) (m, 3F), (−161.22)-(−161.50) (m, 6F). $^{19}$F NMR Chemical shifts are relative to trifluoromethylbenzene, which was used as an external standard. MALDI-TOF MS (M+H): m/z 1057.1, calcd for $C_{49}H_{16}F_{15}N_6O_6$, 1057.0886.

[1b']. $^1$H NMR (500 MHz, $CDCl_3$) δ 9.23-9.21 (two quasi-doublets, each J=1.5 Hz, 3H), 8.60 & 8.59 (two br singlets, 3H), 8.53-8.48 (m, 3H), 5.59 & 5.58 (two br singlets, 6H). $^{13}$C NMR ($CDCl_3$, 125 MHz) δ 164.32, 146.88 (m), 145.17, 144.87 (m), 144.54, 144.37, 144.35, 143.99, 143.80, 143.09 (m), 142.67, 142.62, 141.15 (m), 138.69 (m), 136.71 (m), 136.57, 133.55, 133.51, 132.68, 132.64, 132.52, 131.71, 131.59, 131.02, 130.96, 109.09, 108.96, 54.68 ppm. $^{19}$F NMR ($CDCl_3$, 376 MHz) δ (−141.70)-(−141.92) (m, 6F), (−151.70)-(−152.10) (quartet, J=19.6 Hz, 3F), (−161.20)-(−161.52) (m, 6F). $^{19}$F NMR Chemical shifts are relative to trifluoromethylbenzene which was used as an external standard. MALDI-TOF MS (M+H): m/z 1057.0, calcd for $C_{48}H_{16}F_{15}N_6O_6$, 1057.0886. Anal. calcd. for $C_{48}H_{15}F_{15}N_6O_6$: C, 54.56; H, 1.43; F, 26.97; N, 7.95. Found: C, 53.81; H, 1.46; F, 26.83; N, 7.73.

Figure 64:
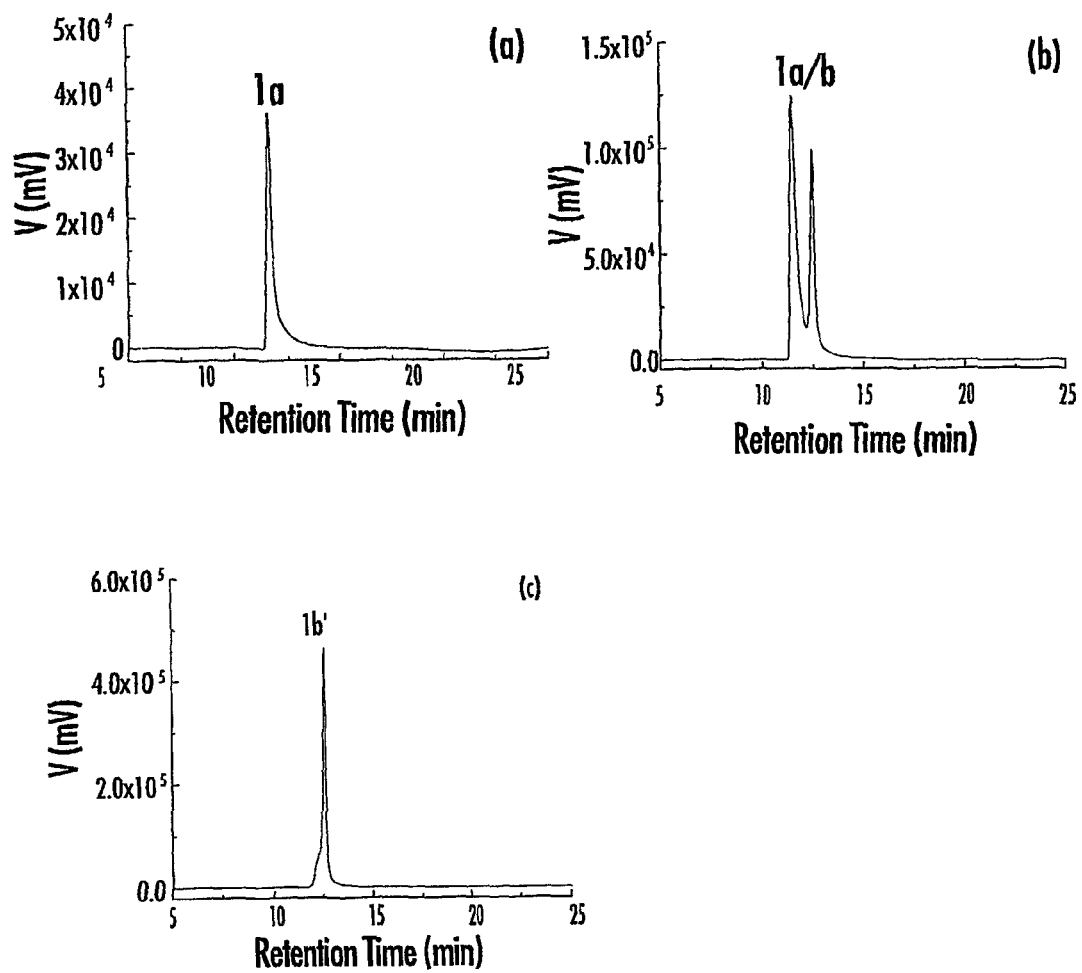
FIG. 64 illustrates HPLC traces of (a) compound 1a, (b) mixture of compounds 1a/b, and (c) compound 1b'.

Thus, a mixture of 2,8,14-isomer and 2,8,15-isomer of 1 can be separated to the individual isomers by using the recrystallization with dichloromethane. This method utilizes the differential solubility between two isomers toward dichloromethane; the solubility of the planer symmetrical 2,8,14-isomer is lower than that of the asymmetrical 2,8,15-isomer. The recrystallization with dichloromethane can yield pure 2,8,14-isomer (1a). Consequently, the filtered solution after the recrystallization should contain the 2,8,15-isomer (1b') or mixture (1a/b). FIG. 64 shows the HPLC traces of 1a separated by the recrystallization with dichloromethane, and 1a/b precipitated from the filtered solution. Also the 2,8,15-isomer can be further purified by column chromatography and HPLC trace of 1b' is shown. A cyano normal phase column and HPLC grade $CH_2Cl_2$ and hexane; the initial % flow of $CH_2Cl_2$ was 20% until 2 min; at 15 min $CH_2Cl_2$ was 100%, were used for HPLC analysis. Both isomer peaks had indistinguishable UV-vis spectra.

Figure 65:
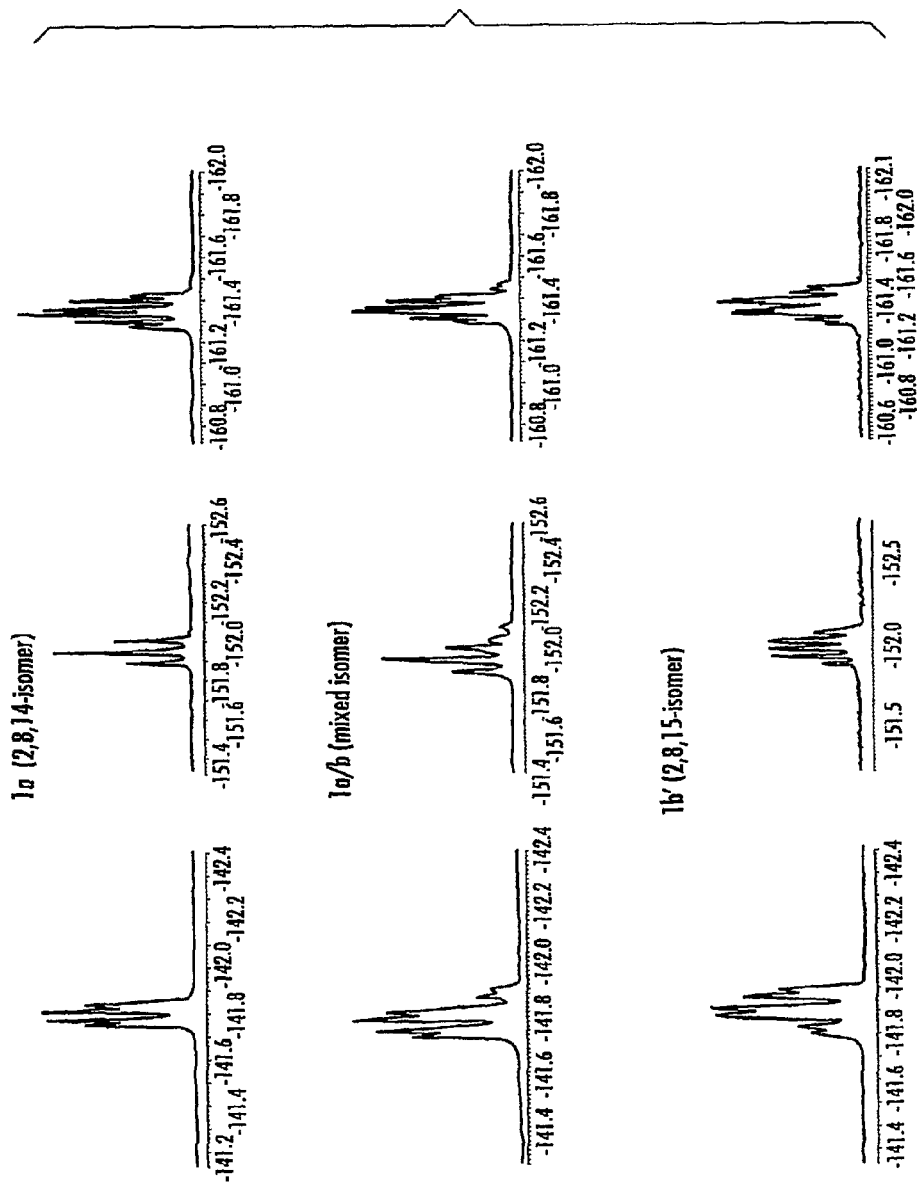
FIG. 65 illustrates $^{19}$F-NMR ($CDCl_3$, 376 MHz) of compound 1a, a mixture of compounds 1a/b, and compound 1b'.
Figure 66:
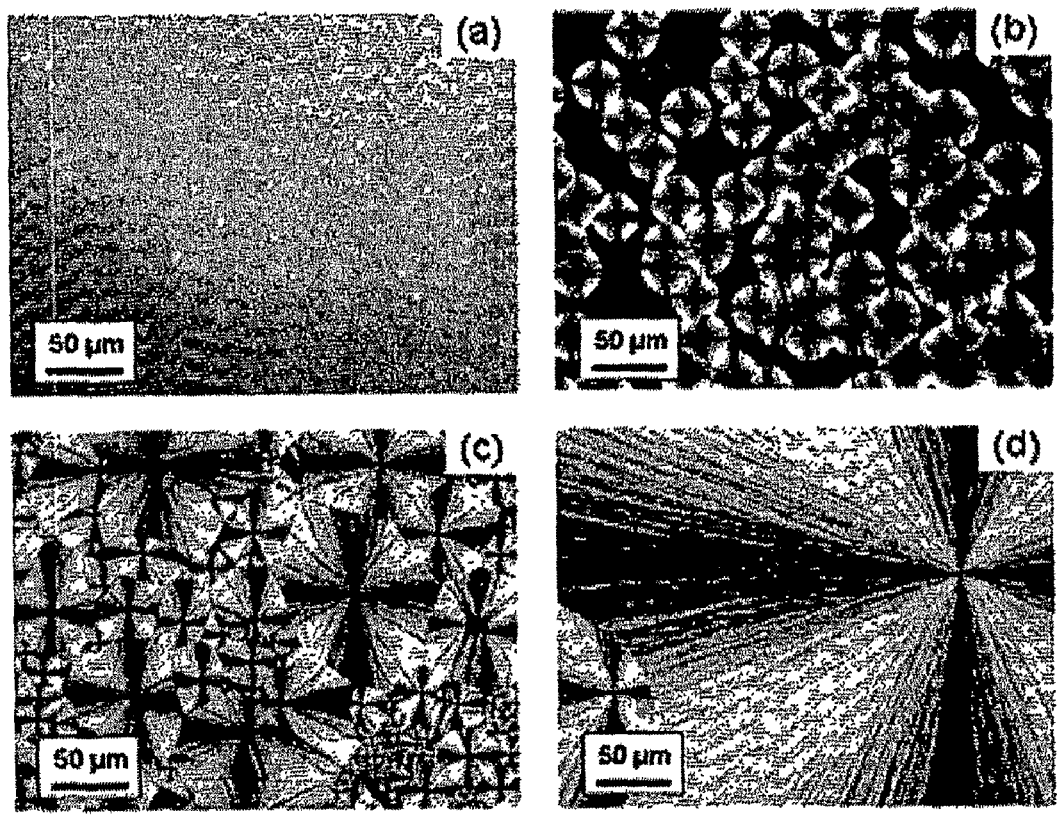
FIG. 66 illustrates cross-polarized optical microscopy images of compound 1b', (a) solidification with 95° C./min cooling rate; (b) with 60° C./min; (c) with 30° C./min; (d) with 10° C./min from isotropic phase. All samples were solidified between two glass slides or ITO glasses.

$^{19}$F-NMR ($CDCl_3$, 376 MHz) of 1a, 1a/b, and 1b' are shown in FIG. 65. In the 2,8,14-isomer, 1a, the $F_p$'s appear as triplets because they are coupled to two $F_m$ whilst $F_o$ appear as doublet of doublets. In the 2,8,15-isomer, 1b', the $F_p$ appear as two overlapped triplets of approximate ratio 2:1 corresponding to two different set of fluorinated aromatic rings.

TABLE 1

Summary of carrier mobility characteristics at room temperature.
Mobility determinations of samples by SCLC method.

| Material | Component | Film morphology | d (μm) | μ(E = 0) (cm²/Vs) | γ (cm/V)^(1/2) | $E_{max}$ (V/cm) | $\mu_{max}$ (cm²/Vs) |
|---|---|---|---|---|---|---|---|
| 1a/b[1] | 2.8.14-isomer 2,8,15-isomer | amorphous | 5 | 0.0124 | $1.72 \times 10^{-3}$ | $3.08 \times 10^4$ | 0.017 |
| 1a/b[2] | 2.8.14-isomer 2,8,15-isomer | amorphous | 5 | 0.0175 | $1.13 \times 10^{-3}$ | $2.80 \times 10^4$ | 0.021 |
| 1b'[2] | 2,8,15-isomer | polycrystalline | 20 | 0.056 | $2.54 \times 10^{-3}$ | $0.75 \times 10^4$ | 0.071 |
| 1b'[3] | 2,8,15-isomer | polycrystalline | 5 | 0.045 | $2.42 \times 10^{-3}$ | $0.60 \times 10^4$ | 0.054 |
| 1b'[3] | 2,8,15-isomer | spherulites | 5 | 0.0096 | $5.65 \times 10^{-3}$ | $0.50 \times 10^4$ | 0.0014 |
| 1a[3] | 2,8,14-isomer | polycrystalline | 5 | — | — | — | — |

[1] the product from first reaction batch
[2] the product from second reaction batch
[3] the product from third reaction batch Therefore the following is claimed:

1. A charge-transport material comprising, a hexaazatrinaphthylene (HATNA)-[X]$_6$ monomer having a structure:

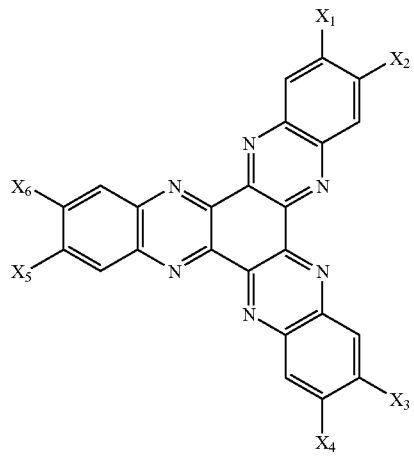

wherein $X_1$, $X_2$, $X_3$, $X_4$, $X_5$, and $X_6$ each are independently selected from: CN; NO$_2$; CHO; linear or branched, alkyl groups with from 2 to 25 carbons; linear or branched, perfluoronated alkyl groups with up to 25 carbons; fused aromatic rings; donor groups; acceptor groups; aryl groups; polymerizable groups; —(CH$_2$CH$_2$O)$_\alpha$—(CH$_2$)$_\beta$OR$_{a1}$; —(CH$_2$CH$_2$O)$_\alpha$—(CH$_2$)$_\beta$NR$_{a2}$R$_{a3}$; —(CH$_2$CH$_2$O)$_\alpha$—(CH$_2$)$_\beta$CONR$_{a2}$R$_{a3}$; —(CH$_2$CH$_2$O)$_\alpha$ —(CH$_2$)$_\beta$CN; —(CH$_2$CH$_2$O)$_\gamma$—(CH$_2$)$_\delta$F; —(CH$_2$CH$_2$O)$_\gamma$—(CH$_2$)$_\delta$NO$_2$; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$ —(CH$_2$)$_\beta$I; —(CH$_2$CH$_2$O)$_\alpha$— (CH$_2$)$_\beta$-Phenyl; —(CH$_2$)$_\beta$—(OCH$_2$CH$_2$)$_\alpha$R$_{a1}$; —(CH$_2$)$_\beta$—(OCH$_2$CH$_2$)$_\alpha$NR$_{a2}$R$_{a3}$; —(CH$_2$)$_\beta$— (OCH$_2$CH$_2$)$_\alpha$CONR$_{a2}$R$_{a3}$; —(CH$_2$)$_\beta$—(OCH$_2$CH$_2$)$_\alpha$CN; —(CH$_2$)$_\beta$—(OCH$_2$CH$_2$)$_\alpha$F; —(CH$_2$)$_\beta$—(OCH$_2$CH$_2$)$_\alpha$NO$_2$; —(CH$_2$)$_\beta$—(OCH$_2$CH$_2$)$_\alpha$Cl; —(CH$_2$)$_\beta$—(OCH$_2$CH$_2$)$_\alpha$Br; —(CH$_2$)$_\beta$—(OCH$_2$CH$_2$)$_\alpha$I; —(CH$_2$)$_\beta$—(OCH$_2$CH$_2$)$_\alpha$Phenyl; —(CF$_2$)$_\beta$OR$_{a1}$; —(CF$_2$)$_\beta$CH$_2$NR$_{a2}$R$_{a3}$; —(CF$_2$)$_\beta$CF$_3$; —O(CF$_2$)$_\beta$ OR$_{a1}$; —OCH$_2$CH$_2$(CF$_2$)$_\beta$OR$_{a1}$; —OCH$_2$CH$_2$(CF$_2$)$_\beta$NR$_{a2}$R$_{a3}$; —O(CF$_2$)$_\beta$ CH$_2$NR$_{a2}$R$_{a3}$; —OCH$_2$CH$_2$(CF$_2$)$_\beta$CF$_3$; —(CF$_2$)$_\beta$ (OCH$_2$CH$_2$)$_\alpha$Phenyl; —(CF$_2$)$_\beta$—(OCH$_2$CH$_2$)$_\alpha$Phenyl; —(CH$_2$)$_\beta$—(OCH$_2$CH$_2$)$_\alpha$Aryl; —(CF$_2$)$_\beta$— (OCH$_2$CH$_2$)$_\alpha$Aryl; —(OCH$_2$CH$_2$)$_\alpha$—(CF$_2$)$_\beta$Aryl; —(OCH$_2$CH$_2$)$_\alpha$—(CH$_2$)$_\beta$Aryl; —O(CH$_2$)$_\beta$Aryl; and —O(CF$_2$)$_\beta$Aryl; and combinations thereof;

wherein R$_{a1}$, R$_{a2}$, and R$_{a3}$ can each be independently selected from, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript α is an integer number from 0 to 25, wherein subscript β is an integer number from 0 to 25; and with the proviso that X$_1$, X$_2$, X$_3$, X$_4$, X$_5$ and X$_6$ are each not an alkoxy group, —OR, where R=C$_n$H$_{2n+1}$, where n=6, 8, 10, or 12; an alkylthio, —SR, where R=C$_n$H$_{2n+1}$, where n=6, 8, 10, or 12; H; Cl; or a methyl (—CH$_3$) group;

further comprising wherein one or more of the X$_1$, X$_2$, X$_3$, X$_4$, X$_5$, and X$_6$ each are independently selected from an aryl group, wherein the aryl group is selected from: aromatic ring systems having 20 carbons in the aromatic ring framework not including carbons on the substituents; and aryls represented by the following structures:

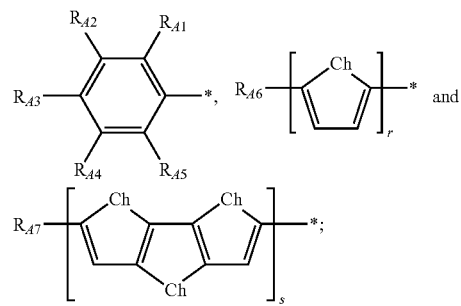

wherein Ch is selected from: Se, S, O, and combinations thereof; wherein R$_{A1}$, R$_{A2}$, R$_{A3}$, R$_{A4}$, R$_{A5}$, R$_{A6}$, and R$_{A7}$, can each be independently selected from: H; a linear or branched alkyl group with up to 25 carbons; —(CH$_2$CH$_2$O)$_\gamma$—(CH$_2$)$_\delta$OCH$_3$; —(CH$_2$CH$_2$O)$_\gamma$—(CH$_2$)$_\delta$N(CH$_3$)$_2$; —(CH$_2$CH$_2$O)$_\gamma$—(CH$_2$)$_\delta$CON (CH$_3$)$_2$; —(CH$_2$CH$_2$O)$_\gamma$—(CH$_2$)$_\delta$CN; —(CH$_2$CH$_2$O)$_\gamma$—(CH$_2$)$_\delta$F; —(CH$_2$CH$_2$O)$_\gamma$—(CH$_2$)$_\delta$NO$_2$; —(CH$_2$CH$_2$O)$_\gamma$—(CH$_2$)$_\delta$Cl; —(CH$_2$CH$_2$O)$_\gamma$—(CH$_2$)$_\delta$Br; —(CH$_2$CH$_2$O)$_\gamma$—(CH$_2$)$_\delta$I; —(CH$_2$CH$_2$O)$_\gamma$—(CH$_2$)$_\delta$-Phenyl; —(CH$_2$)$_\delta$—(OCH$_2$CH$_2$)$_\gamma$CH$_3$;

—(CH$_2$)$_\delta$—(OCH$_2$CH$_2$)$_\delta$N(CH$_3$)$_2$; —(CH$_2$)$_\delta$—(OCH$_2$CH$_2$)$_\gamma$C(O)N(CH$_3$)$_2$; —(CH$_2$)$_\delta$—(OCH$_2$CH$_2$)$_\gamma$CN; —(CH$_2$)$_\delta$—(OCH$_2$CH$_2$)$_\gamma$F; —(CH$_2$)$_\delta$—(OCH$_2$CH$_2$)$_\alpha$NO$_2$; —(CH$_2$)$_\delta$—(OCH$_2$CH$_2$)$_\gamma$Cl; —(CH$_2$)$_\delta$—(OCH$_2$CH$_2$)$_\gamma$Br; —(CH$_2$)$_\delta$—(OCH$_2$CH$_2$)$_\gamma$I; —(CH$_2$)$_\delta$—(OCH$_2$CH$_2$)$_\gamma$Phenyl; —(CF$_2$)$_\beta$OCH$_3$; —(CF$_2$)$_\beta$OCH$_3$; —(CF$_2$)$_\beta$CH$_2$N(CH$_3$)$_2$; —(CF$_2$)$_\beta$CF$_3$; —O(CF$_2$)$_\beta$OCH$_3$; —OCH$_2$CH$_2$(CF$_2$)$_\beta$OCH$_3$; —OCH$_2$CH$_2$(CF$_2$)$_\beta$CH$_2$N(CH$_3$)$_2$; —O(CF$_2$)$_\beta$CH$_2$N(CH$_3$)$_2$; —OCH$_2$CH$_2$(CF$_2$)$_\beta$CF$_3$; —(CH$_2$)$_\beta$—(OCH$_2$CH$_2$)$_\alpha$Phenyl; —(CF$_2$)$_\beta$—(OCH$_2$CH$_2$)$_\alpha$Phenyl; and —(CF$_2$)$_\beta$—(OCH$_2$CH$_2$)$_\alpha$Phenyl; wherein subscript $\gamma$ is an integer number from 0 to 25, wherein subscript $\delta$ is an integer number from 0 to 25; wherein subscript r is an integer number from 0 to 6; wherein subscript s is an integer number from 0 to 3.

2. A charge-transport material comprising,
a hexaazatrinaphthylene (HATNA)-[X]$_6$ monomer having a structure:

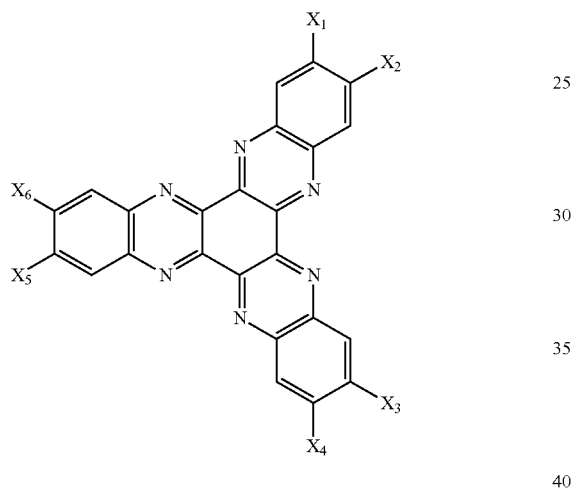

wherein X$_1$, X$_2$, X$_3$, X$_4$, X$_5$, and X$_6$ each are independently selected from: CN; NO$_2$; CHO; linear or branched, alkyl groups with from 2 to 25 carbons; linear or branched, perfluoronated alkyl groups with up to 25 carbons; fused aromatic rings; donor groups; acceptor groups; aryl groups; polymerizable groups; —(CH$_2$CH$_2$O)$_\alpha$—(CH$_2$)$_\beta$OR$_{a1}$; —(CH$_2$CH$_2$O)$_\alpha$—(CH$_2$)$_\beta$NR$_{a2}$R$_{a3}$; —(CH$_2$CH$_2$O)$_\alpha$—(CH$_2$)$_\beta$CONR$_{a2}$R$_{a3}$; —(CH$_2$CH$_2$O)$_\alpha$—(CH$_2$)$_\beta$CN; —(CH$_2$CH$_2$O)$_\gamma$—(CH$_2$)$_\delta$F; —(CH$_2$CH$_2$O)$_\gamma$—(CH$_2$)$_\delta$NO$_2$; —(CH$_2$CH$_2$O)$_\alpha$—(CH$_2$)$_\beta$Cl; —(CH$_2$CH$_2$O)$_\alpha$—(CH$_2$)$_\beta$Br; —(CH$_2$CH$_2$O)$_\alpha$—(CH$_2$)$_\beta$I; —(CH$_2$CH$_2$O)$_\alpha$—(CH$_2$)$_\beta$-Phenyl; —(CH$_2$)$_\beta$—(OCH$_2$CH$_2$)$_\alpha$R$_{a1}$; —(CH$_2$)$_\beta$—(OCH$_2$CH$_2$)$_\alpha$NR$_{a2}$R$_{a3}$; —(CH$_2$)$_\beta$—(OCH$_2$CH$_2$)$_\alpha$CONR$_{a2}$R$_{a3}$; —(CH$_2$)$_\beta$—(OCH$_2$CH$_2$)$_\alpha$CN; —(CH$_2$)$_\beta$—(OCH$_2$CH$_2$)$_\alpha$F; —(CH$_2$)$_\beta$—(OCH$_2$CH$_2$)$_\alpha$NO$_2$; —(CH$_2$)$_\beta$—(OCH$_2$CH$_2$)$_\alpha$Cl; —(CH$_2$)$_\beta$—(OCH$_2$CH$_2$)$_\alpha$Br; —(CH$_2$)$_\beta$—(OCH$_2$CH$_2$)$_\alpha$I; —(CH$_2$)$_\beta$—(OCH$_2$CH$_2$)$_\alpha$Phenyl; —(CF$_2$)$_\beta$OR$_{a1}$; —(CF$_2$)$_\beta$CH$_2$NR$_{a2}$R$_{a3}$; —(CF$_2$)$_\beta$CF$_3$; —O(CF$_2$)$_\beta$OR$_{a1}$; —OCH$_2$CH$_2$(CF$_2$)$_\beta$OR$_{a1}$; —OCH$_2$CH$_2$(CF$_2$)$_\beta$CH$_2$NR$_{a2}$R$_{a3}$; —O(CF$_2$)$_\beta$CH$_2$NR$_{a2}$R$_{a3}$; —OCH$_2$CH$_2$(CF$_2$)$_\beta$CF$_3$; —(CH$_2$)$_\beta$—(OCH$_2$CH$_2$)$_\alpha$Phenyl; —(CF$_2$)$_\beta$—(OCH$_2$CH$_2$)$_\alpha$Phenyl; —(CH$_2$)$_\beta$—(OCH$_2$CH$_2$)$_\alpha$Aryl; —(CF$_2$)$_\beta$—(OCH$_2$CH$_2$)$_\alpha$Aryl; —(OCH$_2$CH$_2$)$_\alpha$—(CF$_2$)$_\beta$Aryl; —(OCH$_2$CH$_2$)$_\alpha$—(CH$_2$)$_\beta$Aryl; —O(CH$_2$)$_\beta$Aryl; and —O(CF$_2$)$_\beta$Aryl; and combinations thereof;

wherein R$_{a1}$, R$_{a2}$, and R$_{a3}$ can each be independently selected from, the following groups: H; linear or branched, alkyl groups with up to 25 carbons; a functional group derived from amino acids, nucleic acids, biotin, ferrocene, ruthenocene, cyanuric chloride, methacryloyl chloride, and derivatives thereof; wherein subscript $\alpha$ is an integer number from 0 to 25, wherein subscript $\beta$ is an integer number from 0 to 25; and with the proviso that X$_1$, X$_2$, X$_3$, X$_4$, X$_5$, and X$_6$ are each not an alkoxy group, —OR, where R=C$_n$H$_{2n+1}$, where n=6, 8, 10, or 12; an alkylthio, —SR, where R=C$_n$H$_{2n+1}$, where n=6, 8, 10, or 12; H; Cl; or a methyl (—CH$_3$) group;

further comprising wherein one or more of the X$_1$, X$_2$, X$_3$, X$_4$, X$_5$, and X$_6$ each are independently selected from an polymerizable group, wherein the polymerizable group is selected from: vinyl; allyl; 4-styryl; acroyl; epoxide; oxetane; cyclic-carbonate; methacroyl; acrylonitrile; isocyanate; isothiocyanate; epoxides; strained ring olefins; (—CH$_2$)$_\eta$SiCl$_3$; (—CH$_2$)$_\eta$Si(OCH$_2$CH$_3$)$_3$; (—CH$_2$)$_\eta$Si(OCH$_3$)$_3$, where $\eta$ is an integer number from 0 to 25; and compounds having the following structures:

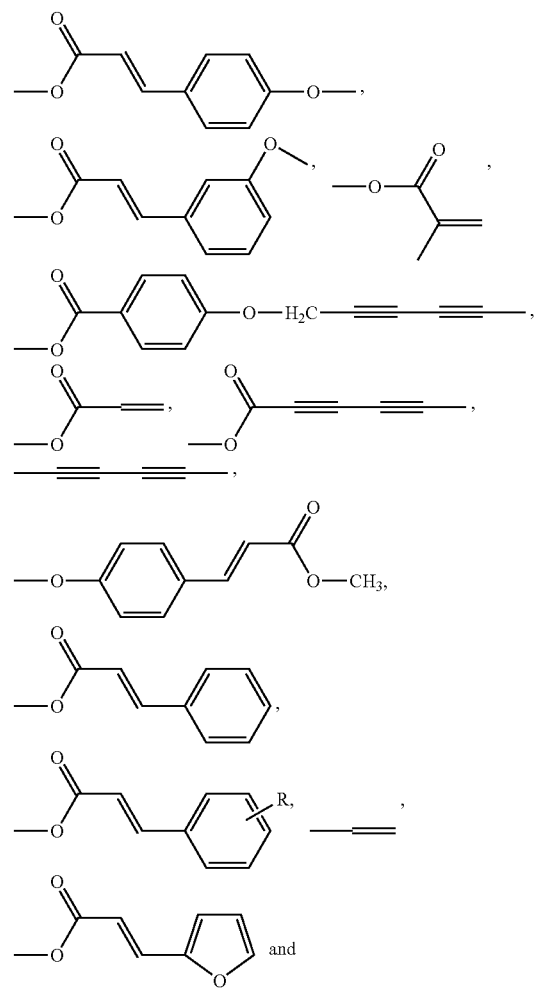

-continued

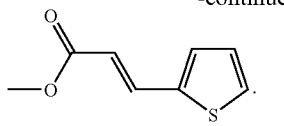

3. A polymer comprising a monomer selected from one of: the HATNA-[X]$_6$ monomer of claim 1, or 2 and a combination thereof.

4. A homopolymer comprising a monomer selected from one of: the HATNA-[X]$_6$ monomer of claim 1, or 2.

5. A copolymer comprising a monomer selected from one of: the HATNA-[X]$_6$ monomer of claim 1, or 2, and a combination thereof.

6. A device, comprising:
a polymer including a compound selected from one of: HATNA-[X]$_6$ of claim 1, or 2, and a combination thereof.

7. The device of claim 6, wherein the polymer is included in a structure selected from: electroluminescent (EL) devices, photovoltaic cells, light-emitting diodes, field-effect transistors, phototransistors, radio-frequency ID tags, semiconductor devices, photoconductive diodes, metal-semiconductor junctions, p-n junction diodes, p-n-p-n switching devices, photodetectors, optical sensors, phototransducers, bipolar junction transistors (BJTs), heterojunction bipolar translators, switching transistors, charge transfer devices, thin film transistors, organic radiation detectors, infra-red emitters, tunable microcavities for variable output wavelength, telecommunications devices and applications, optical computing devices, optical memory devices, chemical detectors, and combinations thereof.

8. A polymer layer, comprising:
a plurality of layers, wherein each layer includes a monomer having a central aromatic core, wherein the central aromatic cores in the layers are stacked substantially over one another to form a one-dimensional charge transport column along the stacked central aromatic cores, wherein the monomer includes a compound selected from: HATNA-[X]$_6$ of claim 1, or 2, and a combination thereof.

9. A material, comprising:
a mixture of components comprising a monomer, a polymer including the monomer, a co-polymer including the monomer, a homopolymer including the monomer, and combinations thereof; wherein the monomer is selected from: the HATNA-[X]$_6$ monomer of claim 1, or 2, and a combination thereof; wherein an amount of each monomer present in the mixture is selected to control at least one property of the mixture; wherein the property is selected from one of: volatility, solubility, crystallinity, melting point, phase transitions, shelf life, charge transport ability, and combinations thereof.

10. A material, comprising:
a mixture of components comprising a compound selected from: HATNA-[X]$_6$ of claim 1, or 2, and a combination thereof; wherein an amount of each compound present in the mixture is selected to control at least one property of the mixture; wherein the property is selected from one of: volatility, solubility, crystallinity, melting point, phase transitions, shelf life, charge transport ability, and combinations thereof.

11. A device, comprising:
a first electrode;
a hole-transport layer disposed adjacent the first electrode;
an electron-transport layer disposed adjacent the hole-transport layer, and wherein the electron-transport material is selected from: HATNA-[X]$_6$ of claim 1, or 2, combination thereof; and
a second electrode disposed adjacent the electron-transport layer.

12. The device of claim 11, wherein the device is an organic light-emitting diode.

13. The device of claim 11, wherein the device is an organic photovoltaic cell.

14. An organic photovoltaic cell comprised of:
a first electrode;
a hole-transport layer disposed adjacent the first electrode;
an electron-transport layer disposed adjacent the hole-transport layer, and wherein the electron-transport material is selected from: HATNA-[X]$_6$ of claim 1, or 2, and a combination thereof;
an exciton blocking layer disposed adjacent the electron-transport layer; and
a second electrode disposed adjacent the exciton blocking layer.

15. An organic field-effect transistor comprised of:
a substrate;
a gate electrode disposed on a first side of the substrate;
a gate insulator disposed on a second side of the substrate;
a source electrode disposed on a first portion of the gate insulator;
a drain electrode disposed on a second portion of the gate insulator; and
an electron-transport layer disposed on a third portion of the gate insulator, the source electrode, and the drain electrode, and wherein the electron-transport material is selected from: HATNA-[X]$_6$ of claim 1, or 2, and a combination thereof.

* * * * *